US009587222B2

(12) United States Patent
Matsuda et al.

(10) Patent No.: US 9,587,222 B2
(45) Date of Patent: Mar. 7, 2017

(54) THREE-DIMENSIONAL TISSUE STRUCTURE

(75) Inventors: Hikaru Matsuda, Hyogo (JP); Yoshiki Sawa, Hyogo (JP); Satoshi Taketani, Osaka (JP); Shigeru Miyagawa, Osaka (JP)

(73) Assignee: CELLSEED INC., Tokyo (JP)

( * ) Notice: Subject to any disclaimer, the term of this patent is extended or adjusted under 35 U.S.C. 154(b) by 1084 days.

(21) Appl. No.: 10/567,728

(22) PCT Filed: Feb. 2, 2004

(86) PCT No.: PCT/JP2004/001024

§ 371 (c)(1), (2), (4) Date: Oct. 27, 2006

(87) PCT Pub. No.: WO2005/011524

PCT Pub. Date: Feb. 10, 2005

(65) Prior Publication Data

US 2007/0092492 A1 Apr. 26, 2007

(30) Foreign Application Priority Data

Aug. 1, 2003 (JP) ................................ 2003-285476

(51) Int. Cl.

| | |
|---|---|
| ***C12N 15/00*** | (2006.01) |
| ***C12N 5/00*** | (2006.01) |
| ***C12N 5/02*** | (2006.01) |
| ***C12N 5/071*** | (2010.01) |
| ***C12N 5/077*** | (2010.01) |
| ***A61L 27/38*** | (2006.01) |
| ***A61K 35/34*** | (2015.01) |
| *A61K 35/12* | (2015.01) |

(52) U.S. Cl.

CPC ............ *C12N 5/0658* (2013.01); *A61K 35/34* (2013.01); *A61L 27/3804* (2013.01); *A61L 27/3834* (2013.01); *A61L 27/3839* (2013.01); *A61L 27/3895* (2013.01); *C12N 5/0068* (2013.01); *C12N 5/0657* (2013.01); *A61K 35/12* (2013.01); *A61L 2430/20* (2013.01); *C12N 2506/02* (2013.01); *C12N 2506/1392* (2013.01); *C12N 2513/00* (2013.01); *C12N 2523/00* (2013.01); *C12N 2533/40* (2013.01); *C12N 2539/10* (2013.01)

(58) Field of Classification Search

CPC ..................................................... C12N 5/068

See application file for complete search history.

(56) References Cited

U.S. PATENT DOCUMENTS

| | | | |
|---|---|---|---|
| 6,207,451 | B1 | 3/2001 | Dennis et al. |
| 6,432,711 | B1 | 8/2002 | Dinsmore et al. |
| 2005/0053585 | A1 | 3/2005 | Black et al. |

FOREIGN PATENT DOCUMENTS

| | | | |
|---|---|---|---|
| EP | 1 358 895 | A1 | 11/2003 |
| JP | H10-511847 | | 11/1998 |
| WO | WO 96/21003 | A1 | 7/1996 |
| WO | WO 01/07568 | A2 | 2/2001 |
| WO | WO 02/08387 | A1 | 1/2002 |
| WO | WO 03/052084 | A2 | 6/2003 |

OTHER PUBLICATIONS

Carnac, G et al , 1998, Mol. Biol. Cell., 9:1891-1902.*

Mathur and Martin, The Lancet, 2004, 264:183-192.*

Jin et al , Jour Pharm and Exp Therapeutics, Feb. 1, 2003, 304:654-660.*

Loh et al, 2009. Macromolecular Bioscience, 6:1069-1079.*

Shimizu, Circulation Res, 2002, 90:e40-e48;.*

Kushida, 1999,J biomed Mater Res, 45:355-362.*

Choi, Journal of Bioscience and Bioengineering, 2008, vol. 105:586-594.*

Frith, Tissue Engineering: PartC, 2010,16:735-749.*

Yamato, Materials Today, May 2004, pp. 42-47.*

Haraguchi, Nature, 2012, 7:850-858.*

Shimizu Tatsua, et al: "Fabrication of pulsatile cardiac tissue grafts using a novel 3-dimensional cell sheet manipulation technique and temeprature-responsive cell culture surfaces", Circulation Research, Feb. 22, 2002, vol. 90, No. 3, pp. E40-E48.

Teruo Okano: "Cardiac tissue reconstruction based on cell sheet engineering" Japanese Circulation Society, Online! 2002, pp. 1-4.

Kellar, Robert, et al.: "Scaffold-based three-dimensional human fibroblast culture provides a structural matrix that supports angiogenesis in infarcted heart tissue", Circulation, vol. 104, No. 17, Oct. 23, 2001, pp. 2063-2068.

Miyagawa, Shigeru, et al.: "A tissue engineered contractile cardiac graft improves the cardiac performance in infarct rat heart", Oct. 23, 2001, Circulation, vol. 104, NR 17 Supplement, pp. II.599, Scientific Sessions 2001 of the American Heart Association.

Bach, A.D., et al.: "Expression of Trisk 51, agrin and nicotinic-acetycholine reception epsilon-subunit during muscle development in a novel three-dimensional muscle-neuronal co-culture system" Cell & Tissue Research, vol. 314, No. 2, Nov. 2003, pp. 263-274.

European Office Action dated Sep. 10, 2007, issued in connection with European Application No. 04 707 319.2.

(Continued)

*Primary Examiner* — Valarie Bertoglio

(74) *Attorney, Agent, or Firm* — Nixon & Vanderhye P.C.

(57) ABSTRACT

The present invention provides a prosthetic tissue or sheet capable of withstanding implantation operations, which can be used in actual operation and can be produced by culture. The present invention also provides a novel therapy which can substitute for cell therapy. Particularly, the present invention provides a method for producing a prosthetic tissue comprising a cell derived from a part other than myocardium and capable of withstanding implantation operation. The above-described objects of the present invention were partially achieved by finding that by culturing cells under specific culture conditions, the cells are unexpectedly organized into a tissue, and the resultant prosthetic tissue is capable of being detached from culture dishes. The present invention also provides a three-dimensional structure applicable to heart, comprising a cell derived from a part other than the myocardium of an adult.

16 Claims, 47 Drawing Sheets

(56) References Cited

OTHER PUBLICATIONS

Shimizu et al, "Tissue engineering for myocardial regeneration", J Artif. Organs., (2002) 5:216-222.

Bruder et al, "Saisei Igaku—tissue engineering no kiso kara saisenntann gijyutu made", pp. 677-678 (Jan. 31, 2002), referred to in Office Acton of Dec. 22, 2008.

Saito et al, "Transcoronary implantation of bone marrow stromal cells ameliorates cardiac function after myocardial infarction", The Journal of Thoracic and Cardiovascular Surgery, Jul. 2003, vol. 126, pp. 114-122.

Memon et al, "Nihon-geka-gakkai zassi", Apr. 2003, vol. 104, p. 422.

Partial translation of Bruder et al, "Saisei Igaku—tissue engineering no kiso kara saisenntann gijyutu made", pp. 677-678 (Jan. 31, 2002), referred to in Office Acton of Dec. 22, 2008.

Presentation of Mr. Memon Imran Ahmad at the $67^{th}$ Annual Scientific Meeting of the Japanese Circulation Society on Mar. 28, 2003.

European Search Report dated Aug. 11, 2011, issued in connection with EP 10 18 3373.9.

Memon, "Tissue Engineered Myoblast Sheet Improves Cardiac Performance", Circulation Journal, vol. 67, Supplement 1, Mar. 1, 2003, p. 89.

Menasche et al, "Myoblast transplantation for heart failure", The Lancet, vol. 357, Jan. 27, 2001, pp. 279-280.

Miyahara et al, "Monolayered mesenchymal stem cells repair scarred myocardium after myocardial infarction", Techincal Reports, Nature Medicine, Advance Online Publication, pp. 1-7, 2006, Nature Publishing Group http://www.nature.comb/naturemedicine.

* cited by examiner

Poly (N-isopropylacrylamide) (PIPAAm
Polyacrylamide (PAAm)
No cell adhesion
Temperature responsive culture dish
Hydrophobic PIPAAm
37°C
Hydrophilic PIPAAm
32°C or less: detached as a sheet
pile up
3D tissue structure with high biocompatibility can be constructed without destroying cell-to-cell adhesion TISSUE IMPLANT
Infarcted Heart
Cell sheet implant on scar area
MYOBLAST INJECTION
Infarcted Heart
Myoblast delivery by inj. in scar area

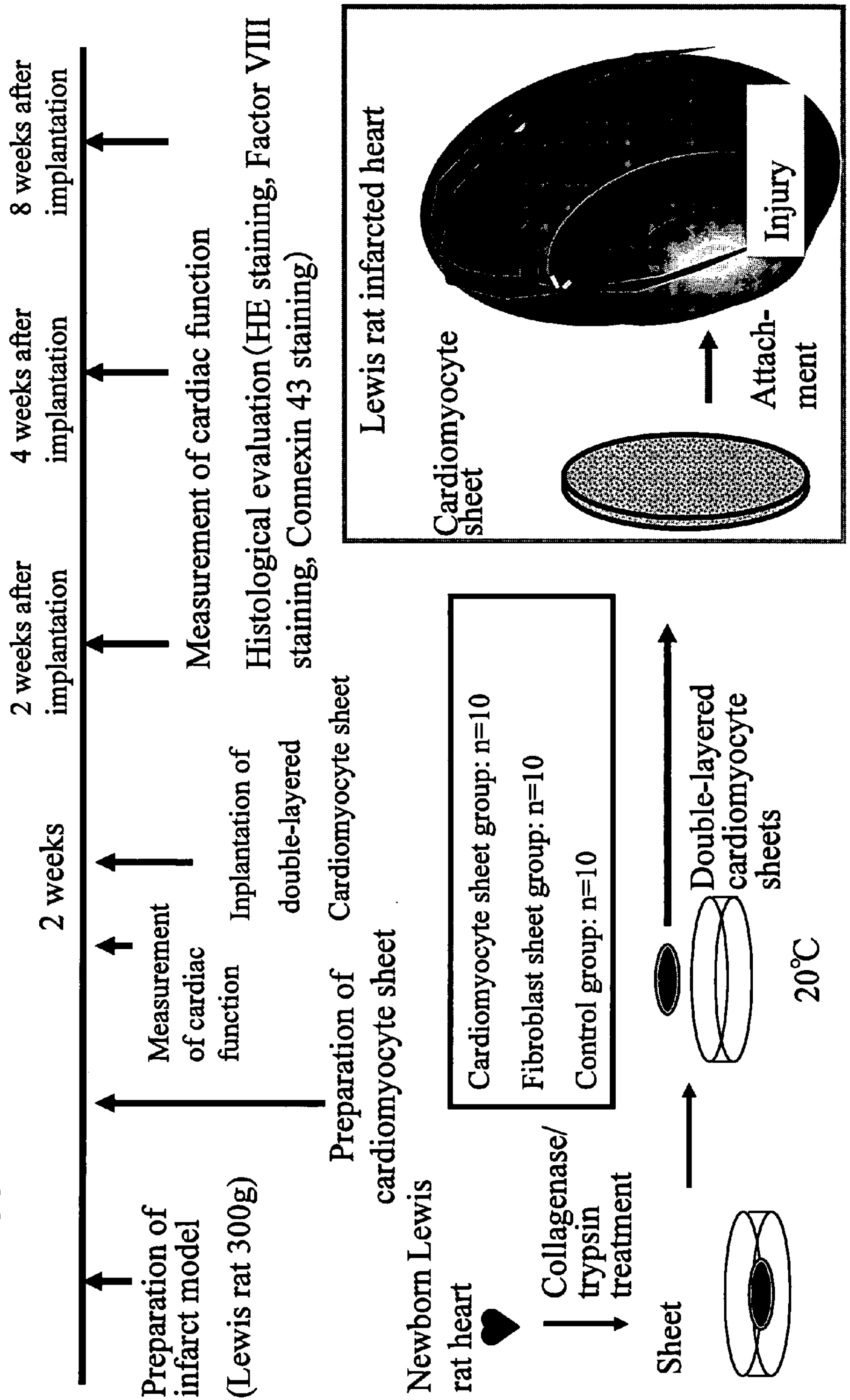
FIG.3
Experimental Protocol
Preparation of infarct model
(Lewis rat 300g)
Preparation of cardiomyocyte sheet
Measurement of cardiac function
2 weeks
Implantation of double-layered Cardiomyocyte sheet
2 weeks after implantation
4 weeks after implantation
8 weeks after implantation
Measurement of cardiac function
Histological evaluation (HE staining, Factor VIII staining, Connexin 43 staining)
Newborn Lewis rat heart
Collagenase/trypsin treatment
Sheet
Cardiomyocyte sheet group: n=10
Fibroblast sheet group: n=10
Control group: n=10
20°C
Double-layered cardiomyocyte sheets
Cardiomyocyte sheet
Attach-ment
Lewis rat infarcted heart
Injury Regenerative therapy for cardiac muscle by cell transplantation FIG.5 Problems with tissue transplantation FIG.6
Implantation of cardiomyocyte sheet into infarcted heart
Cardiomyocyte sheet
Implantation into rat infarct model
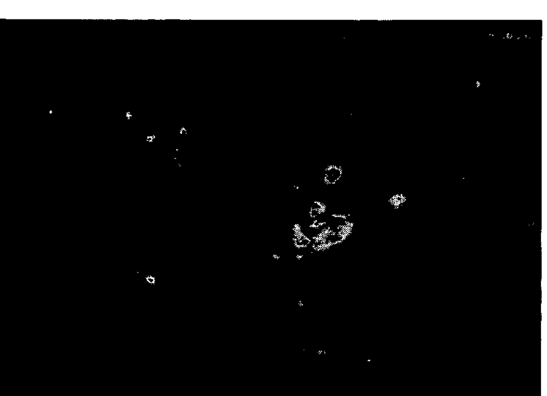
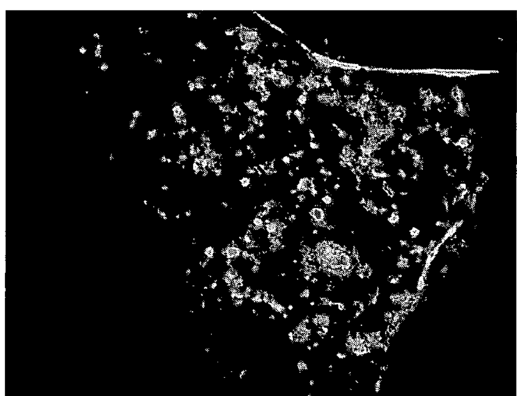
*In vitro* *In vivo*
Implantation of GFP rat newborn cardiomyocyte sheet Tissue FIG.8
Evaluation of Cardiac function - 1
Control
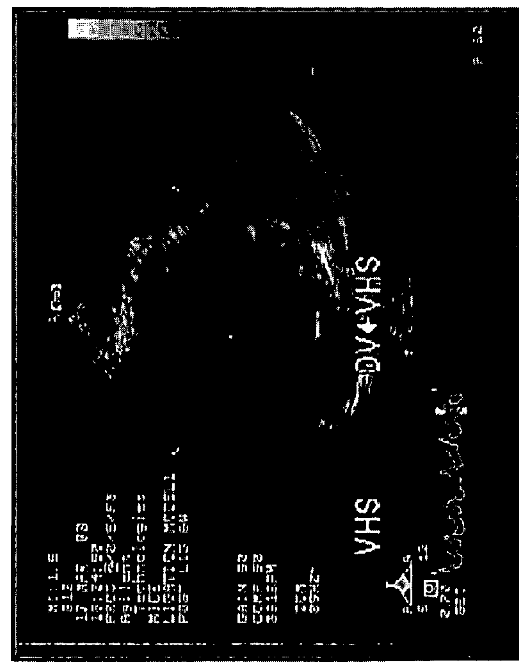
Implantation of prosthetic tissue
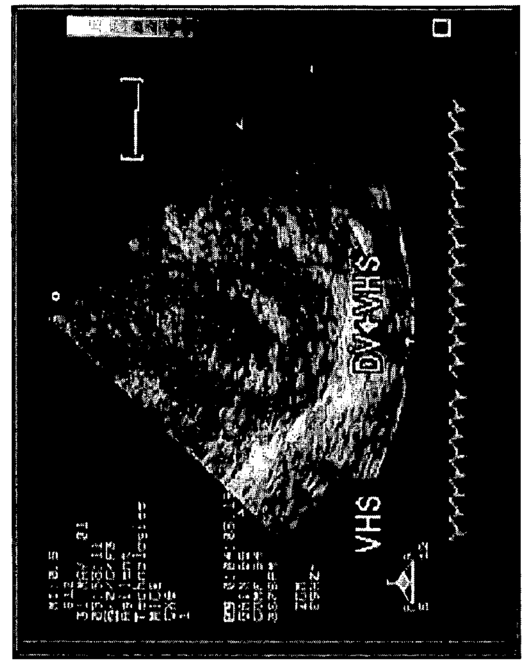
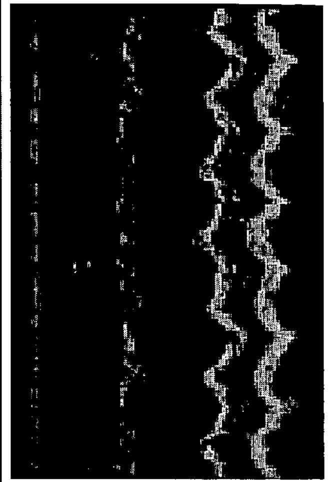

Electrophysiological Evaluation
Threshold
Control
Fibroblast sheet
Cardiomyocyte sheet
Stimulus (300bpm)
Atrium
Injury
Buried electrode at sheet implanted site
Time [Sec]
ECG 1 [mV]
ECG 2 [mV]
Voltage 3 [V]

FIG.11
Electrophysiological Evaluation
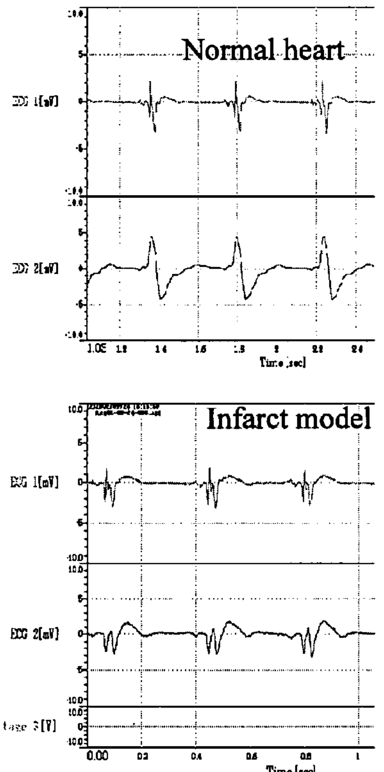
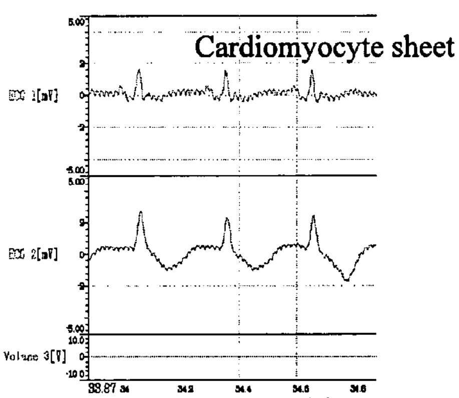
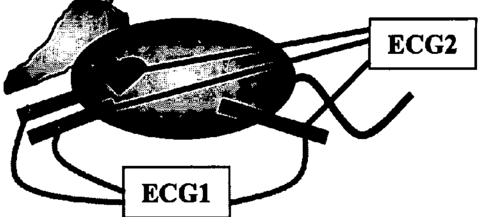
ECG 1:ECG (Surface)
ECG 2: Normal heart (anterior wall)
Ligation model (injured)
Prosthetic tissue implanted
(prosthetic tissue injured)

Myoblast sheet Implantation procedure

FIG.18
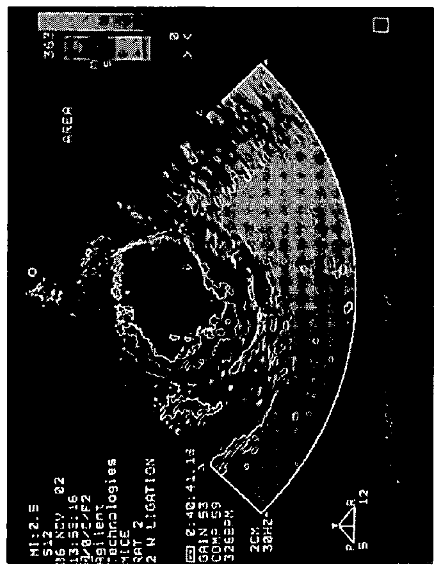
CKA
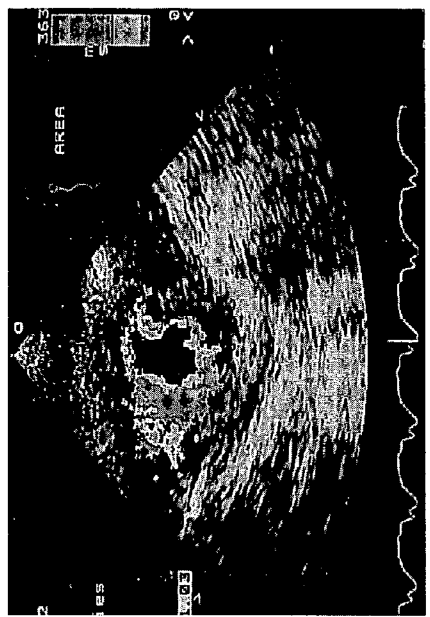
M-mode analysis
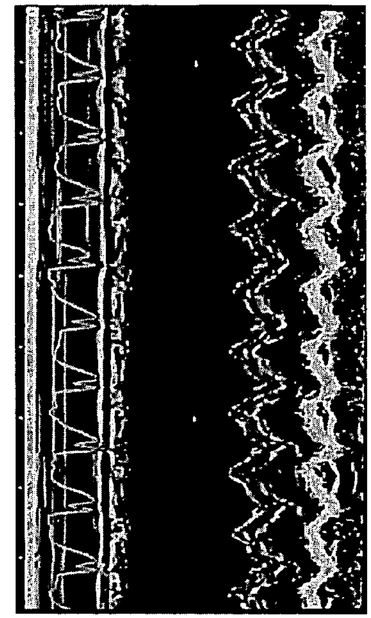

Ejection Fraction
EF (%)
70
60
50
40
30
20
Baseline
2W
4W
8W
Myoblast prosthetic tissue
Myoblast injection
Control
End Diastolic Area
EDA (cm2)
0.9
0.8
0.7
0.6
0.5
E-wave
E-waw (cm2)
140
120
100
80
60
End Systolic Area
ESA (cm2)
0.7
0.6
0.5
0.4
0.3
P< 0.05 for control; *P< 0.05 to for injection needle group Anterior Wall Thickness Comparison
Myoblast prosthetic tissue
x40
Myoblast injection
x40
Control
x40
Anterior wall thickness
Thickness (um)
2000
1500
1000
500
0
*
Control
Myoblast prosthetic tissue
Myoblast injection
P<0.05

FIG.22D
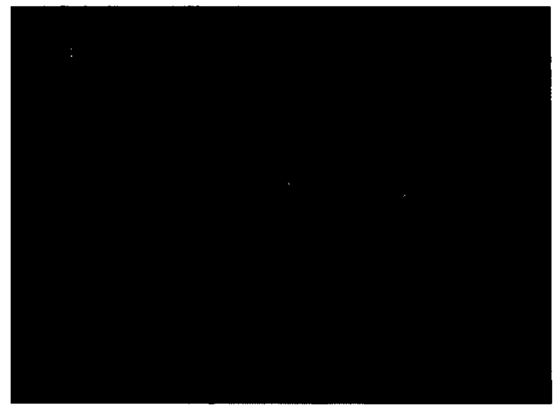
FIG.22E
FIG.22F
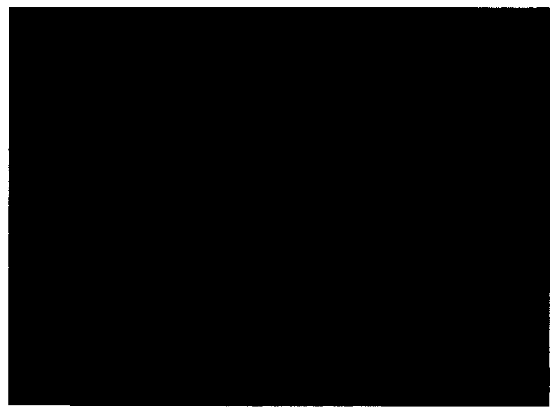

Tissue (Masson's Trichrome staining)

Electrorical propertes of myoblast sheet

FIG.33A Myoblast sheet implantation to dilated cardiomyopathic hamster
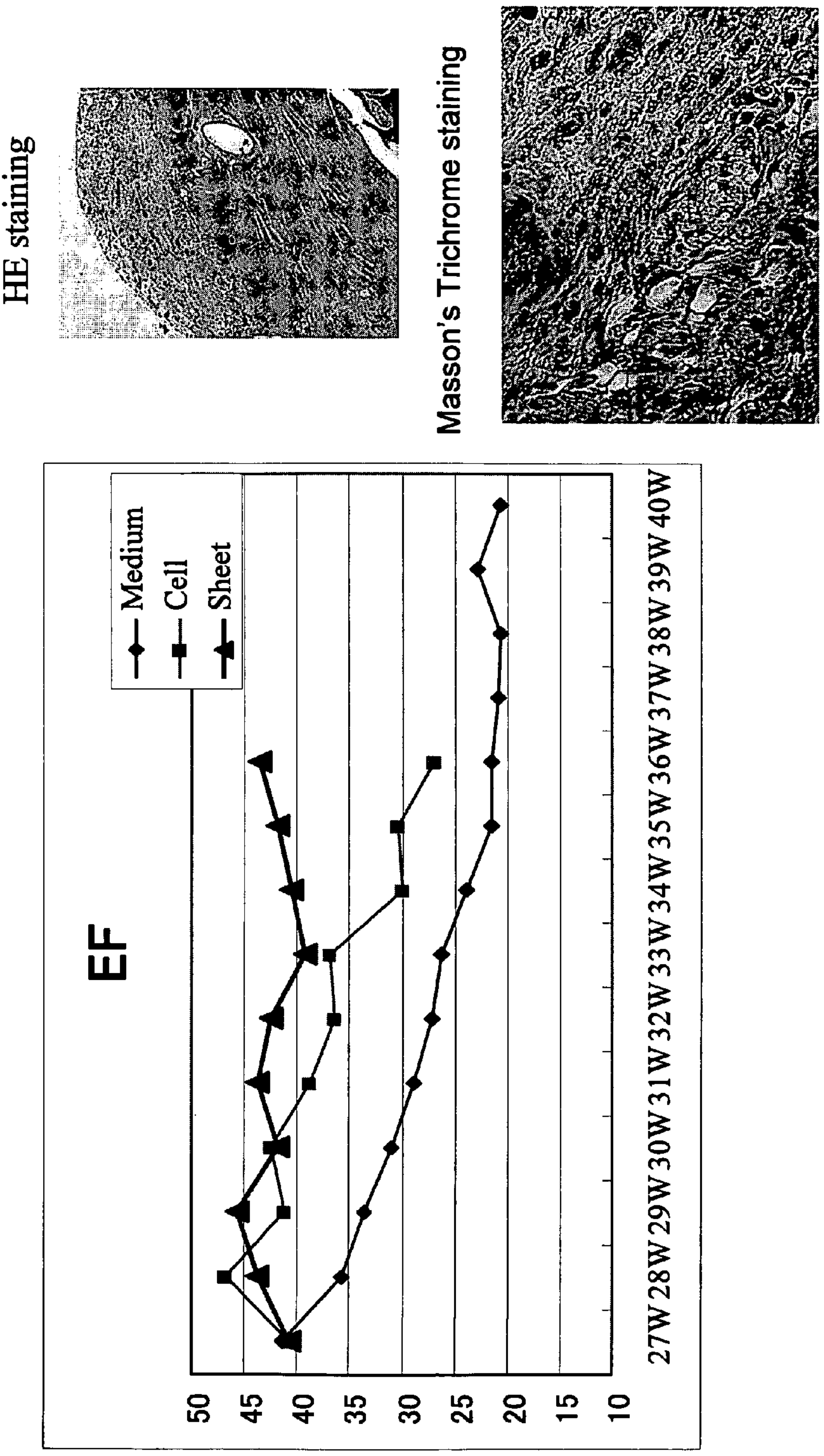

FIG.33C
Control group
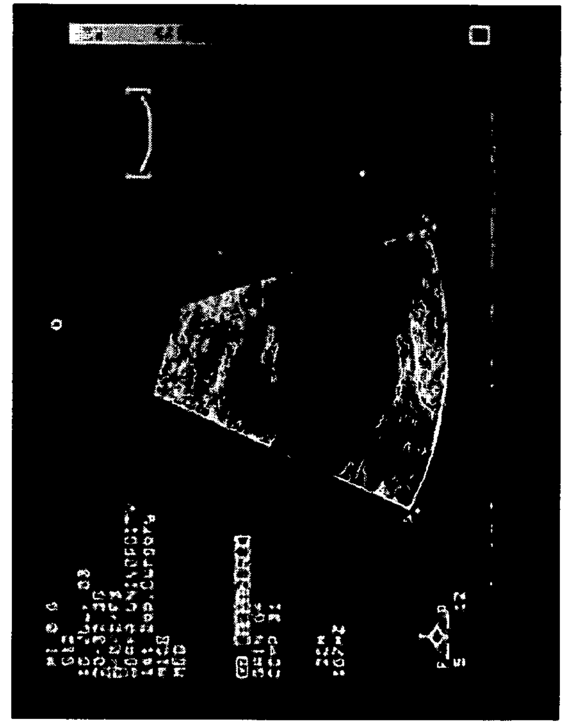
Myoblast sheet implantation group
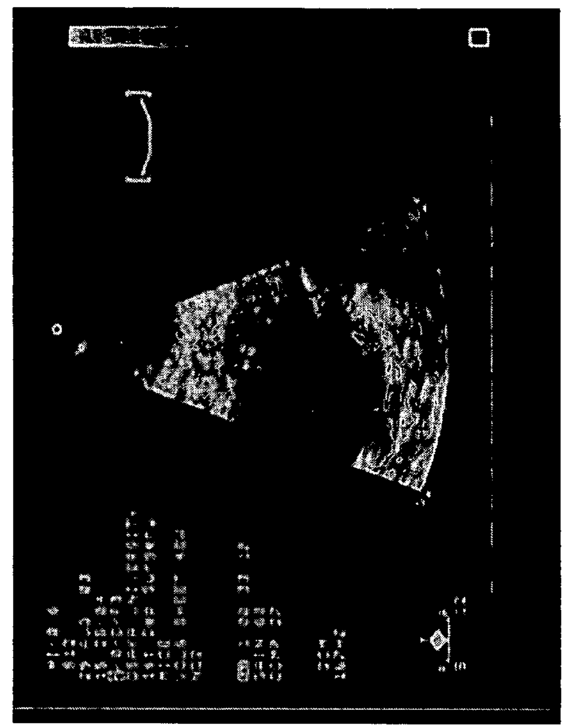

FIG.34 Myoblast sheet implantation into pig infarction model
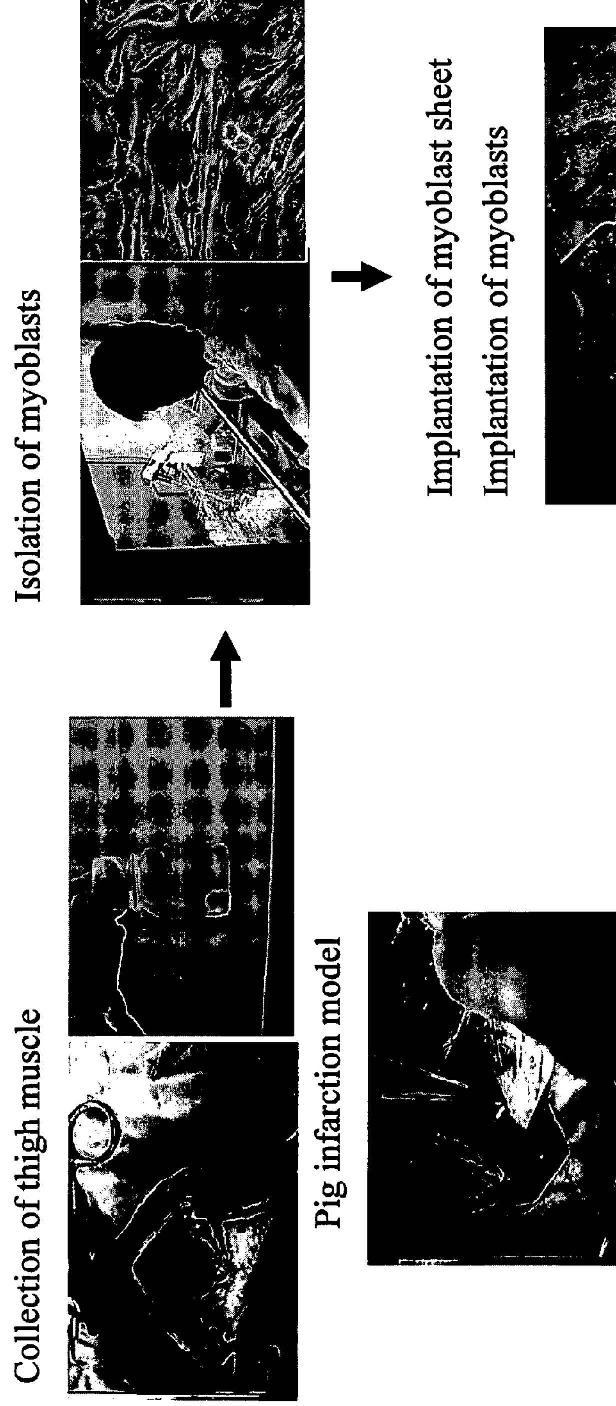

Evaluation of cardiac function (systolic function) of pig infarction model by CKI method Before operation After operation → Implantion site Evaluation of cardiac function (diastolic function) of pig infarction model by CKI method FIG.37
Without ascorbic acid
FIG.38
With ascorbic acid
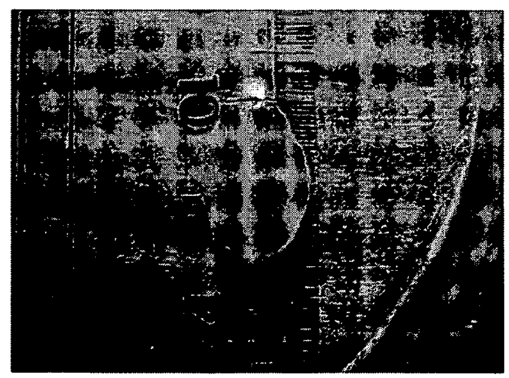
FIG.39
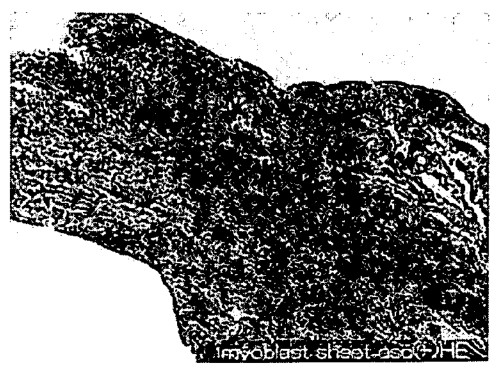

FIG.41

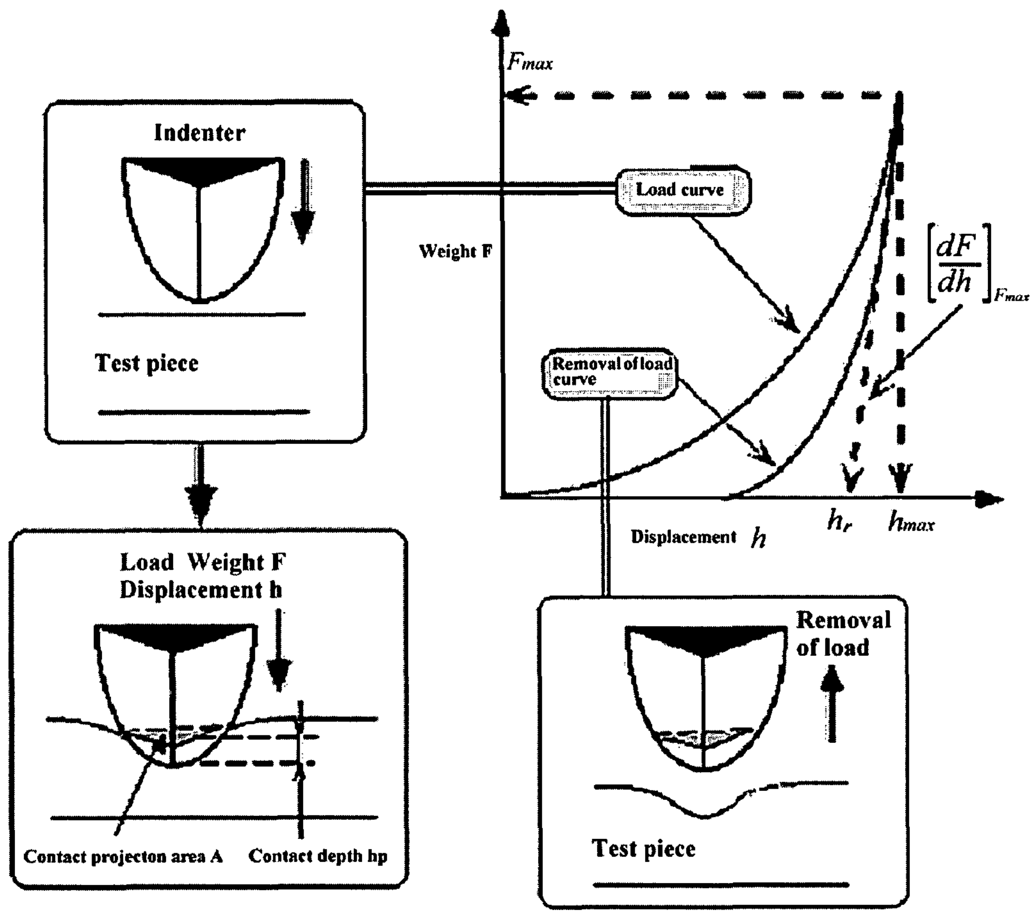

Rigidity $H = \frac{F}{A} = \frac{F}{k_1 h_p^2}$

Young's modulus $E = \left[\frac{dF}{dh}\right]_{F_{max}} \frac{1-\nu^2}{2 \cdot k_2 \cdot h_{pmax}}$ Contact depth $h_p = h_r + 0.25(h_{max} - h_r)$ $F$ : Load $A$ : Contact projection area $h_p$ : Contact depth $k_1 k_2$ : Shape coefficient $F_{max}$ : Maximum load $h_{max}$ : Max. displacement $h_r$ : Point at which tangential line cross weight 0

$dF/dh$ : Gradient of tangential line of the removal of load curve $\nu$ : Poisson's ratio

FIG.42

THREE-DIMENSIONAL TISSUE STRUCTURE

The present application is a 371 U.S. National Phase of PCT/JP2004/001024, filed Feb. 2, 2004, which designated the U.S. and claims benefit of JP 2003-285476, filed Aug. 1, 2003.

TECHNICAL FIELD

The present invention relates to a three-dimensional structure applicable to the heart, and more particularly, to a three-dimensional structure applicable to the heart, which comprises cells derived from parts of an adult other than the heart. The present invention also relates to a method for producing such a three-dimensional structure.

BACKGROUND ART

Myocardial infarct is an irreversible injury (Ho K. K., Anderson K. M., Kannel W. B., Grossman W., Levy D., Circulation, 1993; 88: 107-115). Ischemic heart diseases are the cause of death responsible for 50% of all cardiovascular system-related deaths and the major cause of congestive heart failure. The 1-year mortality observed in patients who are diagnosed as having congestive heart failure and eventually die from chronic heart disease is 20% (American Heart Association, Dallas, Tex.: American Heart Association; 2001). Most therapies currently available to clinicians can significantly improve the prognosis of patients suffering from acute myocardial infarct. Angioplasty and thrombolytic agents may remove the cause of the acute myocardial infarct, though the period of time from the onset of occlusion to reperfusion determines the degree of irreversible myocardial injury (Ryan T. J., Antman E. M., Brooks N. H., Califf R. M., Hillis L. D., Hiratzka L. F., Rapaport E., Riegel B., Russell R. O., Smith E. E. III, Weaver W. D., Gibbons R. J., Alpert J. S., Eagle K. A., Gardner T. J., Garson A. Jr., Gregoratos G., Ryan T. J., Smith S. C. Jr., J. Am. Coll. Cardiol., 1999; 34: 890-911). No clinically used pharmaceutical agent or treatment has an efficacy on the replacement of myocardial scars with functional contraction tissue. There is a demand for a novel therapy for regenerating normal cardiomyocytes.

Cardiomyoplasty has been proposed as a surgical method for improving the function of the left ventricle (LV) of a patient suffering from congestive heart failure, however, the effect thereof on the cardiac function remains unclear (Corin W. J., George D. T., Sink J. D. et al., J. Thorac. Cardiovasc. Surg., 1992, 104:1662-1671; Kratz J. M., Johnson W. S., Mukherjee R. et al., J. Thorac. Cardiovasc. Surg., 1994, 107:868-878; Carpentier A., Chachques J. C., Lancet, 1985, 8840:1267; and Hagege A. A., Desnos M., Chachques J. C. et al., Preliminary report: follow-up after dynamic cardiomyoplasty, Lancet, 1990, 335:1122-1124). Recently, implantation of a biologically modified heart graft, in which a biodegradable scaffold is used, has been proposed as another novel approach. However, the graft hardly attaches to the myocardium, resulting in the least possible benefit for the improvement of the cardiac function (Leor J., Etzion S. A., Dar A. et al., Circulation, 2000; 102 [suppl. III] III-56-III-61; and Li R. K., Jia Z. Q., Weisel R. D. et al., Circulation, 1999; 100 [suppl II]: II-63-II-69). The histological and electrical integration of biologically modified heart tissue and a recipient heart may be crucial for the regeneration of impaired myocardium.

The recent development of tissue engineering is expected to make possible the production of a functional heart tissue using a novel technique, in which cell sheets are three-dimensionally layered without any biodegradable substitute for extracellular matrices (ECM) (Okano T., Yamada N., Sakai H., Sakurai Y., J. Biomed. Mater. Res., 1993; 27:1243-1251). In this novel technique, both intracellular adhesion and adhesion proteins within a confluently cultured cell monolayer are fully maintained. Endogenous ECM supporting a cell sheet whose base portion has been collected by a collecting method (Kushida A., Yamato M., Konno C., Kikuchi A., Sakurai Y., Okano T., J. Biomed. Mater. Res., 45:355-362, 1999) plays an important role as an adhesion factor for the integration to the recipient heart. Further, the cardiomyocyte sheet is a pulsating 3-D heart construct which transmits electricity (Shimizu T., Yamato M., Akutsu T. et al., Circ. Res., Feb. 22, 2002, 90(3):e40). However, it is unknown whether or not cardiomyocyte sheets retain their functions after in vivo implantation.

The recent progress in tissue engineering has the potential of providing an implantable functional tissue comprising various cells and an extracellular matrix.

Implantation of organs (e.g., heart, blood vessel, etc.) using an exogenous tissue is mainly hindered by immunological rejections. Changes occurring in allografts and xenografts were first described 90 or more years ago (Carrel A., 1907, J. Exp. Med. 9:226-228; Carrel A., 1912, J. Exp. Med. 9:389-392; Calne R. Y., 1970, Transplant Proc. 2:550; and Auchincloss 1988, Transplantation 46:1). Rejection to artery grafts pathologically leads either to enlargement (up to rupture) or occlusion of the grafts. The former is caused by decomposition of extracellular matrices, while the latter is caused by proliferation of cells in a blood vessel (Uretsky B. F., Mulari S., Reddy S., et al., 1987, Circulation 76:827-834). Such grafts are often made from non-biological materials which lead to adverse effects.

Recently, cell implantation has attracted attention as a therapy utilizing biological material. However, the implantation of human myoblasts into the infarcted heart has the following drawbacks: 1. damage and loss of implantation cells; 2. tissue injury of the recipient heart during implantation; 3. tissue supply efficiency to the recipient heart; 4. occurrence of arrhythmia; 5. difficulty in treating the entirety of the infarcted site; and the like. Therefore, cell implantation cannot be said to be very successful.

Myocardium-derived sheets have been developed. Typically, autologous myocardium is required for the myocardium-derived sheet in view of immune reactions. Therefore, the applications of the sheet are limited.

Accordingly, there is a keen demand for a prosthetic tissue, a three-dimensional structure, or a sheet capable of withstanding implantation operations, being used in actual operations, and being produced by culture.

DISCLOSURE OF THE INVENTION

An object of the present invention is to provide a prosthetic tissue or sheet capable of withstanding implantation operations, being used in actual operations, and being produced by culture. Another object of the present invention is to provide a novel therapy, which is an alternative to cell therapy. The present invention is particularly directed to production of a prosthetic tissue comprising cells derived from parts other than the myocardium, which can withstand implantation operations.

The above-described objects of the present invention were achieved by providing a three-dimensional structure comprising cells derived from parts other than the myocardium. The objects of the present invention were partially achieved by finding that by culturing cells under specific culture conditions, the cells are unexpectedly organized into a tissue, and the resultant prosthetic tissue is capable of being detached from culture dishes.

The present invention was also achieved by unexpectedly finding that a three-dimensional structure comprising cells derived from parts other than the myocardium can function in a manner similar to that of the myocardium.

Therefore, the present invention provides the following.

(Non-Cardiac Sheet/Three-Dimensional Structure)

(1) A three-dimensional structure applicable to heart, comprising a cell derived from a part other than myocardium of an adult.

(2) A structure according to item 1, wherein the cell is a stem cell or a differentiated cell.

(3) A structure according to item 1, wherein the cell is a mesenchymal cell.

(4) A structure according to item 1, wherein the cell is derived from a myoblast.

(5) A structure according to item 4, wherein the myoblast is a skeletal myoblast.

(6) A structure according to item 1, wherein the cell is a fibroblast.

(7) A structure according to item 1, wherein the cell is a synovial cell.

(8) A structure according to item 1, wherein the cell is derived from a stem cell.

(9) A structure according to item 1, wherein the cell is derived from a subject, the structure being applied to the subject.

(10) A structure according to item 1, wherein the cell is not derived from a subject, the structure being applied to the subject.

(11) A structure according to item 1, wherein the structure expresses at least one non-adult heart marker selected from the group consisting of myosin heavy chain IIa, myosin heavy chain IIb, myosin heavy chain IId(IIx), CD56, MyoD, Myf5, and myogenin.

(12) A structure according to item 11, wherein an expression level of the non-adult heart marker in the structure is at least 50% of an expression level of the non-adult heart marker in skeletal myoblasts.

(13) A structure according to item 1, wherein the three-dimensional structure expresses all of myosin heavy chain IIa, myosin heavy chain IIb, myosin heavy chain IId(IIx), CD56, MyoD, Myf5, and myogenin.

(14) A structure according to item 13, wherein an expression level of each of myosin heavy chain IIa, myosin heavy chain IIb, myosin heavy chain IId(IIx), CD56, MyoD, Myf5, and myogenin in the structure is at least about 50% of an expression level thereof in skeletal myoblasts.

(15) A structure according to item 13, wherein an expression level of each of myosin heavy chain IIa, myosin heavy chain IIb, myosin heavy chain IId(IIx), CD56, MyoD, Myf5, and myogenin in the structure is at least about 100% of an expression level thereof in skeletal myoblasts.

(16) A structure according to item 1, wherein the cell derived from a part other than myocardium is a cell not derived from heart.

(17) A structure according to item 1, wherein the applicability to heart includes applicability to myocardium.

(18) A structure according to item 1, comprising a monolayer cell sheet.

(19) A structure according to item 1, comprising a multilayer cell sheet.

(20) A structure according to item 19, wherein the multilayer cell sheet has biological connection.

(21) A structure according to item 20, wherein the biological connection is selected from the group consisting of connection via extracellular matrix, electrical connection, and connection without scaffold.

(22) A medicament, comprising a three-dimensional structure according to any one of items 1 to 21.

(23) A medicament according to item 22, wherein the heart has a disease or disorder selected from the group consisting of heart failure, ischemic heart disease, myocardial infarct, cardiomyopathy, myocarditis, hypertrophic cardiomyopathy, dilated phase hypertrophic cardiomyopathy, and dilated cardiomyopathy.

(24) A method for producing a three-dimensional structure applicable to heart comprising a cell derived from a part other than myocardium of an adult, the method comprising the steps of:

a) culturing the cell derived from the part other than myocardium of an adult on a cell culture support grafted with a temperature responsive macromolecule having an upper limit critical solution temperature or lower limit critical solution temperature to water of from 0° C. to 80° C.;

b) setting a culture medium temperature to the upper limit critical solution temperature or more or the lower limit critical solution temperature or less; and c) detaching the cultured cell as a three-dimensional structure.

(25) A method according to item 24, wherein a treatment using a protein degrading enzyme is not performed in or before the detaching step.

(26) A method according to item 24, wherein the temperature responsive macromolecule is poly(N-isopropylacrylamide).

Hereinafter, the present invention will be described by way of preferred embodiments. It will be understood by those skilled in the art that the embodiments of the present invention can be appropriately made or carried out based on the description of the present specification and commonly used techniques well known in the art. The function and effect of the present invention can be easily recognized by those skilled in the art.

The present invention provides an implantable prosthetic tissue. This tissue has a large size, which cannot be achieved by conventional techniques, and has an excellent strength. Thereby, it is made possible to treat sites which cannot be conventionally accessible to implantation treatment using conventional prosthetic materials. The present invention makes it possible to provide a prosthetic tissue or three-dimensional structure made of not only myocardial tissue but also parts other than the myocardium. Therefore, parts other than autologous myocardium can be used as material to conduct implantation therapies.

BRIEF DESCRIPTION OF THE DRAWINGS

FIG. 3 shows an exemplary therapy scheme using a prosthetic tissue of the present invention.

FIG. 6 shows an example of implantation of a prosthetic tissue of the present invention into an infarcted heart.

FIG. 8 is an ultrasound echogram showing an example of evaluation of cardiac function ameliorated by a prosthetic tissue of the present invention. The left portion shows a control, while the right portion shows a cardiomyocyte sheet.

FIG. 11 shows electrophysiological evaluation of a prosthetic tissue of the present invention. The upper left portion shows a normal heart, the lower left portion shows an infarct model, and the lower right portion shows a therapy using a cardiomyocyte sheet.

FIG. 18 shows an ultrasound echogram of implantation of a prosthetic myoblast tissue of the present invention (upper) and an exemplary result of M-mode analysis (lower). The left portion shows an, while the right portion shows the infarcted heart after treatment.

FIGS. 22A to 22F show electrophysiological connection when a prosthetic tissue of the present invention is used. FIGS. 22A to 22C show a control, while FIGS. 22D to 22F show a prosthetic myoblast tissue. In the prosthetic myoblast tissue, electrophysiological connection is observed.

FIGS. 23A to 23C provide representative frames as still pictures.

FIGS. 24A to 24C provide representative frames as still pictures.

FIG. 25A shows a control, while FIG. 25B shows use of a prosthetic tissue of the present invention. Results of ultrasound ecography are shown by motion picture display. FIGS. 25A to 25C provide representative frames as still pictures. The left portion shows an infarcted heart control, while the right portion shows a result of a myoblast sheet of the present invention.

FIG. 26A is a photograph showing the same sample as in FIGS. 25A to 25C at a different time point. Results of ultrasound ecography are shown by motion picture display. FIG. 26A provides representative frames as still pictures. The left portion shows an infarcted heart control, while the right portion shows a result of a myoblast sheet of the present invention.

FIG. 26B is a photograph showing the same sample as in FIGS. 25A to 25C at a different time point. Results of ultrasound ecography are shown by motion picture display. FIG. 26B provides representative frames as still pictures. The left portion shows an infarcted heart control, while the right portion shows a result of a myoblast sheet of the present invention.

FIG. 26C is a photograph showing the same sample as in FIGS. 25A to 25C at a different time point. Results of ultrasound ecography are shown by motion picture display. FIG. 26C provides representative frames as still pictures. The left portion shows an infarcted heart control, while the right portion shows a result of a myoblast sheet of the present invention.

FIGS. 27A to 27C provide representative frames as still pictures.

FIG. 33A shows a therapy for dilated cardiomyopathic hamsters using a prosthetic tissue of the present invention. The left portion shows EF, while the right portion shows HE staining. The lower right portion shows Masson's Trichrome staining.

FIG. 33C shows a result of echocardiography (the contractility of a left ventricle) 48 weeks after implantation (myoblast sheet implantation ameliorates the contractility of the left ventricle with dilated cardiomyopathy).

FIG. 34 shows an example of a therapy for a pig infarct model using a prosthetic tissue of the present invention.

FIG. 37 shows a sheet produced by a prosthetic tissue production method without ascorbic acid.

FIG. 38 shows a sheet produced by a prosthetic tissue production method with ascorbic acid according to the present invention.

FIG. 39 shows a sheet produced by a prosthetic tissue production method with ascorbic acid according to the present invention (HE staining).

FIG. 41 shows a method for obtaining a load/removal of a load curve.

FIG. 42 shows a state of a tissue obtained by culturing synovial cells in the presence of ascorbic acid 2-phosphate.

DESCRIPTION OF SEQUENCING LIST

Figure 1A:
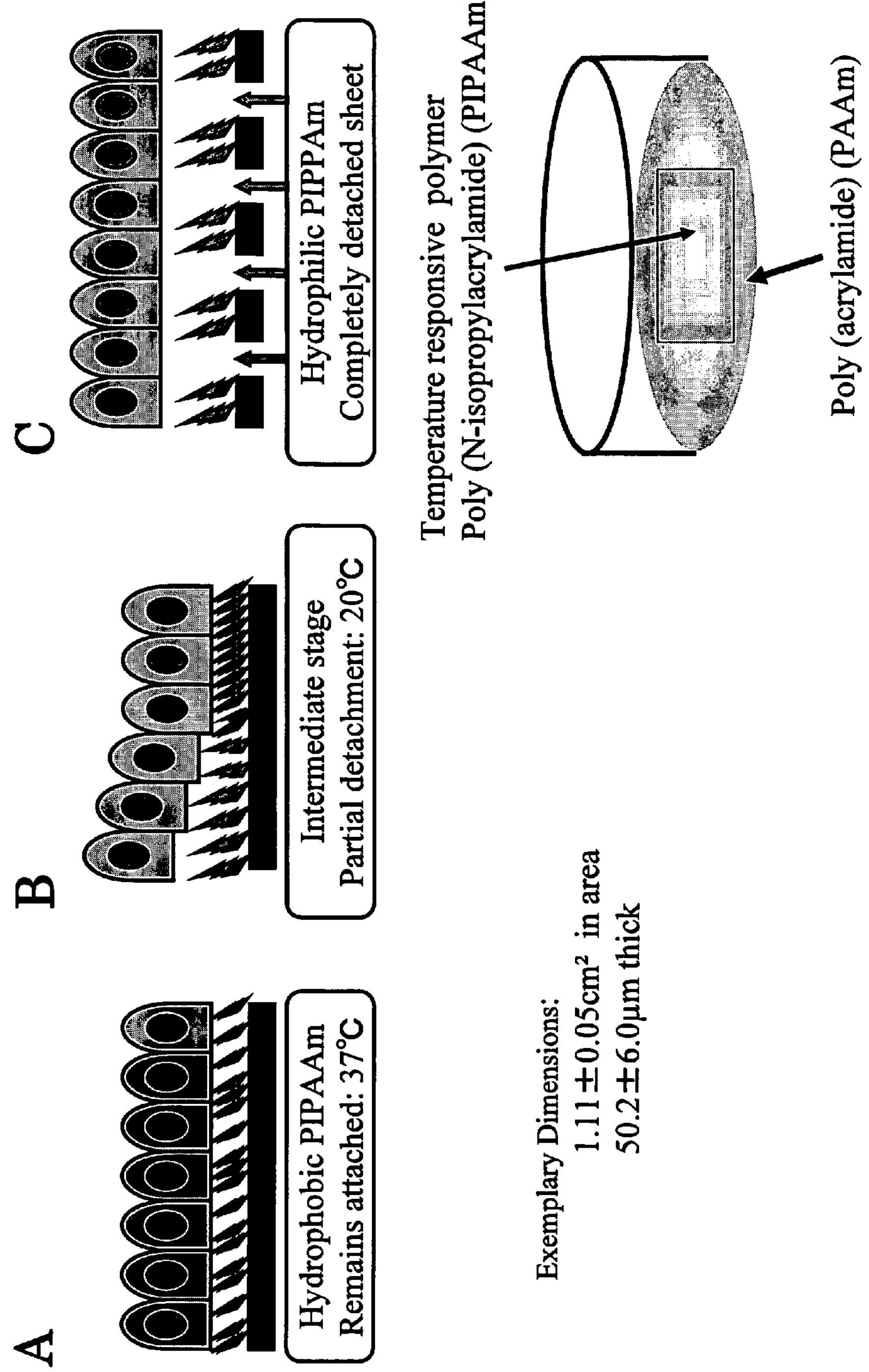
FIG. 1A shows an example in which a prosthetic tissue of the present invention is produced using a temperature responsive polymer.

SEQ ID NO. 1 sets forth a nucleic acid sequence of myosin heavy chain IIa (human: Accession No. NM_017534).

SEQ ID NO. 2 sets forth an amino acid sequence of myosin heavy chain IIa (human: Accession No. NM_017534).

SEQ ID NO. 3 sets forth a nucleic acid sequence of myosin heavy chain IIb (human: Accession No. NM_017533).

SEQ ID NO. 4 sets forth an amino acid sequence of myosin heavy chain IIb (human: Accession No. NM_017533).

SEQ ID NO. 5 sets forth a nucleic acid sequence of myosin heavy chain IId(IIx) (human: Accession No. NM_005963).

SEQ ID NO. 6 sets forth an amino acid sequence of myosin heavy chain IId(IIx) (human: Accession No. NM_005963).

SEQ ID NO. 7 sets forth a nucleic acid sequence of CD56 (human: Accession No. U63041).

SEQ ID NO. 8 sets forth an amino acid sequence of CD56 (human: Accession No. U63041).

SEQ ID NO. 9 sets forth a nucleic acid sequence of human MyoD (GENBANK Accession No. X56677).

SEQ ID NO. 10 sets forth a polypeptide sequence encoded by the nucleic acid sequence set forth in SEQ ID NO. 2.

SEQ ID NO. 11 sets forth a nucleic acid sequence of human myogenic factor 5 (MYF5) (GENBANK Accession No. NM_005593).

SEQ ID NO. 12 sets forth a polypeptide sequence encoded by the nucleic acid sequence set forth in SEQ ID NO. 3.

SEQ ID NO. 13 sets forth a nucleic acid sequence of human myogenin (myogenic factor 4) (GENBANK Accession No. BT007233).

SEQ ID NO. 14 sets forth a polypeptide sequence encoded by the nucleic acid sequence set forth in SEQ ID NO. 5.

SEQ ID NO. 15 sets forth a forward primer in RT-PCR for SRY.

SEQ ID NO. 16 sets forth a reverse primer in RT-PCR for SRY.

SEQ ID NO. 17 sets forth a probe in RT-PCR for SRY.

SEQ ID NO. 18 sets forth a forward primer in RT-PCR for IL2.

SEQ ID NO. 19 sets forth a reverse primer in RT-PCR for IL3.

SEQ ID NO. 20 sets forth a probe in RT-PCR for IL2.

BEST MODE FOR CARRYING OUT THE INVENTION

The present invention will be described below. It should be understood throughout the present specification that articles for singular forms include the concept of their plurality unless otherwise mentioned. Therefore, articles or adjectives for singular forms (e.g., "a", "an", "the", and the like in English) include the concept of their plurality unless otherwise specified. Also, it should be also understood that terms as used herein have definitions ordinarily used in the art unless otherwise mentioned. Therefore, all technical and scientific terms used herein have the same meanings as commonly understood by those skilled in the relevant art. Otherwise, the present application (including definitions) takes precedence.

DEFINITION OF TERMS

The definitions of specific terms used herein are described below.

(Regenerative Medicine)

As used herein, the term "regeneration" refers to a phenomenon in which when an individual organism loses a portion of tissue, the remaining tissue grows and recovers. The extent or manner of regeneration varies depending among animal species or among tissues in the same individual. Most human tissues have limited regeneration capability, and therefore, complete regeneration is not expected if a large portion of tissue is lost. In the case of severe damage, a tissue may grow which has strong proliferation capability different from that of lost tissue, resulting in incomplete regeneration where the damaged tissue is incompletely regenerated and the function of the tissue cannot be recovered. In this case, a structure made of a bioabsorbable material is used to prevent a tissue having strong proliferation capability from infiltrating the defective portion of the tissue so as to secure space for proliferation of the damaged tissue. Further, by supplementing with a cell growth factor, the regeneration capability of the damaged tissue is enhanced. Such a regeneration technique is applied to cartilages, bones, and peripheral nerves, for example. It has been so far believed that nerve cells and cardiac muscles have no or poor regeneration capability. Recently, it was reported that there are tissue stem cells (somatic stem cells), which have both the capability of differentiating into these tissues and self-proliferation capability. Expectations are running high for regenerative medicine using tissue stem cells. Embryonic stem cells (ES cells) are cells, which have the capability of differentiating into all tissues. Efforts have been made to use ES cells for regeneration of complicated organs, such as kidney, liver, and the like, but have not yet been realized.

The term "cell" is herein used in its broadest sense in the art, referring to a structural unit of tissue of a multicellular organism, which is capable of self replicating, has genetic information and a mechanism for expressing it, and is surrounded by a membrane structure which isolates the living body from the outside. In the method of the present invention, any cell can be used as a subject. The number of cells used in the present invention can be counted through an optical microscope. When counting using an optical microscope, the number of nuclei is counted. Tissues are sliced into tissue sections, which are then stained with hematoxylin-eosin (HE) to variegate nuclei derived from extracellular matrices (e.g., elastin or collagen) and cells. These tissue sections are observed under an optical microscope and the number of nuclei in a particular area (e.g., 200 μm×200 μm) can be estimated to be the number of cells. Cells used herein may be either naturally-occurring cells or artificially modified cells (e.g., fusion cells, genetically modified cells, etc.). Examples of cell sources include, but are not limited to, a single-cell culture; the embryo, blood, or body tissue of a normally-grown transgenic animal; a cell mixture of cells derived from normally-grown cell lines; and the like.

As used herein, the term "stem cell" refers to a cell capable of self replication and pluripotency. Typically, stem cells can regenerate an injured tissue. Stem cells used herein may be, but are not limited to, embryonic stem (ES) cells or tissue stem cells (also called tissular stem cell, tissue-specific stem cell, or somatic stem cell). A stem cell may be an artificially produced cell (e.g., fusion cells, reprogrammed cells, or the like used herein) as long as it can have the above-described abilities. Embryonic stem cells are pluripotent stem cells derived from early embryos. An embryonic stem cell was first established in 1981, and has been applied to production of knockout mice since 1989. In 1998, a human embryonic stem cell was established, which is currently becoming available for regenerative medicine. Tissue stem cells have a relatively limited level of differentiation unlike embryonic stem cells. Tissue stem cells are present in tissues and have an undifferentiated intracellular structure. Tissue stem cells have a higher nucleus/cytoplasm ratio and have few intracellular organelles. Most tissue stem cells have pluripotency, a long cell cycle, and proliferative ability beyond the life of the individual. As used herein, stem cells may be preferably embryonic stem cells, though tissue stem cells may also be employed depending on the circumstance.

Tissue stem cells are separated into categories of sites from which the cells are derived, such as the dermal system, the digestive system, the bone marrow system, the nervous system, and the like. Tissue stem cells in the dermal system include epidermal stem cells, hair follicle stem cells, and the like. Tissue stem cells in the digestive system include pancreatic (common) stem cells, hepatic stem cells, and the like. Tissue stem cells in the bone marrow system include hematopoietic stem cells, mesenchymal stem cells, and the like. Tissue stem cells in the nervous system include neural stem cells, retinal stem cells, and the like.

As used herein, the term "somatic cell" refers to any cell other than a germ cell, such as an egg, a sperm, or the like, which does not transfer its DNA to the next generation. Typically, somatic cells have limited or no pluripotency. Somatic cells used herein may be naturally-occurring or genetically modified as long as they can achieve the intended treatment.

The origin of a stem cell is categorized into the ectoderm, endoderm, or mesoderm. Stem cells of ectodermal origin are mostly present in the brain, including neural stem cells. Stem cells of endodermal origin are mostly present in bone marrow, including blood vessel stem cells, hematopoietic stem cells, mesenchymal stem cells, and the like. Stem cells of mesoderm origin are mostly present in organs, including hepatic stem cells, pancreatic stem cells, and the like. As used herein, somatic cells may be derived from any mesenchyme. Preferably, somatic cells derived from mesenchyme may be employed.

As cells for use in construction of a prosthetic tissue or three-dimensional structure of the present invention, differentiated cells or stem cells derived from the above-described ectoderm, endoderm, or mesoderm may be employed, for example. Examples of such cells include mesenchymal cells. In a certain embodiment, as such cells, myoblasts (e.g., skeletal myoblast, etc.), fibroblasts, synovial cells, and the like may be employed. As such cells, differentiated cells or stem cells can be used as they are. Cells differentiated from stem cells into a desired direction can be used.

As used herein, the term "mesenchymal stem cell" refers to a stem cell found in mesenchyme. The term "mesenchymal stem cell" may be herein abbreviated as "MSC". Mesenchyme refers to a population of free cells which are in the asterodal shape or have irregular projections and bridge gaps between epithelial tissues, and which are recognized in each stage of development of multicellular animals. Mesenchyme also refers to tissue formed with intracellular cement associated with the cells. Mesenchymal stem cells have proliferation ability and the ability to differentiate into bone cells, cartilage cells, muscle cells, stroma cells, tendon cells, and fat cells. Mesenchymal stem cells are employed in order to culture or grow bone marrow cells or the like collected from patients, or differentiate them into cartilage cells or osteoblasts. Mesenchymal stem cells are also employed as reconstruction material, such as alveolar bones; bones, cartilages or joints for arthropathy or the like; and the like. There is a large demand for mesenchymal stem cells. Also, mesenchymal stem cells can be differentiated into blood cells and lymphoid cells. Therefore, there is an increasing demand for mesenchymal stem cells. A prosthetic tissue or three-dimensional structure of the present invention comprising mesenchymal stem cells or differentiated mesenchymal stem cells is particularly useful when a structure is required in these applications.

As used herein, the term "isolated" means that naturally accompanying material is at least reduced, or preferably substantially completely eliminated, in normal circumstances. Therefore, the term "isolated cell" refers to a cell substantially free from other accompanying substances (e.g., other cells, proteins, nucleic acids, etc.) in natural circumstances. The term "isolated tissue" refers to a tissue substantially free from substances other than that tissue (e.g., in the case of prosthetic tissues, substances, scaffolds, sheets, coats, etc. used when the prosthetic tissue is produced). The term "isolated" in relation to nucleic acids or polypeptides means that, for example, the nucleic acids or the polypeptides are substantially free from cellular substances or culture media when they are produced by recombinant DNA techniques; or precursory chemical substances or other chemical substances when they are chemically synthesized. Isolated nucleic acids are preferably free from sequences naturally flanking the nucleic acid within an organism from which the nucleic acid is derived (i.e., sequences positioned at the 5' terminus and the 3' terminus of the nucleic acid).

As used herein, the term "intact" in relation to prosthetic tissues, three-dimensional structures, and the like, refers to no physical external injury. For example, when a prosthetic tissue or the like is produced and is then separated from a circumstance in which the production has been conducted, it has substantially no external injury, such as physical impact or the like.

As used herein, the term "established" in relation to cells refers to a state of a cell in which a particular property (pluripotency) of the cell is maintained and the cell undergoes stable proliferation under culture conditions. Therefore, established stem cells maintain pluripotency.

As used herein, the term "non-embryonic" refers to not being directly derived from early embryos. Therefore, the term "non-embryonic" refers to cells derived from parts of the body other than early embryos. Also, modified embryonic stem cells (e.g., genetically modified or fusion embryonic stem cells, etc.) are encompassed by non-embryonic cells.

As used herein, the term "differentiated cell" refers to a cell having a specialized function and form (e.g., muscle cells, neurons, etc.). Unlike stem cells, differentiated cells have no or little pluripotency. Examples of differentiated cells include epidermic cells, pancreatic parenchymal cells, pancreatic duct cells, hepatic cells, blood cells, cardiac muscle cells, skeletal muscle cells, osteoblasts, skeletal myoblasts, neurons, vascular endothelial cells, pigment cells, smooth muscle cells, fat cells, bone cells, cartilage cells, and the like.

As used herein, the term "tissue" refers to a group of cells having the same function and form in cellular organisms. In multicellular organisms, constituent cells are usually differentiated so that the cells have specialized functions, resulting in division of labor. Therefore, multicellular organisms are not simple cell aggregations, but constitute organic or social cell groups having a certain function and structure. Examples of tissues include, but are not limited to, integument tissue, connective tissue, muscular tissue, nervous tissue, and the like. Tissue targeted by the present invention may be derived from any organ or part of an organism. In a preferred embodiment of the present invention, tissue targeted by the present invention includes, but is not limited to, blood vessels, blood vessel-like tissue, cardiac valves, pericardia, dura mater, cornea, joints, and bones.

As used herein, the term "prosthetic tissue" refers to tissue having a state different from natural states. Typically, a prosthetic tissue is herein prepared by cell culture. Tissue which is removed from an organism and is not subjected to any treatment is not referred to as a prosthetic tissue. A prosthetic tissue may include materials derived from organisms and materials not derived from organisms. The prosthetic tissue of the present invention typically comprises a cell and/or a biological material, and may comprise other materials. More preferably, a prosthetic tissue of the present invention is composed substantially only of a cell and/or a biological material. Such a biological material is preferably derived from cells constituting the tissue (e.g., extracellular matrix, etc.).

As used herein, the term "implantable prosthetic tissue" refers to a prosthetic tissue, which can be used for actual clinical implantation and can function as a tissue at the implantation site for a certain period of time after implantation. Implantable prosthetic tissue typically has sufficient strength, sufficient size, sufficient nonporousness, sufficient thickness, sufficient biocompatibility, sufficient affinity, and the like.

The sufficient strength of an implantable prosthetic tissue varies depending on a part targeted by implantation, but can be determined as appropriate by those skilled in the art. However, an implantable prosthetic tissue preferably has at least a certain level of strength. Such a level of strength (e.g., tensile strength) is at least about 50% of the natural strength of a part targeted by implantation, preferably at least about 60%, more preferably about 70%, even more preferably about 80%, and most preferably at least about 100%. The strength can be measured by measuring stress or distortion characteristics or conducting s creep characteristics indentation test as described below.

The sufficient size of an implantable prosthetic tissue varies depending on a part targeted by implantation, but can be determined as appropriate by those skilled in the art. However, an implantable prosthetic tissue preferably has at least a certain size. Such a size (e.g., area) is at least 1 $cm^2$, preferably at least 2 $cm^2$, more preferably at least 3 $cm^2$, even more preferably at least 4 $cm^2$, at least 5 $cm^2$, at least 6 $cm^2$, at least 7 $cm^2$, at least 8 $cm^2$, at least 9 $cm^2$, at least 10 $cm^2$, at least 15 $cm^2$, or at least 20 $cm^2$.

The sufficient nonporousness of an implantable prosthetic tissue varies depending on a part targeted by implantation, but can be determined as appropriate by those skilled in the art. As used herein, the term "nonporousness" refers to a state lacking pore(s). Here, the pore refers to a hole having a substantial size such that body fluid or its equivalent (e.g., an aqueous solution, etc.) leaks from a prosthetic tissue. Therefore, nonporousness can be determined as follows. A prosthetic tissue is placed horizontally. Body fluid or its equivalent is placed on the tissue. It is observed whether or not the body fluid or its equivalent leaks from the tissue. If there is no leak, the tissue is judged to have nonporousness.

The sufficient thickness of an implantable prosthetic tissue varies depending on a part targeted by implantation, but can be determined as appropriate by those skilled in the art. However, an implantable prosthetic tissue preferably has at least a certain thickness. Such a thickness is typically at least about 50 μm, preferably at least about 100 μm, more preferably about 150 μm, even more preferably at least about 200 μm, at least about 300 μMm at least about 400 μm, at least about 500 μm, at least about 600 μm, at least about 700 μm, at least about 800 μm, at least about 900 μm, at least about 1 mm. When an implantable prosthetic tissue is implanted into the heart, the tissue may only have these minimum thicknesses. When implantable prosthetic tissue is used in other applications, the tissue may preferably have a greater thickness. In such a case, for example, implantable prosthetic tissue has preferably a thickness of at least 2 mm, more preferably at least 3 mm, and even more preferably 5 mm.

The sufficient biocompatibility of implantable prosthetic tissue varies depending on a part targeted by implantation, but can be determined as appropriate by those skilled in the art. However, an implantable prosthetic tissue preferably has at least a certain level of biocompatibility. Typically, a desired level of biocompatibility is, for example, such that biological connection to surrounding tissues is achieved without any inflammation, any immune reaction or the like. The present invention is not limited to this. In some cases (e.g., corneas, etc.), an immune reaction is less likely to occur. Therefore, an implantable prosthetic tissue has biocompatibility to an extent, which achieves the object of the present invention even when an immune reaction is likely to occur in other organs. Examples of parameters indicating biocompatibility include, but are not limited to, the presence or absence of an extracellular matrix, the presence or absence of an immune reaction, the degree of inflammation, and the like. Such biocompatibility can be determined by examining the compatibility of a prosthetic tissue at an implantation site after implantation (e.g., confirming that an implanted prosthetic tissue is not destroyed). See "Hito Ishoku Zoki Kyozetsu Hanno no Byori Soshiki Shindan Kijyun Kanbetsu Shindan to Seiken Hyohon no Toriatsukai (Zufu) Jinzo Ishoku, Kanzo Ishoku Oyobi Shinzo Ishoku [Pathological Tissue Diagnosis Criterion for Human Transplanted Organ Rejection Reaction Handling of Differential Diagnosis and Biopsy Specimen (Illustrated Book) Kidney Transplantation, Liver Transplantation and Heart Transplantation]" The Japan Society for Transplantation and The Japanese Society for Pathology editors, Kanehara Shuppan Kabushiki Kaisha (1998). According to this document, biocompatibility is divided into Grade 0, 1A, 1B, 2, 3A, 3B, and 4. At Grade 0 (no acute rejection), no acute rejection reaction, cardiomyocyte failure, or the like is found in biopsy specimens. At Grade 1A (focal, mild acute rejection), there is focal infiltration of large lymphocytes around blood vessels or into interstitial tissue, while there is no damage to cardiomyocytes. This observation is obtained in one or a plurality of biopsy specimens. At Grade 1B (diffuse, mild acute rejection), there is diffuse infiltration of large lymphocytes around blood vessels or into interstitial tissue or both, while there is no damage to cardiomyocytes. At Grade 2 (focal, moderate acute rejection), there is a single observed infiltration focus of inflammatory cells clearly bordered from the surrounding portions. Inflammation cells are large activated lymphocytes and may include eosinophils. Damage to cardiomyocytes associated with modification of cardiac muscle is observed in lesions. At Grade 3A (multifocal, moderate acute rejection), there are multiple infiltration foci of inflammatory cells which are large activated lymphocytes and may include eosinophils. Two or more of the multiple inflammatory infiltration foci of inflammatory cells have damages to cardiomyocytes. In some cases, there is also rough infiltration of inflammatory cells into the endocardium. The infiltration foci are observed in one or a plurality of biopsy specimens. At Grade 3B (multifocal, borderline severe acute rejection), there are more confluent and diffuse infiltration foci of inflammatory cells found in more biopsy specimens than those observed at Grade 3A. There is infiltration of inflammatory cells including large lymphocytes and eosinophils, in some cases neutrophils, as well as damage to cardiomyocytes. There is no hemorrhage. At Grade 4 (severe acute rejection), there is infiltration of various inflammatory cells including activated lymphocytes, eosinophils, and neutrophils. There is always damage to cardiomyocytes and necrosis of cardiomyocytes. Edema, hemorrhage, and/or angitis are also typically observed. Infiltration of inflammatory cells into the endocardium, which is different from the "Quilty" effect, is typically observed. When a therapy is strongly conducted using an immunosuppressant for a considerably long period of time, edema and hemorrhage may be more significant than infiltration.

The sufficient affinity of an implantable prosthetic tissue varies depending on a part targeted by implantation, but can be determined as appropriate by those skilled in the art. Examples of parameters for affinity include, but are not limited to, biological connection ability between an implanted prosthetic tissue and its implantation site, and the like. Such affinity can be determined based on the presence of biological connection at an implantation site after implantation. Preferable affinity is herein such that an implanted prosthetic tissue has the same function as that of a site in which the tissue is implanted, for example.

As used herein, the term "membranous tissue" refers to a tissue in the form of membrane and is also referred to as "planar tissue". Examples of membranous tissue include a portion of tissue having a certain area of an organ (e.g., pericardium, dura mater, cornea, etc.) or bag-shaped tissue, and the like.

As used herein, the term "organ" refers to a structure which is a specific part of an individual organism where a certain function of the individual organism is locally performed and which is morphologically independent. Generally, in multicellular organisms (e.g., animals and plants), organs are made of several tissues in specific spatial arrangement and tissue is made of a number of cells. Examples of such organs include, but are not limited to, skin, blood vessel, cornea, kidney, heart, liver, umbilical cord, intestine, nerve, lung, placenta, pancreas, brain, joint, bone, cartilage, peripheral limbs, retina, and the like. Examples of such organs include, but are not limited to, organs of the skin system, the parenchyma pancreas system, the pancreatic duct system, the hepatic system, the blood system, the myocardial system, the skeletal muscle system, the osteoblast system, the skeletal myoblast system, the nervous system, the blood vessel endothelial system, the pigment system, the smooth muscle system, the fat system, the bone system, the cartilage system, and the like.

As used herein, the term "bag-shaped organ" refers to an organ which has a three-dimensional expanse and the inside of which may be connected via a tubular tissue to the outside. Examples of bag-shaped organs include, but are not limited to, heart, liver, kidney, stomach, spleen, and the like.

In one embodiment, the present invention targets vascular system-related organs, and preferably ischemic organs (e.g., heart having myocardial infarcted heart having ischemia, etc.). In a preferred embodiment, the present invention targets blood vessels, blood vessel-like tissue, heart, heart valves, pericardia, dura mater, cornea, and bones. In another preferred embodiment, the present invention targets heart, heart valves, pericardia, and blood vessels.

As used herein, the term "wrap" in relation to a prosthetic tissue, a three-dimensional structure, or the like, which is wrapped around a certain part (e.g., an injured site, etc.), means that the prosthetic tissue or the like is arranged so as to cover the part (i.e., conceal an injury or the like). The terms "wrap" and "arrange (or locate) so as to cover" are used interchangeably. By observing the spatial relationship between the part and the prosthetic tissue or the like, it can be determined whether or not the part is covered by the prosthetic tissue or the like. In a preferred embodiment, in a wrapping step, a prosthetic tissue or the like can be wrapped one turn around a certain site.

A "sufficient time required for a prosthetic tissue to biologically join with a part" herein varies depending on a combination of the part and the prosthetic tissue, but can be determined as appropriate by those skilled in the art based on the combination. Examples of such a time include, but are not limited to, 1 week, 2 weeks, 1 month, 2 months, 3 months, 6 months, 1 year, and the like, after operation. In the present invention, a prosthetic tissue preferably comprises substantially only cells and materials derived from the cells, and therefore, there is no particular material which needs to be extracted after operation. Therefore, the lower limit of the sufficient time is not particularly important. Thus, in this case, a longer time is more preferable. If the time is substantially extremely long, reinforcement is substantially completed.

As used herein, the term "immune reaction" refers to a reaction due to the dysfunction of immunological tolerance between a graft and a host. Examples of immune reactions include, but are not limited to, a hyperacute rejection reaction (within several minutes after implantation) (immune reaction caused by antibodies, such as β-Gal or the like), an acute rejection reaction (reaction caused by cellular immunity about 7 to 21 days after implantation), a chronic rejection reaction (rejection reaction caused by cellular immunity 3 or more months after operation), and the like.

As used herein, the elicitation of an immune reaction can be confirmed by pathological and histological examination of the type, number, or the like of infiltration of (immunological) cells into implanted tissue using staining (e.g., HE staining, etc.), immunological staining, or microscopic inspection of tissue sections.

As used herein, the term "calcification" refers to precipitation of calcareous substances in organisms.

As used herein, "calcification" in vivo can be determined by measuring calcium concentration. Specifically, implanted tissue is taken out; the tissue section is dissolved by acid treatment or the like; and the atomic absorption of the solution is measured by a trace element quantifying device.

As used herein, the term "within organism(s) (or in organism(s))" or "in vivo" refers to the inner part of organism(s). In a specific context, "within organism(s)" refers to a position at which a subject tissue or organ is placed.

As used herein, "in vitro" indicates that a part of an organism is extracted or released outside the organism for various purposes of research (e.g., in a test tube). The term in vitro is in contrast to the term in vivo.

As used herein, the term "ex vivo" refers to a series of operations where target cells into which a gene will be introduced are extracted from a subject; a therapeutic gene is introduced in vitro into the cells; and the cells are returned into the same subject.

As used herein, the term "material derived from cell(s)" refers to any material originating from the cell(s), including, but not being limited to, materials constituting the cell(s), materials secreted by the cell(s), materials metabolized by the cell(s), and the like. Representative examples of materials derived from cells include, but are not limited to, extracellular matrices, hormones, cytokines, and the like. Materials derived from cells typically have substantially no adverse effect on the cells and their hosts. Therefore, when the material is contained in a prosthetic tissue, a three-dimensional structure, or the like, the material typically has substantially no adverse effect on the prosthetic tissue, three-dimensional structure, or the like.

As used herein, the term "extracellular matrix" (ECM) refers to a substance existing between somatic cells no matter whether the cells are epithelial cells or non-epithelial cells. Extracellular matrices are typically produced by cells, and therefore, are biological materials. Extracellular matrices are involved in supporting tissue as well as in internal environmental structure essential for survival of all somatic cells. Extracellular matrices are generally produced from connective tissue cells. Some extracellular matrices are secreted from cells possessing basal membrane, such as epithelial cells or endothelial cells. Extracellular matrices are roughly divided into fibrous components and matrices filling there between. Fibrous components include collagen fibers and elastic fibers. A basic component of matrices is a glycosaminoglycan (acidic mucopolysaccharide), most of which is bound to non-collagenous protein to form a polymer of a proteoglycan (acidic mucopolysaccharide-protein complex). In addition, matrices include glycoproteins, such as laminin of basal membrane, microfibrils around elastic fibers, fibers, fibronectins on cell surfaces, and the like. Particularly differentiated tissue has the same basic structure. For example, in hyaline cartilage, chondroblasts characteristically produce a large amount of cartilage matrices including proteoglycans. In bones, osteoblasts produce bone matrices which cause calcification. In one embodiment of the present invention, the prosthetic tissue, three-dimensional structure, or the like of the present invention may be advantageously similar to the composition of an extracellular matrix (e.g., elastin, collagen (e.g., Type I, Type IV, etc.), laminin, etc.) of a site of an organ for which implantation is intended. In the present invention, extracellular matrices include cell adhesion molecules. As used herein, the terms "cell adhesion molecule" and "adhesion molecule" are used interchangeably, referring to a molecule capable of mediating the joining of two or more cells (cell adhesion) or adhesion between a substrate and a cell. In general, cell adhesion molecules are divided into two groups: molecules involved in cell-cell adhesion (intercellular adhesion); (cell-cell adhesion molecules) and molecules involved in cell-extracellular matrix adhesion (cell-substrate adhesion) (cell-substrate adhesion molecules). A prosthetic tissue or three-dimensional structure of the present invention typically comprises such a cell adhesion molecule. Therefore, cell adhesion molecules herein include a protein of a substrate and a protein of a cell (e.g., integrin, etc.) in cell-substrate adhesion. A molecule other than proteins falls within the concept of cell adhesion molecule as long as it can mediate cell adhesion.

For cell-cell adhesion, cadherin, a number of molecules belonging in an immunoglobulin superfamily (NCAML1, ICAM, fasciclin II, III, etc.), selectin, and the like are known, each of which is known to join cell membranes via a specific molecular reaction. Therefore, in one embodiment, the prosthetic tissue, three-dimensional structure, or the like of the present invention preferably has substantially the same composition of cadherin, immunoglobulin superfamily molecules, or the like as that of a site for which implantation is intended.

Thus, various molecules are involved in cell adhesion and have different functions. Those skilled in the art can appropriately select a molecule to be contained in a prosthetic tissue or three-dimensional structure of the present invention depending on the purpose. Techniques for cell adhesion are well known as described above and as described in, for example, "Saibogaimatorikkusu—Rinsho heno Oyo—[Extracellular matrix—Clinical Applications—], Medical Review.

It can be determined whether or not a certain molecule is a cell adhesion molecule, by an assay, such as biochemical quantification (an SDS-PAG method, a labeled-collagen method, etc.), immunological quantification (an enzyme antibody method, a fluorescent antibody method, an immunohistological study, etc.), a PCR method, a hybridization method, or the like, in which a positive reaction is detected. Examples of such a cell adhesion molecule include, but are not limited to, collagen, integrin, fibronectin, laminin, vitronectin, fibrinogen, an immunoglobulin superfamily member (e.g., CD2, CD4, CD8, ICM1, ICAM2, VCAM1), selectin, cadherin, and the like. Most of these cell adhesion molecules transmit into a cell an auxiliary signal for cell activation due to intercellular interaction as well as cell adhesion. Therefore, an adhesion factor for use in an implant of the present invention preferably transmits an auxiliary signal for cell activation into a cell. This is because cell activation can promote growth of cells originally present or aggregating in a tissue or organ at an injured site after application of an implant thereto. It can be determined whether or not such an auxiliary signal can be transmitted into a cell, by an assay, such as biochemical quantification (an SDS-PAG method, a labeled-collagen method, etc.), immunological quantification (an enzyme antibody method, a fluorescent antibody method, an immunohistological study, etc.), a PDR method, a hybridization method, or the like, in which a positive reaction is detected.

An example of a cell adhesion molecule is cadherin which is present in many cells capable of being fixed to tissue. Cadherin can be used in a preferred embodiment of the present invention. Examples of a cell adhesion molecule in cells of blood and the immune system which are not fixed to tissue, include, but are not limited to, immunoglobulin superfamily molecules (CD 2, LFA-3, ICAM-1, CD2, CD4, CD8, ICM1, ICAM2, VCAM1, etc.); integrin family molecules (LFA-1, Mac-1, gpIIbIIIa, p150, p95, VLA1, VLA2, VLA3, VLA4, VLA5, VLA6, etc.); selectin family molecules (L-selectin, E-selectin, P-selectin, etc.), and the like. Therefore, such a molecule may be useful for treatment of a tissue or organ of blood and the immune system.

Nonfixed cells need to be adhered to a specific tissue in order to act on the tissue. In this case, it is believed that cell-cell adhesion is gradually enhanced via a first adhesion by a selectin molecule or the like which is constantly expressed and a second adhesion by a subsequently activated integrin molecule. Therefore, in the present invention, a cell adhesion molecule for mediating the first adhesion and another cell adhesion molecule for mediating the second adhesion may be used together.

As used herein, the term "tissue injury rate" refers to a parameter which indicates a function of a tissue or organ; an indicator which indicates how much a treated tissue or organ is injured; and an indicator which indicates whether or not a tissue or organ can have its original function. Methods for determining a tissue injury rate are known in the art. For example, a tissue injury rate can be determined by counting elastin ruptured sites. Herein, a visual field is divided into units of 100 μm×100 μm. In each unit, the presence or absence of an elastin ruptured site is determined. If there is an elastin ruptured site in a unit, the count is incremented. One visual field has 24 units. The extracellular matrices of tissue sections stained by HE staining are subjected to microscopic inspection and counting. Non-treated tissue is defined as having a tissue injury rate of 0%. A tissue injury rate is calculated by x/24. In this case, non-treated tissue corresponds to x=0.

As used herein, the term "tissue strength" refers to a parameter which indicates a function of a tissue or organ and a physical strength of the tissue or organ. Tissue strength can be generally determined by measuring tensile strength (e.g., break strength, modulus of rigidity, Young's modulus, etc.). Such a general tensile test is well known. By analyzing data obtained by a general tensile test, various data, such as break strength, modulus of rigidity, Young's modulus, and the like, can be obtained. These values can be herein used as indicators of tissue strength. Typically, tissue strength which allows clinical applications is herein required.

Figure 40:
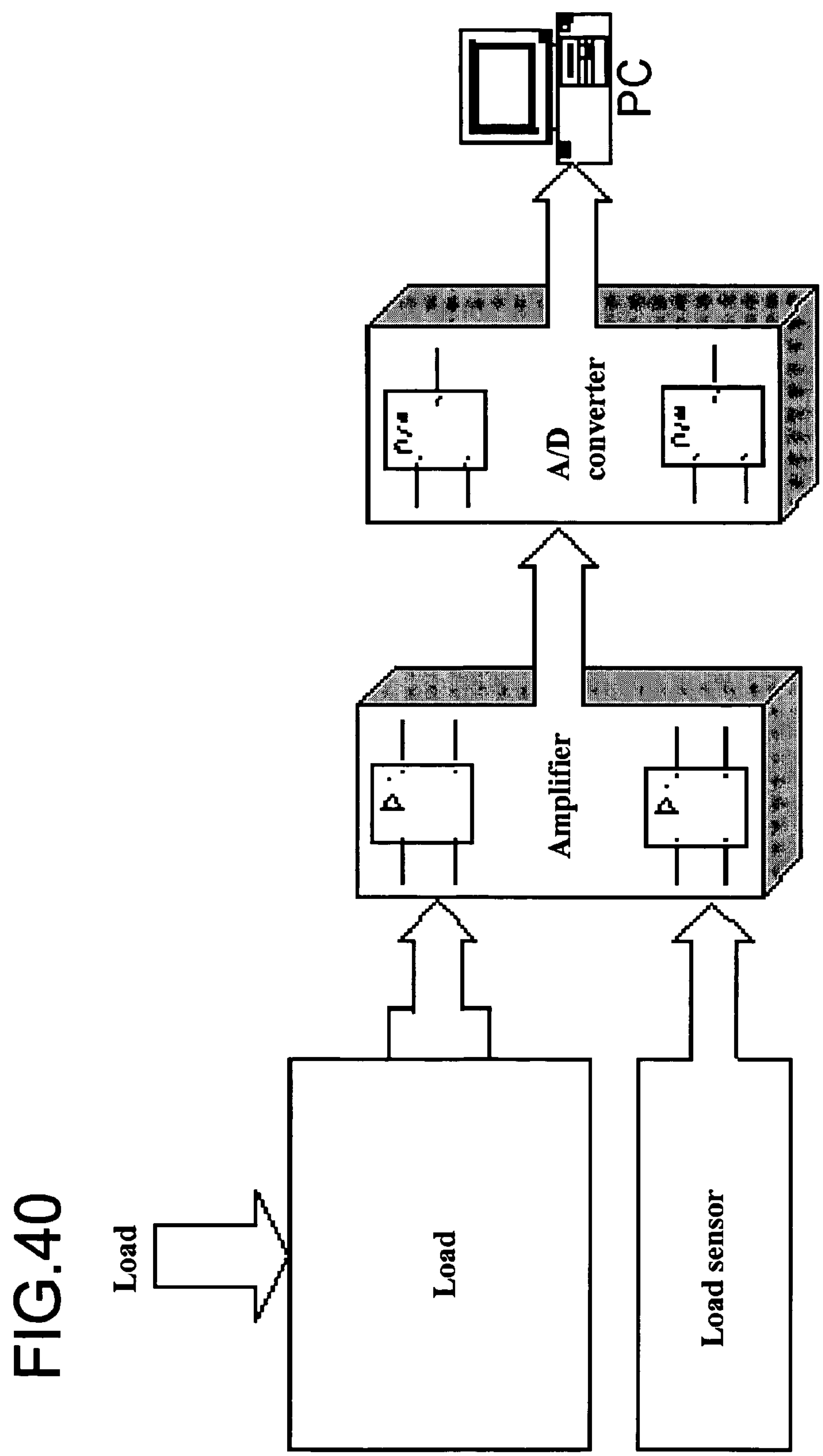
FIG. 40 shows a technique for measuring stress and distortion characteristics to determine tensile strength.

The tensile strength of a prosthetic tissue, three-dimensional structure, or the like of the present invention can be determined by measuring the stress and distortion characteristics thereof. Briefly, a load is applied to a sample; the resultant distortion and the load are input to respective A/D converters (e.g., ELK-5000) (1 ch: distortion, 2 ch: load); the stress and distortion characteristics are measured to determine the tensile strength of the sample (FIG. 40). Tensile strength can also be determined by testing creep characteristics. A creep characteristics indentation test is conducted to investigate how a sample is extended over time while a constant load is applied to the sample. For small materials, thin materials; and the like, an indentation test is conducted using, for example, a triangular pyramid-shaped indenter with a tip having a radius of about 0.1 μm to about 1 μm. Initially, the indenter is pushed into a test piece so that a load is given to the test piece. When the indenter reaches from several tens of nanometers to several micrometers deep in the test piece, the indenter is drawn off to remove the load. FIG. 41 shows a load/removal of load curve obtained by the above-described test method. Rigidity, Young's modulus, or the like can be obtained based on the behavior of the load and the push depth derived from the curve.

In a preferred embodiment, the tensile strength of the prosthetic tissue or three-dimensional structure of the present invention is typically at least about 50% of the natural strength of a part in which implantation is intended, preferably at least about 60%, more preferably about 70%, even more preferably about 80%, and most preferably at least about 100%.

In an alternative embodiment, the prosthetic tissue of the present invention may have a tissue strength of at least about 75% of that of a portion of natural tissue (e.g., a portion in which a clinical application is intended (e.g., heart, etc.)), preferably at least about 80%, more preferably at least about 85%, and even more preferably about 90%. The tissue strength of the prosthetic tissue may be equal to or greater than that of the natural tissue. The tissue strength of a natural tissue refers to a tissue strength which is possessed by a tissue of interest in its natural state. In addition to membranous tissue, other tissues (e.g., tubular tissue, etc.) preferably have a sufficiently strong tissue strength. In the case of tubular tissue, the tissue strength can be represented by a β value. A method for calculating a β value will be described in detail in another portion of the present specification and will also be illustrated in the Examples below. In a certain embodiment, the prosthetic tissue of the present invention has a tissue strength corresponding to a β value of at least about 15, preferably at least about 18, more preferably at least about 20, and even more preferably at least about 22. In another embodiment, the prosthetic tissue of the present invention has a β value of at least about 75% of that of the tissue before treatment, preferably at least about 80%, more preferably at least about 85%, and even more preferably at least about 90%. The β value of the prosthetic tissue may be equal to or greater than that originally possessed by the untreated tissue. A characteristic (e.g., a β value) of untreated tissue refers to a characteristic of the tissue before treatment (e.g., treatment using 1,2-epoxide polymer in the present invention) (e.g., in the natural state). Therefore, for example, if an original tissue has a β value of 25, a prosthetic tissue of the present invention may preferably have a β value of at least 17.5, preferably at least 20, more preferably at least 21.25, and even more preferably at least 22.5.

As used herein, in the case of tubular tissue, the tissue strength can be represented by a rigidity parameter (β value). The β value can be calculated based on the following expression after the P-D (pressure-diameter) relationship is established:

$$\mathrm{Ln}(P/Ps)=\beta(D/Ds-1) \quad (1)$$

where Ps and Ds represents their standard values at 100 mmHg. The value of the diameter (D) is measured under each P (pressure).

Both ends of a tubular tissue (e.g., a blood vessel, etc.) are each fixed to a pipe-like unit. The inside and outside of the tissue are filled with physiological saline. In this situation, pressure is applied to the inside of the tissue by an external device, while the outer diameter of the tissue under the pressure is monitored. The measured pressure and outer diameter are substituted into expression (1) to calculate a β value (Sonoda H., Takamizawa K. et al., J. Biomed. Matr. Res., 2001: 266-276).

As used herein, the term "physiologically active substance" refers to a substance capable of acting on a cell or tissue. Physiologically active substances include cytokines and growth factors. A cellular physiologically active substance may be naturally-occurring or synthesized. Preferably, a cellular physiologically active substance is one that is produced by a cell or one that has a function similar thereto. As used herein, a cellular physiologically active substance may be in the form of a protein or a nucleic acid or in other forms. In actual practice, cellular physiologically active substances are typically proteins. In the present invention, a physiologically active substance may be used to promote the affinity of an implanted prosthetic tissue of the present invention, for example.

The term "cytokine" is used herein in the broadest sense in the art and refers to a physiologically active substance which is produced from a cell and acts on the same or different cell. Cytokines are generally proteins or polypeptides having a function of controlling an immune response, regulating the endocrine system, regulating the nervous system, acting against a tumor, acting against a virus, regulating cell growth, regulating cell differentiation, or the like. Cytokines are herein in the form of a protein or a nucleic acid or in other forms. In actual practice, cytokines are typically proteins.

The terms "growth factor" or "cell growth factor" are used herein interchangeably and each refers to a substance which promotes or controls cell growth. Growth factors are also called "proliferation factors" or "development factors". Growth factors may be added to cell or tissue culture medium, substituting for serum macromolecules. It has been revealed that a number of growth factors have a function of controlling differentiation in addition to a function of promoting cell growth.

Examples of cytokines representatively include, but are not limited to, interleukins, chemokines, hematopoietic factors such as colony stimulating factors, a tumor necrosis factor, interferons, a platelet-derived growth factor (PDGF), an epidermal growth factor (EGF), a fibroblast growth factor (FGF), a hepatocyte growth factor (HGF), an endothelial cell growth factor (VEGF), cardiotrophin, and the like, which have proliferative activity.

Cellular physiologically active substances, such as cytokines, growth factors, and the like, typically have redundancy in function. Accordingly, reference herein to a particular cytokine or growth factor by one name or function also includes any other names or functions by which the factor is known to those of skill in the art, as long as the factor has the activity of a cellular physiologically active substance for use in the present invention. Cytokines or growth factors can be used in a therapeutic or pharmaceutical agent according to a preferred embodiment of the present invention as long as they have preferable activity as described herein.

Therefore, in one embodiment of the present invention, it was revealed that when such a cytokine or growth factor (e.g., HGF) is provided to an implantation site (e.g., an implantation site of the myocardium, etc.) concomitantly with a prosthetic tissue or three-dimensional structure of the present invention, the affinity of the prosthetic tissue or three-dimensional structure and an improvement in the function of the implantation site are observed. Thus, the present invention also provides such a combined therapy.

As used herein, the term "differentiation" refers to a developmental process of the state of the composite parts of organisms, such as cells, tissues, or organs and a process in which a characteristic tissue or organ is formed. The term "differentiation" is mainly used in embryology, developmental biology, and the like. In organisms, various tissues and organs are formed from divisions of a fertilized ovum (a single cell) to an adult. At early developmental stages (i.e., before cell division or after insufficient cell division), each cell or cell group has no morphological or functional feature and is not much distinguishable. Such a state is referred to as "undifferentiated". "Differentiation" may occur at the level of organs. A cell constituting an organ may develop into various cells or cell groups having different features. This phenomenon is also referred to as differentiation within an organ in the formation of the organ. Therefore, a prosthetic tissue or three-dimensional structure of the present invention may comprise a tissue including differentiated cells.

As used herein, the terms "implant", "graft", and "tissue graft" are used interchangeably, referring to homologous or heterologous tissue or a cell group, or an artificial material, which is inserted into a particular site of a body and thereafter forms a part of the body. Therefore, a prosthetic tissue or three-dimensional structure of the present invention can be used as an implant. Examples of conventional grafts include, but are not limited to, organs or portions of organs, blood vessels, blood vessel-like tissue, heart, cardiac valves, pericardia, and the like. Therefore, grafts encompass any one of these which is inserted into a deficient part so as to compensate for the deficiency. Grafts include, but are not limited to, autografts, allografts, and xenografts, which depend on the type of their donor.

As used herein, the term "autograft" (a tissue, a cell, an organ, etc.) refers to a graft (a tissue, a cell, an organ, etc.) which is implanted into the same individual from which the graft is derived. As used herein, the term "autograft" (a tissue, a cell, an organ, etc.) may encompass a graft from a genetically identical individual (e.g. an identical twin) in a broad sense. As used herein, the terms "autologous" and "derived from a subject" are used interchangeably. Therefore, the term "not derived from a subject" in relation to a graft indicates that the graft is not autologous (i.e., heterologous).

As used herein, the term "allograft" (a tissue, a cell, an organ, etc.) refers to a graft (a tissue, a cell, an organ, etc.) which is implanted into an individual which is the same species but is genetically different from that from which the graft is derived. Since an allograft (a tissue, a cell, an organ, etc.) is genetically different from an individual (recipient) to which the graft is implanted, the graft may elicit an immune reaction. Such a graft (a tissue, a cell, an organ, etc.) includes, but is not limited to, for example, a graft (a tissue, a cell, an organ, etc.) derived from a parent.

As used herein, the term "xenograft" (a tissue, a cell, an organ, etc.) refers to a graft (a tissue, a cell, an organ, etc.) which is implanted from a different species. Therefore, for example, when a human is a recipient, a porcine-derived graft (a tissue, a cell, an organ, etc.) is called a xenograft (a tissue, a cell, an organ, etc.).

As used herein, "recipient" (acceptor) refers to an individual which receives a graft (a tissue, a cell, an organ, etc.) or implanted matter (a tissue, a cell, an organ, etc.) and is also called "host". In contrast, an individual providing a graft (a tissue, a cell, an organ, etc.) or implanted matter (a tissue, a cell, an organ, etc.) is called "donor" (provider).

With a prosthetic tissue forming technique of the present invention, a prosthetic tissue derived from any cell can be used. This is because a prosthetic tissue (e.g., membranous tissues, organs, etc.) formed by the method of the present invention can exhibit a desired function while the tissue injury rate is maintained at a level which does not interfere with the therapy (i.e., a low level). Conventionally, tissues or organs are used as grafts without modification. In contrast to this, the present invention provides a tissue comprising three-dimensionally connected cells. Such a prosthetic three-dimensional tissue cannot be achieved by conventional techniques, and therefore, constitutes one significant effect of the present invention.

As used herein, the term "subject" refers to an organism to which treatment of the present invention is applied and is also referred to as "patient". A patient or subject may be preferably a human.

Cells optionally used in a prosthetic tissue, three-dimensional structure, or tissue graft of the present invention may be derived from a syngeneic origin (self origin), an allogenic origin (non-self origin), or a heterologous origin. In view of rejection reactions, syngeneic cells are preferable. If rejection reactions do not raise problems, allogenic cells may be employed. Cells which elicit rejection reactions can be employed by optionally treating the cells in a manner that overcomes rejection reactions. Procedures for avoiding rejection reactions are known in the art (see, for example, "Shin Gekagaku Taikei, Dai 12 Kan, Zoki Ishoku (Shinzo Ishoku Hai Ishoku Gijutsuteki, Rinriteki Seibi kara Jisshi ni Mukete [New Whole Surgery, Vol. 12, Organ Transplantation (Heart Transplantation•Lung Transplantation From Technical and Ethical Improvements to Practice)" (Revised 3rd ed.), Nakayama Shoten]. Examples of such methods include, but are not limited to, a method using immunosuppressants or steroidal drugs, and the like. For example, there are currently the following immunosuppressants for preventing rejection reactions: "cyclosporine" (SANDIMMUNE/NEORAL); "tacrolimus" (PROGRAF); "azathioprine" (IMURAN); "steroid hormone" (prednine, methylprednine); and "T-cell antibodies" (OKT3, ATG, etc.). A method which is used worldwide as a preventive immunosuppression therapy in many facilities, is the concurrent use of three drugs: cyclosporine, azathioprine, and steroid hormone. An immunosuppressant is desirably administered concurrently with a pharmaceutical agent of the present invention. The present invention is not limited to this. An immunosuppressant may be administered before or after a regeneration/therapeutic method of the present invention as long as an immunosuppression effect can be achieved.

Cells used in the present invention may be derived from any organism (e.g., vertebrates and invertebrates). Preferably, cells derived from vertebrates are used. More preferably, cells derived from mammals (e.g., primates, rodents, etc.) are used. Even more preferably, cells derived from primates are used. Most preferably, cells derived from a human are used. Typically, cells from the same species as the host are preferably used.

Examples of a subject treated by a prosthetic tissue of the present invention include, but are not limited to, the heart suffering from a heart disease (e.g., heart failure, ischemic heart diseases, myocardial infarct, cardiomyopathy, myocarditis, hypertrophic cardiomyopathy, dilated hypertrophic cardiomyopathy, and dilated cardiomyopathy); blood vessels in a pericardium patch, infarcted myocardium lower and upper limbs; and the like.

Tissues targeted by the present invention may be any organ of an organism and may be derived from any organism. Examples of organisms targeted by the present invention include vertebrates and invertebrates. Preferably, organisms targeted by the present invention are mammals (e.g., primates, rodents, etc.). More preferably, organisms targeted by the present invention are primates. Most preferably, organisms targeted by the present invention are humans.

When a prosthetic tissue, three-dimensional structure, or the like of the present invention is used as a valve, techniques well known in the art for general use of prosthetic valves can be used to implant the prosthetic tissue or the like. For example, stentless heterologous tissue valves are well known in the art. For example, stentless heterologous tissue valves are known. In heterologous tissue valves, the presence of a stent reduces the effective area of the valve port, leading to calcification or degeneration of valve leaflets. Recently, by utilizing the morphology of the base portion of the porcine aorta, a stentless heterologous tissue valve stent without a stent has attracted attention as a prosthetic valve for the aortic valve (Gross C., et al., Ann. Thorac. Surg., 68:919, 1999). It is considered that the absence of a stent results in a small pressure difference across the valve even when a small-size valve is unavoidably used and is also effective for postoperative enlargement of the left ventricle. Further, the elasticity of the base portion of the aorta is maintained, stress to the cusp is small, and the durability can be expected to be improved as compared to a tissue valve with a stent. Further, stentless heterologous tissue valves can be used in the case of endocarditis due to infection or prosthetic valve infection. At present, substantially satisfactory intermediate-term postoperative results of stentless heterologous tissue valves have been reported in the USA and Europe, and long-term results can be expected to be satisfactory (Gross C., et al., Ann. Thorac. Surg., 68:919, 1999).

As used herein, the term "large size" in relation to a prosthetic tissue refers to the size of a portion thereof which has no pore. Representatively, the term "large size" means that the length in a longitudinal direction of a portion having no pore is at least 1 cm, preferably at least 1.5 cm, and even more preferably at least 2 cm. In this case, the length in a transverse direction thereof is also at least 1 cm, preferably at least 1.5 cm, and even more preferably at least 2 cm. The present invention is not limited to this. When a "large size" is represented by the area of a prosthetic tissue, the area of an inscribed circle in a portion having no pore is typically at least 1 $cm^2$, preferably at least 2 $cm^2$, more preferably at least 3 $cm^2$, even more preferably at least 4 $cm^2$, still even more preferably at least 5 $cm^2$, and most preferably at least 6 $cm^2$.

As used herein, the term "flexibility" in relation to a prosthetic tissue refers to an ability to resist physical stimuli from external environments (e.g., pressure). A prosthetic tissue having flexibility is preferable when the implantation site moves or deforms autonomously or by external effects. Therefore, such a prosthetic tissue having flexibility preferably retains flexibility after implantation.

As used herein, the term "extendibility and contractibility" in relation to a prosthetic tissue refers to an ability to resist extending or contracting stimuli from external environments (e.g., pulsation). A prosthetic tissue having extendibility and contractibility is preferable when the implantation site is subjected to extending or contracting stimuli. Examples of implantation sites, which are subjected to extending or contracting stimuli, include, but are not limited to, heart, muscle, joint, cartilage, tendon, and the like. In one embodiment, extendibility and contractibility capable of withstanding the pulsation motion of the heart may be required.

As used herein, the term "part other than the myocardium of an adult" refers to any part, tissue, cell, or organ other than the myocardium of the terminally differentiated heart. Examples of such parts, tissues, cells, and organs include, but are not limited to, skeletal myoblasts, fibroblasts, synovial cells, stem cells, and the like. These cells have no marker characteristic to cells derived from the myocardium of the adult heart. Such a marker (hereinafter referred to as an "adult myocardial marker") may be in the form of a nucleic acid molecule (expression of mRNA), a protein, an extracellular matrix, a specific phenotype, a specific shape of a cell, or the like. Therefore, adult myocardial markers which are not specified herein may be used to identify a prosthetic tissue of the present invention as long as these markers can indicate cells derived from the myocardium of an adult. Representative examples of parts other than the myocardium of an adult include, but are not limited to, portions of the heart other than the adult myocardium, portions containing mesenchymal stem cells or cells derived therefrom, other tissues, other organs, myoblasts (e.g., skeletal myoblasts), fibroblasts, synovial cells, and the like. Therefore, by identifying a specific marker characteristic to parts other than the myocardium of an adult, the parts other than myocardium can be confirmed.

As used herein, the term "part other than the heart of an adult" refers to any part, tissue, cell, or organ other than the terminally differentiated heart. Examples of such parts, tissues, cells, and organs include, but are not limited to, skeletal myoblasts, fibroblasts, synovial cells, stem cells, and the like. These cells have no marker characteristic to cells derived from the adult heart. Such a marker may be in the form of a nucleic acid molecule (expression of mRNA), a protein, an extracellular matrix, a specific phenotype, a specific shape of cell, or the like. Therefore, adult heart markers which are not specified herein may be used to identify a prosthetic tissue of the present invention as long as these markers can indicate cells derived from adult heart. Representative examples of parts other than the heart of an adult include, but are not limited to, parts containing mesenchymal stem cells or cells derived therefrom, other tissues, other organs, myoblasts (e.g., skeletal myoblasts), fibroblasts, synovial cells, and the like. Therefore, by identifying a specific marker characteristic to parts other than the heart, the parts other than the heart of an adult can be confirmed.

A "part other than the myocardium of an adult" and a "part other than the heart of an adult" can be identified using markers characteristic to cells derived from the myocardium of an adult or the heart of an adult including skeletal myoblasts, fibroblasts, synovial cells, stem cells, or the like (hereinafter referred to as a "non-adult myocardial marker" or a "non-adult heart marker", respectively). If the marker is expressed by less than about 100%, preferably less than about 80%, more preferably less than about 50%, even more preferably less than about 25%, in some cases less than about 1%, the above-described parts can be identified. Examples of such markers include, but are not limited to, myosin heavy chain IIa, myosin heavy chain IIb, myosin heavy chain IId (IIx), CD56, MyoD, Myf5, myogenin, and the like. Therefore, non-adult myocardial markers which are not specified herein may be used to identify a prosthetic tissue of the present invention as long as these markers can indicate cells derived from parts other than the myocardium of an adult. Also, non-adult heart markers which are not specified herein may be used to identify a prosthetic tissue of the present invention as long as these markers can indicate cells derived from parts other than the heart of an adult.

Myosin heavy chain Ha (human: Accession No. NM_017534; SEQ ID NOs. 1 and 2), myosin heavy chain IIb (human: Accession No. NM_017533; SEQ ID NOs. 3 and 4), and myosin heavy chain IId (IIx) (human: Accession No. NM_005963; SEQ ID NOs. 5 and 6) are markers specific to myoblasts (Havenith M. G., Visser R., Schrijvers-van Schendel J. M., Bosman F. T., "Muscle Fiber Typing in Routinely Processed Skeletal Muscle With Monoclonal Antibodies", Histochemistry, 1990; 93(5):497-499). These markers can be confirmed mainly by observing the presence of proteins. An antibody against myosin heavy chain IIa, myosin heavy chain IIb, and myosin heavy chain IId (IIx) is, for example, MY-32 available from Sigma. This antibody is specific to skeletal muscles and does not bind to myocardium (Webster C., Pavlath G. K., Parks D. R., Walsh F. S., Blau H. M., Exp. Cell. Res., 1988 January; 174(1):252-65; and Havenith M. G., Visser R., Schrijvers-van Schendel J. M., Bosman F. T., Muscle Fiber Typing in Routinely Processed Skeletal Muscle with Monoclonal Antibodies, Histochemistry, 1990, 93(5):497-499).

CD56 (human: Accession No. U63041; SEQ ID NOs. 7 and 8) is a marker specific to myoblasts. This marker can be confirmed mainly by observing the presence of mRNA.

MyoD (human: Accession No. X56677; SEQ ID NOs. 9 and 10) is a marker specific to myoblasts. This marker can be confirmed mainly by observing the presence of mRNA.

Myf5 (human: Accession No. NM_005593; SEQ ID NOs. 11 and 12) is a marker specific to myoblasts. This marker can be confirmed mainly by observing the presence of mRNA.

Myogenin (human: Accession No. BT007233; SEQ ID NOs. 13 and 14) is a marker specific to myoblasts. This marker can be confirmed mainly by observing the presence of mRNA.

In other embodiments, other markers specific to other tissues can be utilized. Examples of such markers include, but are not limited to, Oct-3/4, SSEA-1, Rex-1, Otx2, and the like for embryonic stem cells; VE-cadherin, Flk-1, Tie-1, PECAM1, vWF, c-kit, CD34, Thy1, Sca-1, and the like for endothelial cells; skeletal muscle $\alpha$ actin in addition to the above-described markers for skeletal muscles; Nestin, Glu receptor, NMDA receptor, GFAP, neuregulin-1, and the like for nerve cells; c-kit, CD34, Thy1, Sca-1, GATA-1, GATA-2, FOG, and the like for hematopoietic cells.

As used herein, the term "derived" in relation to cells means that the cells are separated, isolated, or extracted from a cell mass, tissue, or organ in which the cells have been originally present, or that the cells are induced from stem cells.

As used herein, the term "applicable to heart" means that the heart applied has an ability to pulsate. A tissue applicable to heart has strength such that the tissue can withstand dilation and contraction of the pulsating heart. Here, applicability to the heart includes applicability to the myocardium. Applicability to heart may be determined by confirming that a recipient having an implanted graft survives.

As used herein, the term "three-dimensional structure" refers to an object which comprises cells having intracellular electrical connection and alignment and extends three-dimensionally. The term "three-dimensional structure" encompasses objects having any shape (e.g., sheet-shape, etc.). A sheet-shaped structure comprises a single layer or a plurality of layers.

As used herein, the term "cell sheet" refers to a structure comprising a monolayer of cells. Such a cell sheet has at least a two-dimensional biological connection. The sheet having biological connection is characterized in that after the sheet is produced, the connection between cells is not substantially destroyed even when the sheet is handled singly. Such biological connection includes intracellular connection via an extracellular matrix.

As used herein, the term "biological connection" in relation to the relationship between cells means that there is certain interaction between the cells. Examples of such interaction includes, but are not limited to, interaction via biological molecules (e.g., extracellular matrix), interaction via signal transduction, electrical interaction (electrical connection, such as synchronization of electrical signals or the like), and the like. In order to confirm interaction, an assay appropriate to a characteristic of the interaction is employed. In order to confirm physical interaction via biological molecules, the strength of a prosthetic tissue, a three-dimensional structure, or the like is measured (e.g., a tensile test). In order to confirm interaction via signal transduction, gene expression or the like is investigated. In order to confirm electrical interaction, the electric potential of a prosthetic tissue, a three-dimensional structure, or the like is measured to determine whether or not the electric potential is propagated with constant waves. Therefore, preferably, physical connection can be determined by observing whether or not the connection is established without a scaffold. In the present invention, it is typically sufficient that at least a two-dimensional biological connection is provided. In a preferred embodiment, it is advantageous that a three-dimensional biological connection is provided. In this case, a three-dimensional structure may be formed. Preferably, there is biological connection substantially uniformly in all directions in three-dimensional space. In another embodiment, the prosthetic tissue, a three-dimensional structure, and the like, which has substantially uniform two-dimensional biological connection and slightly weaker biological connection in the third dimension, may be employed.

A prosthetic tissue, three-dimensional structure, or the like of the present invention may be provided using known preparation methods, as a pharmaceutical product, or alternatively, as an animal drug, a quasi-drug, a marine drug, a cosmetic product, and the like.

Animals targeted by the present invention include any organism as long as it has organs (e.g., animals (e.g., vertebrates, invertebrate)). Preferably, the animal is a vertebrate (e.g., Myxiniformes, Petronyzoniformes, Chondrichthyes, Osteichthyes, amphibian, reptilian, avian, mammalian, etc.), more preferably mammalian (e.g., monotremata, marsupialia, edentate, dermoptera, chiroptera, carnivore, insectivore, proboscidea, perissodactyla, artiodactyla, tubulidentata, pholidota, sirenia, cetacean, primates, rodentia, lagomorpha, etc.). Illustrative examples of a subject include, but are not limited to, animals, such as cattle, pigs, horses, chickens, cats, dogs, and the like. More preferably, primates (e.g., chimpanzee, Japanese monkey, human, etc.) are used. Most preferably, a human is used. This is because there is limitation to implantation therapies.

When the present invention is used as a pharmaceutical agent, it may further comprise a pharmaceutically acceptable carrier or the like. A pharmaceutically acceptable carrier contained in a medicament of the present invention includes any material known in the art.

Examples of such a pharmaceutically acceptable carrier include, but are not limited to, antioxidants, preservatives, colorants, flavoring agents, diluents, emulsifiers, suspending agents, solvents, fillers, bulking agents, buffers, delivery vehicles, agricultural or pharmaceutical adjuvants, and the like.

The amount of a pharmaceutical agent (e.g., a prosthetic tissue, a pharmaceutical compound used in conjunction therewith, etc.) used in the treatment method of the present invention can be easily determined by those skilled in the art with reference to the purpose of use, a target disease (type, severity, and the like), the patient's age, weight, sex, and case history, the form or type of the cell, and the like. The frequency of the treatment method of the present invention applied to a subject (or patient) is also determined by those skilled in the art with respect to the purpose of use, target disease (type, severity, and the like), the patient's age, weight, sex, and case history, the progression of the therapy, and the like. Examples of the frequency include once per day to several months (e.g., once per week to once per month). Preferably, administration is performed once per week to month with reference to the progression.

As used herein, the term "administer" in relation to a prosthetic tissue, three-dimensional structure, or the like of the present invention or a pharmaceutical agent comprising it, means that they are administered singly or in combination with other therapeutic agents. A prosthetic tissue of the present invention may be introduced into therapy sites (e.g., impaired heart, etc.) by the following methods, in the following forms, and in the following amounts. Examples of the introduction methods include, but are not limited to, direct attachment, suture after attachment, insertion, and the like. For example, a prosthetic tissue and a three-dimensional structure of the present invention may be applied by the above-described methods to an impaired site of ischemic myocardial tissue caused by myocardial infarct, angina pectoris, or the like. Combinations may be administered either concomitantly (e.g., as an admixture), separately but simultaneously or concurrently; or sequentially. This includes presentations in which the combined agents are administered together as a therapeutic mixture, and also procedures in which the combined agents are administered separately but simultaneously (e.g., a prosthetic tissue or the like is directly provided by operation, while other pharmaceutical agents are provided by intravenous injection). "Combination" administration further includes the separate administration of one of the compounds or agents given first, followed by the second.

As used herein, the term "reinforcement" means that the function of a targeted part of an organism is improved.

As used herein, the term "instructions" describe a method of administering a medicament, a method for diagnosis, or the like of the present invention for persons who administer, or are administered, the medicament or the like or persons who diagnose or are diagnosed (e.g, physicians, patients, and the like). The instructions describe a statement indicating an appropriate method for administering a diagnostic, a medicament, or the like of the present invention. The instructions are prepared in accordance with a format defined by an authority of a country in which the present invention is practiced (e.g., Health, Labor and Welfare Ministry in Japan, Food and Drug Administration (FDA) in the U.S., and the like), explicitly describing that the instructions are approved by the authority. The instructions are so-called package insert and are typically provided in paper media. The instructions are not so limited and may be provided in the form of electronic media (e.g., web sites, electronic mails, and the like provided on the Internet).

As used herein, the term "stimulus responsive macromolecule" refers to a macromolecule which changes its shape and/or property in response to a stimulus, i.e., the changes occur between before and after the stimulus. Examples of such a stimulus include, but are not limited to, exposure to light, application of electric field, a change in temperature, a change in pH, addition of a chemical substance, and the like. Examples of stimulus responsive macromolecules include, but are not limited to, poly(N-isopropylacrylamide), poly(N-isopropylacrylamide-acrylic acid) copolymer, poly (N-isopropylacrylamide-methylmethacrylate) copolymer, poly(N-isopropylacrylamide-sodium acrylate) copolymer, poly(N-isopropylacrylamide-vinyl ferrocene) copolymer, γ ray-exposed poly(vinylmethylether) (PVME), poly(oxyethylene), a resin obtained by incorporating a biological material (e.g., nucleic acid, etc.) into a macromolecule, and a gel obtained by cross-linking the above-described macromolecules with a cross-linking agent, and the like.

As used herein, the term "temperature responsive macromolecule" refers to a macromolecule which changes its shape and/or property in response to temperature. Examples of temperature responsive macromolecules include, but are not limited to, poly(N-isopropylacrylamide), poly(N-isopropylacrylamide-acrylic acid)copolymer, poly(N-isopropylacrylamide-methylmethacrylate)copolymer, poly(N-isopropylacrylamide-sodium acrylate)copolymer, poly(N-isopropylacrylamide-vinyl ferrocene)copolymer, γ ray-exposed poly(vinylmethylether) (PVME), poly (oxyethylene), and a gel obtained by cross-linking the above-described macromolecules with a cross-linking agent, and the like. Preferable examples of temperature responsive macromolecules include, but are not limited to, poly(N-isopropylacrylamide), poly(N-isopropylacrylamide-methylmethacrylate)copolymer, poly(N-isopropylacrylamide-sodium acrylate)copolymer, and a gel obtained by cross-linking the above-described macromolecules with a cross-linking agent, and the like. For example, a temperature responsive macromolecule used herein has an upper or lower critical solution temperature to water of from 0° C. to 80° C. The present invention is not limited to this. The term "critical solution temperature" refers to a temperature threshold which changes a shape and/or property. Preferably, poly(N-isopropylacrylamide) may be herein used.

For example, γ ray-exposed polyvinylmethylether forms a hydrate at room temperature in aqueous solution which in turn swells. It is known that as the temperature is increased, the substance is dehydrated, so that the solution is contracted and turned into a heat-sensitive macromolecule gel. The PVME gel, which is uniform and transparent like a jelly, is turned cloudy (i.e., its transparency is changed) if it is heated. If the gel is provided with a porous structure or formed into fibers or particles, the gel can extend or contract at high speed. It is believed that a porous and fiber-like PVME gel can extend or contract for less than one second (see http://www.aist.go.jp/NIMC/overview/v27-j.htmL, Japanese Laid-Open Publication No. 2001-213992, and Japanese Laid-Open Publication No. 2001-131249). N-isopropylacrylamide gel (i.e., poly(N-isopropylacrylamide) is also known as a temperature responsive gel. If poly(N-isopropylacrylamide) is copolymerized with a hydrophobic monomer, the temperature which allows it to change its shape and/or property can be lowered. If poly(N-isopropylacrylamide) is copolymerized with a hydrophilic monomer, the temperature which allows it to change its shape and/or property can be raised. By utilizing this character, it is possible to prepare a filler responsive to a desired stimulus. Such a technique can be applied to other temperature responsive macromolecules.

As used herein, the term "protein degrading enzyme" has the same meaning as commonly used in the art and refers to an enzyme which catalyzes the degradation of proteins. This enzyme is also referred to as "protease".

As used herein, the term "regular array film" refers to a film which has a structure in which elements are arrayed under a certain rule. Examples of the structure of such a film include, but are not limited to, honeycomb structure, line structure, dot structure, and the like. A prosthetic tissue of the present invention is preferably produced with such a regular array. The film can be made of a biodegradable material (e.g., poly-L-lactic acid (PLLA), etc.). In order to produce a stretchable film, poly(ϵ-caprolactone) (PCL) or the like can be used.

In cell engineering, tissue engineering, or the like, cell culture often requires base material for scaffolding cells. It is known that cell-to-cell interaction is affected by not only the chemical properties of cell surfaces but also the minute shape of cells. For the purpose of control of cellular functions, it is important to design both the chemical properties of material surfaces contacting cells and the minute structure of cells. It has been revealed that in porous films having honeycomb structure, the honeycomb pattern provides a cell adhesion surface and the porous structure provides access of cell supporting bases and supply routes of nutrients. Therefore, it is preferable to utilize honeycomb structure for the present invention.

The honeycomb structure film may be used as a base to organize cells into a prosthetic organ or a prosthetic tissue, for example. Such a prosthetic organ or tissue or the like may be desired to be absorbed into the body. Therefore, the base is desirably absorbed into the body after a certain period of time. Conventional materials, which have honeycomb structure, stably maintain the structure for a period of time required for cell culture, and thereafter degrade, are described in, for example, Japanese Laid-Open Publication No. 2001-157574, Japanese Laid-Open Publication No. 2002-335949, and the like.

Japanese Laid-Open Publication No. 2001-157574 discloses a honeycomb structure and a film consisting of the honeycomb structure. The honeycomb structure is obtained as follows. A hydrophobic organic solvent solution of a polymer consisting of 50 to 99 w/w % of a biodegradable polymer and 50 to 1 w/w % of an amphipatic polymer is cast on a substrate in atmosphere having a relative humidity of 50 to 95%, followed by gradual evaporation of the organic solvent and concurrent dew condensation on the surface of the cast solution. Small dew drops caused by condensation are evaporated. As a result, a honeycomb structure is obtained. Japanese Laid-Open Publication No. 2002-335949 describes that the above-described film having a honeycomb structure can be used to form a three-dimensional aggregation of orderly organized cells which is similar to biological tissue.

A film for use in the present invention is produced as follows. A hydrophobic organic solvent solution of a single biodegradable and amphipatic polymer or a polymer mixture containing a biodegradable polymer and an amphipatic polymer is cast on a substrate, followed by evaporation of the organic solvent and concurrent dew condensation on the surface of the cast solution. Small dew drops caused by condensation are evaporated.

In the present invention, a single biodegradable and amphipatic polymer may be used, or alternatively, a polymer mixture containing a plurality of polymers including biodegradable polymer(s) and amphipatic polymer(s) may be used.

As biodegradable polymers which can be used in the present invention, biodegradable aliphatic polyesters (e.g., poly(lactic acid), poly(hydroxybutyric acid), polycaprolactone, poly(ethylene adipate), poly(butylenes adipate), etc.), aliphatic polycarbonate (polybutylene carbonate, polyethylene carbonate, etc.), and the like are preferable in view of solubility to organic solvents. Particularly, poly(lactic acid) and polycaprolactone are desirable in view of availability, price, and the like.

Amphipatic polymers which can be used in the present invention are preferably nontoxic in view of use of them as a base material for cell culture. Examples of such amphipatic polymers include, but are not limited to, polyethylene glycol/polypropylene glycol block copolymer; an amphipatic polymer having an acrylamide polymer as a main chain (backbone structure), a dodecy group as a hydrophobic side chain, and a lactose group or a carboxyl group as a hydrophilic side chain; an ionic complex of an anionic macromolecule (e.g., heparin, dextran sulfate, nucleic acid (e.g., DNA, RNA, etc.), etc.) and a long chain alkylammonium salt; an amphipatic polymer having a water-soluble protein (e.g., gelatin, collagen, albumin, etc.) as a hydrophilic group; and the like. Examples of a single biodegradable and amphipatic polymer include, but are not limited to, polylactic acid/polyethylene glycol block copolymer, poly(ε-caprolactone)/polyethylene glycol block copolymer, poly(malic acid)/(an alkyl ester of polymalic acid) block copolymer, and the like.

As used herein, the term "impaired heart" and "impaired myocardium" refer to a heart and a myocardium, respectively, having an impairment including, but being limited to, ischemic impairments and the like. Examples of ischemic impairments include, but are not limited to, myocardial infarct, angina pectoris, and the like.

As used herein, the term "three-dimensional promoting agent" refers to an agent which promotes biological connection in a third dimension after a group of cells are prepared. Examples of such an agent representatively include agents capable of promoting the secretion of a cellular matrix. Examples of a three-dimensional promoting agent include, but are not limited to, ascorbic acid or a derivative thereof (e.g., ascorbic acid 2-phosphate, ascorbic acid 1-phosphate, sodium L-ascorbate, etc.), and the like. Preferably, a three-dimensional promoting agent may be preferably a component of an extracellular matrix of a part targeted by application and/or a component(s) capable of promoting the secretion of an extracellular matrix in an amount similar thereto. When a three-dimensional promoting agent comprises a plurality of components, the components may be components of an extracellular matrix of a part targeted by application and/or components capable of promoting the secretion of an extracellular matrix in an amount similar thereto.

As used herein, the term "ascorbic acid or a derivative thereof" includes ascorbic acid and an analog thereto (e.g., ascorbic acid 2-phosphate, ascorbic acid 1-phosphate, etc.), and a salt thereof (e.g., sodium salt, magnesium salt, etc.).

DESCRIPTION OF THE PREFERRED EMBODIMENTS

Hereinafter, preferred embodiments of the present invention will be described. The following embodiments are provided for a better understanding of the present invention and the scope of the present invention should not be limited to the following description. It will be clearly appreciated by those skilled in the art that variations and modifications can be made without departing from the scope of the present invention with reference to the specification.

According to one aspect of the present invention, a three-dimensional structure applicable to heart, which comprises a cell derived from a part other than the myocardium of an adult, is provided. Conventional three-dimensional structures applicable to heart comprise a cell derived from the myocardium of an adult, and have a small size and poor performance. The present invention is the first in the world to provide a three-dimensional structure applicable to heart, which comprises a cell derived from a part other than the myocardium of an adult (i.e., non-embryo), by culturing the cell derived from the part other than the myocardium of an adult under specific conditions (e.g., in the presence of a three-dimensional promoting agent, etc.). The three-dimensional structure comprises a cell, preferably substantially a cell and a component derived from the cell (e.g., an extracellular matrix, etc.). Thus, in a preferred embodiment, the three-dimensional structure of the present invention comprises a biological material, and therefore, advantageously overcomes drawbacks due to a scaffold (e.g., poor biocompatibility, immunogenicity, etc.) as compared to conventional structures having a scaffold.

In one preferred embodiment, a cell contained in the three-dimensional structure of the present invention may include both a stem cell and a differentiated cell. In a preferred embodiment, a cell contained in the three-dimensional structure of the present invention is a mesenchymal cell. Though not wishing to be bound by any theory, the reason a mesenchymal cell is preferable is that the mesenchymal cell itself is excellently compatible to the heart, and may have an ability to differentiate into the heart tissue.

The above-described mesenchymal cell may be a mesenchymal stem cell or a differentiated mesenchymal cell.

Examples of a mesenchymal cell for use in the present invention include, but are not limited to, bone marrow, fat cells, synovial cells, and the like.

In a more preferred embodiment, a cell used in the present invention is preferably derived from a myoblast. Conventionally, it was not possible to expect that a three-dimensional structure comprising a myoblast is applicable to heart. This finding is an astonishing effect. The reason myoblasts are preferable is that, for example, the supply source thereof is abundant. The reason is not limited to this.

In a more preferred embodiment, a cell used in the present invention is a skeletal myoblast. Skeletal myoblasts are abundant, and therefore, are preferable as an easily available supply source. In addition, the present invention revealed for the first time the possibility that skeletal myoblasts can be implanted into a heart. Thus, skeletal myoblasts can be used in actual medical practice.

Thus, by appropriately culturing cells derived from parts other than the autologous myocardium, a defective heart can be repaired without implantation surgery.

In another embodiment, a cell used in the present invention may be a fibroblast. This is because fibroblasts can provide biological connection three-dimensionally in a three-dimensional structure. A three-dimensional structure comprising a fibroblast can be used in heart applications. Alternatively, such a three-dimensional structure comprising a fibroblast can be used for reinforcement in addition to heart applications.

In another embodiment, a cell used in the present invention may be a synovial cell. This is because synovial cells can provide biological connection three-dimensionally in a three-dimensional structure. A three-dimensional structure comprising a synovial cell can be used in heart applications. Alternatively, such a three-dimensional structure comprising a synovial cell can be used for reinforcement in addition to heart applications.

In another embodiment, a cell used in the present invention is derived from a stem cell. This is because a three-dimensional structure comprising a cell derived from a stem cell can utilize a cell which is differentiated in a desired direction. Therefore, when the structure is applied to a heart, a stem cell which has been differentiated into a heart cell may be preferable. An exemplary method for differentiation may employ LIF. The present invention is not limited to this.

In a preferred embodiment, a cell used in the present invention is advantageously a cell derived from a subject to which a three-dimensional structure is applied. In this case, a cell used herein is also referred to as an autologous cell. By using autologous cells, immune rejection reactions can be prevented or reduced.

In another embodiment, a cell used in the present invention may be a cell not derived from a subject to which a three-dimensional structure is applied. In this case, a measure for preventing immune rejection reactions is preferably taken.

In another embodiment, a cell used in the three-dimensional structure of the present invention expresses at least one non-adult heart marker selected from the group consisting of myosin heavy chain IIa, myosin heavy chain IIb, myosin heavy chain IId(IIx), CD56, MyoD, Myf5, and myogenin. By utilizing such a non-adult heart marker, it is possible to confirm that the cell used in the three-dimensional structure is a non-adult heart-derived cell. The three-dimensional structure of the present invention can avoid the use of the heart of an adult to significantly increase the potential of heart therapies.

The above-described non-adult heart marker is expressed at a level which is typically possessed by a non-adult heart or a tissue thereof. For example, such a level may be at least about 50% of the naturally-occurring level of a non-adult heart or a tissue thereof, preferably at least about 60%, more preferably at least about 70%, more preferably at least about 80%, even more preferably at least about 90%, and still even more preferably at least about 100%. Examples of a technique for determining the level include, but are not limited to, PCR, blotting for determining the expression level of mRNA (e.g., Northern blotting, etc.), blotting for determining the expression level of a protein (e.g., Western blotting, etc.), and the like. PCR is utilized as follows. A specific primer is selected and designed from the above-described non-adult heart markers by using a method well known in the art (e.g., a commercially available PCR primer design device is used). Samples containing mRNA are extracted from a tissue or cell of interest. cDNA is prepared from mRNA using techniques well known in the art. cDNA is subjected to PCR cycles which allow detection of specific expression. The amplified products are subjected to, for example, electrophoresis, followed by staining. As a result, the expression level can be determined. Northern blotting is utilized as follows. The whole or a part of the nucleic acid sequence of the above-described non-adult heart marker is prepared as a probe (particularly, a sequence capable of specific detection). Samples containing mRNA are extracted from a tissue or cell of interest, followed by separation using electrophoresis. The above-described probe is used to detect expression. When a marker is involved in protein expression, antibodies specific to the protein are prepared. These antibodies are used in Western blotting to detect expression by utilizing antigen-antibody reactions.

In another embodiment, a cell used in the three-dimensional structure of the present invention contains substantially no adult heart marker. Based on the fact that the cell contains substantially no adult heart marker, it is possible to confirm that the three-dimensional structure uses a non-adult heart-derived cell. The three-dimensional structure of the present invention can avoid the use of the heart of an adult to significantly increase the potential of heart therapies.

The above-described adult heart marker is expressed at less than a level which is typically possessed by an adult heart or a tissue thereof. For example, such a level may be less than about 100% of the naturally-occurring level of an adult heart or a tissue thereof, preferably less than about 80%, more preferably less than about 50%, even more preferably less than about 20%, still more preferably less than about 10%, and still even more preferably less than about 5%.

In a preferred embodiment, a cell used in the three-dimensional structure of the present invention contains substantially no adult heart markers. By confirming the absence of all adult heart markers, it is possible to more reliably confirm that the structure is not an adult heart. Note that not all adult heart markers are always checked.

Preferably, a cell used in the three-dimensional structure of the present invention is preferably a cell other than heart cells. Cells other than cardiomyocytes can be used in the present invention. However, cells derived from a heart have a limited supply source, and cells derived from an autologous heart are substantially not available. Therefore, the use of cells not derived from a heart is preferable.

The three-dimensional structure of the present invention is typically applicable to heart, and may be applied to other organs. Preferably, the three-dimensional structure of the present invention may be applied to a myocardium.

In one embodiment, the three-dimensional structure of the present invention comprises a cell sheet having at least one layer. In a certain embodiment, the three-dimensional structure of the present invention comprises a cell sheet having only one layer. By providing a cell sheet, the intact or nonporous nature of the three-dimensional structure of the present invention is secured. Therefore, the three-dimensional structure of the present invention comprising a cell sheet having at least one layer is useful in applications in which an injured site is covered.

In a preferred embodiment, the three-dimensional structure of the present invention comprises a cell sheet having a plurality of layers. Preferably, it is advantageous that a plurality of layers in the cell sheet advantageously biologically connect one another. In this case, biological connection is preferably physical connection via an extracellular matrix, or electrical connection (e.g., pulsation, etc.). The connection varies depending on the desired site. When the three-dimensional structure of the present invention is intended to be implanted into a heart, the biological connection typically includes electrical connection. Alternatively, the biological connection may be connection without a scaffold.

The three-dimensional structure of the present invention may be provided as a pharmaceutical agent. Alternatively, the three-dimensional structure of the present invention may be prepared by a medical practitioner or the like at an actual site. Alternatively, after a medical practitioner prepares cells, a third party may culture the cells and prepare a three-dimensional structure comprising the cells, and employ it for surgery. In this case, cell culture can be carried out by those skilled in the art as well as medical practitioners. Therefore, those skilled in the art can determine culture conditions depending on the type of cells and the target implantation site in accordance with the disclosure of the present specification.

In another aspect of the present invention, a method is provided for producing a three-dimensional structure applicable to adult heart, which comprises a cell derived from a part other than the heart. The method comprises the steps of: a) culturing a cell derived from a part other than the myocardium of an adult on a support comprising a temperature responsive macromolecule; b) setting a culture temperature outside a critical solution temperature range of the temperature responsive macromolecule (above the upper limit, if any; or below the lower limit, if any); and c) detaching the cultured cell as a three-dimensional structure. In this case, the cell derived from a part other than a myocardium may be a cell derived from a part other than a heart, including, for example, mesenchymal cells (e.g., myoblasts, skeletal myoblasts, synovial cells, fibroblasts, etc.), and the like. Preferably, the upper limit or lower critical solution temperature to water is from 0° C. to 80° C. A temperature responsive macromolecule having the above-described critical solution temperature is preferably grafted in the support.

In a preferred embodiment of the present invention, in the method for producing a three-dimensional structure, it is preferable that the structure is not treated with a protein degrading enzyme in or before the detaching step. In conventional methods for preparing cell sheets or the like, treatment using a protein degrading enzyme is performed so as to facilitate detachment. In this case, however, the cell sheet is injured, and therefore, cannot be used as a three-dimensional structure. In the method of the present invention, treatment using a protein degrading enzyme can be omitted, whereby an intact three-dimensional structure can be achieved.

In a preferred embodiment, the temperature responsive macromolecule is poly(N-isopropylacrylamide). Poly(N-isopropylacrylamide) has a lower limit critical solution temperature of a little more than 20° C. In this case, therefore, by changing culture medium from a typical culture temperature (e.g., about 37° C.) to about 20° C., it is possible to easily prepare a three-dimensional structure. Thereby, a three-dimensional structure applicable to implantation surgery, which comprises a cell not derived from the myocardium of an adult, can be provided. As a result; a technique substantially other than organ transplantation can be provided to a number of diseases which can be treated only by conventional heart transplantation (e.g., dilated cardiomyopathy, etc.). That is, a therapy which cannot be achieved by conventional techniques can be provided by the present invention.

In a more preferred embodiment, the three-dimensional structure of the present invention preferably comprises a three-dimensional organization promoting agent when cell culture is conducted. Such a three-dimensional organization promoting agent may be ascorbic acid or a derivative thereof.

In another aspect, the prosthetic tissue and three-dimensional structure of the present invention is free from injury caused by a protein degrading enzyme, such as, representatively, dispase, trypsin, or the like, during culture. Therefore, the prosthetic tissue and three-dimensional structure, which is detached from the base material, can be recovered as a cell mass holding proteins between cells (e.g., an extracellular matrix) and having a certain level of strength. The prosthetic tissue and three-dimensional structure also retain intact functions, such as a contraction/relaxation function, intracellular electrical connection, alignment, and the like which are specific to cardiomyocytes. In addition, the three-dimensional structure may have several characteristic, biological tissue-like, cell alignments (e.g., formation of a membrane consisting of connective tissue, formation of a lumen consisting of blood vessel endothelial cells, etc.). When typical protein degrading enzymes (e.g., trypsin, etc.) are used to detach the three-dimensional structure or prosthetic tissue, substantially no desmosome structure between cells, basement membrane-like proteins between cells and base materials, or the like are retained, so that cells are individually separated. Among these protein degrading enzymes, dispase destroys basement membrane-like proteins between cells and base materials substantially completely, but not necessarily desmosome structure. The desmosome structure can be retained if the temperature is from 10° C. to 60° C. In this case, however, the resultant three-dimensional structure or prosthetic tissue has weak strength. In contrast, the three-dimensional structure or prosthetic tissue of the present invention can retain 80% or more of each of the desmosome structure and the basement membrane-like protein, resulting in the above-described various effects. In the cell culture support, a temperature responsive polymer for use in coating the base material has an upper or lower limit critical solution temperature of from 0° C. to 80° C. in aqueous solution, and preferably from 20° C. to 50° C. If the upper or lower limit critical solution temperature exceeds 80° C., cells are likely to be killed. If the upper or lower limit critical solution temperature is lower than 0° C., the cell growth rate is extremely low or cells are killed.

The temperature responsive polymer used in the present invention may be either a homopolymer or a copolymer. An example of such a polymer is a polymer described in, for example, Japanese Laid-Open Publication No. 2-211865, in addition to those described above. Specifically, for example, such a temperature responsive polymer is obtained by homo- or co-polymerization of the following monomers. Examples of usable monomers include, but are not limited to, (meth) acrylamide compounds, N-(or N,N-di)alkyl substituted (meth)acrylamide derivatives, or vinylether derivatives. In the case of copolymers, any two or more of these monomers can be used. Further, copolymers comprising monomers other than the above-described monomers, copolymers obtained by graft- or co-polymerization of polymers, or a mixture of homopolymers and copolymers may be employed. Furthermore, polymers may be cross-linked to an extent such that the inherent properties of the polymer are not impaired. Examples of the base material to be coated include, but are not limited to, materials typically used in cell culture (e.g., glass, modified glass, polystyrene, polymethylmethacrylate, etc.), substantially all materials capable of being generally shaped (e.g., macromolecule compounds in addition to those described above, ceramics, etc.).

A method for coating a support with a temperature responsive polymer is not particularly limited and may be performed in accordance with, for example, Japanese Laid-Open Publication No. 2-211865. Specifically, coating may be performed by subjecting a base material and the above-described monomer or polymer to electron beam irradiation (EB), γ ray irradiation, ultraviolet irradiation, plasma treatment, corona treatment, or organic polymerization reaction, or physical adsorption or the like (e.g., application, crossing, etc.).

In the present invention, cell culture is conducted on the above-described cell culture support (e.g., a cell culture dish, etc.). When the above-described polymer covering the surface of the base material has an upper limit critical solution temperature, the temperature of the medium is set to be equal to or lower than the upper limit critical solution temperature. When the above-described polymer covering the surface of the base material has a lower limit critical solution temperature, the temperature of the medium is set to be equal to or higher than the lower limit critical solution temperature. However, a low temperature range such that cultured cells cannot grow and a high temperature range such that cultured cells are killed is inappropriate. Culture conditions other than temperature may be those well known in the art and are not particularly limited. For example, the medium may be supplemented with known fetal calf serum (FCS) or the like, or alternatively, serum-free medium without supplement of such a serum may be employed.

In the method of the present invention, the period of time required for culture may be determined depending on the application of the prosthetic tissue or three-dimensional structure. In order to detach and recover the cultured prosthetic tissue or three-dimensional structure from the support material, the temperature of the support material having attached cells is increased on or above the upper limit critical solution temperature of a polymer covering the support base material, or is decreased on or below the lower limit critical solution temperature. In this case, the cultured prosthetic tissue or three-dimensional structure is detached directly, or optionally with macromolecular membrane being attached thereto. Note that the prosthetic tissue or three-dimensional structure may be detached in culture medium in which cells have been cultured, or alternatively, in other isotonic solutions. Such solutions may be selected depending on the purpose. Examples of the macromolecular membrane, which is optionally attached to the cell sheet or three-dimensional structure, include, but are not limited to, hydrophilized polyvinylidene difluoride (PVDF), polypropylene, polyethylene, cellulose and derivatives thereof, chitin, chitosan, collagen, paper (e.g., Japan paper, etc.), urethane, net-like or stockinette-like macromolecular materials (e.g., spandex, etc.), and the like. When a net-like or stockinette-like macromolecular material is employed, the prosthetic tissue or three-dimensional structure has a higher degree of freedom, so that the contraction/relaxation function thereof can be increased. A method for producing the prosthetic tissue or three-dimensional structure comprising cells of the present invention is not particularly limited. For example, the prosthetic tissue or three-dimensional structure of the present invention can be produced by utilizing the above-described cultured cell sheet attached to a macromolecular membrane.

In order to detach and recover the prosthetic tissue or three-dimensional structure with a high yield from the cell culture support, the cell culture support is tapped or shaken, or the medium is stirred with a pipette. These procedures may be performed singly or in combination. In addition, the prosthetic tissue or three-dimensional structure may be optionally rinsed with isotonic solution or the like before detaching and recovering. By stretching the prosthetic tissue or three-dimensional structure in a specific direction after being detached from the base material, the cell sheet or three-dimensional structure is provided with alignment. Stretching may be performed by using a tensile device (e.g., Tensilon, etc.), or simply forceps, or the like. A stretching method is not particularly limited. By providing alignment, it is possible to confer directionality to the motion of the cell sheet or three-dimensional structure itself. Therefore, for example, it is possible to allow the prosthetic tissue or three-dimensional structure to move in accordance with the motion of a specific organ. The prosthetic tissue or three-dimensional structure can be efficiently applied to organs.

The thus-obtained prosthetic tissue or three-dimensional structure cannot be obtained by conventional techniques. The prosthetic tissue or three-dimensional structure retains the basement membrane which in conventional techniques is ruptured. Therefore, the prosthetic tissue or three-dimensional structure can be satisfactorily accepted by the surrounding tissue and can pulsate in situ when it is buried in any part of an organism (e.g., heart, bone, muscle, arm, shoulder, foot, and other organs). Though not wishing to be bound by any theory, the reason is believed to be as follows. The prosthetic tissue or three-dimensional structure buried within an organism is accepted by a biological tissue, and is contracted or relaxed. In this case, the prosthetic tissue or three-dimensional structure is in the low oxygen state. To compensate the state, blood vessel endothelial cells aggressively enter the prosthetic tissue or three-dimensional structure from the surrounding biological tissue. As a result, blood vessels are formed, so that sufficient oxygen and nutrients can be supplied via blood. Thus, the prosthetic tissue or three-dimensional structure buried within an organism can form a functional tissue within the organism. Such a prosthetic tissue or three-dimensional structure is strongly expected to be used in clinical applications, such as implantation and the like. Specifically, the prosthetic tissue or three-dimensional structure of the present invention can be used as a therapeutic instrument for heart diseases (e.g., myocardial infarct, etc.). In this case, for example, the prosthetic tissue or three-dimensional structure is implanted to a site of a heart which has a weak contraction force. Alternatively, the prosthetic tissue or three-dimensional structure may be applied around a blood vessel to improve circulation. For example, the prosthetic tissue or three-dimensional structure is useful as a therapeutic instrument for severe Raynaud's disease, a severe stiff shoulder, the dysfunction of the aorta, and the like. Note that a cell culture support for use in the present invention can be repeatedly used.

(Preparation of Prosthetic Tissue Using Three-Dimensional Promoting Agent)

In another aspect, the present invention provides a method for producing a prosthetic tissue. The method for producing a prosthetic tissue comprises the steps of: A) providing a cell; B) placing the cell in a container containing a cell culture medium including a three-dimensional promoting agent, wherein the container has a base with an area sufficient to accommodate a desired size of the prosthetic tissue; and C) culturing the cell in the container for a period of time sufficient to form the prosthetic tissue having the desired size.

The above-described cell may be any cell. A method for providing a cell is well known in the art. For example, a tissue is extracted and cells are isolated from the tissue. Alternatively, cells are isolated from body fluid containing blood cells or the like. Alternatively, a cell line is prepared in an artificial culture. The present invention is not limited to this.

The method for producing a prosthetic tissue of the present invention employs a cell culture medium containing a three-dimensional promoting agent. Examples of such a three-dimensional promoting agent include, but are not limited to, ascorbic acid or a derivative thereof, ascorbic acid 1-phosphate, ascorbic acid 2-phosphate, L-ascorbic acid, and the like.

The cell culture medium used in the present invention may be any medium which allows a cell of interest to grow. Examples of such a medium include, but are not limited to, DMEM, MEM, F12, DME, RPMI1640, MCDB104, 199, MCDB153, L15, SkBM, Basal medium, and the like which are supplemented with glucose, FCS (fetal calf serum), antibiotics (penicillin, streptomycin, etc.) as appropriate.

The container used in the present invention may be any container typically used in the art which has a base with an area sufficient to accommodate a desired size of the prosthetic tissue. Examples of such a container include, but are not limited to, petri dishes, flasks, mold containers, and the like, and preferably containers having a large area of the base (e.g., at least 1 $cm^2$). The material of the container may be any material and include, but are not limited to, glass, plastic (e.g., polystyrene, polycarbonate, etc.), silicone, and the like.

In a preferred embodiment, the three-dimensional promoting agent used in the method for producing a prosthetic tissue of the present invention includes ascorbic acid 2-phosphate. Conventionally, it is known that ascorbic acid is used for cell culture. However, there was no report that ascorbic acid 2-phosphate is intentionally used for formation of tissue. In the present invention, by adding a certain amount of ascorbic acid 2-phosphate, it is possible to prevent an extracellular matrix from being produced in an excessively large amount, the composition has an implantable level of extracellular matrices, and therefore, the ratio of the cell to the extracellular matrix results in an implantable level of strength and the like. These effects are unexpected.

In a preferred embodiment, ascorbic acid 2-phosphate used in the present invention typically has a concentration of at least 0.01 mM, preferably at least 0.05 mM, more preferably at least 0.1 mM, even more preferably at least 0.2 mM, still more preferably at least 0.5 mM, and still even more preferably 1.0 mM.

Alternatively, ascorbic acid 2-phosphate used in the present invention may be used in conjunction with ascorbic acid 1-phosphate. In this case, ascorbic acid 1-phosphate and ascorbic acid 2-phosphate may be preferably used at a specific ratio. Such a preferable ratio is, for example, in the range of from 1:10 to 10:1. Alternatively, the preferable ratio is such that the molar amount of ascorbic acid 1-phosphate is smaller than the molar amount of ascorbic acid 2-phosphate.

In another embodiment, the three-dimensional promoting agent used in the present invention includes ascorbic acid 2-phosphate. However, there was no report that ascorbic acid 2-phosphate is explicitly used for formation of a tissue. In the present invention, by adding a certain amount of ascorbic acid 2-phosphate, it is possible to prevent an extracellular matrix from being produced in an excessively large amount, the composition has an implantable level of extracellular matrices, and therefore, the ratio of cells to the extracellular matrix results in an implantable level of strength and the like. These effects are unexpected.

In a preferred embodiment, when the molar amount of ascorbic acid 1-phosphate is smaller than the molar amount of ascorbic acid 2-phosphate, ascorbic acid 2-phosphate used in the present invention is typically present at a concentration of at least 0.01 mM, preferably at least 0.05 mM, more preferably at least 0.1 mM, even more preferably at least 0.2 mM, and still more preferably at least 0.5 mM, and still even more preferably 1.0 mM.

In a certain preferred embodiment, the three-dimensional promoting agent of the present invention includes ascorbic acid 1-phosphate or a salt thereof, ascorbic acid 2-phosphate or a salt thereof, and L-ascorbic acid or a salt thereof.

The container used in a prosthetic tissue production method of the present invention is preferably coated with a temperature responsive macromolecule. In another preferred embodiment, the container is preferably provided with a scaffold having a honeycomb structure. The present invention is not limited to this. Use of a honeycomb structure is described in, for example, Tanaka K. et al, "Atarashii Baiomedikaru Intafesu [New Biomedical Interface]", Kagaku Kogyo [Chemical Industry], December 2002, 901-906, Kagaku Kogyo Sha.

The temperature responsive macromolecule which may be used in the prosthetic tissue production method of the present invention, includes poly(N-isopropylacrylamide).

In a preferred embodiment, after the culturing step, the prosthetic tissue production method of the present invention further comprises, D) detaching the prosthetic tissue and allowing the prosthetic tissue to perform self contraction. The detachment can be accelerated by applying a physical stimulus (e.g., applying a physical stimulus to a corner of the container, etc.). When a temperature responsive macromolecule is used, the detachment can be accelerated by changing the environment to a temperature higher or lower than the critical solution temperature of the temperature responsive macromolecule. Self-contraction naturally takes place after the detachment. By self-contraction, biological connection is accelerated particularly in the third dimension (the direction perpendicular to the two-dimensional directions in the case of tissue on a sheet). Therefore, a prosthetic tissue of the present invention may have a three-dimensional structure.

In a prosthetic tissue production method of the present invention, the sufficient time preferably means at least 3 days and may be more than or less than 3 days, though it varies depending on the application of a prosthetic tissue of interest. By 3-day culture, it is possible to prepare a graft which can be applied at least to the reinforcement of a heart.

In another aspect, the present invention provides a functional prosthetic tissue. The functional prosthetic tissue of the present invention is herein an implantable prosthetic tissue. Attempts have been heretofore made to produce prosthetic tissues by cell culture. However, there were no prosthetic tissues suitable for implantation in terms of size, strength, physical injuries when it is detached, or the like. The present invention provides a tissue culture method in which cells are cultured in the presence of a three-dimensional promoting agent as described above, so that there is no problem in terms of size, strength, and the like and there is no difficulty in detaching tissues. An implantable prosthetic tissue is provided only after such a tissue culture method is achieved. For diseases which are conventionally treated only by organ transplantation (e.g., refractory heart diseases (myocarditis, hypertrophic cardiomyopathy, dilated phase hypertrophic cardiomyopathy, dilated cardiomyopathy, etc.)), an alternative therapy having general versatility is provided, which is of immeasurable usefulness.

A “disease” targeted by the present invention may be any heart disease in which tissue is injured. Examples of such a heart disease include, but are not limited to, heart failure, myocardial infarct, cardiomyopathy, and the like. A combined therapy of the present invention may be applied to organs in addition to the heart as long as it aims the regeneration of injured tissues. In a specific embodiment, a disease targeted by a method of the present invention is refractory heart failure.

The term “heart failure” refers to the inability of the heart to circulate blood in a required quantity and quality to organs in the entire body due to an impairment of the heart itself, such as failure of cardiac functions, failure of circulatory functions, a reduction in contractile power, or the like. Heart failure is a terminal symptom of heart diseases, such as myocardial infarct, cardiomyopathy, and the like. Severe heart failure means that the state of the heart is severe and is also referred to as terminal heart failure.

The term “refractory heart failure” refers to heart failure which is resistant to therapy and is difficult to ameliorate by medical therapy and drug therapy. The term “refractory heart failure” is substantially synonymically referred to as chronic heart failure or terminal heart failure. Refractory heart failure cannot be controlled by triple therapy using a typical Digitalis drug, diuretic, ACE inhibitor, and the like, or a drug therapy supplemented with a β-blocker. These therapies require a mechanical aid for circulation, such as IABP (intra-aortic balloon pumping), PCPS (percutaneous cardiopulmonary support), or the like, or alternatively, heart transplantation. Therefore, there was a demand for the development of a simple and radical therapy. Particularly, heart transplantation has a serious donor shortage problem. When heart transplantation cannot be used (e.g., elderly, patients in need of dialysis, etc.), refractory heart failure poses serious problems. Therefore, there is a keen demand for an alternative to heart transplantation therapy.

The term “myocardial infarct” refers to a disease in which ischemic necrosis occurs in a perfusion area associated with highly developed constriction or occlusion caused by various lesions of the coronary artery. The severity of myocardial infarct is divided into classes in various manners. Classification may be based on, for example, progress over time; morphology (e.g., the range, site, necrosis size, or the like within the myocardium); the necrosis form of a myocardium; the reconstruction of a ventricle after infarction; the dynamics of blood circulation (associated with therapy, prognosis, etc.); clinical severity; and the like. Myocardial infarct having a high level of severity is particularly called severe myocardial infarct.

The term “cardiomyopathy” is a generic term for diseases caused by organic and functional abnormality in a myocardium, which are divided into secondary cardiomyopathy following a basic disease (e.g., hypertension, dysbolism, ischemia, etc.), and spontaneous cardiomyopathy which develops without an apparent basic disease. As a pathological change, myocardial hypertrophy, formation of fibrous tissue, degeneration, or the like is observed.

The term “dilated cardiomyopathy” refers to a functional failure of the left ventricle associated with the deflation thereof, and is also referred to as “congestive cardiomyopathy”. The term “dilated cardiomyopathy” may be abbreviated as “DCM”. Dilated cardiomyopathy is associated with contraction failure, leading to chronic heart failure. Examples of a cause of dilated cardiomyopathy include various things, such as viral infection, gene mutation, and the like. Generally, dilated cardiomyopathy does not include specific myocardial diseases (conventionally referred to as secondary myocardial diseases), such as ischemic cardiomyopathy caused by an unambiguous other cause, myocardial diseases associated with dysbolism or the like. However, these specific myocardial diseases are also included within the scope of the present invention as long as the present invention has a therapeutic effect thereon. Most patients have a reduction in contractile power in the entire myocardium. It is also said that abnormality may occur in the motion of an isolated portion of a wall. Typically, dilated cardiomyopathy has heart failure symptoms associated with congestion and sometimes has malaise due to low cardiac output. Dilated cardiomyopathy has no known cause and is an idiopathic myocardial disease. The pathology of dilated cardiomyopathy mainly includes a reduction in contractile power of a myocardium, which leads to the dilation of the left ventricular cavity. The pathology also includes a reduction in blood amount, an increase in left ventricular diastolic pressure, and the like. Dilated cardiomyopathy has acute or insidious onset and refractory heart failure at its end stage. Pathologically or histologically, the degeneration, formation of fibrous tissue, or atrophy of myocardial tissue is diffusely or locally observed. Residual cardiomyocytes often cause hypertrophy. In addition to heart failure, severe arrhythmia or thromboembolism occurs, resulting in a very poor prognosis. Echocardiogram is particularly useful for diagnosis of dilated cardiomyopathy, which demonstrates a diffuse reduction in wall motion, the thinning of a ventricular wall, and the dilation of a ventricular cavity. In addition, coronary angiography (coronary arterial lesion) and myocardial biopsy can be conducted to achieve a more reliable diagnosis. Therefore, in the present invention, a test technique well known in the art, such as heart ultrasonography, a heart catheter test method, a nuclear medical test method (myocardial scintigraphy), myocardial biopsy, or the like, can be used to confirm an amelioration in dilated cardiomyopathy.

Conventionally, for dilated cardiomyopathy, a drug therapy using an ACE inhibitor, a diuretic, a β-blocker, a cardiotonic drug, or the like; guidance in regulating the intake of salt and water and exercise; and the like, are conducted. However, none of them cure the disease itself. For arrhythmia, an antiarrhythmic agent, such as amiodarone or the like, may be administered, which is however only a symptomatic treatment. For thrombi and emboli, an anticoagulant, such as warfarin or the like, is used, which is however only a symptomatic treatment. As a surgical treatment, a pacemaker, a buried defibrillator, an assisted circulation device (bypass), heart transplantation, or the like is used. However, these treatments other than heart transplantation cannot be said to eradicate the disease. At present, serious donor shortage limits heart transplantation. A therapeutic technique of the present invention is effective for dilated cardiomyopathy and the like and provides an advantageous therapeutic effect.

The term "hypertrophic cardiomyopathy" (HCM) refers to a type of cardiomyopathy whose main symptom is a reduction in diastolic compliance due to an abnormal enlargement of a myocardium and left ventricle hypertrophy. The contractile function of the heart is typically retained. The 5-year and 10-year survival rates are satisfactorily about 90% and about 80%, respectively. However, hypertrophic cardiomyopathy is believed to be a cause of sudden death, which poses a clinical problem. Therefore, there is a demand for a radical therapy for the disease. A therapeutic technique of the present invention is also effective to hypertrophic cardiomyopathy and provides an advantageous therapeutic effect.

The term "dilated phase hypertrophic cardiomyopathy" refers to a type of hypertrophic cardiomyopathy in which the formation of fibrous tissue is developed in a myocardium in the course of the disease, leading to the thinning of a ventricular wall and a reduction in contractile power, and as a result, a ventricular cavity is enlarged, so that a symptom of dilated cardiomyopathy appears. Dilated phase hypertrophic cardiomyopathy is said as having a very poor prognosis. There are a number of subclinical cases, posing a clinical problem. Therefore, there is also a demand for a radical therapy for dilated phase hypertrophic cardiomyopathy. A therapeutic technique of the present invention is effective for dilated phase hypertrophic cardiomyopathy and the like and provides an advantageous therapeutic effect.

Conventional therapies and diagnostic techniques for refractory heart failure or the like as described above are described in, for example, "Junkanki Shikkan Saishin no Tiryo [Latest Therapy for Circulatory Diseases] 2002-2003, Shigetake Sasayama and Yoshio Yazaki editors, Nankodo, 2002, and the like. As described in "Junkanki Shikkan Saishin no Tiryo [Latest Therapy for Circulatory Diseases] 2002-2003, Shigetake Sasayama and Yoshio Yazaki editors, Nankodo, 2002, which was most recently published, there was no radical therapy for refractory heart failure. The present invention is the first to provide a therapy for the above-described heart diseases, particularly refractory heart failure.

As used herein, the term "prophylaxis" or "prevention" in relation to a certain disease or disorder refers to a treatment which keeps such a condition from happening before the condition is caused, or causes the condition to occur at a reduced level or to be delayed.

As used herein, the term "therapy" in relation to a certain disease or disorder means that when such a condition occurs, such a disease or disorder is prevented from deteriorating, preferably is retained as it is, more preferably is diminished, and even more preferably extinguished. As used herein, the term "radical therapy" refers to a therapy which eradicates the root or cause of a pathological process. Therefore, when a radical therapy is made for a disease, there in principle is no recurrence of the disease.

As used herein, the term "prognosis" is also referred to as "prognostic treatment". The term "prognosis" in relation to a certain disease or disorder refers to a diagnosis or treatment of such a condition after a therapy.

In a preferred embodiment, the prosthetic tissue of the present invention has a three-dimensional, biological connection. As described in other portions of the specification, examples of biological connection include, but are not limited to, physical connection via extracellular matrices, electrical connection, and the like. In the present invention, physical connection via extracellular matrices is particularly important in view of the strength of tissue.

In one embodiment, the prosthetic tissue of the present invention is different from conventional prosthetic tissues in that the former comprises a cell.

Preferably, a prosthetic tissue of the present invention consists substantially of a cell or a material derived from the cell. Since the prosthetic tissue is composed substantially of only a cell and a cell-derived material (e.g., extracellular matrix, etc.), the prosthetic tissue can have an increased level of biocompatibility and affinity. The cell-derived material representatively includes extracellular matrices. Particularly, the prosthetic tissue preferably comprises a cell and an extracellular matrix at an appropriate ratio thereof. Such an appropriate ratio of a cell and an extracellular matrix is from about 1:9 to about 9:1, preferably about 3:7 to about 7:3, and more preferably about 3:7 to about 5:5. A preferable ratio varies depending on the purpose. Such variations may be prepared by those skilled in the art. An appropriate ratio can be estimated by investigating the ratio of a cell and an extracellular matrix in an organ of interest.

In another embodiment, the prosthetic tissue of the present invention is preferably isolated. In this case, the term "isolate" means that the prosthetic tissue is separated from a scaffold, a support, and a culture medium used in culture. If a prosthetic tissue of the present invention is substantially free from materials, such as a scaffold and the like, it is possible to suppress adverse reactions after implantation, such as immune rejection reactions, inflammation reactions, and the like.

In another embodiment, the prosthetic tissue of the present invention is preferably intact. An intact prosthetic tissue can be provided substantially only after the prosthetic tissue production method of the present invention using a three-dimensional promoting agent is provided. Conventionally, when a prosthetic tissue is detached from the culture environment, a physical stimulus is necessarily applied to the tissue, so that the tissue is unavoidably hurt. Therefore, an attempt has been made to compile a plurality of cell sheets prepared by conventional methods. However, such a multilayer of cell sheets cannot be easily used for actual implantation. Therefore, such a problem is overcome by the intactness of the prosthetic tissue of the present invention.

In a preferred embodiment, the prosthetic tissue of the present invention has a large size. The term "large size" in relation to a prosthetic tissue typically means that the prosthetic tissue has an area sufficient to cover a site to which the prosthetic tissue is implanted. Such an area is, for example, at least 1 $cm^2$, more preferably at least 2 $cm^2$, at least 3 $cm^2$, at least 4 $cm^2$, even more preferably at least 5 $cm^2$, and still even more preferably at least 6 $cm^2$.

In a preferred embodiment, the prosthetic tissue of the present invention is thick. The term "thick" in relation to a prosthetic tissue typically means that the prosthetic tissue has a thickness which provides a strength sufficient to cover a site to which the prosthetic tissue is implanted. Such a thickness is, for example, at least about 50 μm, more preferably at least about 100 μm, at least about 200 μm, at least about 300 μm, even more preferably at least about 400

μm, still more preferably at least about 500 μm, and still even more preferably about 1 mm.

A prosthetic tissue of the present invention is preferably imperforate. The imperforate prosthetic tissue is suitable for implantation. The imperforate prosthetic tissue is particularly preferable for reinforcement of a defective site of a bag-shaped tissue which needs to be covered.

In another embodiment, the prosthetic tissue of the present invention is flexible. Due to the flexibility, the prosthetic tissue is particularly suitable for reinforcement of motile organs. Examples of motile organs include, but are not limited to, hearts, blood vessels, muscles, and the like.

In another embodiment, the prosthetic tissue of the present invention has dilation/contraction ability. Due to the dilation/contraction ability, the prosthetic tissue is suitable for organs which expand and contract, including, for example, hearts, muscles, and the like. The dilation/contraction ability cannot be achieved by cell sheet or the like prepared by conventional methods. Preferably, a prosthetic tissue of the present invention has a sufficient strength to withstand the pulsation motion of a heart. The strength sufficient to withstand pulsation motion is, but is not limited to, at least about 50% of the strength of naturally-occurring myocardium, preferably at least about 75%, and more preferably at least about 100%.

In a preferred embodiment, the prosthetic tissue of the present invention has biological connection in all three dimensions. There are some prosthetic tissues prepared by conventional methods, which have biological connection in two dimensions to some degree. However, no tissue having biological connection in all three dimensions can be prepared by conventional methods. Therefore, since the prosthetic tissue of the present invention has biological connection in all three dimensions, the prosthetic tissue is substantially implantable in any application.

Examples of biological connection which is an indicator of a prosthetic tissue of the present invention, include, but are not limited to, interconnection of extracellular matrices, electrical connection, the presence of intracellular signal transduction, and the like. The interaction of extracellular matrices can be observed with a microscope by staining intracellular adhesion as appropriate. Electrical connection can be observed by measuring electric potential.

In a preferred embodiment, the prosthetic tissue of the present invention has a sufficient tissue strength for clinical applications. The sufficient tissue strength for clinical applications varies depending on a site to which the prosthetic tissue is applied. Such a strength can be determined by those skilled in the art with reference to the disclosure of the specification and techniques well known in the art. For example, in a preferred embodiment, a strength required by the present invention is at least 80% of the tissue strength of a portion targeted by a clinical application.

In a specific embodiment, the above-described portion targeted by a clinical application includes the heart, and in some cases, portions other than the heart.

In another aspect, the present invention provides a cell culture composition for producing prosthetic tissue from a cell. The cell culture composition contains an ingredient (e.g., commercially available medium, etc.) for maintaining or growing the cell, and a three-dimensional promoting agent. The three-dimensional promoting agent has been described in detail in the above description of the prosthetic tissue production method. Therefore, the three-dimensional promoting agent includes ascorbic acid or a derivative thereof (e.g., ascorbic acid 1-phosphate or a salt thereof, ascorbic acid 2-phosphate or a salt thereof, L-ascorbic acid or a salt thereof, etc.). The culture composition of the present invention contains ascorbic acid 2-phosphate or a salt thereof at a concentration of at least 0.1 mM. Alternatively, in the case of a condensed culture composition, the condensed culture composition contains ascorbic acid 2-phosphate or a salt thereof at a concentration which becomes at least 0.1 mM after preparation. Alternatively, the lower limit concentration of ascorbic acid 2-phosphate or a salt thereof may be 0.01 mM, 0.05 mM, 0.2 mM, or 0.3 mM, even more preferably 0.5 mM, or alternatively 1.0 mM.

In a preferred embodiment, the three-dimensional promoting agent contained in the cell culture composition of the present invention includes ascorbic acid 1-phosphate or a salt thereof and ascorbic acid 2-phosphate or a salt thereof.

Ascorbic acid 2-phosphate used in the present invention is used concomitantly with ascorbic acid 1-phosphate. In this case, ascorbic acid 1-phosphate and ascorbic acid 2-phosphate may be preferably present at a specific ratio. Such a preferable ratio is, for example, in the range of from 1:10 to 10:1. Alternatively, the preferable ratio is such that the molar amount of ascorbic acid 1-phosphate is smaller than the molar amount of ascorbic acid 2-phosphate.

In another embodiment, the three-dimensional promoting agent used in the present invention includes ascorbic acid 2-phosphate. However, there was no report that ascorbic acid 2-phosphate is explicitly used for formation of a tissue. In the present invention, by adding a certain amount of ascorbic acid 2-phosphate, it is possible to prevent an extracellular matrix from being produced in an excessively large amount, the composition has an implantable level of extracellular matrices, and therefore, the ratio of the cell to the extracellular matrix results in an implantable level of strength and the like. These effects are unexpected.

In a preferred embodiment, ascorbic acid 2-phosphate used in the present invention is typically present at a concentration of at least 0.01 mM, preferably at least 0.05 mM, more preferably at least 0.1 mM, even more preferably at least 0.2 mM, and still more preferably at least 0.5 mM, and still even more preferably 1.0 mM.

In a certain preferred embodiment, the three-dimensional promoting agent of the present invention includes ascorbic acid 1-phosphate or a salt thereof, ascorbic acid 2-phosphate or a salt thereof, and L-ascorbic acid or a salt thereof.

(Prosthetic Tissue for "Wrapping")

In another aspect, the present invention provides a prosthetic tissue for reinforcement of a portion of an animal organism. The prosthetic tissue capable of such reinforcement is a technique achieved only after the prosthetic tissue production method of the present invention is provided.

In a preferred embodiment, the above-described portion includes bag-shaped organs. For bag-shaped organs, it is important for the prosthetic tissue to possess intactness and/or nonporousness. A prosthetic tissue having such a property and a certain size cannot be provided by conventional techniques. Therefore, it can be said that a substantial therapy for bag-shaped organs can be achieved only after the above-described prosthetic tissue of the present invention is provided. Therefore, for bag-shaped organs which have specific diseases (e.g., refractory diseases (e.g., dilated cardiomyopathy, etc.), etc.), a therapy can be first provided other than organ transplantation.

In a specific embodiment, examples of the above-described bag-shaped organ include, but are not limited to, hearts, livers, kidneys, and the like.

In a specific embodiment of the present invention, the above-described reinforcement may be achieved by disposing a prosthetic tissue of the present invention to cover the above-described portion. It is not possible to use a prosthetic tissue provided by conventional methods to perform treatment by covering the above-described portion (i.e., "wrapping" application). Thus, the prosthetic tissue of the present invention can provide applications which cannot be achieved by conventional techniques.

Therefore, in the above-described specific embodiment, the prosthetic tissue of the present invention is resistant to dilation/contraction of the above-described portion.

In a preferred embodiment, the prosthetic tissue of the present invention advantageously has biological connection.

In another preferred embodiment, the biological connection includes at least one of interconnection of extracellular matrices, electrical connection, and intracellular signal transduction.

In another preferred embodiment, the prosthetic tissue for reinforcement of the present invention is formed by culturing a cell in the presence of a three-dimensional promoting agent.

In another embodiment, the prosthetic tissue for reinforcement of the present invention comprises a cell (autologous cell) derived from an animal to be treated (e.g., a human). More preferably, a prosthetic tissue for reinforcement of the present invention comprises only a cell(s) (autologous cell) derived from an animal to be treated (e.g., a human).

("Wrapping" Therapy)

In another aspect, the present invention provides a method for reinforcement of a portion of an animal organism. The method comprises the steps of: A) disposing a prosthetic tissue to cover the portion; and B) holding the prosthetic tissue for a time sufficient to connect to the portion. The step of disposing the prosthetic tissue to cover the portion can be carried out using a technique well known in the art. The sufficient time varies depending on a combination of the portion and the prosthetic tissue, and can be easily determined as appropriate by those skilled in the art depending on the combination. Examples of such a time include, but are not limited to, 1 week, 2 weeks, 1 month, 2 months, 3 months, 6 months, 1 year, and the like. In the present invention, a prosthetic tissue preferably comprises substantially only cell(s) and material(s) derived from the cell. Therefore, there is no particular material which needs to be extracted after operation. The lower limit of the sufficient time is not particularly important. In this case, it can be said that the longer the time, the more preferable the prosthetic tissue. If the time is sufficiently extremely long, it can be said that reinforcement is substantially completed. Therefore, the time is not particularly limited.

In another embodiment, in a reinforcement method of the present invention, the above-described portion preferably includes bag-shaped organs (e.g., hearts, livers, kidneys, etc.). In order to reinforce such a bag-shaped tissue, it is necessary to wrap the organ (e.g., cover an injured portion. A prosthetic tissue resistant to wrapping applications is first provided by the present invention. Therefore, the reinforcement method of the present invention is advantageous over conventional techniques.

Particularly, in the reinforcement method of the present invention, a prosthetic tissue of the present invention is resistant to dilation/contraction of the above-described portion. Examples of such dilation/contraction include, but are not limited to, the pulsation motion of a heart, the contraction of a muscle, and the like.

In another preferred embodiment, in the reinforcement method of the present invention, a prosthetic tissue of the present invention has biological connection (e.g., interconnection of extracellular matrices, electrical connection, intracellular signal transduction, etc.). The biological connection is preferably provided in all three dimensions.

In another preferred embodiment, the reinforcement method of the present invention further comprises culturing a cell in the presence of a three-dimensional promoting agent to form a prosthetic tissue of the present invention. An implantation/regeneration technique using the method which comprises the step of culturing a cell in the presence of a three-dimensional promoting agent cannot be provided by conventional techniques. The method provides a therapy for diseases (e.g., refractory heart diseases (e.g., dilated cardiomyopathy, etc.), etc.), which cannot be achieved by conventional therapies.

In a preferred embodiment, in the reinforcement method of the present invention, the cell used in the prosthetic tissue of the present invention is derived from an animal to which the prosthetic tissue is to be implanted (i.e., an autologous cell). By using an autologous cell, adverse side effects, such as immune rejection reactions or the like, can be avoided.

In another preferred embodiment, the portion is a heart. The heart has a disease or disorder, such as heart failure, ischemic heart disease, myocardial infarct, cardiomyopathy, myocarditis, hypertrophic cardiomyopathy, dilated phase hypertrophic cardiomyopathy, dilated cardiomyopathy, or the like.

For some organs, it is said that it is difficult to radically treat a specific disease, disorder, or condition thereof (e.g., refractory heart diseases). However, the present invention provides the above-described effect, thereby making possible a treatment which cannot be achieved by conventional techniques. It has been clarified that the present invention can be applied to radical therapy. Therefore, the present invention has usefulness which cannot be achieved by conventional medicaments.

(Combined Therapy)

In another aspect, the present invention provides a regeneration therapy which uses a cytokine, such as HGF or the like, in combination with a prosthetic tissue.

Cytokines used in the present invention are already commercially available (e.g., HGF-101 from Toyo Boseki, etc.). However, these cytokines can be prepared by various methods and can be used in the present invention if they are purified to an extent which allows them to be used as a medicament. HGF can be obtained as follows: primary cultured cells or an established cell line capable of producing HGF is cultured; and HGF is separated from the culture supernatant or the like, followed by purification. Alternatively, a gene encoding HGF is incorporated into an appropriate vector by a genetic engineering technique; the vector is inserted into an appropriate host to transform the host; recombinant HGF of interest can be obtained from the supernatant of the transformed host culture (e.g., Nature, 342, 440(1989); Japanese Laid-Open Publication No. 5-111383; Biochem-Biophys. Res. Commun., 163, 967 (1989), etc.). The above-described host cell is not particularly limited and can be various host cells conventionally used in genetic engineering techniques, including, for example, *Escherichia coli*, yeast, animal cells, and the like. The thus-obtained HGF may have one or more amino acid substitutions, deletions and/or additions in the amino acid sequence as long as it has substantially the same action as that of naturally-occurring HGF. Examples of a method for introducing HGF into patients in the present invention include, but are not limited to, a Sendai virus (HVJ) liposome method with high safety and efficiency (Molecular Medicine, 30, 1440-1448(1993); Jikken Igaku (Experimental Medicine), 12, 1822-1826 (1994)), an electrical gene introduction method, a shotgun gene introduction method, and the like. Preferably, the HVJ liposome method is used.

Hereinafter, the present invention will be described by way of examples. Examples described below are provided only for illustrative purposes. Accordingly, the scope of the present invention is not limited except as by the appended claims.

EXAMPLES

In the examples below, animals were treated in accordance with rules defined by Osaka University (Japan) and were cared for in the spirit of animal protection.

Example 1

Production and Utilization of Prosthetic Tissue and Three-Dimensional Structure Made of Cardiomyocyte Sheet—Tissue Engineered Contractile Cardiomyocyte Sheet Regenerates Impaired Myocardium (Bioengineered Contractile Cardiomyocyte Sheet Regenerates Infarcted Myocardium)

In Example 1, the present inventors investigated (1) whether or not a cardiomyocyte sheet (prosthetic tissue) survives after implantation and shows histological electrical connection with impaired myocardium; (2) whether or not the implanted cardiomyocyte sheet (prosthetic tissue) can induce an improvement in a cardiac function. As a result, it was demonstrated that the present invention provides the electrical connection and the improvement of cardiac function.

The present inventors introduced the concept of bioengineered tissue implantation into the treatment of impaired myocardium. It was demonstrated that a tissue engineered contractile cardiomyocyte sheet without a scaffold provides histological electrical connection with impaired myocardium and regeneration of an infarcted myocardium.

(Materials and Methods)

(Myocardial Infarct Model)

30 male Lewis rats (300 g, 8 weeks old; Seac Yoshitomi Ltd, Fukuoka, Japan) were used in this study. Humane animal care complied with "Principles of Laboratory Animal Care" prepared by the National Society for Medical Research and "Guide for the Care and Use of Laboratory Animals" (NIH Publication, No. 86-23, 1985, revised) prepared by the Institute of Laboratory Animal Resource and published by the National Institute of Health. Acute myocardial infarct was induced as described in Weisman H. F., Bush D. E., Mannisi J. A., et al., Cellular Mechanism of Myocardial Infarct Expansion, Circulation, 1988; 78: 186-201. Briefly, the rats were anesthetized with sodium pentobarbital, followed by positive pressure breathing through an endotracheal tube. A left 4th intercostal space thoracotomy was used and the left anterior descending coronary artery (LAD) was completely ligated with an 8-0 polypropylene thread at a distance of 3 mm from the root of the LAD.

(Preparation of Rectangle-Designed PIPAAm Grafted Polystyrene Cell Culture Dishes)

A rectangle-designed PIPAAm grafted cell culture dish was prepared with a specific procedure as described in, for example, Okano T., Yamada N., Sakai H., Sakurai Y., J. Biomed. Mater. Res., 1993; 27:1243-1251. Briefly, an IPAAm monomer solution in 2-propanol (kindly provided by Kohjin, Tokyo, Japan) was spread onto tissue culture polystyrene (TCPS) dishes (Falcon 3002, Becton Dickinson). Thereafter, these dishes were subject to irradiation (electron beam dose: 0.25 MGy) using an Area Beam Electron Processing System (Nisshin High Voltage), resulting in polymerization of IPAAm and covalent bonding of IPAAm to the dish surface. The PIPAAm grafted dishes were rinsed with cold distilled water to remove non-grafting IPAAm, followed by drying the dishes in nitrogen gas. In the second step, the PIPAAm grafted surface was masked with a rectangular cover glass (24×24 mm, Matsunami, Tokyo, Japan). Acrylamide (AAm) monomer solution of 2-propanol was spread onto the surface of the masked dish. Thereafter, the dish surface was electron beam irradiated and washed. As a result, the rectangular region at the center of each dish was PIPAAm-grafted (temperature responsive), while the surrounding border was poly-AAm grafted (non-cell adhesive). The rectangle-designed PIPAAm grafted dish was sterilized with ethylene oxide gas before use in culture.

(Primary Culture of Newborn Rat Ventricular Muscle Cells)

Primary newborn rat cardiomyocytes were prepared in accordance with a procedure previously described in, for example, Shimizu T., Yamato M., Akutsu T. et al., Circ. Res., Feb. 22, 2002; 90(3):e40. Briefly, 1 to 2 day old newborn rats were sacrificed while deeply anesthetized, and the hearts were rapidly removed, followed by digestion with Hanks solution containing collagenase (class II, Worthington Biochemical) at 37° C. The isolated cells were suspended in culture medium containing 6% FCS, 40% Medium 199 (Gibco BRL), 0.2% penicillin-streptomycin solution, 2.7 mmol/L glucose, and 54% balanced salt solution (116 mmol/L NaCl, 1.0 mmol/L $NaH_2PO_4$, 0.8 mmol/L $MgSO_4$, 1.18 mmol/L KCl, 0.87 mmol/L $CaCl_2$, and 26.2 mmol/K $NaHCO_3$). The cell suspension was plated at a density of $8\times10^6$ cells/dish, followed by incubation in a humidified atmosphere containing 5% $CO_2$ at 37° C.

(Primary Culture of Fibroblasts)

Primary fibroblasts were prepared in accordance with a procedure previously published in, for example, Yablonka-Reuveni Z., Nameroff M., Skeletal Muscle Cell Populations Separation and Partial Characterization of Fibroblast-Like Cells from Embryonic Tissue Using Density Centrifugation, Histochemistry, 1987; 87:27-38. Briefly, a suspension of cells derived from leg muscle of 8 week old Lewis rats was separated into fibroblasts and muscle cells by Percoll™ density centrifugation (Amersham Biosciences Sweden). The isolated fibroblasts were used for a control fibroblast sheet.

(Production of Cardiomyocyte Sheet)

The isolated cardiomyocytes of the newborn rat were cultured on the rectangle-designed PIPAAm grafted polystyrene cell culture dish. By lowering the temperature to 20° C., the cells were detached as a rectangular cell sheet. Two cardiomyocyte sheets were piled up to produce a thicker heart graft. Cross sectional observation of the double-layered cardiac sheet demonstrated intimate connection and homogenous heart-like tissue. Synchronous motion of a four-layer cardiomyocyte sheet was detected by the naked eye (data not shown). In the case of the fibroblast sheet, isolated fibroblasts were cultured on the same dish for 2 days, and were detached as a rectangular cell sheet by the same method.

(Implantation of Cardiomyocyte Sheet)

The cardiomyocyte sheet was implanted into Lewis rats 2 weeks after LAD ligation. Specifically, a left 4th intercostal space thoracotomy was performed on the rat under general anesthetization. The infarct region was visually identified based on the surface scar and the abnormal wall motion. The cardiomyocyte sheet or the fibroblast sheet was implanted into an infarcted myocardium. A control group was not treated.

The cardiac function was evaluated 2 weeks, 4 weeks, and 8 week after implantation. 8 weeks after implantation, the heart was collected and sectioned, and processed for histological and immunohistological tests.

In order to identify the implanted cardiomyocyte sheet, EGFP newborn rat cardiomyocytes were isolated with the same protocol, and a cardiomyocyte sheet was prepared. The present inventors implanted the EGFP newborn rat cardiomyocyte sheet into an infarcted myocardium of nude rats. The present inventors could detect EGFP positive cardiomyocytes in the infarcted myocardium (FIG. 6, lower left portion and lower right portion).

(Measurement of Cardiac Function of Rat Heart)

Rats were anesthetized with sodium pentobarbital. Anesthetization was supplemented with ethanol to maintain light anesthetization. The rats were lightly secured in a supine position and the precordia of the rats were shaved. Heart ultrasonography was performed using a commercially available echocardiograph SONOS 5500 (PHILIPS Medical Systems, USA). A 12-MHz annular array transducer was placed on an acoustic coupler gel layer applied onto the left hemithorax. The transducer was carefully made to have adequate contact with the thorax while avoiding an excessive level of pressure on the thorax. The rats were imaged in a shallow left lateral decubitus position. The heart was first imaged in a two-dimensional mode in a short axis cross section at a level of the greatest left ventricle (LV) diameter. The systolic left ventricle (LV) area and the diastolic left ventricle (LV) area were determined at the same time. The volume of the left ventricle (LV) was estimated based on a short axis area of the left ventricle (LV) (Gorcsan J. 3rd, Morita S., Mandarino W. A., Deneault L. G., Kawai A., Kormos R. L., Griffith B. P., Pinsky M. R., Two-dimensional Echocardiographic Automated Border Detection Accurately Reflects Changes in Left ventricular Volume, J. Am. Soc. Echocardiogr., 1993; 6: 482-9). The resultant image was used to locate an M mode cursor perpendicular to the left ventricle (LV) anterior wall and the left ventricle (LV) posterior wall. All measurements are performed on line using a monitor. Diastolic measurements were performed at the time of an apparent maximum left ventricle (LV) diastolic dimension. A left ventricle (LV) endsystolic dimension was measured at the time of the most anterior systolic excursion of the left ventricle (LV) posterior wall. The left ventricle (LV) dimension in diastole (LVDd) and the left ventricle (LV) dimension in systole were measured. Dimension data and area data were represented by an average of measured values of two or three selected beats. A left ventricle (LV) ejection fraction (EF) was calculated by:

$$\text{LVEF}\ (\%)=[(\text{LVDd}^3-\text{LVDs}^3)/\text{LVDd}^3]\times 100.$$

LV % fractional shortening (FS) was calculated by:

$$\text{LV}\ \%\ \text{FS}=[(\text{LVDd}-\text{LVDs})/\text{LVDd}]\times 100.$$

(Endocardiography Quantification of Regional Left Ventricular Wall Motion Using Color Kinesis)

Color kinesis is an extension of this technology, which compares tissue backscatter values between successive acoustic frames as a means of automatically tracking and displaying endocardial motion in real time. Color kinesis was incorporated into a commercially available ultrasound system (SONOS 5500, PHILIPS Medical Systems, USA) (Auchincloss 1988, Transplantation 46:1; Robert M. L., Philippe V., Lynn W., James B., Claudia K., Joanne S., Rick K., David P., Victor M. A., et al., "Echocardiographic quantification of regional left ventricular wall motion with color kinesis", Circulation, 1996, 93:1877-1885).

In all study subjects, ultrasound imaging was performed with a 12-MHz annular array transducer. Midpapillary parasternal short-axis was obtained during end expiration in the lateral decubitus position. After image quality was optimized, the acoustic quantification system for endocardial boundary detection was activated. Gain control (total and lateral gain, time gain compensation) were adjusted to optimize tracking of the blood-endocardial interface within a predefined region of interest. Color kinesis then was activated for on-line color encoding of endocardial excursion throughout systole. Image sequences containing color kinesis data were obtained throughout the cardiac cycle and stored in a digital format on optical disks for off-line analysis.

(Histopathology)

Left ventricular myocardium specimens were obtained at 2 and 8 weeks after cardiomyocyte sheet implantation. Each specimen was placed in 10% neutral formaldehyde and embedded in paraffin. A few serial sections were cut from each specimen and stained with hematoxylin and eosin for light microscopic examination.

To label vascular endothelial cells, immunohistochemical staining of factor VIII-related antigen was performed. Frozen sections were fixed with a 2% paraformaldehyde solution in PBS for 5 minutes at room temperature, immersed in methanol with 3% hydrogen peroxide for 15 minutes, then washed with PBS. The samples were covered with bovine serum albumin solution (DAKO LSAB Kit DAKO CORPORATION, Denmark) for 10 minutes to block nonspecific reactions. The specimens were incubated overnight with an EPOS-conjugated antibody against factor VIII-related antigen coupled with HRP (DAKO EPOS Anti-Human Von Wille brand Factor/HRP, DAKO Denmark). After the samples were washed with PBS, they were immersed in diaminobenzidine solution (0.3 mg/ml diaminobenzidine in PBS) to obtain positive staining.

To detect Connexin 43, immunohistochemical staining of Connexin 43-related antigen was performed. Frozen sections were immersed in methanol with 3% hydrogen peroxide for 5 minutes, and then washed with PBS. The specimens were incubated for 20 minutes with a mouse monoclonal antibody to Connexin 43 (CHEMICON International, Inc. USA). After the samples were washed with PBS, they were immersed in biotinylated anti-mouse immunogulobulins (DAKO Denmark) for 10 minutes, and then washed with PBS. The samples were immersed in peroxidase-conjugated streptavidin (DAKO Denmark) for 10 minutes. After the samples were washed with PBS, they were immersed in diaminobenzidine solution (0.3 mg/ml diaminobenzidine in PBS) to obtain positive staining.

(Electrophysiological Analysis)

One microelectrode (100 μm in diameter, Unique Medical Co., Ltd., Tokyo) for capture of the electrical potentials was positioned over the cardiomyocyte sheets implanted scar, fibroblast sheets implanted scar, or no treatment scar. The other two electrodes were put on left subcostal and right femoral region. For stimulation of the host myocardium, two microelectrodes were positioned over an atrium. For detection of host electrocardiogram, three electrodes were attached on right upper breast, left subcostal, and right femoral regions. Both electrograms were amplified by bioelectric amplifiers (UA-102, Unique Medical Co., Ltd., Tokyo) and were recorded by a data acquisition system (UAS-108S, Unique Medical Co., Ltd., Tokyo). The atrium was stimulated at the rate of 300 bpm by stimulator (NIHON KODEN Japan). Thereafter, the electrical potential was captured in the regions of interest.

Thereafter, in order to analyze the threshold, two microelectrodes for stimulation were positioned over the no treatment scar, cardiomyocyte sheet implanted scar, or fibroblast sheets implanted scar. For detection of paced host electrocardiogram, one electrode was attached on a normal myocardium, and the other two electrodes were put on left subcostal and right femoral regions. Thereafter, the present inventors stimulated the no treatment scar, cardiomyocyte sheet implanted scar, or fibroblast sheets implanted scar at the rate of 300 bpm by the same stimulator.

(Data Analysis)

Data are expressed as means±standard deviation (SD). In order to assess the significance of the differences between individual groups, statistical evaluation was performed with the nonparametric Mann-Whitney two-sample test. Statistical significance was determined as a p-value less than 0.05.

(Results)

(Characteristics of Cardiac Grafts)

Detached cardiomyocyte sheets shrank from 5.76 $cm^2$ to 1.11±0.05 $cm^2$ (n=3) in area due to cytoskeletal reorganization. On the other hand, the thickness increased from 20.1±0.9 μm to 52.4±6.0 μm (n=3). The cardiac sheets contracted spontaneously by macroscopic observation.

(Histological Assessment)

Figure 7:
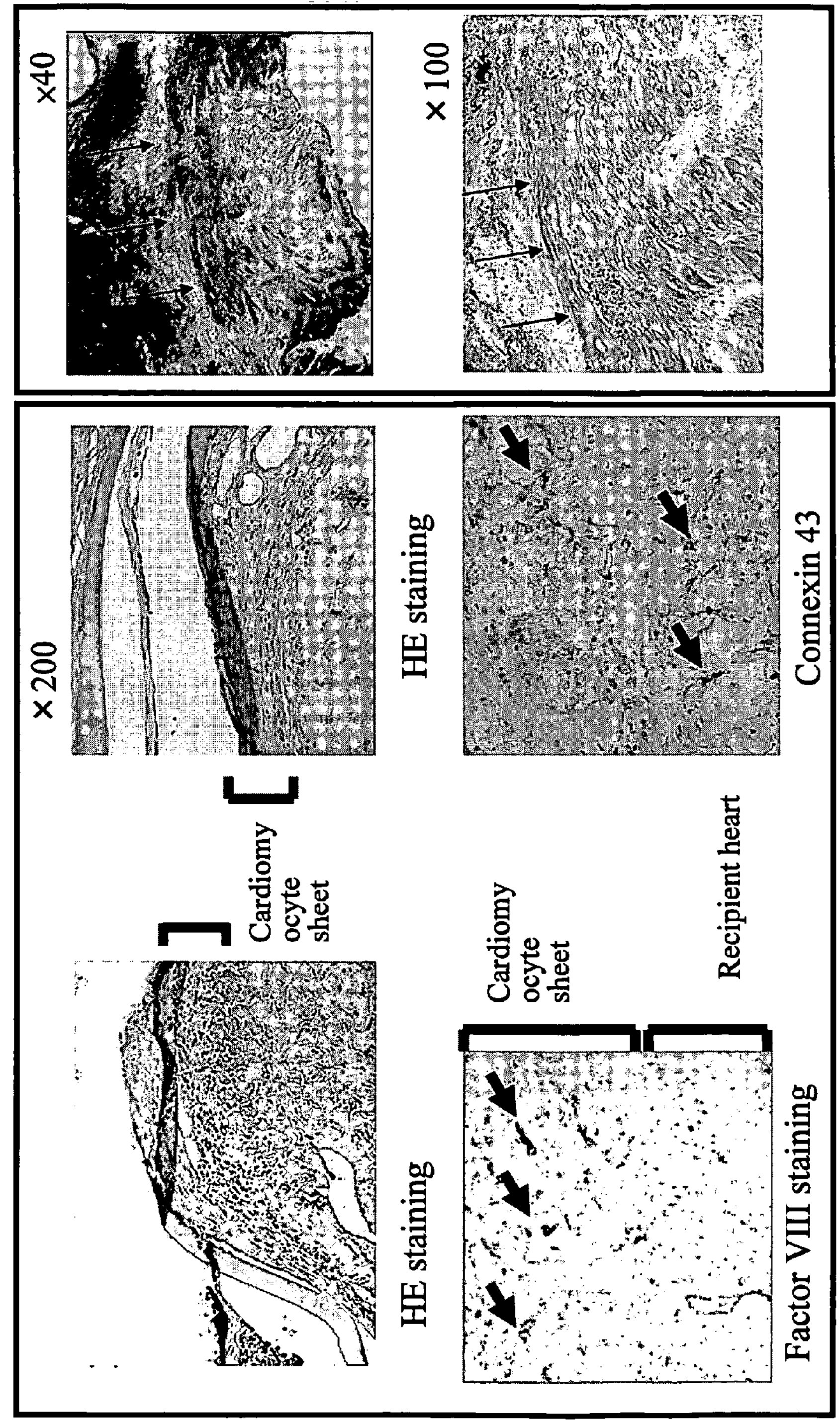
FIG. 7 shows a state of a prosthetic tissue of the present invention after implantation. The left portion shows the tissue 2 weeks after implantation, while the right portion shows the tissue 8 weeks after implantation. HE staining is shown over the left panel (left: ×100; right: ×200). Factor VIII staining is shown below the left panel, while Connexin 43 staining is shown to the right. The right panel shows HE staining (upper: ×40; lower: ×100).

The present inventors could detach a mono-layered cardiomyocyte sheet under low temperature (FIG. 6, upper left portion). The cardiomyocyte sheet was attached on an infarcted myocardium immediately after implantation without ligature (FIG. 6, upper right portion). 2 weeks after implantation, histological examination of Hematoxylin-Eosin (HE) stain of the implanted cardiomyocyte sheet showed good attachment in alignment on the infarcted myocardium without accumulation of inflammatory cells. The yellow arrow indicates a collagen sheet, which is necessary to deliver the cardiomyocyte sheet to the infarcted myocardium (FIG. 7). Visual inspection of the implanted cardiomyocyte sheet at eight weeks after implantation revealed the intimate attachment between the implanted cardiomyocyte sheet and a recipient heart. HE stain of the implanted cardiomyocyte sheet after eight weeks of implantation demonstrated the integration of the cardiomyocyte sheet with the host myocardium in alignment in the center of the scar (FIG. 7, lower right portion). Immunohistochemical staining showed randomly oriented Connexin 43 in the implanted cardiomyocyte sheet and around a contact region between the implanted cardiomyocyte sheet and the recipient heart (FIG. 7, lower middle portion). Factor VIII immunohistochemical staining demonstrated many Factor VIII positive cells in and around the implanted cardiomyocyte sheet (FIG. 7, lower left portion).

(Functional Recovery of Infarcted Myocardium)

B-mode analysis showed that dilatation of the left ventricle was well suppressed and global wall motion was well preserved in the T group compared with the C group (FIG. 8). An ejection fraction (EF), a fractional shortening (FS), and a left ventricular endsystolic area (LVESA) at a baseline were not significantly different between the three groups.

Figure 9:
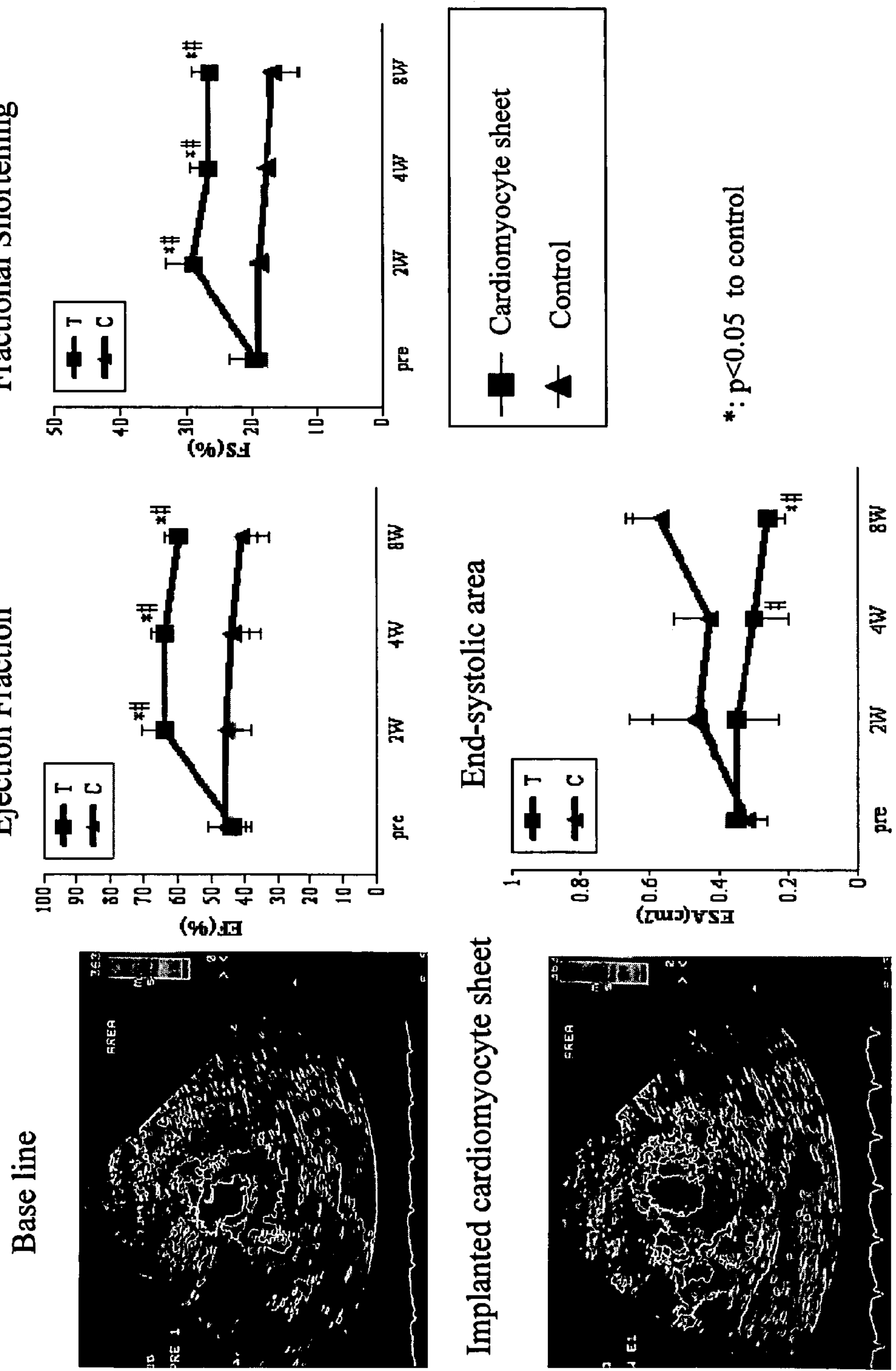
FIG. 9 shows an example of evaluation of cardiac function ameliorated by a prosthetic tissue of the present invention. In the figure, the ejection fraction (EF), the fractional shortening (FS), and the endo-systolic area (ESA) are shown. Squares indicate the cardiomyocyte sheet, while triangles indicate the control. A left panel photograph is an ultrasound echo photograph (upper: control; lower: cardiomyocyte sheet).

2 and 4 weeks after implantation, 2D endocardiography showed a significant improvement of EF and FS in the T group compared with those in the other groups. LVESA was significantly smaller in the T group than that in the other groups. These functional improvements were preserved 8 weeks after implantation (FIG. 9).

(Electrophysiological Experiments)

Electrophysiological experiments showed the one peak component of QRS wave of the treated scar area in the T group in spite of two peaks of QRS wave like branch blocks in the C group (FIG. 11). An effect was observed in the F group, though the level of the effect was lower than that of the T group. Furthermore, electrophysiological experiments demonstrated an improvement of the amplitude (volts) of the QRS complex in the T group in spite of low amplitude in the F and C group (C group vs T group: 2.79±0.9 V vs 0.83±0.64 V, P<0.05) (FIG. 11).

Figure 10:
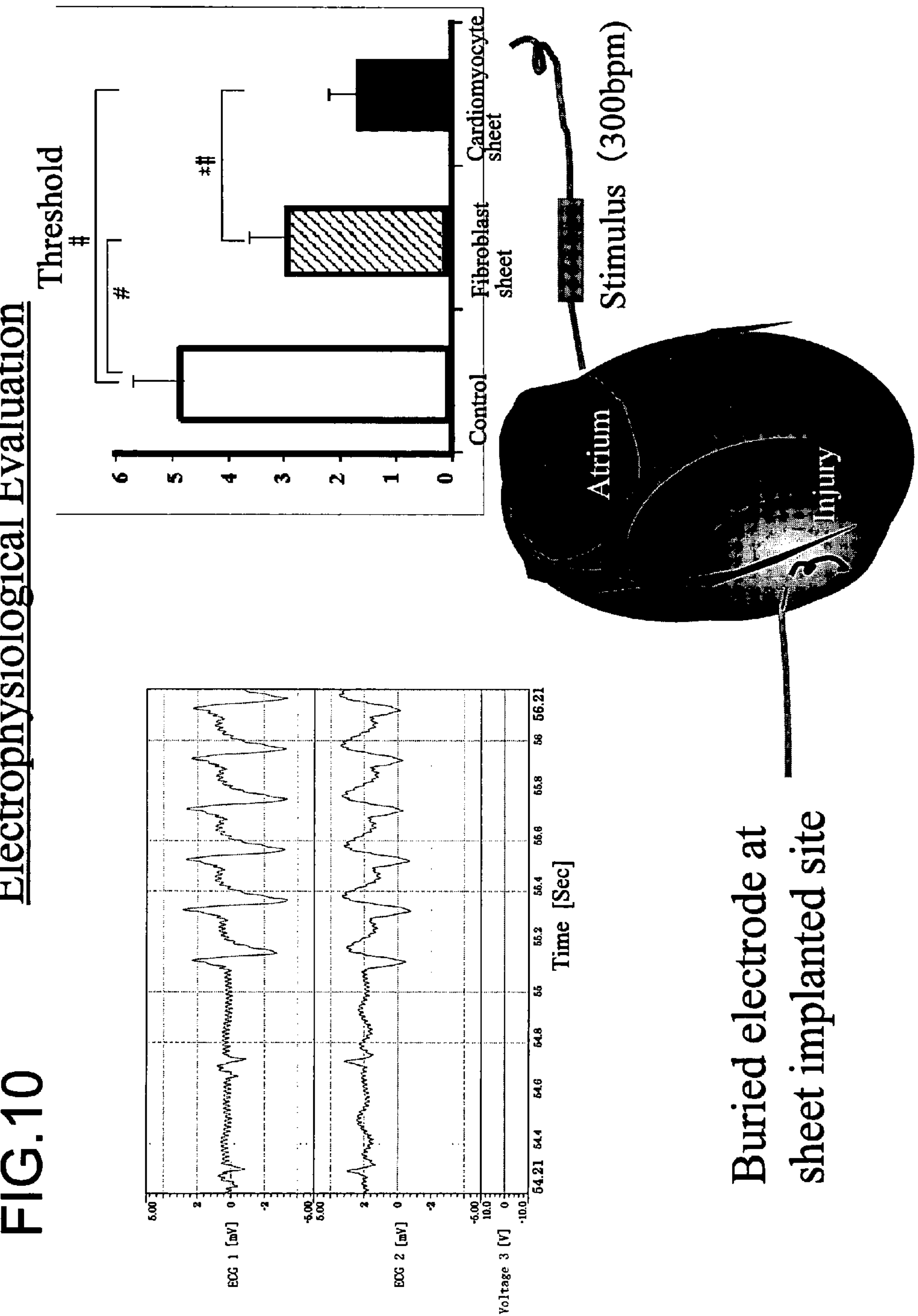
FIG. 10 shows a technique for electrophysiological evaluation of a prosthetic tissue of the present invention. The right portion schematically shows changes in electric potential, while the right portion shows numerical values of threshold. The right portion shows a control, and a fibroblast sheet of the present invention and a cardiomyocyte sheet of the present invention.
Figure 12:
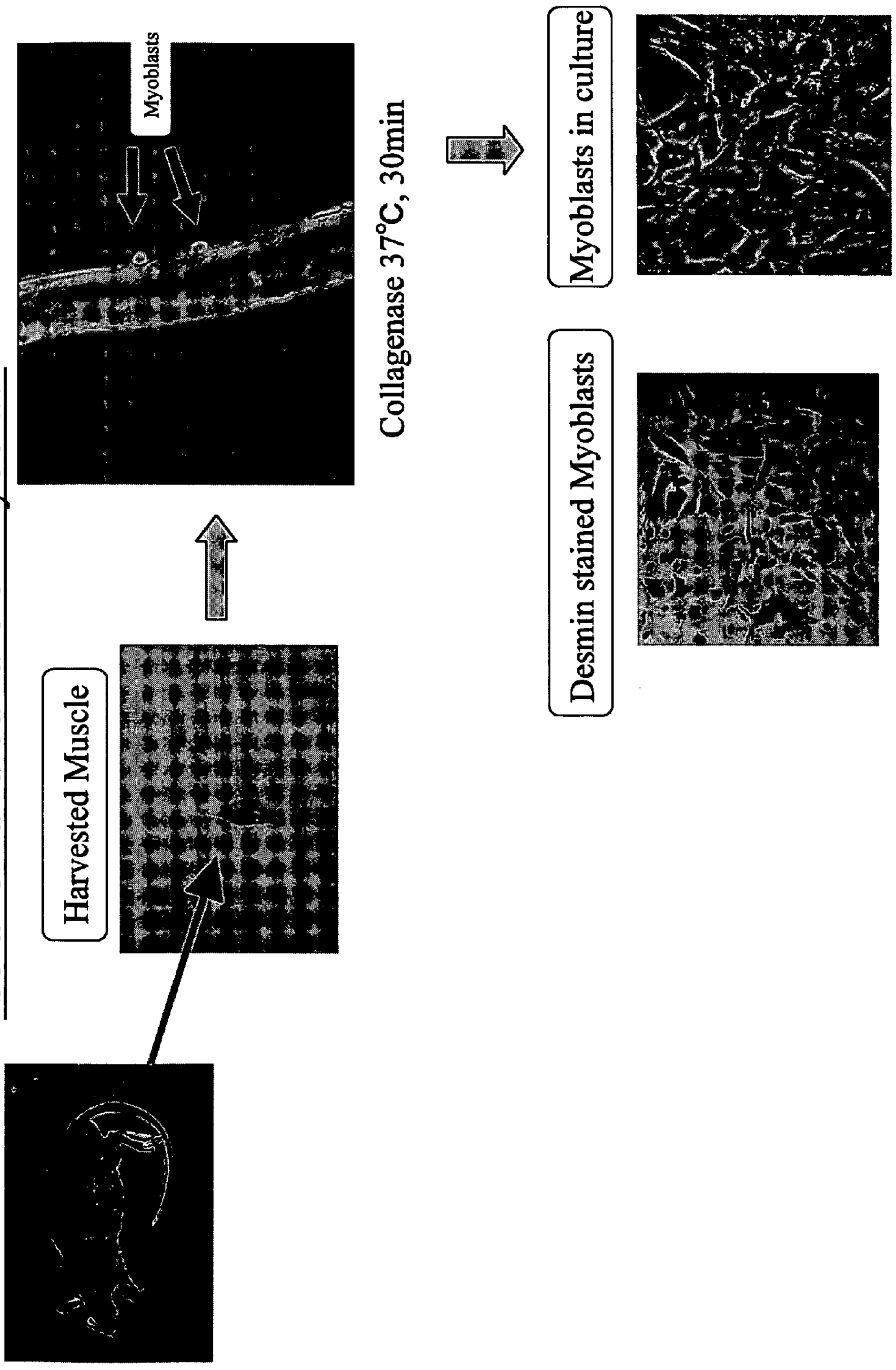
FIG. 12 shows an example of procedures for isolating and culturing myoblasts in a method according to the present invention.

In the T group, when an atrium was stimulated at the frequency of 300 bpm by a stimulator, synchronous electrical spikes were detected in the implanted area (FIG. 10, lower left portion). Furthermore, a threshold for pacing of a recipient heart was lower in the T group than the F and C groups (C group vs F group vs T group: 4.9±0.9 V vs 3.0±0.7 V vs 1.7±0.5 V, P<0.05) (FIG. 10, right portion).

(Results)

A temperature-responsive domain made of poly(N-isopropylacrylamide) was grafted on polystyrene cell culture surfaces. Newborn rat cardiomyocytes were cultured on these dishes and detached as a rectangular cell sheet below 20° C. without trypsin. Two sheets were piled up to make thicker cardiac grafts. These cardiomyocyte sheets contracted spontaneously. Cross sectional observation of the two sheets demonstrated intimate connection and homogenous heart-like tissue.

Two weeks after left anterior descending (LAD) ligation, two different treatments were conducted: 1) cardiomyocyte sheet implantation (T group, n=10); and 2) fibroblast sheet implantation (F group, n=10). The control group was not treated (C group, n=10). Endocardiography demonstrated that cardiac function was significantly ameliorated in the T group two, four, and 8 weeks after implantation. Color kinesis showed that regional systolic wall motion was excellently recovered as compared with values before implantation. Cardiomyocyte sheets attached on the infarcted myocardium were in alignment and seemed to be homogeneous tissue in the myocardium. Immunohistochemical staining demonstrated neoangiogenesis and randomly oriented Connexin 43 in the implanted cardiomyocyte sheets. Electrophysiological experiments showed the improvement of the R-wave and the one peak component of the QRS complex in the treated scar area in the T group in spite of the two peak components of the QRS complex like branch block in the F and C group. Furthermore, a threshold for pacing of a recipient heart was lower in the T group than the F and C group (C group vs F group vs T group: 4.9±0.9 V vs 3.0±0.7 V vs 1.7±0.5 V, P<0.05).

DISCUSSION

The recent development of cellular cardiomyopathy introduced by needle injection has provided a novel approach to restore impaired cardiac function (Taylor D. A., Atkins B. Z., Hungspreugs P., Jones T. R., Reedy M. C., Hutcheson K. A., Glower D. D., Kraus W. E., Regeneration of Functional Myocardium: Improved Performance after Skeletal Myoblast Transplantation, Nature Med., 1998; 4:929-933). Additional potential advantages of the cardiomyocyte sheet implantation method are better control of the tissue formation process (the shape, size, and consistency of a graft), an easy implantation technique, and implantation of a number of cells with minimum cell loss. In contrast, an injection method provides a loss of a certain amount of cells or its surface protein (e.g., Connexin 43) by means of trypsin treatment. In addition to myocardial infarction, the cardiomyocyte sheet implantation method may be useful for repair of global myocardial dysfunction (e.g., dilated cardiomyopathy). To achieve clinical applications, total implanted myocardial tissue mass is critically important for the repair of impaired myocardium, and enhancement of angiogenesis may make it possible for cardiac sheets to be thicker and deliver more cells to impaired myocardium.

In this example, the present inventors have developed a contractile cardiomyocyte sheet without a scaffold and have analyzed cardiac function and histological assessment after implantation. The cardiomyocyte sheet has attached to an infarcted myocardium accompanied with angiogenesis. The cardiomyocyte sheet looked like homogeneous myocyte tissue expressing Connexin 43 and contracted synchronously in vivo. Cardiomyocytes in the cardiomyocyte sheet exhibited alignment and few inflammatory cells accumulated in the implanted cardiomyocyte sheet. The cardiomyocyte sheet implantation promised excellent improvement of systolic and diastolic cardiac performance. Electrophysiological experiments revealed that the cardiomyocyte sheet improves electrical conductivity in scar and reconstructs one peak component of the QRS complex in the treated scar area. These data proved the present inventors' hypothesis that contractile cardiomyocyte sheets exhibit histological and electrical integration with impaired myocardium accompanied with angiogenesis and expression of Connexin 43 and induces the significant improvement of cardiac performance. To the present inventors' best knowledge, this is the first report in which myocardial regeneration therapy was successful in impaired myocardium using a tissue engineered cardiac sheet.

The main factors of integration in the regenerative therapy are dynamic integration, electrical integration, and histological integration.

Concerning dynamic integration, cardiomyocytes of the implanted cardiomyocyte sheet showed alignment and promoted significant improvement of regional and global systolic function in infarcted myocardium. Impaired remodeling is responsible for the cardiac structural deformation and cardiac function deterioration in an infarcted heart (Tyagi S. C., Extracellular Matrix Dynamics in Heart Failure: A Prospect for Gene Therapy, J. Cell. Biochem., 1998, 68:403-410). Kelley et al. showed that restraint of the dilation of a left ventricle (LV) with mesh placed over an infarcted myocardium preserves the left ventricle (LV) geometry and resting function in a sheep myocardial infarction model (Kelley S. T., Malekan R., Gorman J. H. et al., Restraining Infarct Expansion Preserves Left Ventricular Geometry and Function after Acute Anteroapical Infarction, Circulation, 1999, 99:135-142). Although both the preservation of the left ventricle (LV) geometry and the improvement of a regional systolic function in dysfunctioned tissues may be essential for repair of systolic performance in an impaired heart, only the attenuation of left ventricular (LV) dilatation is not adequate treatment. The present inventors' data, in which non-contractile sheets failed to improve the systolic performance compared with contractile sheets, supports this finding. Moreover, the present inventors' data demonstrated significant angiogenesis in infarcted myocardium. One of the mechanisms for the improvement of cardiac function may be angiogenesis induced by an implanted cardiomyocyte sheet. To sum up, the significant improvement of systolic function induced by an implanted cardiomyocyte sheet is responsible for the preservation of left ventricular (LV) geometry, the improvement of regional systolic function, and induction of angiogenesis.

Concerning electrical integration, the present inventors' study demonstrated that an electrical conductor (i.e., a cardiomyocyte sheet expressing Connexin 43) promoted conductivity in scar, leading to the improvement of the amplitude of the QRS complex and the repair of two peak components of the QRS complex like branch block in infarcted myocardium. Branch block patterns are likely to be related to fibrosis or necrosis in myocardium (Agarwal A. K., Venugopalan P., Right Bundle Branch Block: Varying Electrocardiogram Patterns., An Etiological Correlation, Mechanisms and Electrophysiology, International Journal of Cardiology, 1999, 71:33-39). The histological change was reflected to the amplitude of the QRS complex in electrocardiogram recording (Sakamoto A., Ono K., Abe M., Jasmin G., Eki T., Murakami Y., Masaki T., Toyo-oka T., Hanaoka F., Both Hypertrophic and Dilated Cardiomyopathies Are Caused by Mutation of the Same Gene, delta-sarcoglycan, in Hamster: An Animal Model of Disrupted Dystrophin-associated Glycoprotein Complex, Proc. Natl. Acad. Sci. USA, Dec. 9, 1997, 94(25):13873-8). The facts of synchronous wall motion demonstrated in the US, repair of two peak components of the QRS complex like branch block, and decrease of a threshold in scar might reveal electrical connection between an implanted cardiomyocyte sheet and a host myocardium. For this reason, cell sheets kept good surface condition with Connexin 43 when the present inventors used temperature-responsive dishes, and not trypsin, to detach the cell sheets from culture dishes.

Concerning histological integration, implanted cardiomyocyte sheets showed good attachment with infarcted myocardium with angiogenesis. Already, the present inventors demonstrated that histological integration by the enhancement of cell/cell and cell/ECM interaction by a growth factor in blood is essential for myocardial regeneration of infarcted myocardium (Miyagawa S., Sawa Y., Taketani S., Kawaguchi N., Nakamura T., Matsuura N., Matsuda H., Myocardial Regeneration Therapy for Heart Failure, Hepatocyte Growth Factor Enhances the Effect of Cellular Cardiomyoplasty, Circulation, 2002, 105: 2556-2561). Kushida et al. reported that adhesive agents in cell sheets were well preserved after detachment from temperature-responsive dishes (Kushida A., Yamato M., Konno C., Kikuchi A., Sakurai Y., Okano T., J. Biomed. Mater. Res. 45:355-362, 1999). Therefore, these sheets show good attachment and integration with several organs with good preservation of adhesive molecules in its surface (Shimizu T., Yamato M., Kikuchi A., et al., Two-dimensional Manipulation of Cardiac Myocyte Sheets Utilizing Temperature-responsive Culture Dishes Augments the Pulsatile Amplitude, Tissue Eng., 2001, 7(2):141-51, 24; and von Recum H. A., Kim S. W., Kikuchi A., Okuhara M., Sakurai Y., Okano T., Retinal Pigmented Epithelium Culture on Thermally Responsive Polymer Porous Substrates, J. Biomater. Sci. Polym. Ed 9: 1998, 1241-1254). Moreover, delivery of cells with preservation of cellular community may be important for cell survival and viability in contrast to cell delivery through an injection method. These results indicate that cardiomyocyte sheets without scaffolds make a syncytium with a host myocardium.

A cell source for sheets is a very important matter in clinical applications. Recently, myoblasts are most widely used for clinical applications of cell transplantation. Myoblasts have a potential of ischemic tolerance rather than cardiomyocytes. Therefore, myoblasts are one of the suitable cell sources for cell sheet implantation in clinical applications at present.

In conclusion, the present inventors have demonstrated that contractile cardiomyocyte sheets integrated with impaired myocardium dynamically, electrically, and histologically.

Cardiomyocyte sheet implantation may be a novel and promising strategy for repairing functional performance and cardiac structure in impaired myocardium.

Fibroblast sheets also provide a slight improvement which is less than that of heart cell sheets. Therefore, it was demonstrated that fibroblast sheets have a potential to be utilized at least for first aid.

CONCLUSION

Figure 1B:
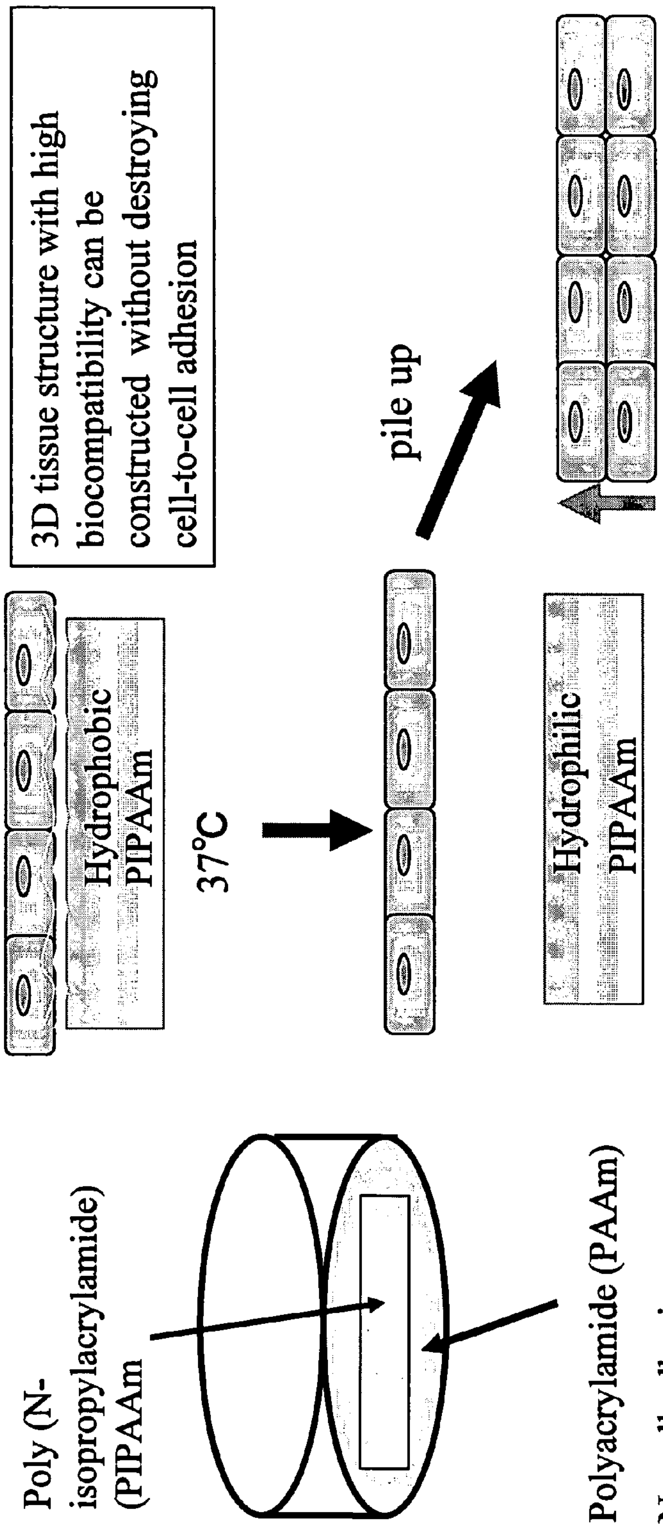
FIG. 1B shows another example in which a prosthetic tissue of the present invention is produced using a temperature responsive polymer.
Figure 2:
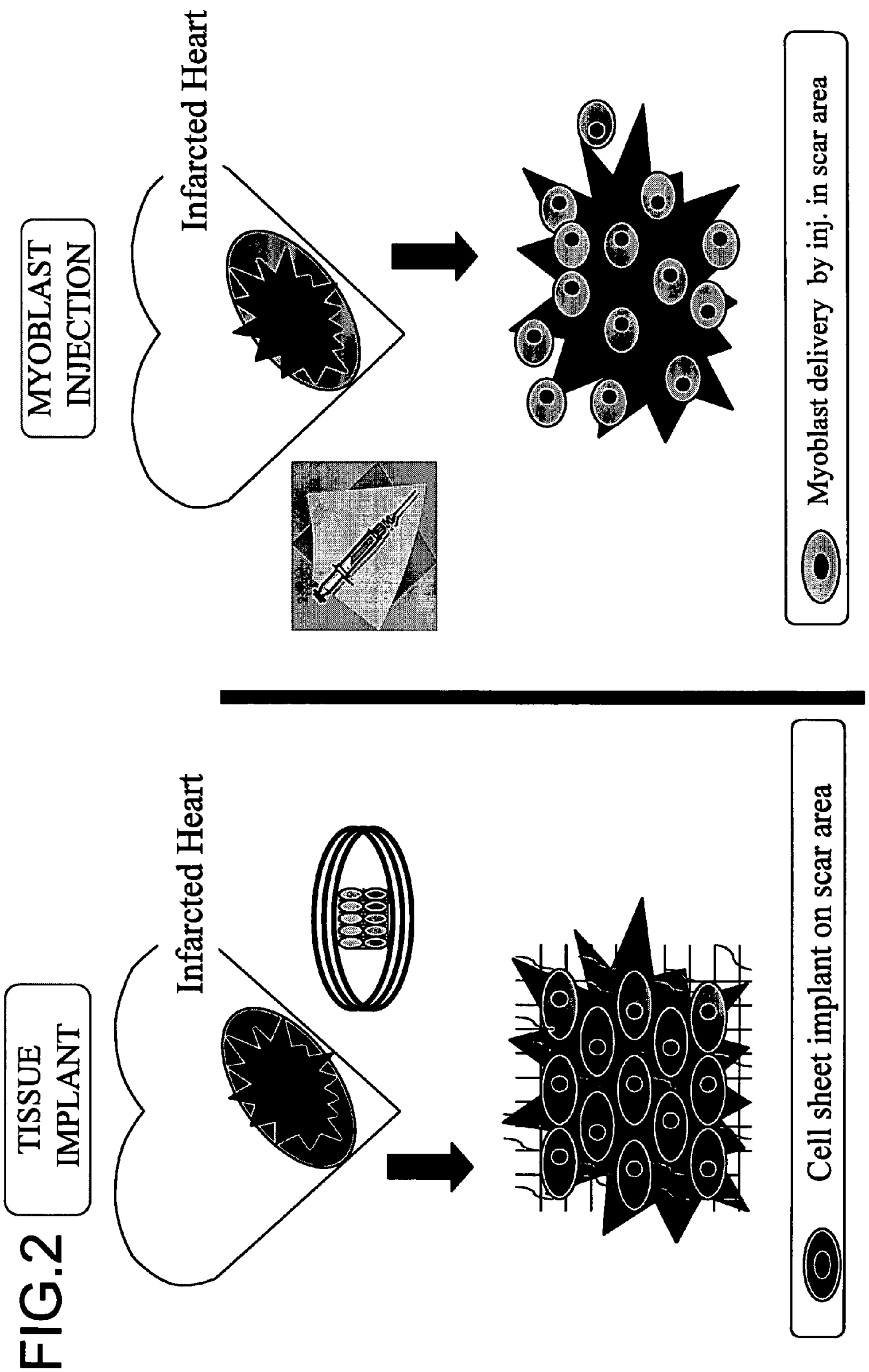
FIG. 2 shows an example in which a therapy using a prosthetic tissue of the present invention is compared with a cell therapy.
Figure 4:
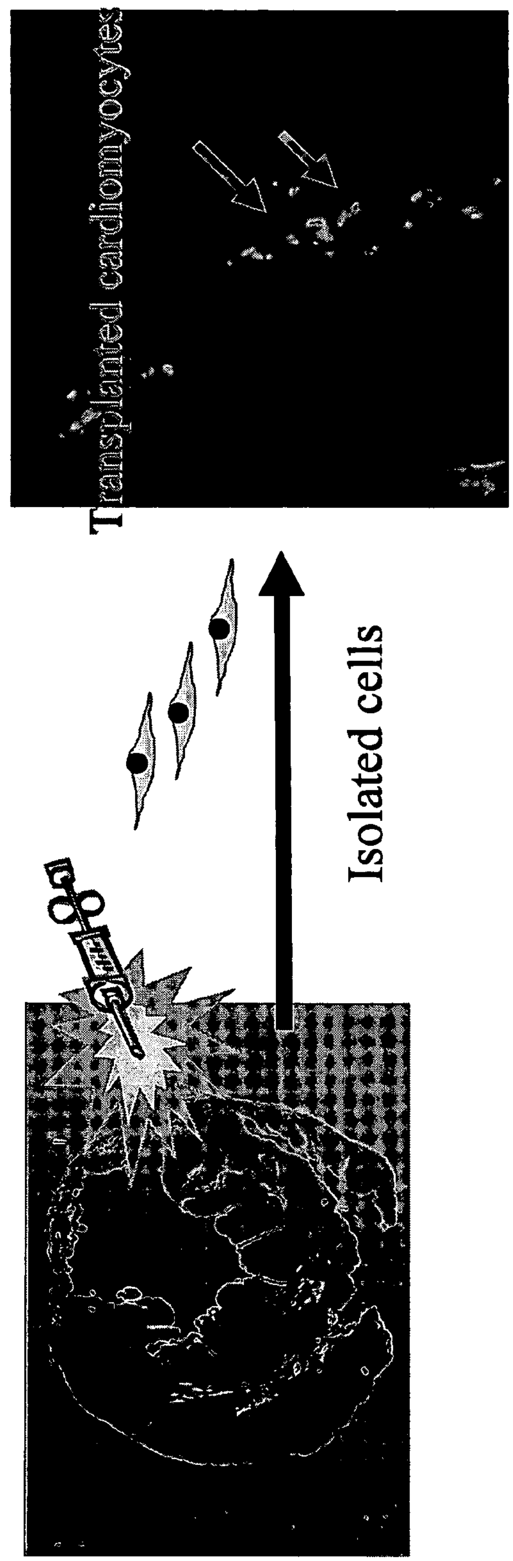
FIG. 4 shows a limit of myocardial regenerative therapies using cell implantation. As shown in the right portion, an injured site is not completely healed by cells in cell implantation.
Figure 5:
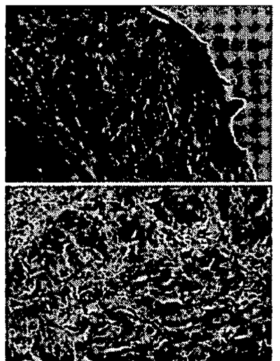
FIG. 5 shows a limit of tissue implantation using a scaffold.

A prosthetic tissue using newborn rat cardiomyocytes integrated with impaired myocardium and ameliorated cardiac function in an ischemic cardium model. Although the present inventors herein used cardiomyocytes, a prosthetic tissue organized using a cell sheet technique introduces a novel concept of tissue implantation and is useful in the field of regenerative medicine. This technique is schematically shown in FIGS. 1A and 1B.

Example 2

Self-Derived Myoblast Sheet Regenerates Impaired Myocardium

A Way to Clinical Application—Demonstrating Examples Using Rats

Recent progress in tissue engineering is likely to provide implantable functional tissue comprising various cells other than myocardial cells, and extracellular matrices. The present inventors designed autologous myoblast sheets. The present inventors considered that these sheets are beneficial for clinical applications. In this example, therefore, myoblasts were used as material to construct a prosthetic tissue or three-dimensional structure and an effect of the prosthetic tissue or three-dimensional structure on clinical applications was demonstrated.

(Methods)

Figure 13:
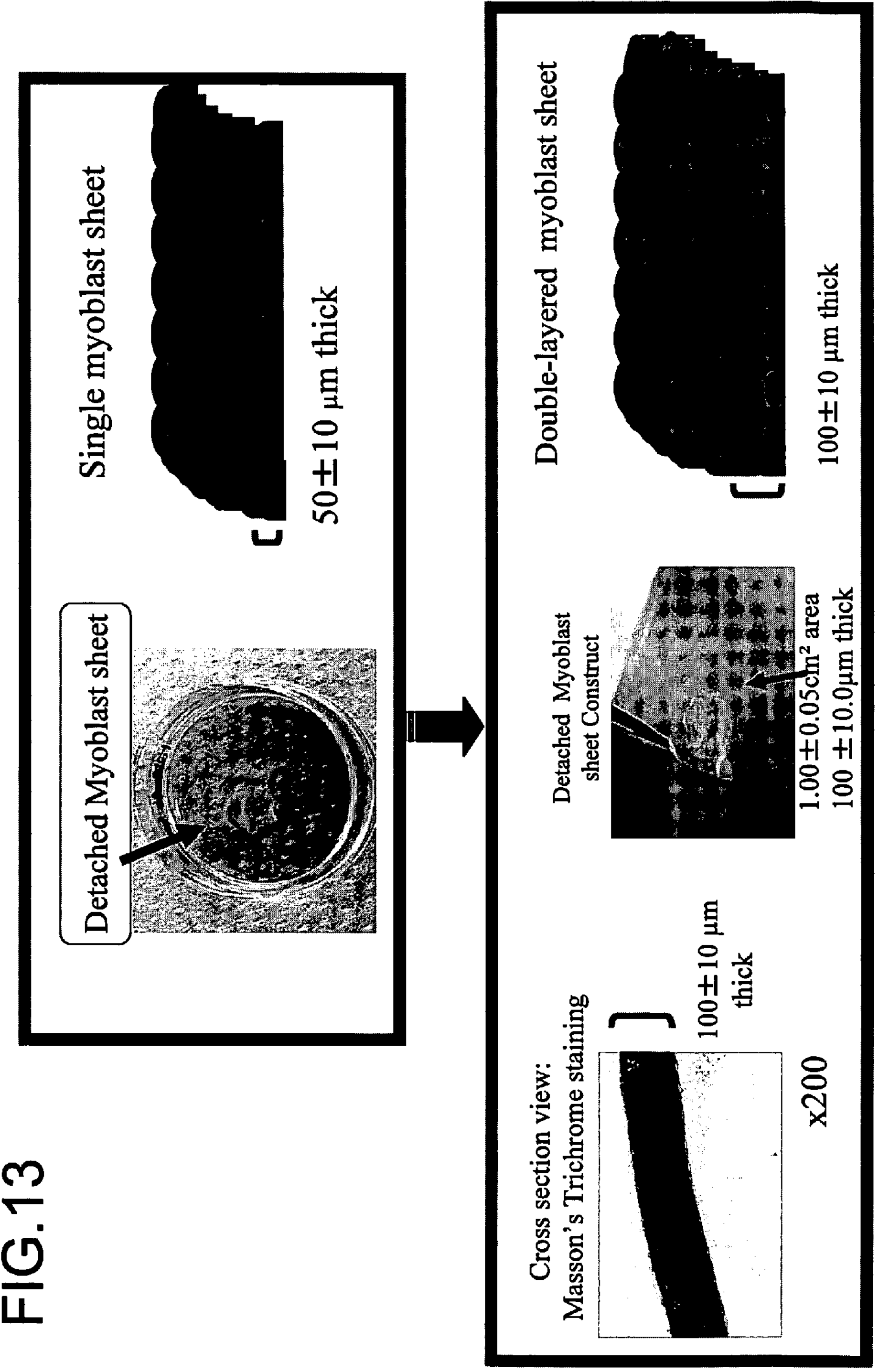
FIG. 13 shows an example of prosthetic tissue culture containing myoblasts in a method according to the present invention.

An impaired heart was created in 28 rats by ligating the left anterior descending (LAD) for 2 weeks. A temperature responsive domain made of a polymer (N-isopropylacrylamide) was coated on culture dishes. Skeletal myoblasts (SMs) isolated from leg muscle were cultured and detached from the dishes as a single monolayer cell-sheet (tissue) at 20° C. (FIG. 13). Two myoblast sheets were implanted in nine rats (myoblast sheet (S) group=$10^7$ cells). Myoblast cells were injected into 9 rats (I group=$10^7$ cells). Non-cellular therapy was conducted in 10 rats (C group=only medium was injected).

(Measurement of Cardiac Function)

Figure 14:
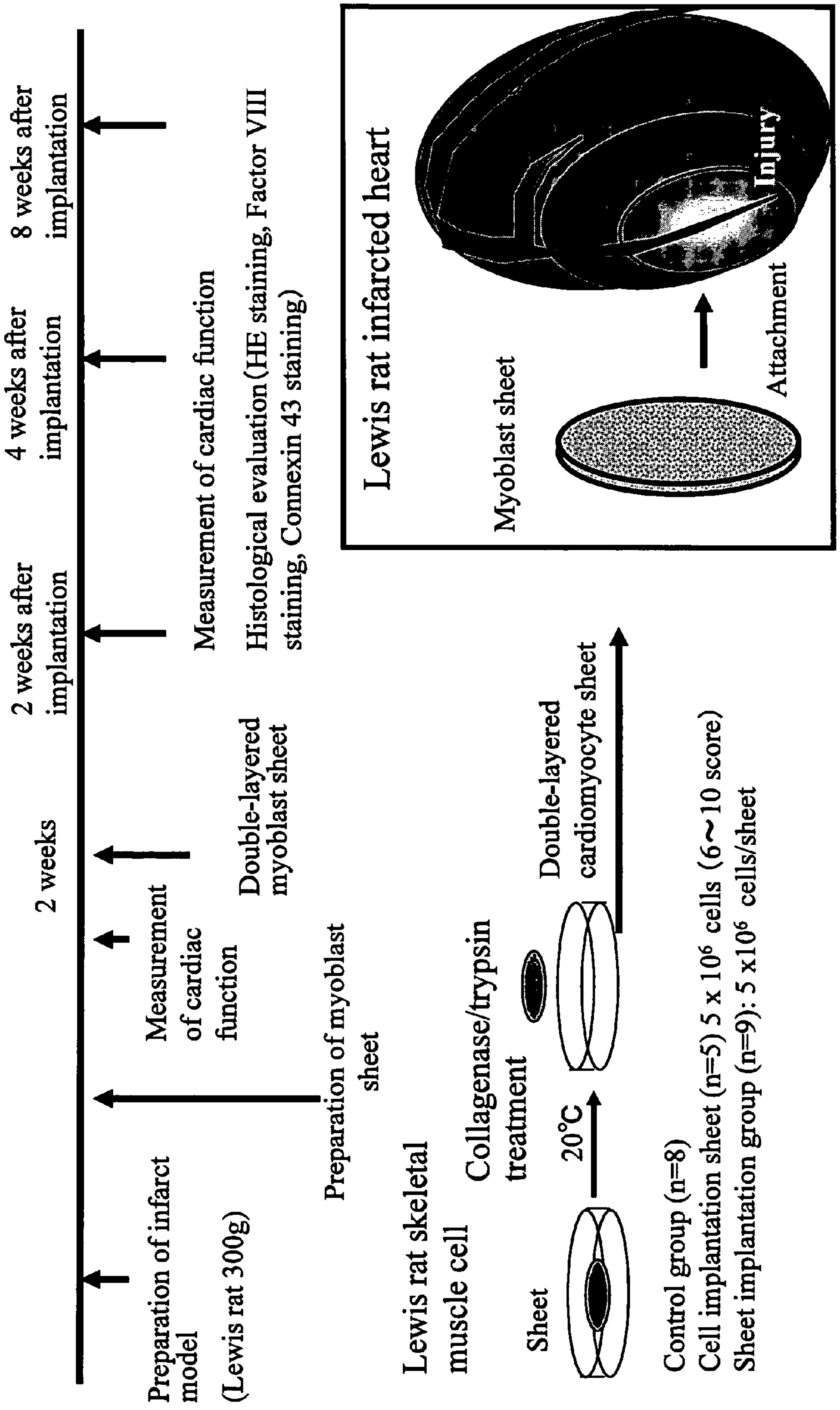
FIG. 14 shows an exemplary experimental scheme using a prosthetic myoblast tissue of the present invention.

Rats were operated on under anesthetization. The cardiac function was monitored at Day 14 and 28 after operation. An ultrasound device (SONOS 5500) with a 12-MHz annular array transducer was used to perform endocardiography (FIG. 18). Parasternal short axis imaging and parasternal long axis imaging were performed in the B- and M-imaging modes. In addition to anterior wall pressure, global parameters (e.g., left ventricle end-diastolic diameter, left ventricle endsystolic diameter, fractional shortening, and ejection fraction) were measured (FIG. 14).

(Histology)

Figure 15:
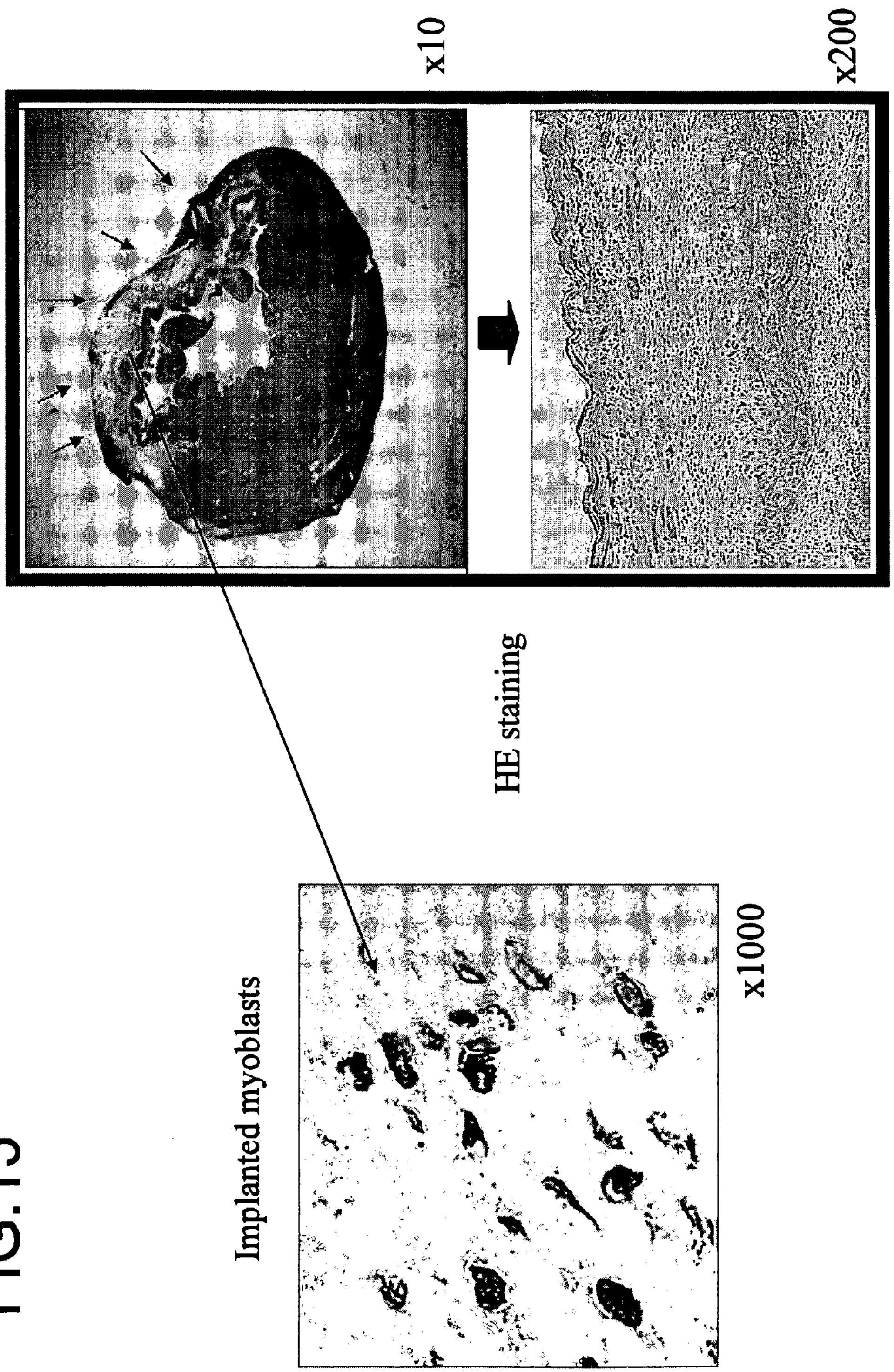
FIG. 15 shows photographs indicating a myoblast prosthetic tissue of the present invention 4 weeks after implantation (×10, ×200, and ×1000).
Figure 16:
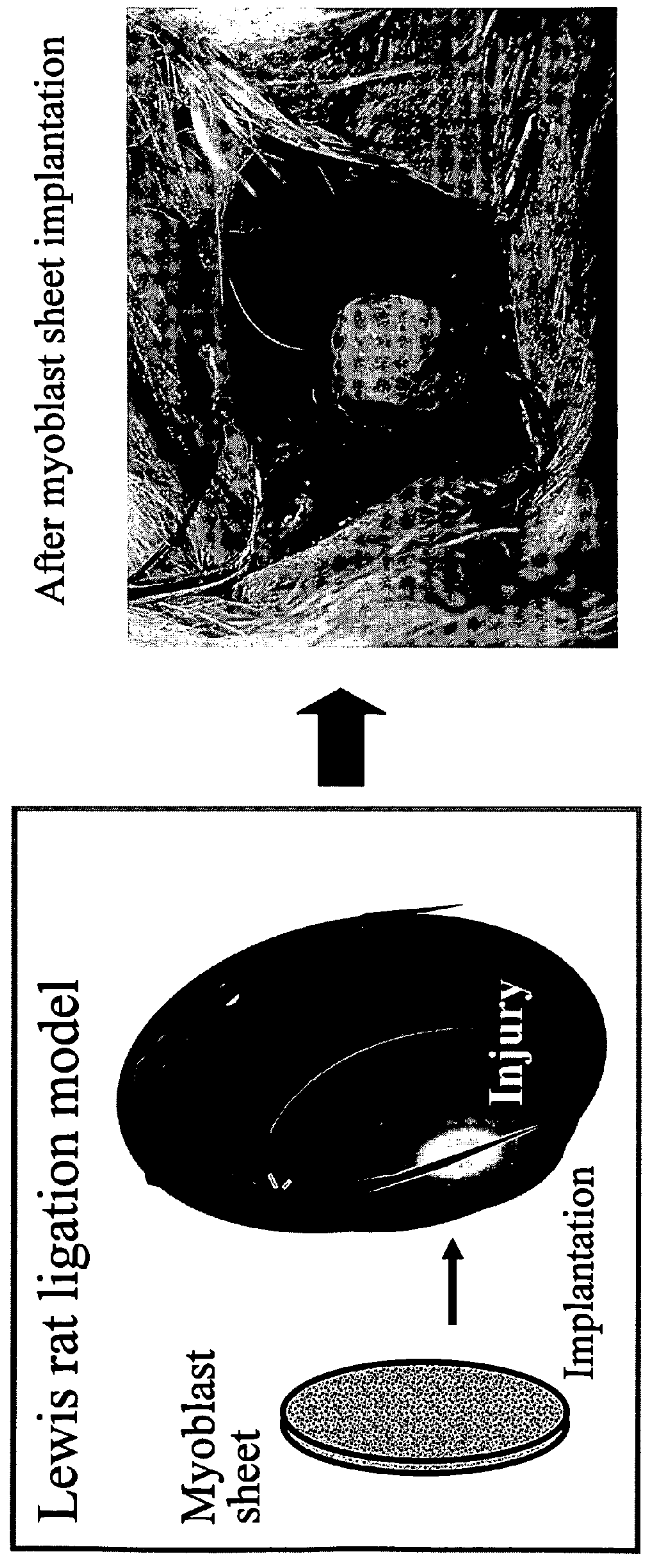
FIG. 16 shows an exemplary implantation operation using a prosthetic myoblast tissue of the present invention.
Figure 17:
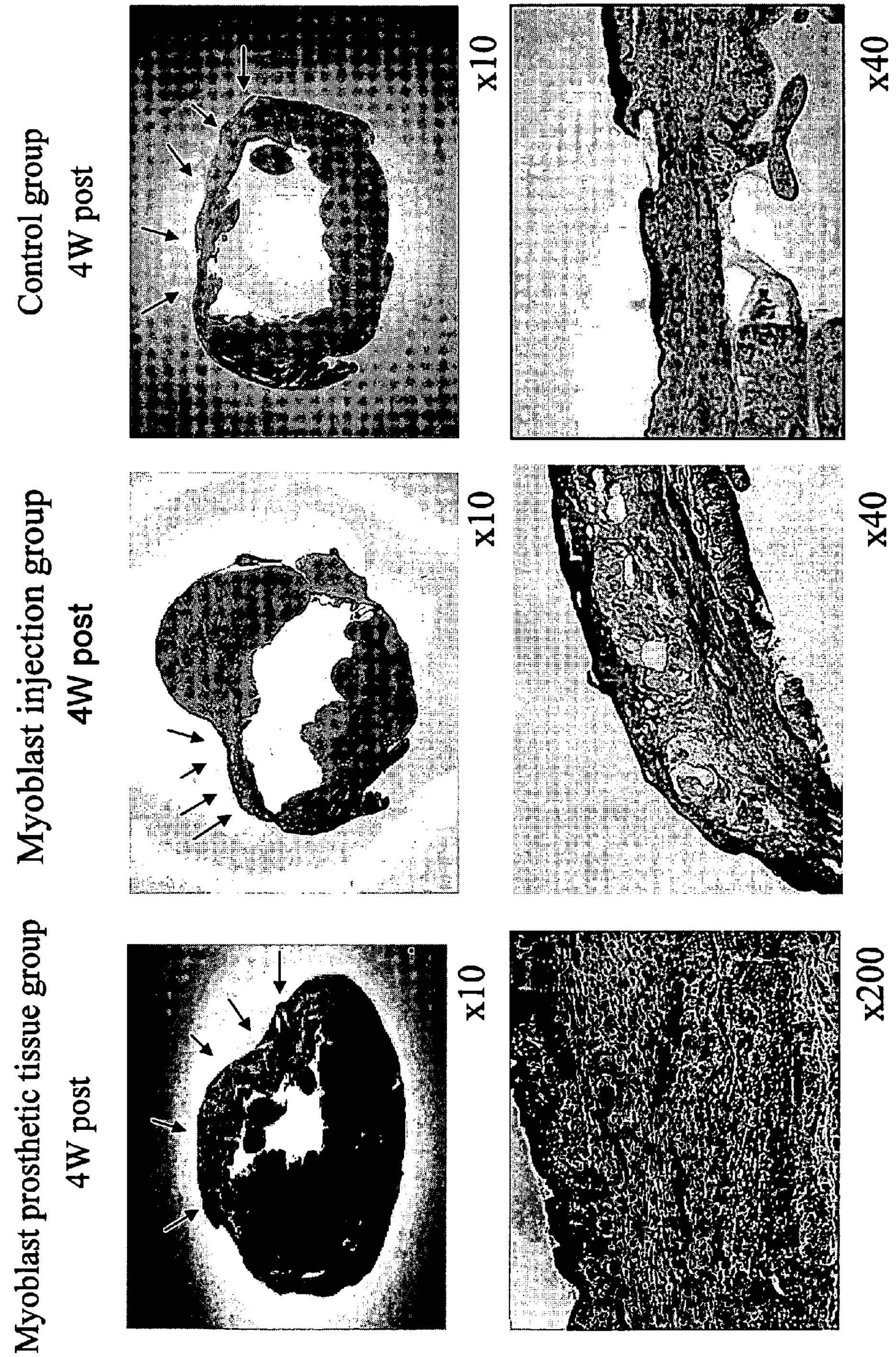
FIG. 17 shows an exemplary implantation of a prosthetic myoblast tissue of the present invention (histological staining). The upper portion shows the prosthetic tissue, cell injection, and control from the right (×10). The lower portion shows a photograph (×400) for each.

2 and 4 weeks after, the rats were sacrificed with excessive pentobarbital, and the hearts were excised. The hearts were fixed with 10% formaldehyde and embedded in paraffin. Serial 5-mm thick sections were cut from the base to the apex of the heart along a longitudinal axis thereof using a low temperature bath. Thereafter, treatment was performed for standard histology (as shown in FIGS. 15 and 17, hematoxylin-eosin staining was performed for visualization of muscle, and Masson's Trichrome staining for evaluating collagen content was performed for evaluation of collagen content).

(Results)

(Effect of Myoblast Implantation on Cardiac Function)

According to the experiments, myocardial infarction resulted in acute mortality of less than 20% within 24 hours after operation. The cell implantation procedure did not cause additional animal death.

Figure 19:
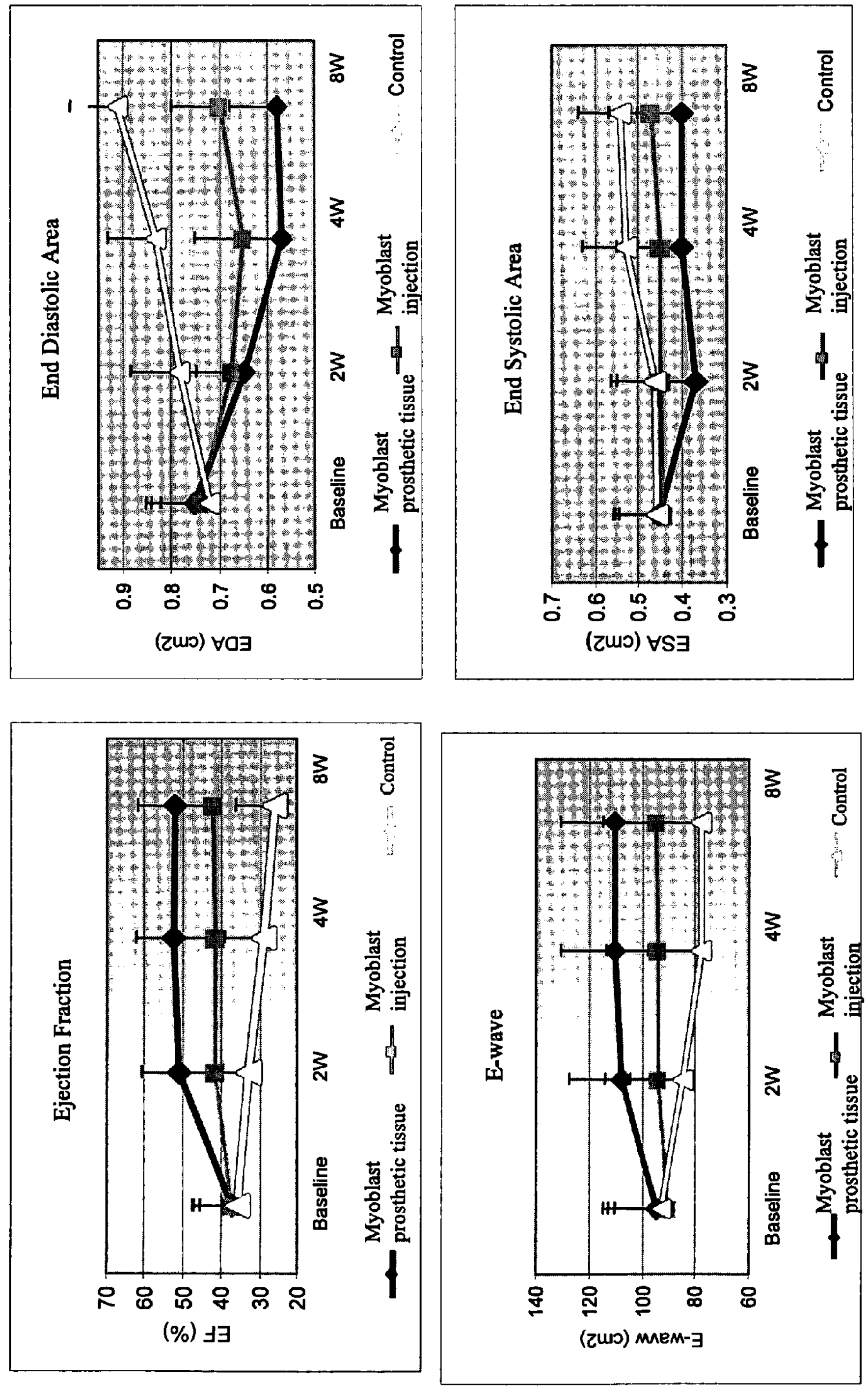
FIG. 19 shows exemplary results of a test for the cardiac function of a prosthetic myoblast tissue of the present invention after implantation. The ejection fraction (EF), fractional shortening (FS), endo-systolic area (ESA), and E-Wave are shown. Diamonds indicate a prosthetic myoblast tissue, squares indicate myoblast injection, and triangles indicate a control.

Ventricle remodeling characteristically caused global enlargement of heart cavity and pump failure. At 2, 4, and 8 weeks after operation, tissue (MS group) and the MI group had a significant decrease in left ventricular diameter, and both the left ventricular end-diastolic area (LVEDA) and left ventricular endsystolic area (LVESA) were improved after the treatment. Further, the ejection fraction (EF) value and fractional shortening (FS) value of the myoblast sheet group were also high compared with those of the MI group (FIG. 19).

Hearts in the control group which were not subjected to cell therapy showed further dilation of a ventricle, hypertrophy of an anterior wall, and clearly low ejection fraction (EF) and fractional shortening (FS) values.

(Histological Findings)

Figure 20:
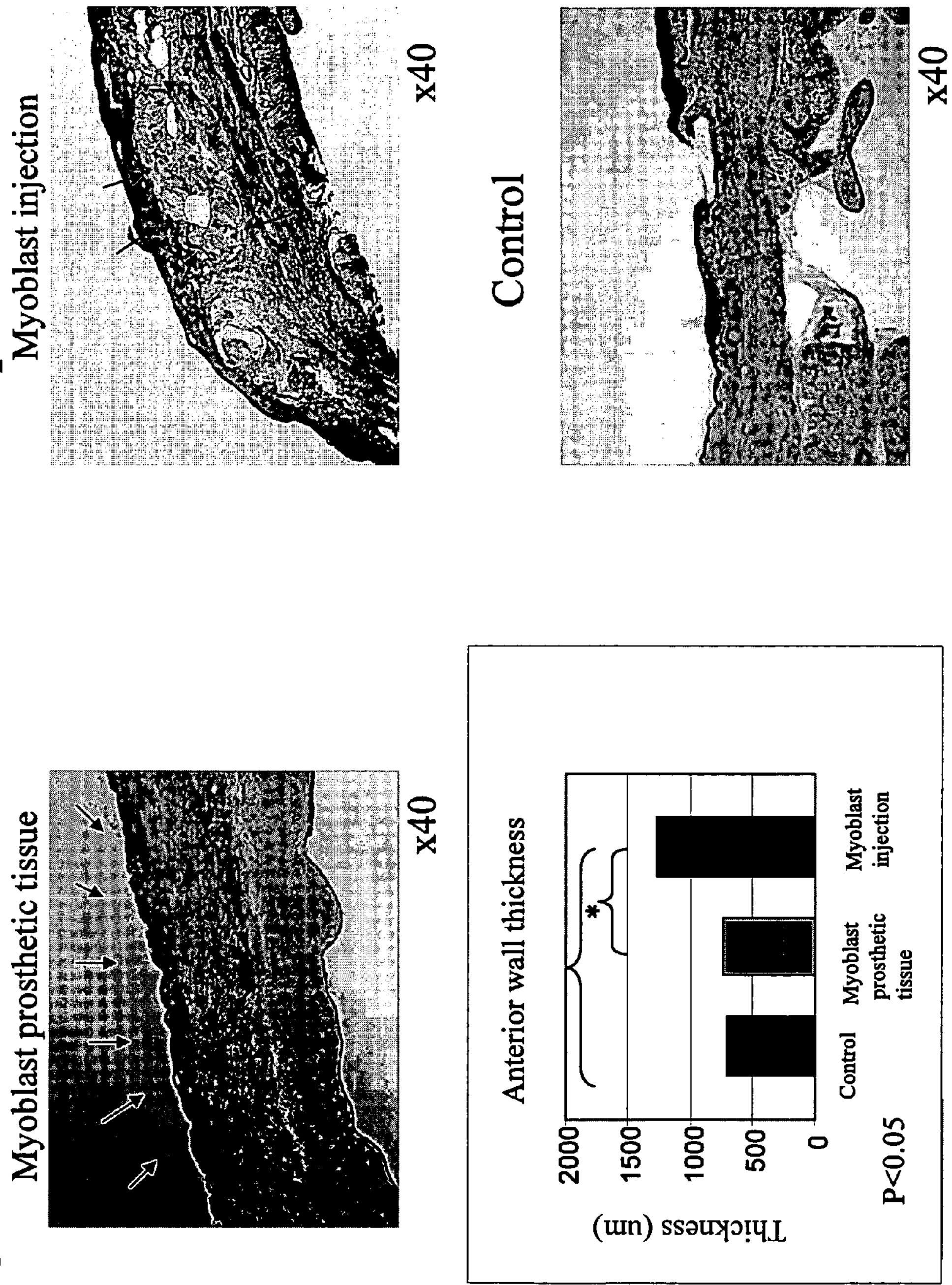
FIG. 20 shows an example of comparison in wall pressure between a prosthetic myoblast tissue of the present invention and myoblast. The results of photographs (upper left prosthetic tissue; upper right: cell injection; lower right: control) are summarized to a lower left graph.
Figure 21:
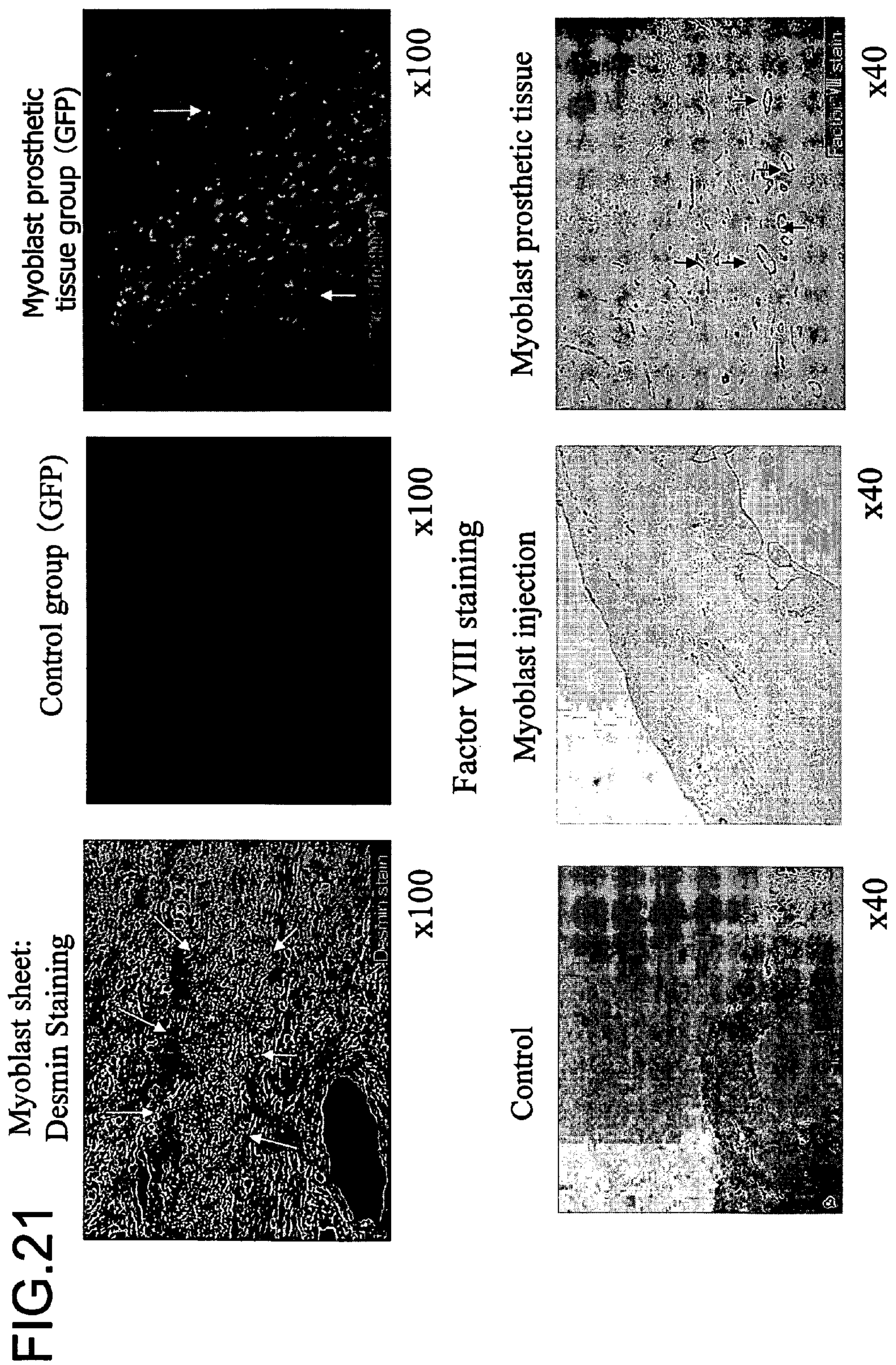
FIG. 21 shows comparison between a prosthetic myoblast tissue of the present invention and a control visualized by desmin staining, Factor VIII staining, and GFP expression. The upper portion shows desmin staining (left: prosthetic tissue), GFP expression (right: prosthetic tissue), and GFP expression (middle: control). The lower portion shows Factor VIII staining (prosthetic tissue, cell injection, and control from the right).

Histology revealed that the impaired hearts of the MI group had a dilated wall having nonuniform thickness (FIG. 20), and contained substantially no patches of implanted cells (FIG. 21). In contrast, the infarcted heart with the implanted sheet had a wall which did not dilate and was uniformly thick, and adequately cellularized, and did not have scarring. The survival of the implanted sheet was identified at 2, 4, and 8 weeks after implantation.

Technical loss of implantation cells was analyzed by RT-PCR based on the presence of the Y chromosome. As a result, the loss was smaller at 15 minutes and 1 day after operation in the MS group than in the MI group (3.7±0.5% vs 1.7±0.5% of the total number of heart cells).

(Sequential Photographs)

By taking a motion picture, it was confirmed that the myoblast implantation of the present invention actually caused pulsation (FIGS. 22A-F to 29).

Figures 22A, 22B, 22C:
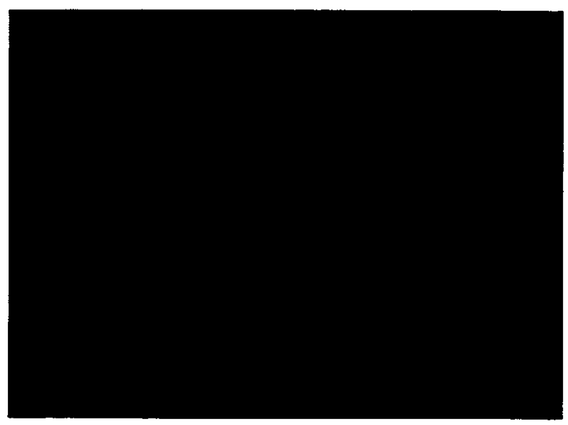

FIGS. 22A to 22F show a motion picture display of a result of an electrophysiological examination, presenting representative frames (still images). FIGS. 22A to 22C indicate the control, and FIG. 22D to 22F indicate results of a myoblast sheet of the present invention.

Figures 23A, 23B, 23C:
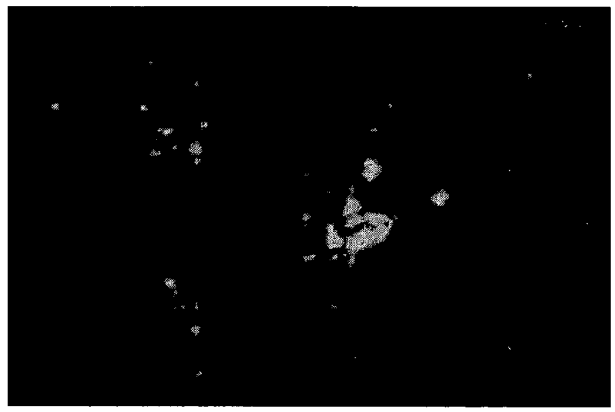
FIGS. 23A to 23C show GFP expression when a prosthetic tissue of the present invention is used. GFP expression is shown by motion picture display.

FIGS. 23A to 23C show a motion picture display of expression of GFP, presenting representative frames (still images). It is observed that a myoblast sheet of the present invention was actually pulsating.

Figure 24A:
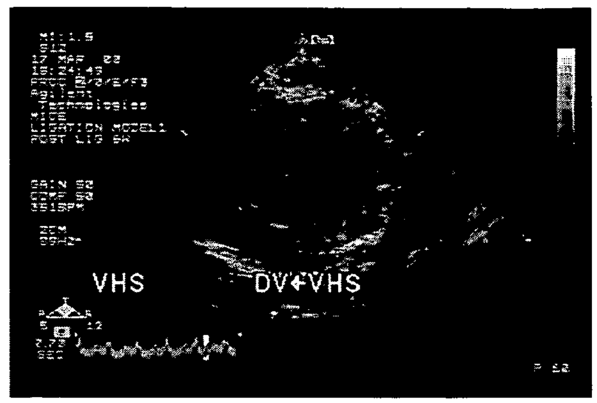
FIGS. 24A to 24C; show an exemplary ultrasound echography temporal analysis of treatment using a prosthetic tissue of the present invention. Results of ultrasound ecography for an infarcted heart treated according to the present invention are shown by motion picture display.
Figure 24B:
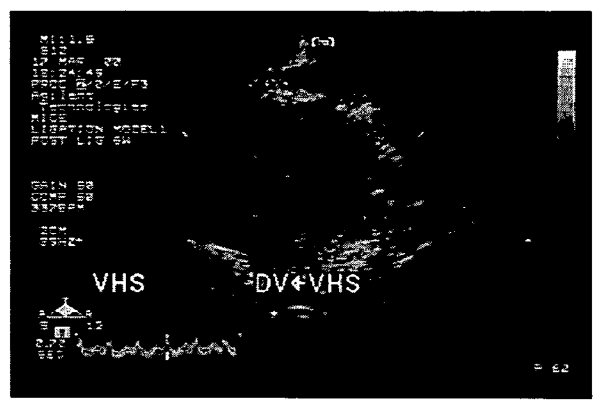
Figure 24C:
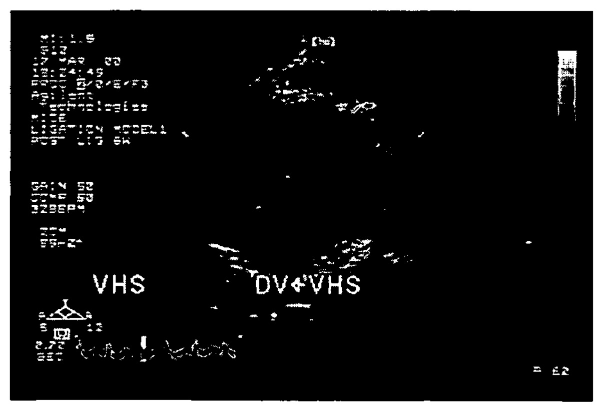

FIGS. 24A to 24C show a motion picture display of an ultraechogram of an infarcted heart treated according to the present invention, presenting representative frames (still images).

Figure 25A:
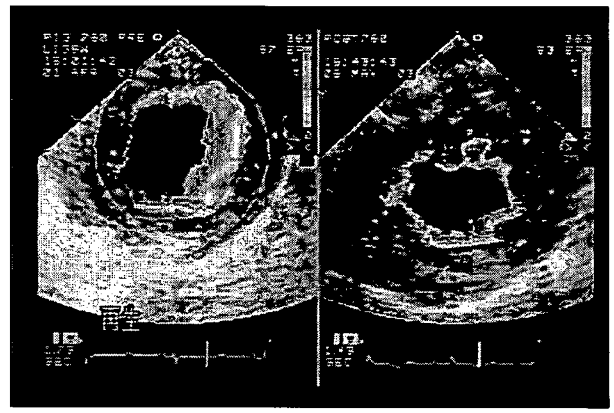
FIGS. 25A to 25C show an exemplary ultrasound echography temporal analysis of treatment using a prosthetic tissue of the present invention.
Figure 25B:
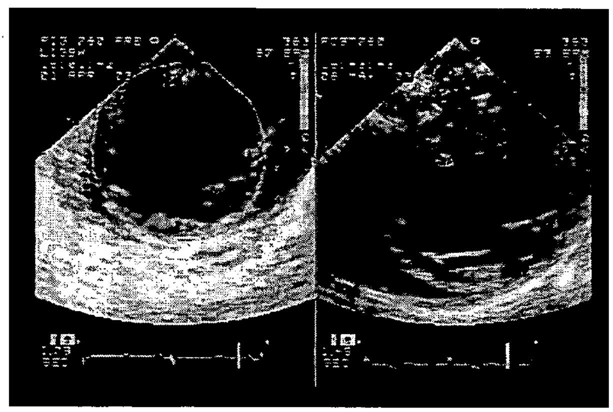
Figure 25C:
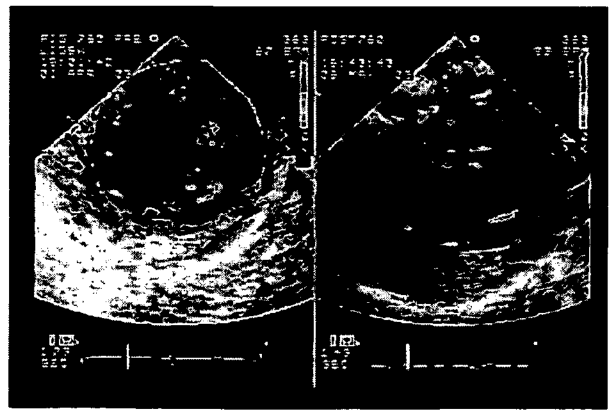

FIGS. 25A to 25C also show a motion picture display of an ultraechogram of an infarcted heart treated according to the present invention, presenting representative frames (still images). The left portion of the figure shows a control infarcted heart, while the right portion shows a result of a myoblast sheet of the present invention. As can be seen from the figure, the present invention substantially cured infarct, so that the heart pulsated substantially normally.

Figure 26A:
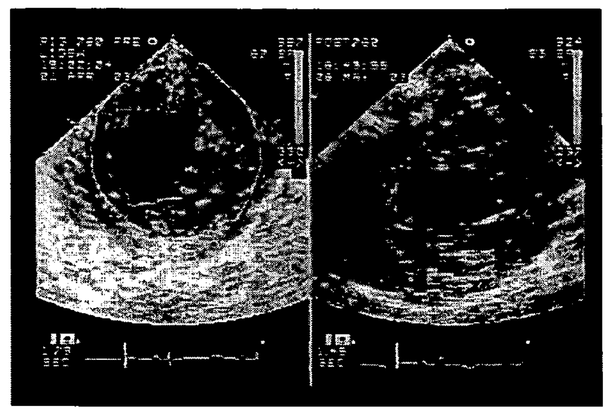
FIG. 26A shows an exemplary ultrasound echography analysis of treatment using a prosthetic tissue of the present invention.
Figure 26B:
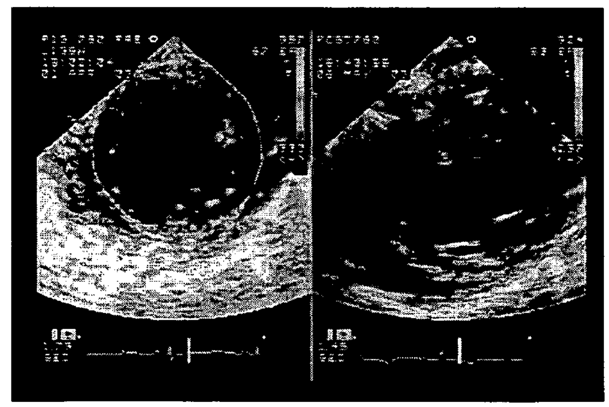
FIG. 26B shows an exemplary ultrasound echography analysis of treatment using a prosthetic tissue of the present invention.
Figure 26C:
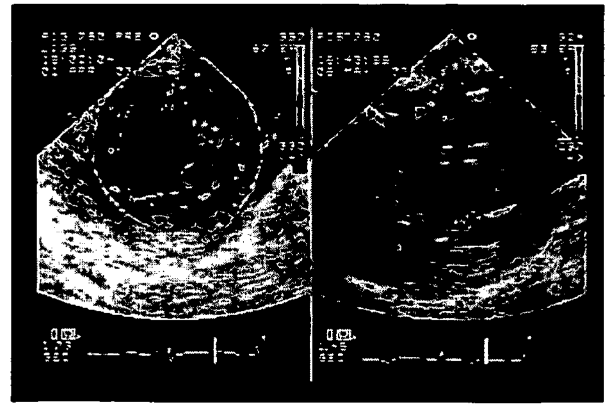
FIG. 26C shows an exemplary ultrasound echography analysis of treatment using a prosthetic tissue of the present invention.

FIGS. 26A to 26C are photographs showing the same sample as in FIGS. 25A to 25C at different time points. As can be seen from these figures, the infarcted heart was substantially cured by the present invention.

Figure 27A:
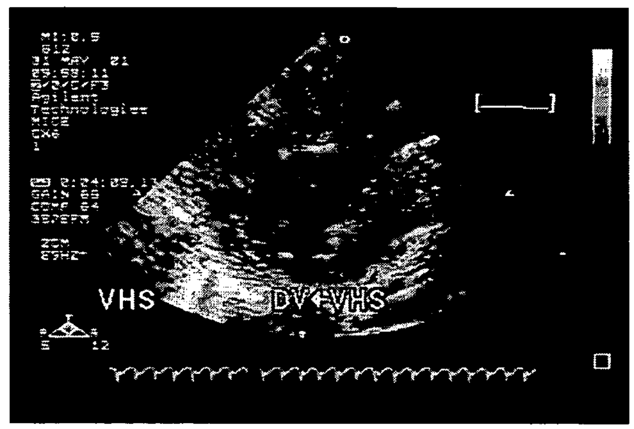
FIGS. 27A to 27C show an exemplary ultrasound echography analysis of treatment using a prosthetic tissue of the present invention. Results of ultrasound ecography for an infarcted heart treated according to the present invention are shown by motion picture display.
Figure 27B:
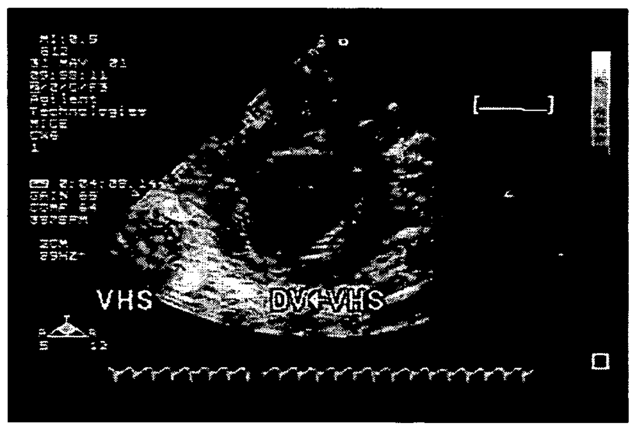
Figure 27C:
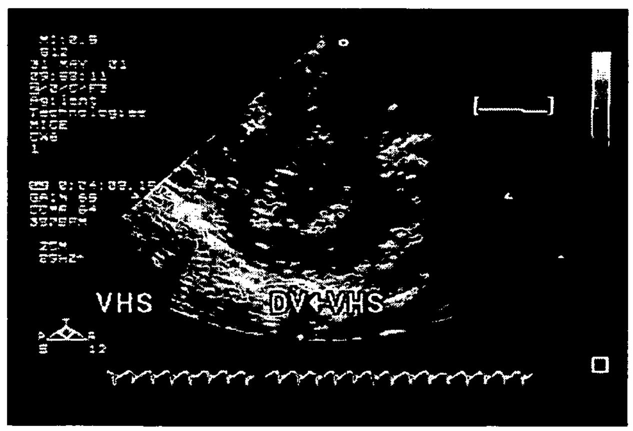

FIGS. 27A to 27C show a motion picture display of an ultraechogram of an infarcted heart treated according to the present invention, presenting representative frames (still images). As can be seen from the figure, the infarct was cured by the treatment of the present invention.

(RT-PCR)

Next, in order to show cell affinity, the number of implanted cells was quantified by RT-PCR. In this example, the number of gene copies was evaluated by TaqMan assay for SRY and IL2.

RT-PCR was performed using a primer which was a portion of a gene derived from the Y chromosome in the male cells. By measuring the amount of the gene in the chromosomes in a female host, affinity was confirmed.

The following primer was used.

As a reaction solution, the following PCR mixed reaction solution was used.

| | |
|---|---|
| Universal Mix (provided by the manufacturer) | 12.5 μl |
| Primer (100 μM) forward | 0.05 μl |
| Primer (100 μM) reverse | 0.05 μl |
| Probe (50 μM) | 0.1 μl |
| $dH_2O$ | 10.3 μl |
| Template (DNA) | 2.0 μl |

The primer and probe sequences are described below.

```
SRY
(forword primer) GCC TCA GGA CAT    (SEQ ID NO. 15)
                 ATT AAT CTC TGG AG

(reverse primer) GCT GAT CTC TGA    (SEQ ID NO. 16)
                 ATT CTG CAT GC

(probe)          AGG CGC AAG TTG    (SEQ ID NO. 17)
                 GCT CAA CAG AAT CC

IL2
(forword primer) GCC TTG TGT GTT    (SEQ ID NO. 18)
                 ATA AGT AGG AGG C

(reverse primer) AGT GCC AAT TCG    (SEQ ID NO. 19)
                 ATG ATG AGC

(probe)          TCT CCT CAG AAA    (SEQ ID NO. 20)
                 TTC CAC CAC AGT
                 TGC TG
```

100 ng of each genomic DNA was used to perform PCR. The mixed reaction solution was placed in wells of MicroAmp Optical 96-well reaction plates. The wells were capped with MicroAmp Optical Caps. Air bubbles were briefly removed, and the liquid present in the bottom of each well was collected. Each gene was measured in triplicate. PCR was performed using the ABI Prism 7700 Sequence Detection System.

Standard DNA was the following: (200 ng. 40 ng. 8 ng. 1.6 ng 0.32 ng 0.064 ng); (SRY 200 ng=$3\times10^4$ copies; IL2 200 ng=$6\times10^4$ copies).

Parameters for thermal cycling were described below.

| Stage 1 | Stage 2 | Stage 3 |
|---|---|---|
| 50° C./2 min | 95° C./10 min | 95° C./15 sec–60° C./1 min 40 cycles |

The index of male cells was obtained by the following expression:

$$(2\times SRY/IL2)\times100.$$

Figure 28:
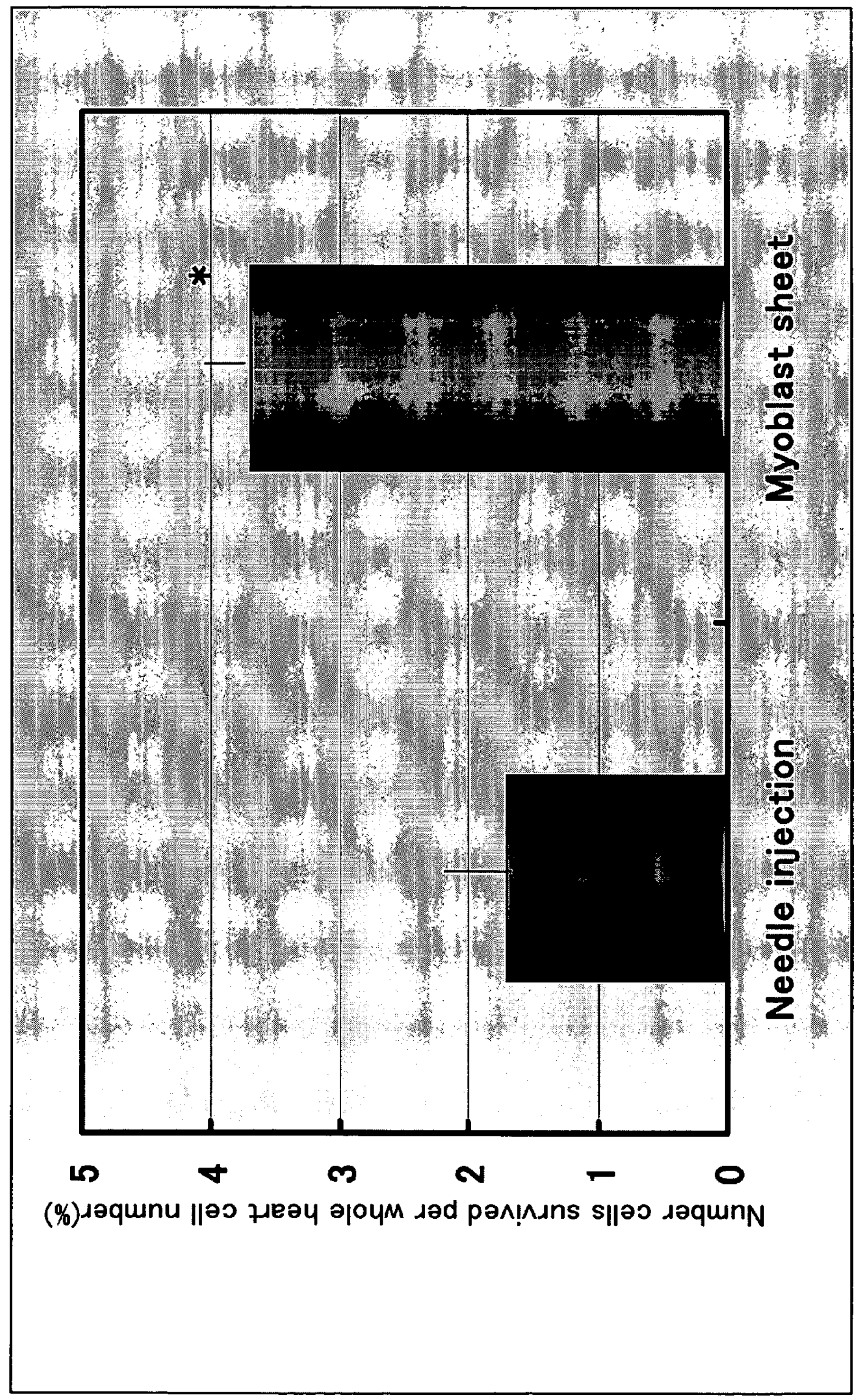
FIG. 28 shows cell affinity by RT-PCR.

As a result, as shown in FIG. 28, it was demonstrated that the sheet (three-dimensional tissue) implantation has a more satisfactory level of affinity than that of needle (cell itself) implantation.

(Demonstration of Cellularity)

What kind of cell type cells contained in an implanted cardiomyocyte sheet were differentiated into, was examined.

Therefore, Masson's Trichrome staining, HE (hematoxylin-eosin) staining,

MHC fast staining, and MHC slow staining were performed.

These procedures were performed as follows.

<Masson's Trichrome Staining>

Masson's Trichrome staining is performed as follows. Masson's Trichrome staining stains nuclei with iron hematoxylin. Thereafter, small pigment molecules (acid fuchsin, xylidine ponceau) having a high diffusion rate enter cell reticular channels, and next, large pigment molecules (aniline blue) having a low diffusion rate enter the rough structure of collagen fibers, thereby staining the cell with blue.

Masson's Trichrome staining uses the following reagents.

A) Dye mordant

| | |
|---|---|
| aqueous 10% trichloroacetic acid solution | 1 part |
| aqueous 10% potassium dichromate solution | 1 part |

B) Weigert's iron hematoxylin solution (equal amounts of solution 1 and solution 2 are mixed in use)

| solution 1 | |
|---|---|
| hematoxylin | 1 g |
| 100% ethanol | 100 ml |
| **solution 2** | |
| ferric chloride | 2.0 g |
| hydrochloric acid (25%) | 1 ml |
| distilled water | 95 ml |

C) 1% hydrochloric acid 70% alcohol

D) I solution

| | |
|---|---|
| 1% Biebrich red | 90 ml |
| 1% acid fuchsin | 10 ml |
| acetic acid | 1 ml |

E) II solution

| | |
|---|---|
| phosphomolybdic acid | 5 g |
| phosphotungstic acid | 5 g |
| distilled water | 200 ml |

F) III solution

| | |
|---|---|
| aniline blue | 2.5 g |
| acetic acid | 2 ml |
| distilled water | 100 ml |

G) 1% acetic acid water

Procedure for Masson's Trichrome Staining:

1. deparaffinization, washing with water, distilled water;
2. mordanting (10 to 15 min);
3. washing with water (5 min);
4. Weigert's iron hematoxylin solution (5 min);
5. light washing with water;
6. separation with 1% hydrochloric acid 70% alcohol;
7. color development, washing with water (10 min);
8. distilled water;
9. I solution (2 to 5 min);
10. light washing with water;
11. II solution (30 min or more);
12. light washing with water;
13. III solution (5 min);
14. light washing with water;
15. 1% acetic acid/water (5 min);
16. washing with water (quick); and
17. dehydration, clearing, mounting.

With Masson's Trichrome staining, collagen fiber, reticular fiber and glomerular basement membrane are stained vividly blue, nuclei are stained black-violet, plasma is stained pale-red, erythrocytes are stained orange-yellow to deep-red, mucus is stained blue, basophilic granules are stained blue and eosinphilic granules are stained red, and fibrin is stained red. Therefore, a blue-stained area can be calculated as a fibrous site.

<Hematoxylin-Eosin (HE) Staining>

The acceptance or vanishment of cells in a sheet was observed by HE staining. The procedure is described as follows. A sample is optionally deparaffinized (e.g., with pure ethanol), followed by washing with water. The sample is immersed in Omni's hematoxylin for 10 min. Thereafter, the sample is washed with running water, followed by color development with ammonia water for 30 sec. Thereafter, the sample is washed with running water for 5 min and is stained with eosin hydrochloride solution for 2 min, followed by dehydration, clearing, and mounting.

<MHC Fast Staining>

MONOCLONAL ANTI-SKELETAL MYOSIN (FAST) MYOSIN HEAVY CHAIN: MY-32 (skeletal myoblasts)

Specific reactivity with rats and human

1. Make 5 um thick sections from frozen block.
2. Sections are fixed in acetone at −20° C. for 5-10 mins. (Paraffin blocks should be deparaffinized and rehydrated).
3. Endogenous peroxide activity is blocked in 0.3% $H_2O_2$ in methanol for 20 mins at RT. (1 ml 30% $H_2O_2$+99 ml methanol)
4. Wash with PBS (3×5 mins).
5. Incubate with primary monoclonal antibody (MY-32) in the moist chamber at 4° C. for overnight (1 μl antibody+200 μl PBS per slide).
6. Next day wash with PBS (3×5 mins).
7. Apply anti mouse and anti rabbit no. 1 Biotynalated link for 30 mins−1 hrs at RT. (apply about 3 drops directly on slide).
8. Wash with PBS (3×5 mins).
9. Apply about 3 drops directly Streptavidin HRP no. 2 for LSAB. 10-15 mins.
10. Wash with PBS (3×5 mins).
11. Apply DAB (5 ml DAB+5 μl $H_2O_2$).
12. Observe under microscope for brownish colour.
13. Dip in water for 5 mins.
14. Apply HE for 30 sec-1 min.
15. Wash few times.
16. Ion exchange water wash 1 time.
17. 80% ethanol wash for 1 min.
18. 90% ethanol wash for 1 min.
19. 100% ethanol wash for 1 min (3 times).
20. Xylene wash for 1 min (3 times), Coverslip.
21. Examine color development.

<MHC Slow Staining>

Monoclonal Anti Myosin: (skeletal slow)

Specific reactivity with dog, rats and human

1. Make 5 μm thick sections from frozen block.
2. Sections are fixed in acetone at −20° C. for 5-10 mins. (Paraffin blocks should be deparaffinized and rehydrated).
3. Endogenous peroxide activity is blocked in 0.3% $H_2O_2$ in methanol for 20 mins at RT. (1 ml 30% $H_2O_2$+99 ml methanol)
4. Wash with PBS (3×5 mins).
5. Incubate with primary monoclonal antibody NOQ7 in the moist chamber at 4° C. for overnight (1 μl antibody+200 μl PBS per slide).
6. Next day wash with PBS (3×5 mins).
7. Apply anti mouse and anti rabbit no. 1 Biotynalated link for 30 mins−1 hrs at RT. (apply about 3 drops directly on slide).
8. Wash with PBS (3×5 mins).
9. Apply about 3 drops directly Streptavidin HRP no. 2 for LSAB. 10-15 mins.
10. Wash with PBS (3×5 mins).
11. Apply DAB (5 ml DAB+5 μl $H_2O_2$).
12. Observe under microscope for brownish colour.
13. Dip in water for 5 mins.
14. Apply HE for 30 sec-1 min.
15. Wash few times.
16. Ion exchange water wash 1 time.
17. 80% ethanol wash for 1 min.
18. 90% ethanol wash for 1 min.
19. 100% ethanol wash for 1 min (3 times).
20. Xylene wash for 1 min (3 times), Coverslip.
21. Examine color development.

Figure 29:
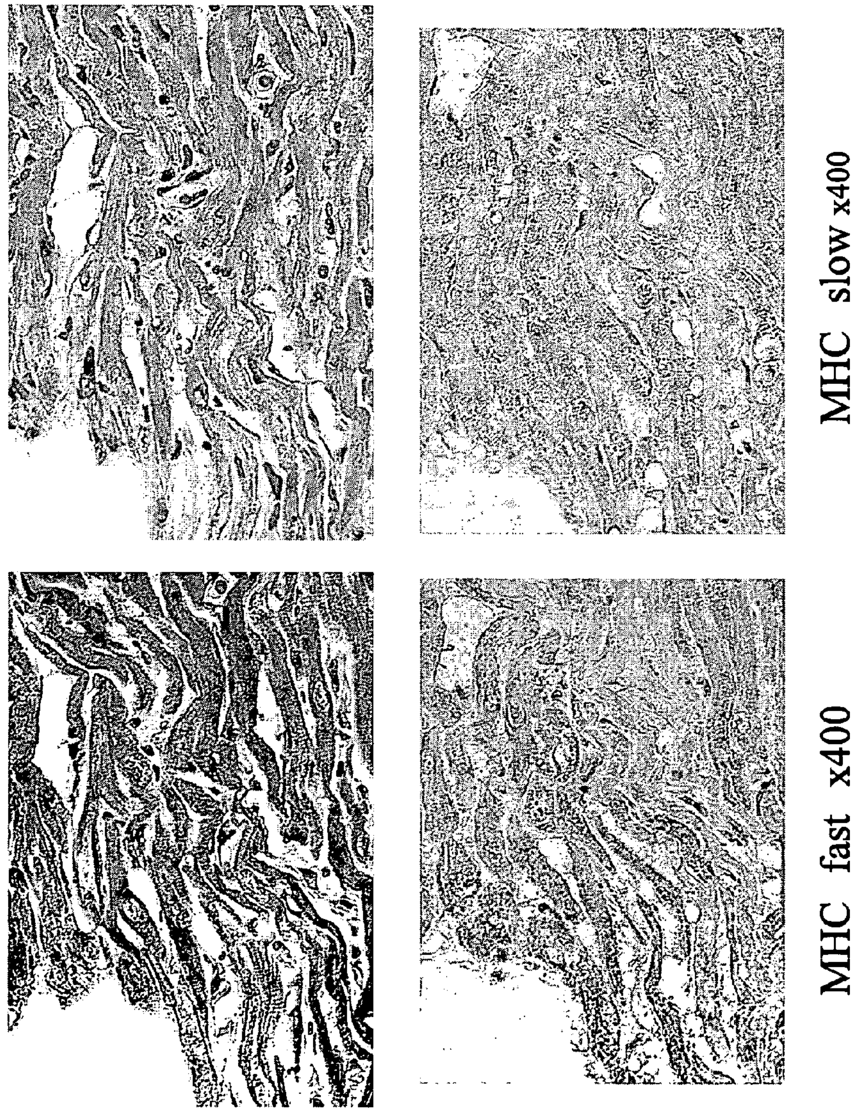
FIG. 29 shows a change in an implanted myoblast sheet after implantation.

As a result, as shown in FIG. 29, it was demonstrated that the implanted myoblast sheet was differentiated from fast fiber to slow fiber. These markers can be used to identify a three-dimensional tissue structure of the present invention.

CONCLUSION

Skeletal myoblast implantation attenuated heart remodeling and regenerated impaired myocardium to ameliorate global cardiac function as compared with cell implantation. This finding suggests a promising strategy for regenerative therapy for myocardium.

Therefore, it was demonstrated that when a myoblast sheet was implanted as a three-dimensional structure, the cardiac function of impaired myocardium was ameliorated.

In this example, by using direct injection, autologous skeletal myoblast (SM) implantation was clinically applied. Loss of implanted cells and implanted extracellular matrix (ECM) due to direct injection limits the number of skeletal myoblasts and the ability of skeletal myoblasts.

Concerning clinical tests using an autologous cell source, autologous myoblasts are preferably used. It was also demonstrated that tissue implantation is more advantageous to regenerate an injured heart than cell implantation.

Example 3

Skeletal Myoblast—Implantation of Tissue-Engineered Myoblast Sheet Improves Cardiac Function with Attenuation of Cardiac Remodeling in Cardiomyopathic Hamsters Next, it was examined whether or not a prosthetic tissue or three-dimensional structure produced using skeletal myoblasts ameliorates cardiomyopathy.

Cell therapy is a promising strategy for ischemic cardiomyopathy. However, direct injection methods seem to have limitations for generalized cell delivery in dilated cardiomyopathy (DCM). Given this body of evidence, the present inventors considered that a tissue-engineered myoblast sheet implantation might be a superior and promising method to ameliorate the cardiac function in DCM. Therefore, the present inventors carried out this example.

(Method)

Male 27-week old BIO TO-2 (dilated cardiomyopathy (DCM)) hamsters which showed moderate cardiac remodeling were used as recipients. Myoblasts isolated from BIO FIB hamsters (FIB) were cultured on dishes grafted with a temperature-responsive polymer made of poly(N-isopropylacrylamide), and detached as a cell sheet at 20° C. without enzymatic treatment.

Three different therapies were conducted: (1) myoblast sheet implantation group (S group, n=8); (2) myoblast (isolated from FIB) injection group (T group, n=10); and (3) Sham operation group (C group, n=10). In the S group, a myoblast sheet was implanted on the left ventricular (LV) wall. In the T group, myoblasts were injected into the right ventricular (RV) wall and the left ventricular (LV) wall.

(Results)

(Functional Recovery of Infarcted Myocardium)

B-mode analysis demonstrated that the dilation of a left ventricle was adequately suppressed and global wall motion was adequately preserved in the T group as compared with the C group (FIG. 18).

Figure 30A:
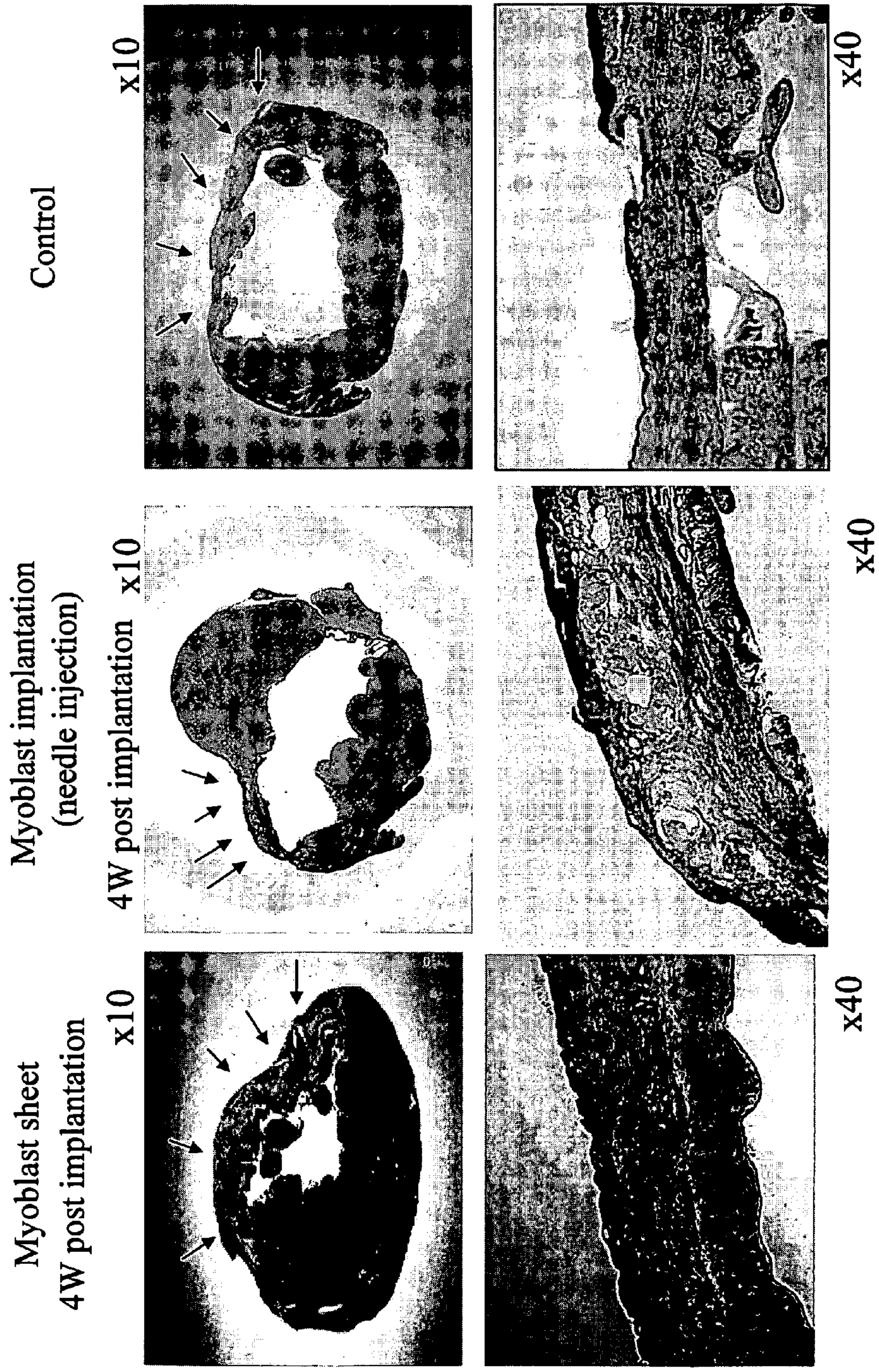
FIG. 30A shows an example of Masson's Trichrome staining of a prosthetic tissue of the present invention using myoblasts, which was applied to a cardiomyopathic hamster. The upper portion shows sheet (prosthetic tissue) implantation, cell implantation, and a control (×10). The lower portion shows an enlarged view for each (×40).
Figure 30B:
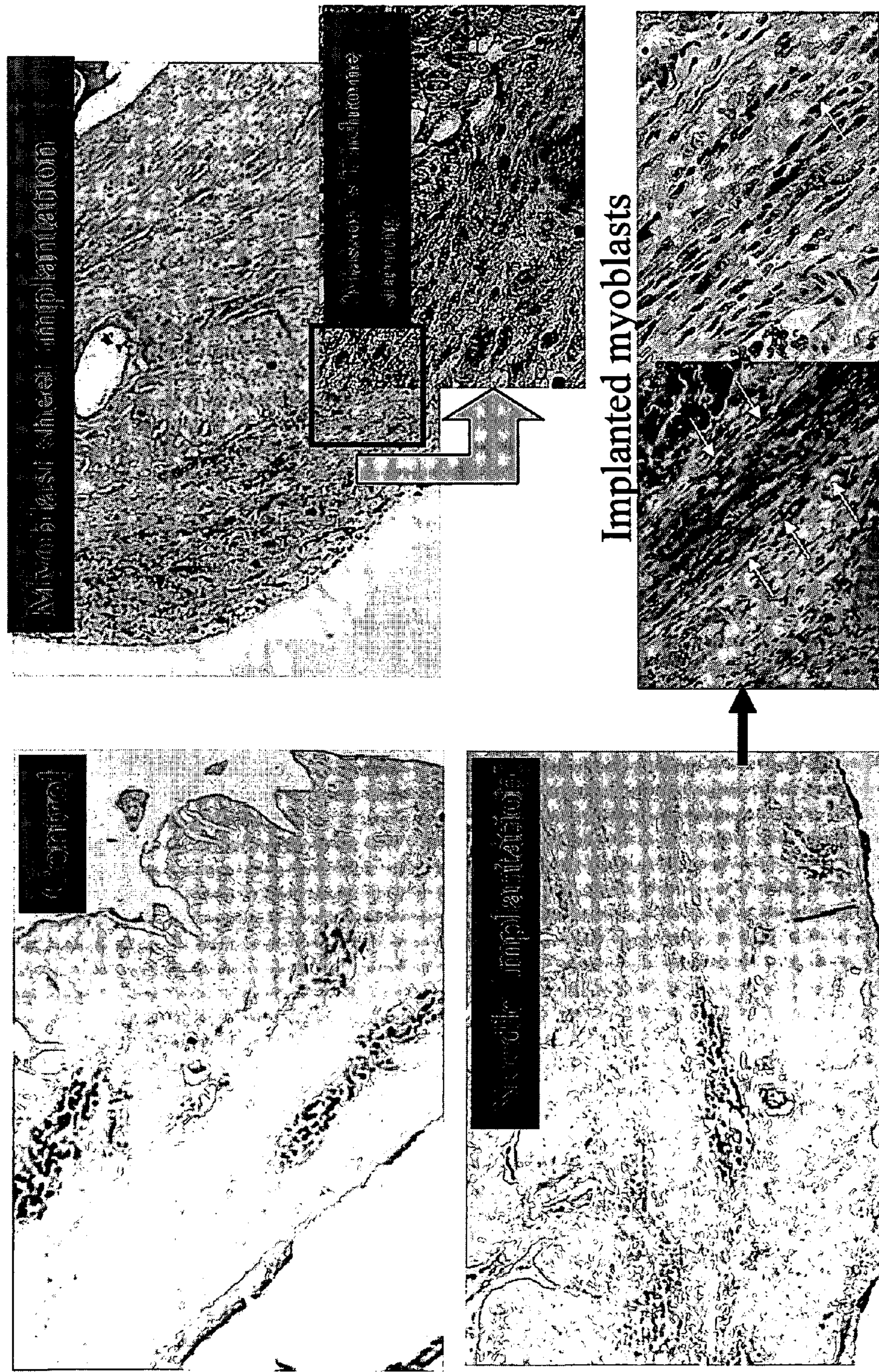
FIG. 30B shows histology (myoblast sheet is accepted by a dilated cardiomyopathic heart and enlarges a ventricular wall).
Figure 30C:
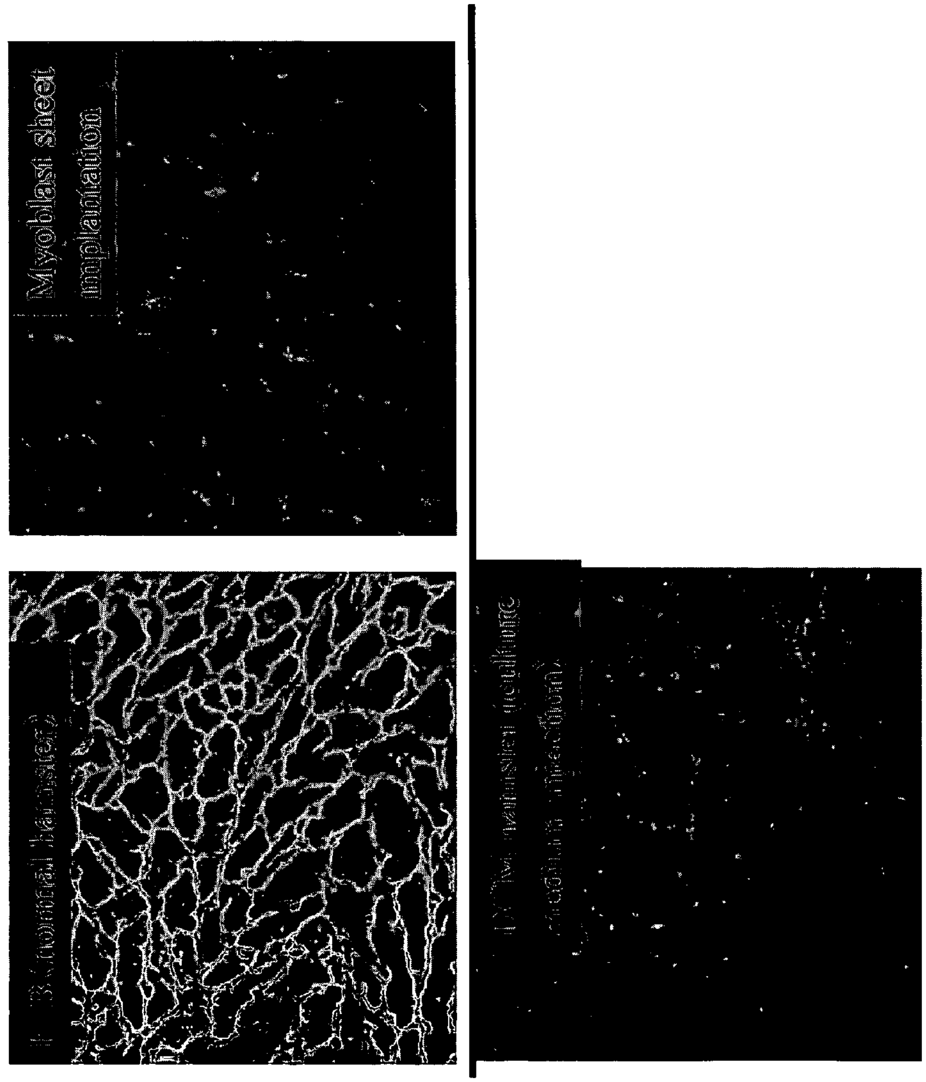
FIG. 30C shows comparison of expression levels of $\alpha$-sarcoglycan (myoblast sheet implantation enhances expression of $\alpha$-sarcoglycan).
Figure 30D:
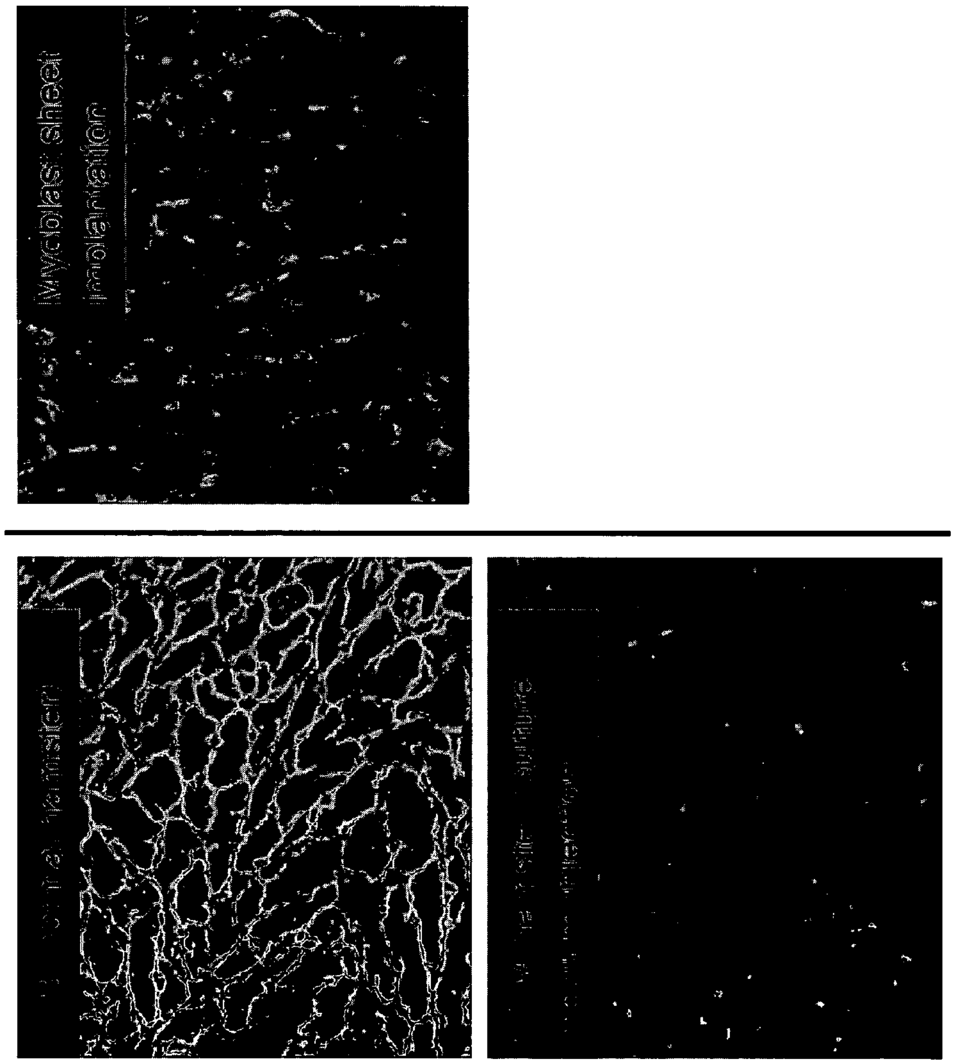
FIG. 30D shows comparison of expression levels of $\beta$-sarcoglycan (myoblast sheet implantation enhances expression of $\beta$-sarcoglycan).
Figure 31:
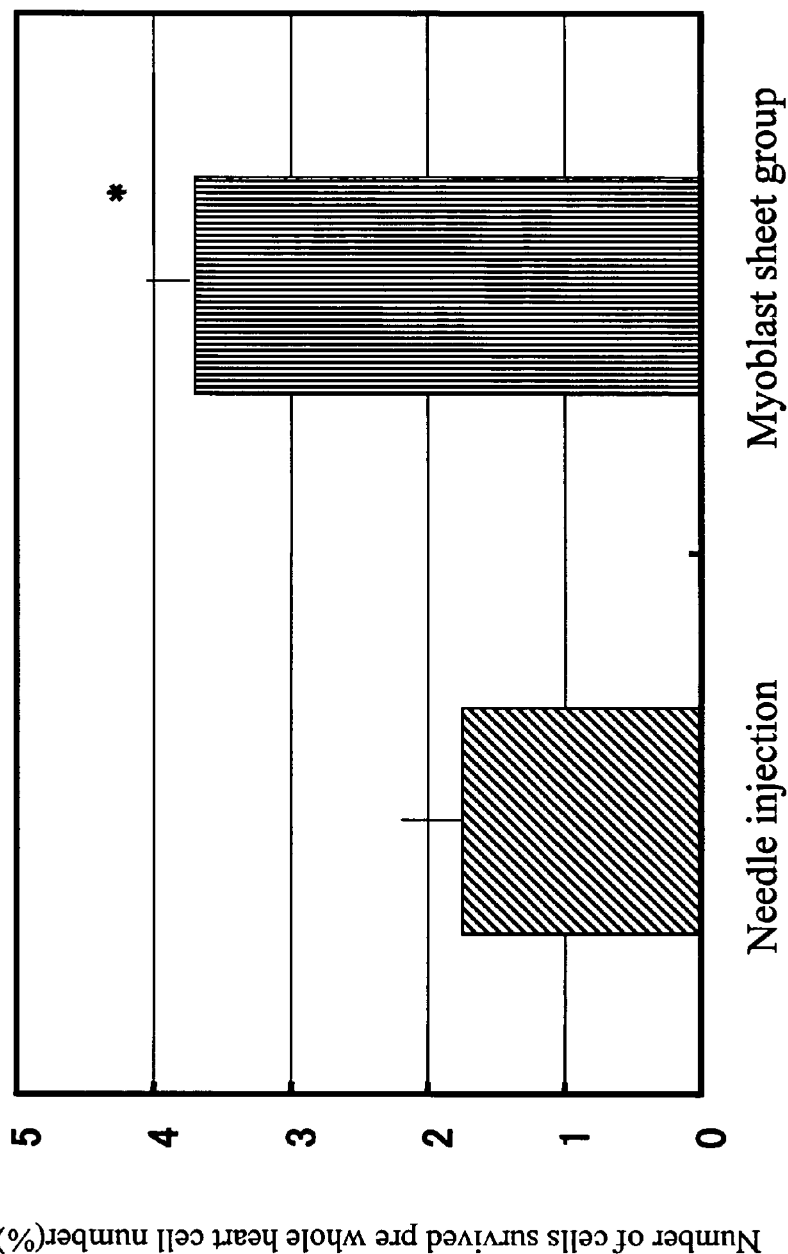
FIG. 31 shows a survival rate of cardiomyopathic hamsters into which a prosthetic tissue (sheet) comprising myoblasts of the present invention has been implanted myoblast. Injection of cells as they are is compared with administration of a prosthetic tissue.
Figure 32:
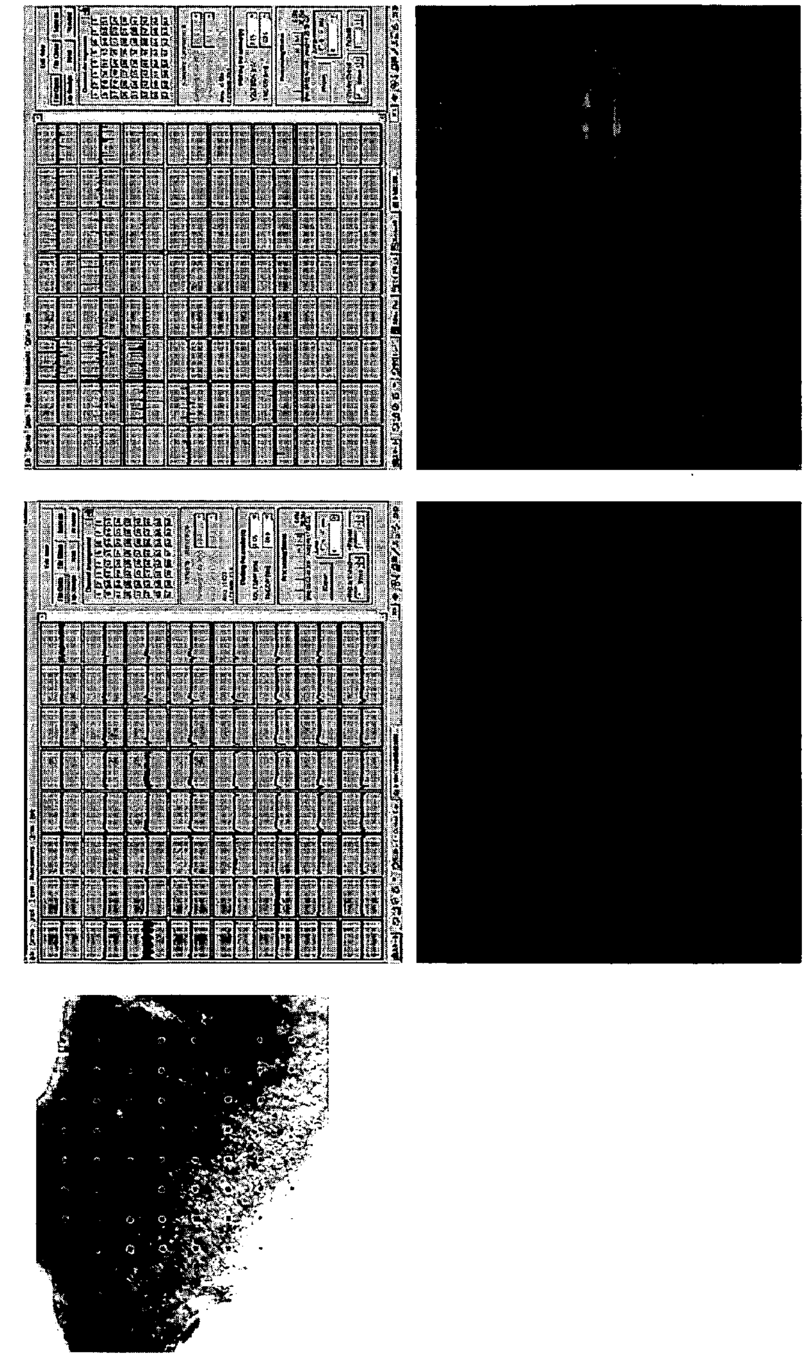
FIG. 32 shows electrical characteristics after implantation of a prosthetic tissue of the present invention. The left portion shows a prosthetic tissue comprising cardiomyocytes, while the right portion shows a prosthetic tissue comprising myoblasts.

After the myoblast sheet was implanted, an ultrasound echogram demonstrated that dilated LV dimension was significantly reduced, whereas the hearts in T and C groups showed a progression of left ventricular (LV) dilation (FIG. 33A). Six weeks after operation, fractional shortening (FS) was significantly improved in the S and T groups compared with that in the C group. After seven weeks, FS in the S group was maintained at the preoperative level, while FS in the other groups decreased gradually. Although the max velocity of the mitral valve E-wave in the S group dropped slightly one week after the sheet implantation, this was recovered to the preoperative level 2 weeks after operation. The averaged E-wave in the S and T groups was significantly higher than that in the C group 4 weeks after operation and thereafter. Histological examinations in the S group demonstrated that the implanted sheet almost covered the whole heart and the left ventricle (LV) wall thickness was increased with surviving myoblasts (FIGS. 30A to 30D). As can be seen from FIG. 30B, the implanted myoblasts, which constituted a tissue structure, were intimately attached to and accepted by the heart to aid the cardiac function. FIGS. 30C and 30D clearly show that expression of α-sarcoglycan and β-sarcoglycan had a score of 2 to 3 and about 3, respectively, i.e., the heart was substantially moderately recovered, where normal expression has a score of 5 and DCM hamsters have a score of about 3. It is known that DCM hamsters have a symptom of partial dilated cardiomyopathy caused by a decrease in expression of sarcoglycan. It was demonstrated that a three-dimensional tissue structure of the present invention has an effect of supplementing such gene expression.

Figure 33B:
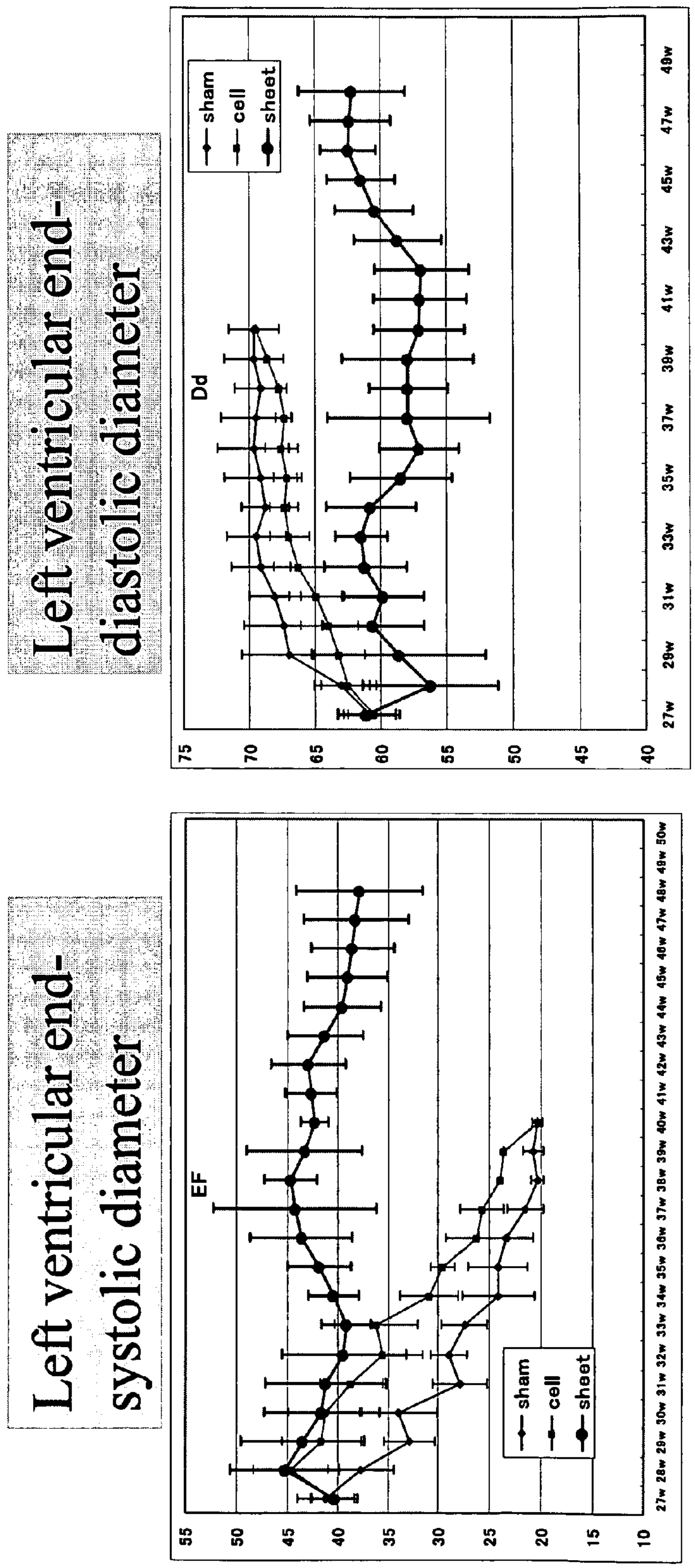
FIG. 33B shows a result of echocardiography 48 weeks after implantation (myoblast sheet implantation ameliorates the cardiac function of a dilated cardiomyopathy heart).

FIG. 33B clearly shows that use of the three-dimensional tissue structure of the present invention allowed DCM hamsters to survive beyond 48 weeks. This is a significant and unexpected effect compared with injection (only cells) or control (in either case, all DCM hamsters died after 38 to 40 weeks). As shown in FIG. 33C, the contractility of the left ventricle with dilated cardiomyopathy was significantly ameliorated. This result shows that the structure of the present invention can be applied to hearts. The result corresponds to about a 25-year extension of life span, demonstrating a significant effect of the three-dimensional tissue structure of the present invention. The average life-span of the DCM hamsters was about 40 weeks, while the longest life-span of the DCM hamsters having an implanted sheet was about 70 weeks. Assuming that the life-span of a normal hamster is about 2 years and the life-span of a human is 80 years, the life-span of the implanted hamster was prolonged by about 30 weeks which is equivalent to about 25 years in a human. Thus, it was demonstrated that the three-dimensional structure of the present invention has a significant effect on cardiomyopathy.

CONCLUSION

Myoblast sheet implantation reduced the progression of heart hypertrophy with improvement of cardiac function in dilated cardiomyopathic (DCM) hearts. Myoblast sheet implantation may be a promising method to restore the cardiac function with attenuation of cardiac remodeling in DCM hearts.

Example 4

Therapy for Infarct Pig Model

In this example, aiming for more clinical findings, skeletal myoblast sheets were implanted into a larger animal model of myocardial infarct to study amelioration of cardiac function.

(Method)

A thoracotomy was performed on 30 kg pigs under general anesthetization and the LAD was ligated to produce myocardial infarct models. Three different therapies were conducted: 1) skeletal myoblast sheet group; 2) skeletal myoblast injection group; and 3) control group. For these groups, changes in cardiac function and myocardial tissue were examined (FIG. 34). Skeletal myoblasts were collected from autologous thigh muscle. Collagenase, trypsin EDTA, gentamicin sulfate, and amphotericin B were prepared and filtered through a 0.22-μm filter to formulate a dissociating solution. SkBM Basal Medium, bovine fetal serum, EGF, sodium dexamethasone phosphate, gentamicin sulfate, and amphotericin B were prepared and filtered through a 0.22 μm filter to formulate primary culture medium. The dissociated cells were cultured on dishes grafted with a temperature responsive macromolecule made of poly(N-isopropylamide) and were detached as a cell sheet by changing temperature instead of enzymatic treatment.

(Results)

Figure 35:
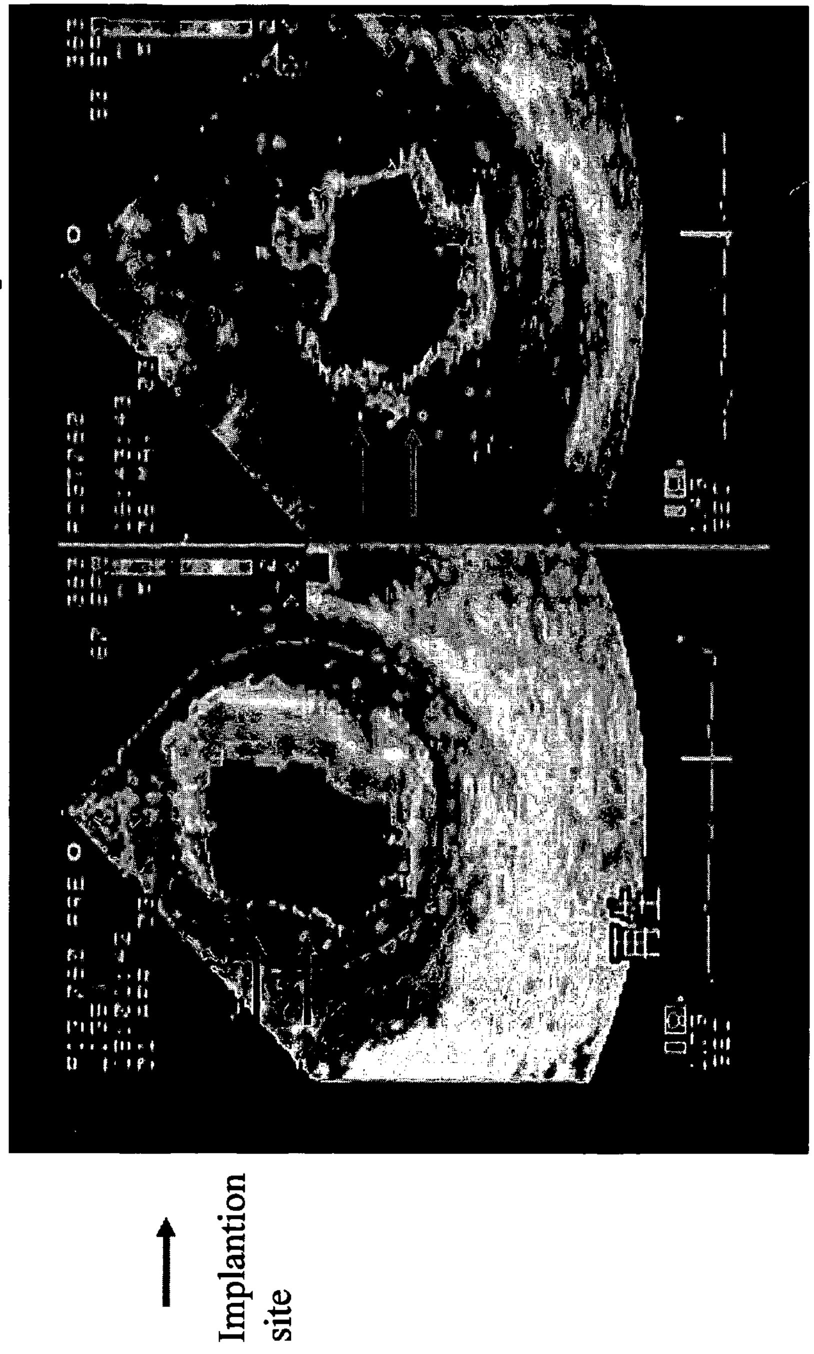
FIG. 35 shows a therapeutic effect (contractility) in a pig infarct model using a prosthetic tissue of the present invention.
Figure 36:
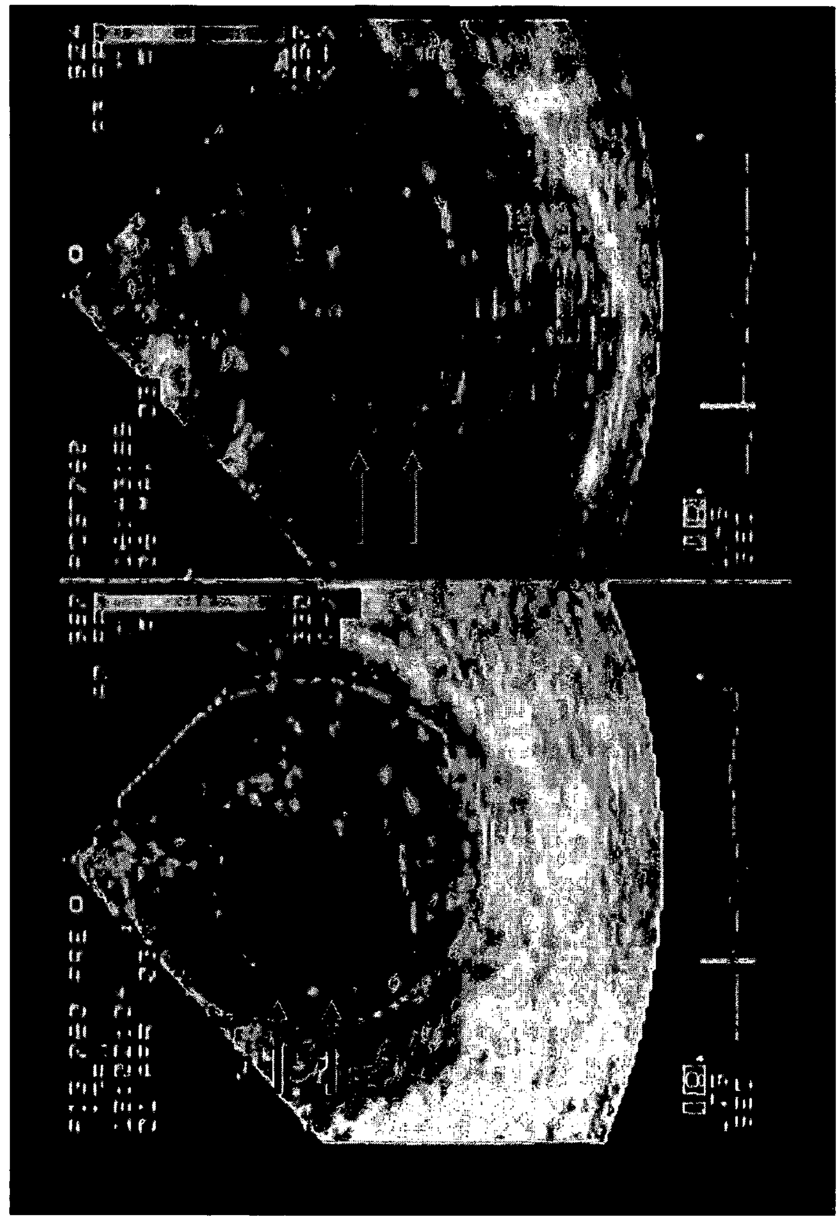
FIG. 36 shows a therapeutic effect (expansibility) in a pig infarct model using a prosthetic tissue of the present invention.

The group with cell sheet implantation had ameliorated cardiac functions, i.e., contractility and expansibility (FIGS. 35 and 36). In addition, it was confirmed that the implanted cells were accepted by the myocardial infarct portion.

CONCLUSION

In experiments using animals other than rodents, it was confirmed that a therapy using a myoblast sheet of the present invention had an effect of ameliorating cardiac function.

Example 5

Synovial Cells

To demonstrate an effect of the present invention in the case of another type of cell, a sheet of synovial cells (cells containing tissue stem cells) was prepared and implanted into myocardial infarct models to examine an effect of ameliorating cardiac function.

(Methods)

Knee joints were removed from 8-week old rats. Synovial tissue was cut off the internal surface of the joint. The tissue was attached to culture medium containing 20% FCS and DMEM high glucose for cell culture. The resultant cells were cultured on dishes grafted with a temperature responsive macromolecule made of poly(N-isopropylamide) and were detached as a cell sheet by changing temperature instead of enzymatic treatment. For myocardial infarct models prepared by LAD ligation, three different therapies were conducted: 1) cell sheet group; 2) cell injection group; and 3) control group. For these groups, changes in cardiac function and myocardial tissue were examined.

(Results)

The group with cell sheet implantation had ameliorated cardiac functions, i.e., contractility and expansibility. In addition, it was confirmed that the implanted cells were accepted by the myocardial infarct portion.

CONCLUSION

In the case of cells differentiated from cell obtained from synovial tissue, it was confirmed that a sheet of such cells had an effect of ameliorating cardiac function.

Example 6

Stem Cells

As an example of undifferentiated cells, there is a mouse embryonic stem cell known to be capable of differentiating into a cardiomyocyte. In this example, a sheet of such cardiomyocytes was prepared and implanted into myocardial infarct models to study the effect on ameliorating cardiac function.

(Methods)

A resistance gene was introduced into a promoter site of a gene expressing MHC in mouse embryonic stem cells. The cells were cultured in a selective culture containing a high concentration of a drug in which differentiated cells other than cardiomyocytes are killed, so that cardiomyocytes were selected. The resultant cells were cultured on dishes grafted with a temperature responsive macromolecule made of poly(N-isopropylamide) and were detached as a cell sheet by changing temperature instead of enzymatic treatment. For myocardial infarct models prepared by LAD ligation, three different therapies were conducted: 1) cell sheet group; 2) cell injection group; and 3) control group. For these groups, changes in cardiac function and myocardial tissue were examined.

(Results)

The group with cell sheet implantation had ameliorated cardiac functions, i.e., contractility and expansibility. In addition, it was confirmed that the implanted cells were accepted by the myocardial infarct portion.

CONCLUSION

In the case of cells differentiated from cells obtained from synovial tissue, it was confirmed that a sheet of such cells had an effect of ameliorating cardiac function.

Example 7

Preparation of Prosthetic Tissue Using Ascorbic Acid

Next, an influence of ascorbic acid or a derivative thereof on production of a prosthetic tissue was studied.

After an adequate amount of myoblasts were produced, $5\times10^6$ cells were cultured on 10-cm temperature responsive culture dishes. For culture, SkBM Basal Medium (Clonetics (Cambrex)) was used. Next, ascorbic acid 2-phosphate (0.5 mM), magnesium ascorbic acid 1-phosphate (0.1 mM), and sodium L-ascorbate (0.1 mM) were added to the medium. 4 days after culture start, the cells were detached at 20° C. As a control, a prosthetic tissue was prepared in a culture system without ascorbic acids.

(Results)

When ascorbic acid was added, the prosthetic tissue was detached much more easily than that in the culture system without any ascorbic acids. In addition, tissue was not cultured to a size of several millimeters in the culture system without ascorbic acids. If the tissue exceeded such a size, cracks occurred and the growth stopped. It was also substantially difficult to detach the tissue. Thus, implantable prosthetic tissue could not be provided. In contrast, a prosthetic tissue of the present invention, which was cultured in a medium supplemented with an ascorbic acid, grown into an implantable size, and was easy to detach. In addition, the prosthetic tissue was isolated while substantially no hole or scar was generated. Inspection of biological connections demonstrated that extracellular matrix-mediated interaction was significant (FIGS. 37 to 39).

Example 8

Effect of Addition of Ascorbic Acid 2-Phosphate

Next, an influence of ascorbic acid 2-phosphate on production of a prosthetic tissue was studied.

After an adequate amount of synovial cells or myoblasts were produced, $5\times10^6$ cells were cultured on 10-cm temperature responsive culture dishes. For culture, SkBM Basal Medium (myoblasts) containing ascorbic acid 2-phosphate (1 mM) or DMEM (synovial cells) containing ascorbic acid 2-phosphate (1 mM) was used. As a control, a prosthetic tissue was prepared in a culture system having the same medium without ascorbic acids or in another culture system having the same medium with ascorbic acid 1-phosphate (1 mM).

9 days after culture start, the tissue was detached and contracted. The tissue was contracted by a factor of about 3.

Figure 42:
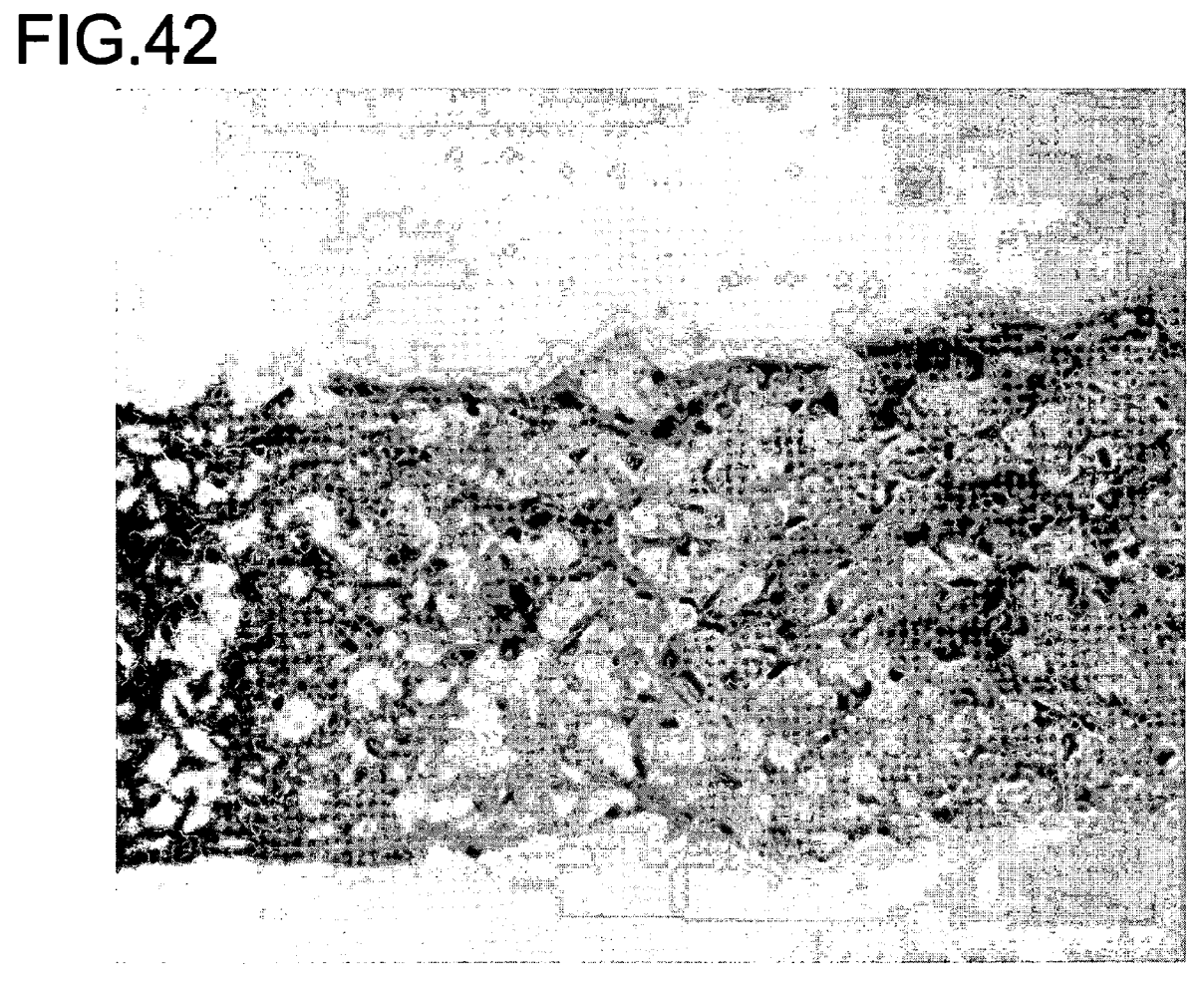

The contracted tissue was histologically analyzed by HE staining or the like (FIG. 42, synovial cells). It was found that the cells constructed 10 or more layers and the matrix was in the form of collagen mesh or sponge. The matrix had rigidity such that the matrix could be easily pinched with forceps.

(Stress-Distortion Examination (Tensile Test))

To confirm strength, a tensile test was conducted to obtain a load-time (stress distortion) curve where a sample is stretched. According to this curve, the limit of proportionality, modulus of elasticity, yield point, maximum strength, rupture point, elastic energy, and tenacity are obtained.

(Creep Characteristics (Indentation Test))

Indentation test, which measures creep characteristics, was carried out by determining viscoelasticity. It is possible to observe a phenomenon in which distortion is increased. An instrument, such as a rod or the like, is pushed into a gel material, and the deformation of the material is monitored.

(Results)

A prosthetic tissue can be detached much more easily when ascorbic acid 2-phosphate is added than in a culture system without ascorbic acids and in a culture system which contains commonly used ascorbic acid 1-phosphate. In addition, tissue was not cultured to a size of several millimeters in the culture system without ascorbic acids. If the tissue exceeded such a size, cracks occurred and the growth stopped. The size, strength, and the like are greater in the culture system with ascorbic acid 2-phosphate than in the culture system containing commonly used ascorbic acid 1-phosphate. In the system without ascorbic acids, it was also substantially difficult to detach the tissue. Thus, implantable prosthetic tissue could not be provided.

Particularly, the prosthetic tissue cultured in the system containing ascorbic acid 2-phosphate had rigidity such that it can be pinched with forceps. Prosthetic tissues cultured in other systems had less rigidity than that of the prosthetic tissue cultured in the ascorbic acid 2-phosphate-containing system. The prosthetic tissue cultured in ascorbic acid 2-phosphate-containing medium was grown to an implantable size and was easy to detach. In addition, the prosthetic tissue was isolated while substantially no hole or scar was generated. Inspection of biological connection demonstrated that extracellular matrix-mediated interaction was significant.

Example 9

Effect of Prosthetic Tissue Cultured in the Presence of Ascorbic Acids

The prosthetic tissue produced in the presence of ascorbic acids in Examples 7 and 8 was implanted into dilated cardiomyopathy hamsters. All the implanted mice were cured, and survived as long as ordinary hamsters do. Therefore, it was demonstrated that the present invention can cure diseases, which are conventionally believed to be refractory, by providing a specific three-dimensional promoting agent.

Example 10

Combined Therapy

A combined therapy of a sheet as prepared in the above-described examples, and gene therapy, was carried out. The combined therapy aims for promoting angiogenesis in sheet implanted sites, promoting acceptance of implanted sheets, and suppressing cell necrosis within sheets.

(Methods)

A complex of Sendai virus (HVJ) and a liposome was prepared in accordance with the description of a document (Kaneda Y., Iwai K., Uchida T., Increased Expression of DNA Co-introduced with Nuclear Protein in Adult Rat Liver, Science, 1989, 243:375-378). Hereinafter, this procedure will be briefly described. 200 μl of DNA solution was prepared and shaken for 30 sec. The solution was allowed to stand in a 37° C. constant temperature bath for 30 sec. This procedure was performed 8 times. The solution was subjected to ultrasonic treatment for 5 sec, and shaken for 30 sec. 0.3 mL of BSS was added to the solution, followed by shaking in a 37° C. constant temperature bath. Inactivated HVJ was added to the solution which was in turn placed on ice for 10 min. The solution was shaken in a 37° C. constant temperature bath for 1 hour. 1 mL of 60% sucrose solution and 6 mL of 30% sucrose solution were layered in an ultracentrifugation tube. HVJ liposome solution was placed on the layered solution. BSS was added to the tube. The tube was ultracentrifuged at 62,800×g 4 times for 1.5 hours. A layer immediately above the 30% sucrose solution layer was removed and preserved at 4° C. This liposome was used for gene introduction.

About 0.2 mL of Sendai virus liposome-plasmid complex (containing 15 μg of human HGF cDNA) was injected into a myocardial infarct region. In a control group, an empty vector was used for gene introduction into infarcted myocardium. The human HGF concentration of heart tissue was measured by enzyme-linked immunosolvent assay (ELISA) using an anti-human HGF monoclonal antibody (Institute of Immunology, Tokyo, Japan)) (Ueda H., Sawa Y., Matsumoto K. et al., Gene Transfection of Hepatocyte Growth Factor Attenuates Reperfusion Injury in the Heart, Ann. Thorac. Surg., 1999, 67:1726-1731). The resultant cells were cultured on dishes grafted with a temperature responsive macromolecule made of poly(N-isopropylamide) and were detached as a cell sheet by changing temperature instead of enzymatic treatment. For myocardial infarct models prepared by LAD ligation, three different therapies were conducted: 1) cell sheet group; 2) gene therapy group; 3) combined therapy group; and 4) control group. For these groups, changes in cardiac function and myocardial tissue were examined.

(Results)

The cell sheet implantation group and the combined therapy group have ameliorated cardiac functions, i.e., contractility and expansibility. In addition, it is confirmed that in the combined therapy group, angiogenesis is observed and the implanted cells are accepted by the myocardial infarct portion.

CONCLUSION

A combination of sheet tissue and gene therapy has an effect of amelioration of cardiac function, an effect of angiogenesis, and an effect of cell protection. It is also confirmed that cardiac function is further ameliorated.

Although certain preferred embodiments have been described herein, it is not intended that such embodiments be construed as limitations on the scope of the invention except as set forth in the appended claims. Various other modifications and equivalents will be apparent to and can be readily made by those skilled in the art, after reading the description herein, without departing from the scope and spirit of this invention. All patents, published patent applications and publications cited herein are incorporated by reference as if set forth fully herein.

INDUSTRIAL APPLICABILITY

The present invention provides a radical therapeutic method, a technique, and a medicament for diseases which are difficult to treat by conventional therapies (particularly, heart diseases exhibiting sever heart failure, etc.).

We claim:

1. A method for producing a three-dimensional structure applicable to a heart comprising mesenchymal stem cells, or synovial cells and synovium tissue stem cells that are derived from internal surface of a joint, the method comprising the steps of:

a) culturing the cells on a cell culture support grafted with a temperature responsive macromolecule;

b) setting a culture medium temperature to an upper limit critical solution temperature or more or a lower limit critical solution temperature or less; and c) detaching the cultured cells as the three-dimensional structure applicable to a heart.

2. A method according to claim 1, wherein a treatment using a protein degrading enzyme is not performed in or before the detaching step.

3. A method according to claim 1, wherein the temperature responsive macromolecule is poly (N-isopropylacrylamide).

4. A method for producing a three-dimensional structure applicable to a heart, comprising mesenchymal stem cells, or synovial cells and synovium tissue stem cells that are derived from internal surface of a joint, the method comprising the steps of:

a) culturing the cells on a cell culture support grafted with a temperature responsive macromolecule, in the presence of ascorbic acid, to form a three-dimensional structure;

b) setting a culture medium temperature to an upper limit critical solution temperature or more or a lower limit critical solution temperature or less; and c) detaching the three-dimensional structure as the three-dimensional structure applicable to a heart.

5. A method for treating myocardial ischemia, which comprises the steps of disposing the three-dimensional structure applicable to a heart to cover a portion of a heart to be treated and holding the structure for a time sufficient to connect to the portion, thereby ameliorating the effects of ischemia, said three-dimensional structure applicable to a heart, comprising mesenchymal stem cells, or synovial cells and synovium tissue stem cells that are derived from internal surface of a joint, wherein:

the three-dimensional structure applicable to a heart is a cell sheet, is free from scaffold, and is obtained by the process comprising:

a) culturing the cells on a cell culture support grafted with a temperature responsive macromolecule to form a cell sheet;

b) setting a culture medium temperature to an upper limit critical solution temperature or more or a lower limit critical solution temperature or less; and c) detaching the cell sheet as the three-dimensional structure applicable to a heart.

6. The method according to claim 5, wherein a surface of the heart is treated with HGF.

7. The method according claim 5, wherein the myocardial ischemia is selected from the group consisting of ischemic heart disease, myocardial infarct, and dilated cardiomyopathy.

8. The method according to claim 5, wherein the cells are derived from a subject, the structure being applied to the subject.

9. The method according to claim 5, wherein the cells are not derived from a subject, the structure being applied to the subject.

10. The method of claim 5 wherein said structure is in the form of a medicament.

11. A method for treating myocardial ischemia, which comprises the steps of disposing the three-dimensional structure applicable to a heart to cover a portion of a heart to be treated and holding the structure for a time sufficient to connect to the portion, thereby ameliorating the effects of myocardial ischemia, said three-dimensional structure applicable to a heart, comprising mesenchymal stem cells, or synovial cells and synovium tissue stem cells that are derived from internal surface of a joint, wherein:

the three-dimensional structure applicable to a heart is free from scaffold, and is obtained by the process comprising:

a) culturing the cells on a cell culture support grafted with a temperature responsive macromolecule, in the presence of ascorbic acid, to form a three-dimensional structure;

b) setting a culture medium temperature to an upper limit critical solution temperature or more or a lower limit critical solution temperature or less; and c) detaching the three-dimensional structure as the three-dimensional structure applicable to a heart.

12. The method according to claim 11, wherein a surface of the heart is treated with HGF.

13. The method according claim 11, wherein the myocardial ischemia is selected from the group consisting of ischemic heart disease, myocardial infarct, and dilated cardiomyopathy.

14. The method according to claim 11, wherein the cells are derived from a subject, the structure being applied to the subject.

15. The method according to claim 11, wherein the cells are not derived from a subject, the structure being applied to the subject.

16. The method of claim 11 wherein said structure is in the form of a medicament.

* * * * *

SEQUENCE LISTING

<160> NUMBER OF SEQ ID NOS: 20

<210> SEQ ID NO 1
<211> LENGTH: 5956
<212> TYPE: DNA
<213> ORGANISM: Homo sapiens

<400> SEQUENCE: 1

```
atgagttctg actcagaatt ggctgttttt ggggaggctg ctcctttcct ccgaaagtct     60

gaaagggaac gcattgaggc ccagaatagg ccctttgatg ccaaaacatc tgtctttgtg    120

gcggagccca aagaatcctt tgtcaaaggg accatccaga gcagagaagg aggaaaagtg    180

acggtgaaga ctgagggagg agcgactctg acagtgaagg atgatcaggt cttccccatg    240

aaccctccca aatatgacaa gatcgaggat atggccatga tgactcatct gcatgagcct    300

gctgtgctgt acaacctcaa agaacgttat gcagcctgga tgatctacac ctattcaggt    360

ctcttctgtg tcactgtcaa cccctacaag tggctgcctg tgtataagcc cgaggtggtg    420

acagcctacc gaggcaaaaa gcgccaggag gccccgcccc acatcttctc catctctgac    480

aacgcctatc agttcatgct gactgaccga gagaatcagt caatcctgat cactggagaa    540

tctggtgcag ggaagactgt gaacaccaag cgtgtcatcc agtactttgc aacaattgca    600

gttactggtg agaagaagaa ggaagaaatt acttctggca aaatacaggg gactctggaa    660

gatcaaatca tcagtgccaa cccccctactg gaggcctttg gcaacgccaa gaccgtgagg    720

aatgacaact cctctcgctt tggtaaattc atcagaatcc actttggcac tactggaaaa    780

ctggcatctg ctgatattga aacatatctg ctagagaagt ctagagttgt tttccagctt    840

aaggctgaga gaagttatca tattttttac cagattacat cgaataagaa accagaactt    900

attgaaatgc ttctgattac cacgaaccca tatgattacc catttgtcag tcaaggggag    960

atcagtgtgg ccagcatcga tgatcaggaa gaactgatgg ccacagatag tgctattgat   1020

attttgggct ttactaatga agaaaaggtc tccatttaca agctcacggg ggctgtgatg   1080

cattatggga acctaaaatt taagcaaaag cagcgtgagg agcaagcaga gccagatggc   1140

acagaagttg ctgacaaggc ggcctacctc cagagtctga actctgcaga tctgctcaaa   1200

gctctctgct accccagggt caaggtcggc aatgagtatg tcaccaaagg ccagactgta   1260

gaacaggtgt ccaacgcagt aggtgctctg gccaaagccg tctacgagaa gatgttcctg   1320

tggatggttg cccgcatcaa ccagcagctg gacaccaagc agcccaggca gtacttcatc   1380

ggggtcttgg acattgctgg ttttgagatt tttgatttca acagcctgga gcagctgtgc   1440

atcaatttca ccaatgagaa actgcaacag tttttcaacc accacatgtt cgtgctggag   1500

caggaggagt acaagaagga aggcatcgag tggacgttca tcgacttcgg gatggacctg   1560

gctgcctgca tcgagctcat cgagaagcct atgggcatct tctccatcct ggaagaggag   1620

tgcatgttcc ctaaggcaac agacacctcc ttcaagaaca agctgtatga ccagcacctg   1680

ggcaagtctg ccaacttcca gaagcccaag gtggtcaaag gcaaggccga ggcccacttc   1740

gctctgattc actatgctgg tgttgtggac tacaacatta ctggctggct ggagaagaac   1800

aaggaccccc tgaatgagac cgtggttgga ctgtaccaga agtctgcaat gaaaactcta   1860

gctcagctct tctctggggc tcaaactgct gaaggagagg gagctggtgg aggggccaag   1920

aaaggtggta agaagaaggg ctcttctttc cagacagtgt ctgccctttt cagagagaat   1980

ttgaacaagc tgatgaccaa cctcaggagt acccatcctc actttgtgag gtgtatcatc   2040

cccaatgaga caaaaactcc tggtgccatg gagcatgagc ttgtcctcca ccagctgagg   2100
```

```
tgtaacggtg tgctggaagg catccgcatc tgtaggaaag gatttccaag cagaatcctt   2160
tatgcagact tcaaacagag atacaaggta ttaaatgcaa gtgcaatccc tgaagggcaa   2220
ttcattgata gcaagaaggc ctctgagaag ctccttgcat ccatcgacat tgaccacacc   2280
cagtataaat ttgggcacac caaggtcttt ttcaaagctg gtcttctggg gctcctagag   2340
gagatgcgag atgacaagct ggcccagctg attacccgaa cccaggccag gtgcagaggg   2400
ttcttggcaa gagtggagta ccagaggatg gtggagagaa gggaggccat cttctgtatc   2460
cagtacaata tcagatcctt catgaatgtc aagcactggc cctggatgaa actcttcttc   2520
aagatcaagc ctctgttgaa gagtgcagaa actgagaagg agatggccac catgaaggaa   2580
gaatttcaga aaattaaaga cgaacttgcc aagtcagagg caaaaaggaa ggaactggaa   2640
gaaaagatgg tgacgctgtt gaaagaaaaa aatgacttgc agctccaagt tcaggctgaa   2700
gccgaaggct tggctgatgc agaggaaagg tgtgaccagc taatcaaaac caaaatccag   2760
ctagaagcca aaatcaaaga ggtgactgag agagctgagg atgaggaaga gatcaatgct   2820
gagctgacag ccaagaagag gaaactggag gatgaatgtt cagaactcaa gaaagacatt   2880
gatgaccttg agctgacact ggccaaggtt gagaaggaga aacatgccac agaaaacaag   2940
gtgaaaaacc tcacagaaga gatggcaggt ctggatgaaa ccattgctaa gctgaccaag   3000
gagaagaagg ctctccagga ggcccaccag cagaccctgg atgacctgca ggcagaggag   3060
gacaaagtca acaccctgac caagctaaa atcaaacttg aacaacaagt ggatgatctt   3120
gaagggtcct tggagcaaga aaagaaactt cgcatggacc tagaaagggc taagaggaaa   3180
cttgagggtg acttgaagtt ggcccaagaa tccataatgg acattgaaaa tgagaaacag   3240
caacttgatg aaaagctcaa aaagaaagag tttgaaatca gcaatctgca aagcaagatt   3300
gaagatgaac aggcacttgg cattcaattg cagaagaaaa ttaaagaatt gcaagcccgc   3360
attgaggagc tggaggagga aatcgaggcg gagcgggcct cccgggccaa agcagagaag   3420
cagcgctctg acctctcccg ggagctggag gagatcagcg agaggctgga agaagccggt   3480
ggggccactt cagcccagat tgagatgaac aagaagcggg aggctgagtt ccagaaaatg   3540
cgcagggacc tggaggaggc caccctacag catgaagcca cagcggccac cctgaggaag   3600
aagcatgcag atagtgtggc cgagcttggg gagcagattg acaacctgca gcgagtgaag   3660
cagaagctgg agaaggagaa gagtgagatg aagatggaga ttgatgacct tgctagtaat   3720
gtagaaacgg tctccaaagc caagggaaac ctagagaaaa tgtgccggac tctagaggac   3780
caactgagtg aactgaaatc aaaggaagag gagcagcagc ggctgatcaa tgacctgact   3840
gcgcagaggg ggcgcctgca gactgaatct ggtgagtttt cacgccagct tgatgaaaag   3900
gaagctctgg tgtctcagtt atcaagaggc aaacaagcct ttactcaaca gattgaagaa   3960
ttaaagaggc aacttgaaga ggagataaaa gccaagaacg ccctggcgca tgccctgcag   4020
tcttcccgcc acgactgtga cctgctgcgg gaacagtatg aggaggagca ggaatccaag   4080
gccgagctgc agagagcact gtccaaggcc aacaccgagg ttgcccaatg gaggaccaaa   4140
tacgagacgg acgccatcca gcgcacagag gagctggagg aggccaagaa gaagctggcc   4200
cagcggctgc aggcagctga ggaacatgta gaagctgtga acgccaaatg tgcttccctc   4260
gaaaagacga agcagcggct gcagaatgag gtcgaggacc tcatgcttga tgtggagagg   4320
acaaatgccg cctgtgccgc ccttgacaaa aagcaaagga acttcgataa gatcctggca   4380
gaatggaaac agaaatgtga ggaaacgcat gctgagcttg aggcctccca gaaggaggcc   4440
```

```
cgttcccttg gcactgagct gttcaagata aagaatgcct atgaggaatc tttggatcag   4500

ctagaaaccc tgaagcgaga gaacaaaaac ttacagcagg agatttctga cctcacggaa   4560

cagattgcag aaggagggaa acgtatccat gaactggaga aaataaagaa acaagtggaa   4620

caagaaaagt gtgaacttca ggctgcttta gaagaagcag aggcatctct tgaacatgaa   4680

gagggaaaga tcctgcgcat ccagcttgag ttgaaccaag tcaagtctga ggttgatagg   4740

aaaattgctg aaaaagatga ggaaattgac cagctgaaga gaaaccacat tagaatcgtg   4800

gagtccatgc agagcacgct ggatgctgag atcaggagta ggaatgatgc cattaggctc   4860

aagaagaaga tggagggaga cctcaatgaa atggaaatcc agctgaacca tgccaaccgc   4920

atggctgctg aggccctgag gaactacagg aacacccaag gcatcctcaa ggatacccag   4980

atccacctgg atgatgctct ccggagccag gaggacctga aggaacagct ggccatggtg   5040

gagcgcagag ccaacctgct gcaggctgag atcgaggagc tgcgggccac tctggaacag   5100

acagagagga gcagaaaaat cgcagaacag gagctcctgg atgccagtga gcgtgttcag   5160

ctactgcaca cccagaacac cagcctgatc aacaccaaga agaagctgga gacagatatt   5220

tcccaaatgc aaggagagat ggaggacatt ctccaggaag cccgcaatgc agaagaaaag   5280

gccaagaagg ccatcactga tgccgccatg atggctgagg agctgaagaa ggagcaggac   5340

accagcgccc acctggagcg gatgaagaag aacatggagc agaccgtgaa ggatctgcag   5400

ctccgtctgg atgaggctga gcagctggcc ctgaagggtg ggaagaagca gatccagaaa   5460

ctggaggcca gggtacggga gctggaagga gaggttgaga gtgagcaaaa gcgtaatgct   5520

gaggctgtca aaggtctgcg caaacatgag aggcgagtga aggaactcac ttaccagacg   5580

gaagaagata gaaagaatat tctcaggctt caagatttgg tagataaact tcaggcaaaa   5640

gtgaaatctt ataagagaca agctgaggag gctgaggaac aatccaacac caatctagct   5700

aaattccgca agctccagca tgagctggag gaggccgagg aacgggctga cattgctgag   5760

tcccaggtga acaaactgcg ggtgaagagc cgggaggttc acacaaaagt cataagtgaa   5820

gagtgatcat gtcctgatgc catggaatga ctgaagacag gcacaaaatg tgacatcttt   5880

ggtcatttcc ctctgtaatt attgtgtatt ctaccctgtt gcaaaggaaa taaagcatag   5940

ggtagtttgc aaacaa                                                   5956
```

<210> SEQ ID NO 2
<211> LENGTH: 1941
<212> TYPE: PRT
<213> ORGANISM: Homo sapiens

<400> SEQUENCE: 2

```
Met Ser Ser Asp Ser Glu Leu Ala Val Phe Gly Glu Ala Ala Pro Phe
1               5                   10                  15

Leu Arg Lys Ser Glu Arg Glu Arg Ile Glu Ala Gln Asn Arg Pro Phe
            20                  25                  30

Asp Ala Lys Thr Ser Val Phe Val Ala Glu Pro Lys Glu Ser Phe Val
        35                  40                  45

Lys Gly Thr Ile Gln Ser Arg Glu Gly Gly Lys Val Thr Val Lys Thr
    50                  55                  60

Glu Gly Gly Ala Thr Leu Thr Val Lys Asp Asp Gln Val Phe Pro Met
65                  70                  75                  80

Asn Pro Pro Lys Tyr Asp Lys Ile Glu Asp Met Ala Met Met Thr His
                85                  90                  95

Leu His Glu Pro Ala Val Leu Tyr Asn Leu Lys Glu Arg Tyr Ala Ala
```

```
            100                 105                 110

Trp Met Ile Tyr Thr Tyr Ser Gly Leu Phe Cys Val Thr Val Asn Pro
        115                 120                 125

Tyr Lys Trp Leu Pro Val Tyr Lys Pro Glu Val Val Thr Ala Tyr Arg
    130                 135                 140

Gly Lys Lys Arg Gln Glu Ala Pro Pro His Ile Phe Ser Ile Ser Asp
145                 150                 155                 160

Asn Ala Tyr Gln Phe Met Leu Thr Asp Arg Glu Asn Gln Ser Ile Leu
                165                 170                 175

Ile Thr Gly Glu Ser Gly Ala Gly Lys Thr Val Asn Thr Lys Arg Val
            180                 185                 190

Ile Gln Tyr Phe Ala Thr Ile Ala Val Thr Gly Glu Lys Lys Lys Glu
        195                 200                 205

Glu Ile Thr Ser Gly Lys Ile Gln Gly Thr Leu Glu Asp Gln Ile Ile
    210                 215                 220

Ser Ala Asn Pro Leu Leu Glu Ala Phe Gly Asn Ala Lys Thr Val Arg
225                 230                 235                 240

Asn Asp Asn Ser Ser Arg Phe Gly Lys Phe Ile Arg Ile His Phe Gly
                245                 250                 255

Thr Thr Gly Lys Leu Ala Ser Ala Asp Ile Glu Thr Tyr Leu Leu Glu
            260                 265                 270

Lys Ser Arg Val Val Phe Gln Leu Lys Ala Glu Arg Ser Tyr His Ile
        275                 280                 285

Phe Tyr Gln Ile Thr Ser Asn Lys Lys Pro Glu Leu Ile Glu Met Leu
    290                 295                 300

Leu Ile Thr Thr Asn Pro Tyr Asp Tyr Pro Phe Val Ser Gln Gly Glu
305                 310                 315                 320

Ile Ser Val Ala Ser Ile Asp Asp Gln Glu Glu Leu Met Ala Thr Asp
                325                 330                 335

Ser Ala Ile Asp Ile Leu Gly Phe Thr Asn Glu Glu Lys Val Ser Ile
            340                 345                 350

Tyr Lys Leu Thr Gly Ala Val Met His Tyr Gly Asn Leu Lys Phe Lys
        355                 360                 365

Gln Lys Gln Arg Glu Glu Gln Ala Glu Pro Asp Gly Thr Glu Val Ala
    370                 375                 380

Asp Lys Ala Ala Tyr Leu Gln Ser Leu Asn Ser Ala Asp Leu Leu Lys
385                 390                 395                 400

Ala Leu Cys Tyr Pro Arg Val Lys Val Gly Asn Glu Tyr Val Thr Lys
                405                 410                 415

Gly Gln Thr Val Glu Gln Val Ser Asn Ala Val Gly Ala Leu Ala Lys
            420                 425                 430

Ala Val Tyr Glu Lys Met Phe Leu Trp Met Val Ala Arg Ile Asn Gln
        435                 440                 445

Gln Leu Asp Thr Lys Gln Pro Arg Gln Tyr Phe Ile Gly Val Leu Asp
    450                 455                 460

Ile Ala Gly Phe Glu Ile Phe Asp Phe Asn Ser Leu Glu Gln Leu Cys
465                 470                 475                 480

Ile Asn Phe Thr Asn Glu Lys Leu Gln Gln Phe Phe Asn His His Met
                485                 490                 495

Phe Val Leu Glu Gln Glu Glu Tyr Lys Lys Glu Gly Ile Glu Trp Thr
            500                 505                 510

Phe Ile Asp Phe Gly Met Asp Leu Ala Ala Cys Ile Glu Leu Ile Glu
        515                 520                 525
```

```
Lys Pro Met Gly Ile Phe Ser Ile Leu Glu Glu Glu Cys Met Phe Pro
    530                 535                 540

Lys Ala Thr Asp Thr Ser Phe Lys Asn Lys Leu Tyr Asp Gln His Leu
545                 550                 555                 560

Gly Lys Ser Ala Asn Phe Gln Lys Pro Lys Val Val Lys Gly Lys Ala
                565                 570                 575

Glu Ala His Phe Ala Leu Ile His Tyr Ala Gly Val Val Asp Tyr Asn
            580                 585                 590

Ile Thr Gly Trp Leu Glu Lys Asn Lys Asp Pro Leu Asn Glu Thr Val
        595                 600                 605

Val Gly Leu Tyr Gln Lys Ser Ala Met Lys Thr Leu Ala Gln Leu Phe
    610                 615                 620

Ser Gly Ala Gln Thr Ala Glu Gly Glu Gly Ala Gly Gly Gly Ala Lys
625                 630                 635                 640

Lys Gly Gly Lys Lys Lys Gly Ser Ser Phe Gln Thr Val Ser Ala Leu
                645                 650                 655

Phe Arg Glu Asn Leu Asn Lys Leu Met Thr Asn Leu Arg Ser Thr His
            660                 665                 670

Pro His Phe Val Arg Cys Ile Ile Pro Asn Glu Thr Lys Thr Pro Gly
        675                 680                 685

Ala Met Glu His Glu Leu Val Leu His Gln Leu Arg Cys Asn Gly Val
    690                 695                 700

Leu Glu Gly Ile Arg Ile Cys Arg Lys Gly Phe Pro Ser Arg Ile Leu
705                 710                 715                 720

Tyr Ala Asp Phe Lys Gln Arg Tyr Lys Val Leu Asn Ala Ser Ala Ile
                725                 730                 735

Pro Glu Gly Gln Phe Ile Asp Ser Lys Lys Ala Ser Glu Lys Leu Leu
            740                 745                 750

Ala Ser Ile Asp Ile Asp His Thr Gln Tyr Lys Phe Gly His Thr Lys
        755                 760                 765

Val Phe Phe Lys Ala Gly Leu Leu Gly Leu Leu Glu Glu Met Arg Asp
    770                 775                 780

Asp Lys Leu Ala Gln Leu Ile Thr Arg Thr Gln Ala Arg Cys Arg Gly
785                 790                 795                 800

Phe Leu Ala Arg Val Glu Tyr Gln Arg Met Val Glu Arg Arg Glu Ala
                805                 810                 815

Ile Phe Cys Ile Gln Tyr Asn Ile Arg Ser Phe Met Asn Val Lys His
            820                 825                 830

Trp Pro Trp Met Lys Leu Phe Phe Lys Ile Lys Pro Leu Leu Lys Ser
        835                 840                 845

Ala Glu Thr Glu Lys Glu Met Ala Thr Met Lys Glu Glu Phe Gln Lys
    850                 855                 860

Ile Lys Asp Glu Leu Ala Lys Ser Glu Ala Lys Arg Lys Glu Leu Glu
865                 870                 875                 880

Glu Lys Met Val Thr Leu Leu Lys Glu Lys Asn Asp Leu Gln Leu Gln
                885                 890                 895

Val Gln Ala Glu Ala Glu Gly Leu Ala Asp Ala Glu Glu Arg Cys Asp
            900                 905                 910

Gln Leu Ile Lys Thr Lys Ile Gln Leu Glu Ala Lys Ile Lys Glu Val
        915                 920                 925

Thr Glu Arg Ala Glu Asp Glu Glu Glu Ile Asn Ala Glu Leu Thr Ala
    930                 935                 940
```

```
Lys Lys Arg Lys Leu Glu Asp Glu Cys Ser Glu Leu Lys Lys Asp Ile
945                 950                 955                 960

Asp Asp Leu Glu Leu Thr Leu Ala Lys Val Glu Lys Glu Lys His Ala
                965                 970                 975

Thr Glu Asn Lys Val Lys Asn Leu Thr Glu Glu Met Ala Gly Leu Asp
            980                 985                 990

Glu Thr Ile Ala Lys Leu Thr Lys  Glu Lys Lys Ala Leu  Gln Glu Ala
        995                 1000                1005

His Gln  Gln Thr Leu Asp Asp  Leu Gln Ala Glu Glu  Asp Lys Val
    1010                 1015                 1020

Asn Thr  Leu Thr Lys Ala Lys  Ile Lys Leu Glu Gln  Gln Val Asp
    1025                 1030                 1035

Asp Leu  Glu Gly Ser Leu Glu  Gln Glu Lys Lys Leu  Arg Met Asp
    1040                 1045                 1050

Leu Glu  Arg Ala Lys Arg Lys  Leu Glu Gly Asp Leu  Lys Leu Ala
    1055                 1060                 1065

Gln Glu  Ser Ile Met Asp Ile  Glu Asn Glu Lys Gln  Gln Leu Asp
    1070                 1075                 1080

Glu Lys  Leu Lys Lys Lys Glu  Phe Glu Ile Ser Asn  Leu Gln Ser
    1085                 1090                 1095

Lys Ile  Glu Asp Glu Gln Ala  Leu Gly Ile Gln Leu  Gln Lys Lys
    1100                 1105                 1110

Ile Lys  Glu Leu Gln Ala Arg  Ile Glu Glu Leu Glu  Glu Glu Ile
    1115                 1120                 1125

Glu Ala  Glu Arg Ala Ser Arg  Ala Lys Ala Glu Lys  Gln Arg Ser
    1130                 1135                 1140

Asp Leu  Ser Arg Glu Leu Glu  Glu Ile Ser Glu Arg  Leu Glu Glu
    1145                 1150                 1155

Ala Gly  Gly Ala Thr Ser Ala  Gln Ile Glu Met Asn  Lys Lys Arg
    1160                 1165                 1170

Glu Ala  Glu Phe Gln Lys Met  Arg Arg Asp Leu Glu  Glu Ala Thr
    1175                 1180                 1185

Leu Gln  His Glu Ala Thr Ala  Ala Thr Leu Arg Lys  Lys His Ala
    1190                 1195                 1200

Asp Ser  Val Ala Glu Leu Gly  Glu Gln Ile Asp Asn  Leu Gln Arg
    1205                 1210                 1215

Val Lys  Gln Lys Leu Glu Lys  Glu Lys Ser Glu Met  Lys Met Glu
    1220                 1225                 1230

Ile Asp  Asp Leu Ala Ser Asn  Val Glu Thr Val Ser  Lys Ala Lys
    1235                 1240                 1245

Gly Asn  Leu Glu Lys Met Cys  Arg Thr Leu Glu Asp  Gln Leu Ser
    1250                 1255                 1260

Glu Leu  Lys Ser Lys Glu Glu  Glu Gln Gln Arg Leu  Ile Asn Asp
    1265                 1270                 1275

Leu Thr  Ala Gln Arg Gly Arg  Leu Gln Thr Glu Ser  Gly Glu Phe
    1280                 1285                 1290

Ser Arg  Gln Leu Asp Glu Lys  Glu Ala Leu Val Ser  Gln Leu Ser
    1295                 1300                 1305

Arg Gly  Lys Gln Ala Phe Thr  Gln Gln Ile Glu Glu  Leu Lys Arg
    1310                 1315                 1320

Gln Leu  Glu Glu Glu Ile Lys  Ala Lys Asn Ala Leu  Ala His Ala
    1325                 1330                 1335

Leu Gln  Ser Ser Arg His Asp  Cys Asp Leu Leu Arg  Glu Gln Tyr
```

```
    1340                1345                1350

Glu Glu  Glu Gln Glu Ser Lys  Ala Glu Leu Gln Arg  Ala Leu Ser
    1355                1360                1365

Lys Ala  Asn Thr Glu Val Ala  Gln Trp Arg Thr Lys  Tyr Glu Thr
    1370                1375                1380

Asp Ala  Ile Gln Arg Thr Glu  Glu Leu Glu Glu Ala  Lys Lys Lys
    1385                1390                1395

Leu Ala  Gln Arg Leu Gln Ala  Ala Glu Glu His Val  Glu Ala Val
    1400                1405                1410

Asn Ala  Lys Cys Ala Ser Leu  Glu Lys Thr Lys Gln  Arg Leu Gln
    1415                1420                1425

Asn Glu  Val Glu Asp Leu Met  Leu Asp Val Glu Arg  Thr Asn Ala
    1430                1435                1440

Ala Cys  Ala Ala Leu Asp Lys  Lys Gln Arg Asn Phe  Asp Lys Ile
    1445                1450                1455

Leu Ala  Glu Trp Lys Gln Lys  Cys Glu Glu Thr His  Ala Glu Leu
    1460                1465                1470

Glu Ala  Ser Gln Lys Glu Ala  Arg Ser Leu Gly Thr  Glu Leu Phe
    1475                1480                1485

Lys Ile  Lys Asn Ala Tyr Glu  Glu Ser Leu Asp Gln  Leu Glu Thr
    1490                1495                1500

Leu Lys  Arg Glu Asn Lys Asn  Leu Gln Gln Glu Ile  Ser Asp Leu
    1505                1510                1515

Thr Glu  Gln Ile Ala Glu Gly  Gly Lys Arg Ile His  Glu Leu Glu
    1520                1525                1530

Lys Ile  Lys Lys Gln Val Glu  Gln Glu Lys Cys Glu  Leu Gln Ala
    1535                1540                1545

Ala Leu  Glu Glu Ala Glu Ala  Ser Leu Glu His Glu  Glu Gly Lys
    1550                1555                1560

Ile Leu  Arg Ile Gln Leu Glu  Leu Asn Gln Val Lys  Ser Glu Val
    1565                1570                1575

Asp Arg  Lys Ile Ala Glu Lys  Asp Glu Glu Ile Asp  Gln Leu Lys
    1580                1585                1590

Arg Asn  His Ile Arg Ile Val  Glu Ser Met Gln Ser  Thr Leu Asp
    1595                1600                1605

Ala Glu  Ile Arg Ser Arg Asn  Asp Ala Ile Arg Leu  Lys Lys Lys
    1610                1615                1620

Met Glu  Gly Asp Leu Asn Glu  Met Glu Ile Gln Leu  Asn His Ala
    1625                1630                1635

Asn Arg  Met Ala Ala Glu Ala  Leu Arg Asn Tyr Arg  Asn Thr Gln
    1640                1645                1650

Gly Ile  Leu Lys Asp Thr Gln  Ile His Leu Asp Asp  Ala Leu Arg
    1655                1660                1665

Ser Gln  Glu Asp Leu Lys Glu  Gln Leu Ala Met Val  Glu Arg Arg
    1670                1675                1680

Ala Asn  Leu Leu Gln Ala Glu  Ile Glu Glu Leu Arg  Ala Thr Leu
    1685                1690                1695

Glu Gln  Thr Glu Arg Ser Arg  Lys Ile Ala Glu Gln  Glu Leu Leu
    1700                1705                1710

Asp Ala  Ser Glu Arg Val Gln  Leu Leu His Thr Gln  Asn Thr Ser
    1715                1720                1725

Leu Ile  Asn Thr Lys Lys Lys  Leu Glu Thr Asp Ile  Ser Gln Met
    1730                1735                1740
```

```
Gln Gly  Glu Met Glu Asp Ile  Leu Gln Glu Ala Arg  Asn Ala Glu
    1745                 1750                 1755

Glu Lys  Ala Lys Lys Ala Ile  Thr Asp Ala Ala Met  Met Ala Glu
    1760                 1765                 1770

Glu Leu  Lys Lys Glu Gln Asp  Thr Ser Ala His Leu  Glu Arg Met
    1775                 1780                 1785

Lys Lys  Asn Met Glu Gln Thr  Val Lys Asp Leu Gln  Leu Arg Leu
    1790                 1795                 1800

Asp Glu  Ala Glu Gln Leu Ala  Leu Lys Gly Gly Lys  Lys Gln Ile
    1805                 1810                 1815

Gln Lys  Leu Glu Ala Arg Val  Arg Glu Leu Glu Gly  Glu Val Glu
    1820                 1825                 1830

Ser Glu  Gln Lys Arg Asn Ala  Glu Ala Val Lys Gly  Leu Arg Lys
    1835                 1840                 1845

His Glu  Arg Arg Val Lys Glu  Leu Thr Tyr Gln Thr  Glu Glu Asp
    1850                 1855                 1860

Arg Lys  Asn Ile Leu Arg Leu  Gln Asp Leu Val Asp  Lys Leu Gln
    1865                 1870                 1875

Ala Lys  Val Lys Ser Tyr Lys  Arg Gln Ala Glu Glu  Ala Glu Glu
    1880                 1885                 1890

Gln Ser  Asn Thr Asn Leu Ala  Lys Phe Arg Lys Leu  Gln His Glu
    1895                 1900                 1905

Leu Glu  Glu Ala Glu Glu Arg  Ala Asp Ile Ala Glu  Ser Gln Val
    1910                 1915                 1920

Asn Lys  Leu Arg Val Lys Ser  Arg Glu Val His Thr  Lys Val Ile
    1925                 1930                 1935

Ser Glu  Glu
    1940
```

<210> SEQ ID NO 3
<211> LENGTH: 6016
<212> TYPE: DNA
<213> ORGANISM: Homo sapiens

<400> SEQUENCE: 3

```
atccttcctc aaaattcttg aagtagttgt ctgctttgag cctgccacct tcttcatctg     60

ataatacaag aggtatacct agtccagcac tgccatcaat aacctgcagc catgagttct    120

gactctgaga tggccatttt tggggaggct gctcctttcc tccgaaagtc tgaaaaggag    180

cgaattgaag ctcagaacaa gccttttgat gccaagacat cagtctttgt ggtggaccct    240

aaggagtcct acgtgaaagc aatagtgcag agcagggaag gggggaaggt gacagccaag    300

accgaagctg gagctactgt aactgtgaaa gaagaccaag tcttctccat gaaccctccc    360

aaatatgaca agatcgagga catggccatg atgactcacc tgcatgagcc tgctgtgctg    420

tataacctca aagagcgtta cgcagcctgg atgatctaca cctactcggg cctcttctgt    480

gtcaccgtca acccctacaa gtggctgccg gtgtacaacc ctgaggtggt gacagcctac    540

cgaggcaaaa agcgccagga ggccccaccc catatcttct ccatctctga caatgcctat    600

cagttcatgc taactgatcg tgaaaaccag tcaatcttga ttactggaga atctggtgca    660

gggaagactg tgaacacgaa gcgtgtcatc cagtactttg caacaattgc agttactgga    720

gagaagaaaa aagaggaacc tgcctctggc aaaatgcagg ggacccttga agatcaaatc    780

atcagtgcta acccccctact ggaagccttc ggcaatgcca agaccgtgag gaatgacaac    840
```

```
tcctctcgct ttggtaaatt catcaggatc cattttggtg ccacaggcaa actggcttct    900
gcagatattg aaacatatct gctagagaag tcccgagtta cttttcagct aaaggctgaa    960
agaagctacc acatatttta tcaaatcctg tccaataaga aaccagagct cattgaaatg   1020
cttctgatca ccaccaaccc atatgacttc gcatttgtca gccaagggga aattactgtg   1080
cccagcattg atgaccagga agagctgatg gccacagata gtgctgtgga catcctgggt   1140
ttcactgctg atgaaaaggt ggccatttac aagctcactg gagccgtgat gcattatggg   1200
aacatgaaat tcaagcaaaa gcaaagggaa gagcaggcag agccagatgg cacggaagtt   1260
gctgacaaag ctgcttatct gacaagtctg aactctgctg acctgctcaa atctctctgc   1320
tatcccagag tcaaggtcgg caatgagttc gtaaccaaag gccagactgt gcagcaggtg   1380
tacaacgcag tgggtgctct ggccaaagcc atctacgaga agatgttcct gtggatggtc   1440
acccgcatca accagcagct ggacaccaag cagcccaggc agtacttcat cggggtcttg   1500
gacattgctg gctttgagat ctttgatttc aacagcctgg agcagctgtg catcaacttc   1560
accaacgaga aactgcaaca gtttttcaac caccacatgt tcgtgctgga gcaggaagag   1620
tacaagaagg aaggcatcga gtgggagttc attgacttcg ggatggacct ggctgcctgc   1680
atcgagctca tcgagaagcc tatgggcatc ttctccatcc tagaagagga gtgcatgttc   1740
cccaaggcaa cagacacctc cttcaagaac aagctgtatg aacaacatct tggaaaatcc   1800
aacaacttcc agaagcccaa gcctgccaaa ggcaagcctg aggctcactt ctcactggtg   1860
cactatgccg gcaccgtgga ctacaacatc gccggctggc tggacaaaaa caaggacccc   1920
ctgaatgaga ctgtggtggg gctgtaccag aagtctgcaa tgaagactct ggctttcctc   1980
ttctctgggg cacaaactgc tgaagcagag ggtggtggtg gaaagaaagg tggcaaaaag   2040
aagggttctt ctttccagac agtgtcagct cttttcaggg agaatttgaa taagctgatg   2100
accaacttga ggagcactca cccccacttt gtgcggtgca tcatccccaa tgaaactaaa   2160
actcctggtg ccatggagca tgagcttgtc ctgcatcagc tgaggtgtaa cggtgtgctg   2220
gaaggcatcc gcatctgcag gaaaggcttc cccagcagaa tcctttatgc agacttcaaa   2280
cagagataca aggttctaaa tgcgagtgct atcccagagg gtcagttcat tgacagcaag   2340
aaggcttctg agaaacttct agggtctatt gaaattgacc acacccagta caaattcggt   2400
cataccaagg ttttcttcaa agctggcctg ctgggaactc tagaagaaat gcgagatgaa   2460
aagctagctc aactcatcac gcgcactcaa gccatatgca gggggttcct gatgagagtg   2520
gagttcagaa agatgatgga gaggagagag tccatcttct gcattcagta caacatccgt   2580
gctttcatga atgtgaagca ctggccctgg atgaagctgt atttcaagat caagcccctc   2640
ctcaagagtg cagagacaga gaaggagatg gccaacatga aggaagaatt tgagaaaacc   2700
aaagaagagc tggctaagac agaggcaaaa aggaaagaac tagaagaaaa gatggtgacg   2760
ctaatgcaag agaaaaatga cttacaactc caagttcaag ctgaagcaga tgccttggct   2820
gatgcagagg aaagatgtga tcagttgatt aaaaccaaaa tccaacttga ggccaaaatc   2880
aaagaggtaa ctgaaagagc tgaggatgag gaagagatca atgctgagct gacagccaag   2940
aagaggaaac tggaggatga atgttcagag ctcaagaaag acattgatga ccttgagctg   3000
acactggcca aggttgagaa ggagaaacat gccacagaga acaaggtgaa aaacctcaca   3060
gaagagatgg caggtctgga tgaaaccatt gctaagctga ccaaggagaa gaaggctctc   3120
caggaggccc accagcagac cctggatgac ctgcagatgg aggaggacaa agtcaacacc   3180
ctgaccaaag ctaaaaccaa gctagaacag caagtggacg atcttgaagg atctctggaa   3240
```

```
caagaaaaga aactttgcat ggacttagaa agagccaaga gaaaactgga gggtgaccta   3300
aaattggccc aagaatccac aatggataca gaaaatgaca aacagcaact taatgagaaa   3360
ctcaaaaaga aagagtttga aatgagcaat ctgcaaggca agattgaaga tgaacaagcc   3420
cttgcaatgc agctacaaaa gaagatcaaa gaattacagg cccgcattga ggagctggag   3480
gaggaaatcg aggcagagcg ggcctcccgg gccaaagcag aaaagcagcg ctctgacctc   3540
tcccgggagc tggaggagat cagtgagagg ctggaagaag ccggtggggc cacttcagcc   3600
cagattgagt tgaacaagaa gcgggaggct gagttccaga aaatgcgcag ggacctggaa   3660
gagtccaccc tgcagcacga agccacggca gctgctcttc ggaagaagca cgcagatagt   3720
gtggctgagc ttgggaagca gatcgacagc cttcagcggg tcaagcagaa gctggagaag   3780
gaaaagagtg agctgaagat ggagatcaat gaccttgcta gtaacatgga gactgtctcc   3840
aaagccaagg caaactttga gaaaatgtgc cgcaccctag aggaccagct tagtgaaata   3900
aaaacaaagg aagaagagca gcaacgctta ataaatgagt tgtcagccca gaaggcacgt   3960
ttacacacag aatcaggtga gttttcacga cagctagatg aaaaagatgc tatggtttct   4020
cagctatccc gaggcaaaca agcatttaca caacagattg aagaattaaa gaggcagcta   4080
gaagaggaga ctaaggccaa gagcactctg gcccatgccc tgcagtcagc ccgccatgac   4140
tgtgacctgc tgcgggaaca gtatgaggag gagcaggaag ccaaggctga gctgcagagg   4200
ggaatgtcca aggccaacag tgaggttgcc cagtggagga ccaagtacga gacggacgcc   4260
atccagcgca cagaggagct ggaggaggcc aagaagaagc tagcccagcg tctgcaggat   4320
gcagaagaac atgtagaagc tgtgaattcc aaatgtgctt ctcttgaaaa gacaaagcag   4380
aggctacaga atgaagtaga ggacctcatg attgatgtgg aacgatctaa tgctgcctgc   4440
atagctctcg ataagaagca aagaaacttt gacaaggttc tggcagaatg gaaacagaag   4500
tatgaggaaa ctcaggctga acttgaggcc tcccagaagg agtcgcgttc tctcagcact   4560
gagctgttca aggtgaagaa tgcctacgag gaatccctgg atcatcttga aactctaaag   4620
cgagagaata agaacttaca acaggagatt tctgacctga cagagcaaat tgcagagggt   4680
ggaaagcata tccatgaact ggagaaagta aagaaacaac ttgatcatga gaagagtgaa   4740
ctacagactt ccctagagga agcagaggca tctcttgagc atgaagaagg caaaattctt   4800
cgcattcaac ttgagctaaa tcaggtgaaa tctgagattg accgaaaaat tgctgaaaaa   4860
gatgaagaac tcgatcagct aaagaggaac catctcagag ttgtggagtc aatgcagagt   4920
acactggatg ctgagatcag gagcagaaat gatgctctga ggatcaagaa gaagatggag   4980
ggagatctta atgaaatgga aatccagctg aaccatgcca accgccaggc tgctgaggca   5040
ctaaggaatc ttagaaacac acaaggaata ctgaaggaca ctcagctaca tttggatgat   5100
gccatcagag gccaagatga ccttaaggaa caattggcaa tggttgagcg cagagctaac   5160
ctgatgcagg ctgaagttga agagctcagg gcatccctgg aacggactga gagaggcagg   5220
aaaatggcag agcaagagct tctggatgcc agtgaacgtg tgcaacttct gcacactcag   5280
aacaccagcc tgatcaacac caagaagaag ctggaaacag acatttccca aatccaggga   5340
gagatggagg acatcgtcca ggaagcccgc aatgcagagg agaaggccaa gaaggccatc   5400
actgatgctg ccatgatggc tgaggagctg aagaaggaac aggacaccag cgcccacctg   5460
gagcggatga agaagaacat ggagcagacc gtgaaggatc tgcagctccg tctgggtgag   5520
gctgagcagc tggcgctgaa gggtgggaag aagcagatcc agaaactgga ggccagggtg   5580
```

```
agagagcttg aaagtgaggt ggaaagtgaa cagaagcaca atgttgaggc tgtcaagggt   5640

cttcgcaaac atgagagaag agtgaaggaa ctcacttacc agactgagga ggaccgcaag   5700

aatattctca ggctgcagga cttggtggac aaattgcaaa ccaaagtcaa agcttacaag   5760

agacaagctg aagaggctga ggaacaatcc aatgtcaacc ttgccaagtt ccgcaagctc   5820

cagcacgagc tggaggaggc cgaggaacgg gctgacattg ctgagtccca agtcaacaag   5880

ctgagagtga agagtcggga ggttcacaca aaagtcataa gtgaagagta attcattcta   5940

atgaaagaaa atgtgaccaa agaaatgcac gaaatgtgaa gttctttgtc actgtcctgt   6000

atatcaagga aataaa                                                   6016


<210> SEQ ID NO 4
<211> LENGTH: 1939
<212> TYPE: PRT
<213> ORGANISM: Homo sapiens

<400> SEQUENCE: 4

Met Ser Ser Asp Ser Glu Met Ala Ile Phe Gly Glu Ala Ala Pro Phe
1               5                   10                  15

Leu Arg Lys Ser Glu Lys Glu Arg Ile Glu Ala Gln Asn Lys Pro Phe
            20                  25                  30

Asp Ala Lys Thr Ser Val Phe Val Val Asp Pro Lys Glu Ser Tyr Val
        35                  40                  45

Lys Ala Ile Val Gln Ser Arg Glu Gly Gly Lys Val Thr Ala Lys Thr
    50                  55                  60

Glu Ala Gly Ala Thr Val Thr Val Lys Glu Asp Gln Val Phe Ser Met
65                  70                  75                  80

Asn Pro Pro Lys Tyr Asp Lys Ile Glu Asp Met Ala Met Met Thr His
                85                  90                  95

Leu His Glu Pro Ala Val Leu Tyr Asn Leu Lys Glu Arg Tyr Ala Ala
            100                 105                 110

Trp Met Ile Tyr Thr Tyr Ser Gly Leu Phe Cys Val Thr Val Asn Pro
        115                 120                 125

Tyr Lys Trp Leu Pro Val Tyr Asn Pro Glu Val Val Thr Ala Tyr Arg
    130                 135                 140

Gly Lys Lys Arg Gln Glu Ala Pro Pro His Ile Phe Ser Ile Ser Asp
145                 150                 155                 160

Asn Ala Tyr Gln Phe Met Leu Thr Asp Arg Glu Asn Gln Ser Ile Leu
                165                 170                 175

Ile Thr Gly Glu Ser Gly Ala Gly Lys Thr Val Asn Thr Lys Arg Val
            180                 185                 190

Ile Gln Tyr Phe Ala Thr Ile Ala Val Thr Gly Glu Lys Lys Lys Glu
        195                 200                 205

Glu Pro Ala Ser Gly Lys Met Gln Gly Thr Leu Glu Asp Gln Ile Ile
    210                 215                 220

Ser Ala Asn Pro Leu Leu Glu Ala Phe Gly Asn Ala Lys Thr Val Arg
225                 230                 235                 240

Asn Asp Asn Ser Ser Arg Phe Gly Lys Phe Ile Arg Ile His Phe Gly
                245                 250                 255

Ala Thr Gly Lys Leu Ala Ser Ala Asp Ile Glu Thr Tyr Leu Leu Glu
            260                 265                 270

Lys Ser Arg Val Thr Phe Gln Leu Lys Ala Glu Arg Ser Tyr His Ile
        275                 280                 285

Phe Tyr Gln Ile Leu Ser Asn Lys Lys Pro Glu Leu Ile Glu Met Leu
```

```
    290                 295                 300

Leu Ile Thr Thr Asn Pro Tyr Asp Phe Ala Phe Val Ser Gln Gly Glu
305                 310                 315                 320

Ile Thr Val Pro Ser Ile Asp Asp Gln Glu Glu Leu Met Ala Thr Asp
                325                 330                 335

Ser Ala Val Asp Ile Leu Gly Phe Thr Ala Asp Glu Lys Val Ala Ile
            340                 345                 350

Tyr Lys Leu Thr Gly Ala Val Met His Tyr Gly Asn Met Lys Phe Lys
        355                 360                 365

Gln Lys Gln Arg Glu Glu Gln Ala Glu Pro Asp Gly Thr Glu Val Ala
    370                 375                 380

Asp Lys Ala Ala Tyr Leu Thr Ser Leu Asn Ser Ala Asp Leu Leu Lys
385                 390                 395                 400

Ser Leu Cys Tyr Pro Arg Val Lys Val Gly Asn Glu Phe Val Thr Lys
                405                 410                 415

Gly Gln Thr Val Gln Gln Val Tyr Asn Ala Val Gly Ala Leu Ala Lys
            420                 425                 430

Ala Ile Tyr Glu Lys Met Phe Leu Trp Met Val Thr Arg Ile Asn Gln
        435                 440                 445

Gln Leu Asp Thr Lys Gln Pro Arg Gln Tyr Phe Ile Gly Val Leu Asp
    450                 455                 460

Ile Ala Gly Phe Glu Ile Phe Asp Phe Asn Ser Leu Glu Gln Leu Cys
465                 470                 475                 480

Ile Asn Phe Thr Asn Glu Lys Leu Gln Gln Phe Phe Asn His His Met
                485                 490                 495

Phe Val Leu Glu Gln Glu Glu Tyr Lys Lys Glu Gly Ile Glu Trp Glu
            500                 505                 510

Phe Ile Asp Phe Gly Met Asp Leu Ala Ala Cys Ile Glu Leu Ile Glu
        515                 520                 525

Lys Pro Met Gly Ile Phe Ser Ile Leu Glu Glu Glu Cys Met Phe Pro
    530                 535                 540

Lys Ala Thr Asp Thr Ser Phe Lys Asn Lys Leu Tyr Glu Gln His Leu
545                 550                 555                 560

Gly Lys Ser Asn Asn Phe Gln Lys Pro Lys Pro Ala Lys Gly Lys Pro
                565                 570                 575

Glu Ala His Phe Ser Leu Val His Tyr Ala Gly Thr Val Asp Tyr Asn
            580                 585                 590

Ile Ala Gly Trp Leu Asp Lys Asn Lys Asp Pro Leu Asn Glu Thr Val
        595                 600                 605

Val Gly Leu Tyr Gln Lys Ser Ala Met Lys Thr Leu Ala Phe Leu Phe
    610                 615                 620

Ser Gly Ala Gln Thr Ala Glu Ala Glu Gly Gly Gly Gly Lys Lys Gly
625                 630                 635                 640

Gly Lys Lys Lys Gly Ser Ser Phe Gln Thr Val Ser Ala Leu Phe Arg
                645                 650                 655

Glu Asn Leu Asn Lys Leu Met Thr Asn Leu Arg Ser Thr His Pro His
            660                 665                 670

Phe Val Arg Cys Ile Ile Pro Asn Glu Thr Lys Thr Pro Gly Ala Met
        675                 680                 685

Glu His Glu Leu Val Leu His Gln Leu Arg Cys Asn Gly Val Leu Glu
    690                 695                 700

Gly Ile Arg Ile Cys Arg Lys Gly Phe Pro Ser Arg Ile Leu Tyr Ala
705                 710                 715                 720
```

```
Asp Phe Lys Gln Arg Tyr Lys Val Leu Asn Ala Ser Ala Ile Pro Glu
                725                 730                 735

Gly Gln Phe Ile Asp Ser Lys Lys Ala Ser Glu Lys Leu Leu Gly Ser
            740                 745                 750

Ile Glu Ile Asp His Thr Gln Tyr Lys Phe Gly His Thr Lys Val Phe
        755                 760                 765

Phe Lys Ala Gly Leu Leu Gly Thr Leu Glu Glu Met Arg Asp Glu Lys
    770                 775                 780

Leu Ala Gln Leu Ile Thr Arg Thr Gln Ala Ile Cys Arg Gly Phe Leu
785                 790                 795                 800

Met Arg Val Glu Phe Arg Lys Met Met Glu Arg Arg Glu Ser Ile Phe
                805                 810                 815

Cys Ile Gln Tyr Asn Ile Arg Ala Phe Met Asn Val Lys His Trp Pro
            820                 825                 830

Trp Met Lys Leu Tyr Phe Lys Ile Lys Pro Leu Leu Lys Ser Ala Glu
        835                 840                 845

Thr Glu Lys Glu Met Ala Asn Met Lys Glu Glu Phe Glu Lys Thr Lys
    850                 855                 860

Glu Glu Leu Ala Lys Thr Glu Ala Lys Arg Lys Glu Leu Glu Glu Lys
865                 870                 875                 880

Met Val Thr Leu Met Gln Glu Lys Asn Asp Leu Gln Leu Gln Val Gln
                885                 890                 895

Ala Glu Ala Asp Ala Leu Ala Asp Ala Glu Glu Arg Cys Asp Gln Leu
            900                 905                 910

Ile Lys Thr Lys Ile Gln Leu Glu Ala Lys Ile Lys Glu Val Thr Glu
        915                 920                 925

Arg Ala Glu Asp Glu Glu Glu Ile Asn Ala Glu Leu Thr Ala Lys Lys
    930                 935                 940

Arg Lys Leu Glu Asp Glu Cys Ser Glu Leu Lys Lys Asp Ile Asp Asp
945                 950                 955                 960

Leu Glu Leu Thr Leu Ala Lys Val Glu Lys Glu Lys His Ala Thr Glu
                965                 970                 975

Asn Lys Val Lys Asn Leu Thr Glu Glu Met Ala Gly Leu Asp Glu Thr
            980                 985                 990

Ile Ala Lys Leu Thr Lys Glu Lys  Lys Ala Leu Gln Glu  Ala His Gln
        995                 1000                 1005

Gln Thr  Leu Asp Asp Leu Gln  Met Glu Glu Asp Lys  Val Asn Thr
    1010                 1015                 1020

Leu Thr  Lys Ala Lys Thr Lys  Leu Glu Gln Gln Val  Asp Asp Leu
    1025                 1030                 1035

Glu Gly  Ser Leu Glu Gln Glu  Lys Lys Leu Cys Met  Asp Leu Glu
    1040                 1045                 1050

Arg Ala  Lys Arg Lys Leu Glu  Gly Asp Leu Lys Leu  Ala Gln Glu
    1055                 1060                 1065

Ser Thr  Met Asp Thr Glu Asn  Asp Lys Gln Gln Leu  Asn Glu Lys
    1070                 1075                 1080

Leu Lys  Lys Lys Glu Phe Glu  Met Ser Asn Leu Gln  Gly Lys Ile
    1085                 1090                 1095

Glu Asp  Glu Gln Ala Leu Ala  Met Gln Leu Gln Lys  Lys Ile Lys
    1100                 1105                 1110

Glu Leu  Gln Ala Arg Ile Glu  Glu Leu Glu Glu Glu  Ile Glu Ala
    1115                 1120                 1125
```

```
Glu Arg  Ala Ser Arg Ala Lys  Ala Glu Lys Gln Arg  Ser Asp Leu
    1130                 1135                 1140

Ser Arg  Glu Leu Glu Glu Ile  Ser Glu Arg Leu Glu  Glu Ala Gly
    1145                 1150                 1155

Gly Ala  Thr Ser Ala Gln Ile  Glu Leu Asn Lys Lys  Arg Glu Ala
    1160                 1165                 1170

Glu Phe  Gln Lys Met Arg Arg  Asp Leu Glu Glu Ser  Thr Leu Gln
    1175                 1180                 1185

His Glu  Ala Thr Ala Ala Ala  Leu Arg Lys Lys His  Ala Asp Ser
    1190                 1195                 1200

Val Ala  Glu Leu Gly Lys Gln  Ile Asp Ser Leu Gln  Arg Val Lys
    1205                 1210                 1215

Gln Lys  Leu Glu Lys Glu Lys  Ser Glu Leu Lys Met  Glu Ile Asn
    1220                 1225                 1230

Asp Leu  Ala Ser Asn Met Glu  Thr Val Ser Lys Ala  Lys Ala Asn
    1235                 1240                 1245

Phe Glu  Lys Met Cys Arg Thr  Leu Glu Asp Gln Leu  Ser Glu Ile
    1250                 1255                 1260

Lys Thr  Lys Glu Glu Glu Gln  Gln Arg Leu Ile Asn  Glu Leu Ser
    1265                 1270                 1275

Ala Gln  Lys Ala Arg Leu His  Thr Glu Ser Gly Glu  Phe Ser Arg
    1280                 1285                 1290

Gln Leu  Asp Glu Lys Asp Ala  Met Val Ser Gln Leu  Ser Arg Gly
    1295                 1300                 1305

Lys Gln  Ala Phe Thr Gln Gln  Ile Glu Glu Leu Lys  Arg Gln Leu
    1310                 1315                 1320

Glu Glu  Glu Thr Lys Ala Lys  Ser Thr Leu Ala His  Ala Leu Gln
    1325                 1330                 1335

Ser Ala  Arg His Asp Cys Asp  Leu Leu Arg Glu Gln  Tyr Glu Glu
    1340                 1345                 1350

Glu Gln  Glu Ala Lys Ala Glu  Leu Gln Arg Gly Met  Ser Lys Ala
    1355                 1360                 1365

Asn Ser  Glu Val Ala Gln Trp  Arg Thr Lys Tyr Glu  Thr Asp Ala
    1370                 1375                 1380

Ile Gln  Arg Thr Glu Glu Leu  Glu Glu Ala Lys Lys  Lys Leu Ala
    1385                 1390                 1395

Gln Arg  Leu Gln Asp Ala Glu  Glu His Val Glu Ala  Val Asn Ser
    1400                 1405                 1410

Lys Cys  Ala Ser Leu Glu Lys  Thr Lys Gln Arg Leu  Gln Asn Glu
    1415                 1420                 1425

Val Glu  Asp Leu Met Ile Asp  Val Glu Arg Ser Asn  Ala Ala Cys
    1430                 1435                 1440

Ile Ala  Leu Asp Lys Lys Gln  Arg Asn Phe Asp Lys  Val Leu Ala
    1445                 1450                 1455

Glu Trp  Lys Gln Lys Tyr Glu  Glu Thr Gln Ala Glu  Leu Glu Ala
    1460                 1465                 1470

Ser Gln  Lys Glu Ser Arg Ser  Leu Ser Thr Glu Leu  Phe Lys Val
    1475                 1480                 1485

Lys Asn  Ala Tyr Glu Glu Ser  Leu Asp His Leu Glu  Thr Leu Lys
    1490                 1495                 1500

Arg Glu  Asn Lys Asn Leu Gln  Gln Glu Ile Ser Asp  Leu Thr Glu
    1505                 1510                 1515

Gln Ile  Ala Glu Gly Gly Lys  His Ile His Glu Leu  Glu Lys Val
```

```
    1520                1525                1530

Lys Lys  Gln Leu Asp His Glu  Lys Ser Glu Leu Gln  Thr Ser Leu
    1535                1540                1545

Glu Glu  Ala Glu Ala Ser Leu  Glu His Glu Glu Gly  Lys Ile Leu
    1550                1555                1560

Arg Ile  Gln Leu Glu Leu Asn  Gln Val Lys Ser Glu  Ile Asp Arg
    1565                1570                1575

Lys Ile  Ala Glu Lys Asp Glu  Glu Leu Asp Gln Leu  Lys Arg Asn
    1580                1585                1590

His Leu  Arg Val Val Glu Ser  Met Gln Ser Thr Leu  Asp Ala Glu
    1595                1600                1605

Ile Arg  Ser Arg Asn Asp Ala  Leu Arg Ile Lys Lys  Lys Met Glu
    1610                1615                1620

Gly Asp  Leu Asn Glu Met Glu  Ile Gln Leu Asn His  Ala Asn Arg
    1625                1630                1635

Gln Ala  Ala Glu Ala Leu Arg  Asn Leu Arg Asn Thr  Gln Gly Ile
    1640                1645                1650

Leu Lys  Asp Thr Gln Leu His  Leu Asp Asp Ala Ile  Arg Gly Gln
    1655                1660                1665

Asp Asp  Leu Lys Glu Gln Leu  Ala Met Val Glu Arg  Arg Ala Asn
    1670                1675                1680

Leu Met  Gln Ala Glu Val Glu  Glu Leu Arg Ala Ser  Leu Glu Arg
    1685                1690                1695

Thr Glu  Arg Gly Arg Lys Met  Ala Glu Gln Glu Leu  Leu Asp Ala
    1700                1705                1710

Ser Glu  Arg Val Gln Leu Leu  His Thr Gln Asn Thr  Ser Leu Ile
    1715                1720                1725

Asn Thr  Lys Lys Lys Leu Glu  Thr Asp Ile Ser Gln  Ile Gln Gly
    1730                1735                1740

Glu Met  Glu Asp Ile Val Gln  Glu Ala Arg Asn Ala  Glu Glu Lys
    1745                1750                1755

Ala Lys  Lys Ala Ile Thr Asp  Ala Ala Met Met Ala  Glu Glu Leu
    1760                1765                1770

Lys Lys  Glu Gln Asp Thr Ser  Ala His Leu Glu Arg  Met Lys Lys
    1775                1780                1785

Asn Met  Glu Gln Thr Val Lys  Asp Leu Gln Leu Arg  Leu Gly Glu
    1790                1795                1800

Ala Glu  Gln Leu Ala Leu Lys  Gly Gly Lys Lys Gln  Ile Gln Lys
    1805                1810                1815

Leu Glu  Ala Arg Val Arg Glu  Leu Glu Ser Glu Val  Glu Ser Glu
    1820                1825                1830

Gln Lys  His Asn Val Glu Ala  Val Lys Gly Leu Arg  Lys His Glu
    1835                1840                1845

Arg Arg  Val Lys Glu Leu Thr  Tyr Gln Thr Glu Glu  Asp Arg Lys
    1850                1855                1860

Asn Ile  Leu Arg Leu Gln Asp  Leu Val Asp Lys Leu  Gln Thr Lys
    1865                1870                1875

Val Lys  Ala Tyr Lys Arg Gln  Ala Glu Glu Ala Glu  Glu Gln Ser
    1880                1885                1890

Asn Val  Asn Leu Ala Lys Phe  Arg Lys Leu Gln His  Glu Leu Glu
    1895                1900                1905

Glu Ala  Glu Glu Arg Ala Asp  Ile Ala Glu Ser Gln  Val Asn Lys
    1910                1915                1920
```

Leu Arg Val Lys Ser Arg Glu Val His Thr Lys Val Ile Ser Glu
    1925                1930                1935

Glu

<210> SEQ ID NO 5
<211> LENGTH: 5925
<212> TYPE: DNA
<213> ORGANISM: Homo sapiens

<400> SEQUENCE: 5
atgagttctg actctgagat ggccattttt ggggaggctg ctcctttcct ccgaaagtct 60
gaaagggagc gaattgaagc ccagaacaag ccttttgatg ccaagacatc agtctttgtg 120
gtggacccta aggagtcctt tgtgaaagca acagtgcaga gcagggaagg ggggaaggtg 180
acagctaaga ccgaagctgg agctactgta acagtgaaag atgaccaagt cttccccatg 240
aaccctccca aatatgacaa gatcgaggac atggccatga tgactcatct acacgagcct 300
gctgtgctgt acaacctcaa agagcgctac gcagcctgga tgatctacac ctactcaggc 360
ttgttctgtg tcactgtcaa cccctacaag tggttgccag tgtataatgc agaagtggtg 420
acagcctacc gaggcaaaaa gcgccaggaa gccccaccc acatcttctc catctctgac 480
aatgcctatc agttcatgct gactgatcgg gagaatcagt ctatcttgat caccggagaa 540
tctggcgcag ggaagactgt gaacaccaag cgtgtcatcc agtactttgc aacaattgca 600
gttactgggg agaagaagaa ggaagaagtt acttctggca aaatgcaggg gactctggaa 660
gatcaaatca tcagtgccaa cccctactg gaggcctttg gcaacgccaa gaccgtgagg 720
aatgacaact cctctcgctt tggtaaattc atcaggatcc acttcggtac cacagggaaa 780
ctggcttctg ctgatattga aacatatctt ctggagaagt ctagagttac tttccagcta 840
aaggctgaaa gaagctatca tatttttat cagatcatgt ctaacaagaa gccagatcta 900
attgaaatgc tcctgatcac caccaaccca tacgattatg ccttcgtcag tcaaggggag 960
atcacagtgc ccagcattga tgaccaagaa gagttgatgg ctacagatag tgccattgaa 1020
attctgggct ttacttcaga tgaaagagtg tccatctata agctcacagg ggctgtgatg 1080
cattatggga acatgaaatt caagcaaaag cagcgtgagg agcaagctga gccagatggc 1140
actgaagttg ctgacaaggc agcctatctc caaaatctga actctgcaga tctgctcaaa 1200
gccctctgct accctagggt caaggtcggc aatgagtatg tcaccaaagg tcaaactgtg 1260
cagcaggtgt acaatgcagt gggtgctctg gccaaagctg tctacgataa gatgttcttg 1320
tggatggtca cccgcatcaa ccagcagctg gacaccaagc agcccaggca gtacttcatt 1380
ggggtcttgg acattgctgg ctttgagatc tttgatttca acagcctgga gcagctgtgc 1440
atcaacttca ccaatgagaa actgcaacag tttttcaacc accacatgtt cgtgctggag 1500
caggaggagt acaagaagga aggcattgag tggacgttca ttgactttgg gatggacctg 1560
gctgcctgca tcgagctcat cgagaagcct atgggcatct tctccatcct ggaagaggag 1620
tgcatgttcc ccaaggcgac agacacctcc ttcaagaaca agctgtatga acaacatctt 1680
ggaaaatcca ataacttcca gaagcccaag cctgccaaag gcaagcctga ggcccacttc 1740
tctttgattc actatgctgg caccgtggac tacaacattg ccggctggct tgacaagaac 1800
aaggaccccc tgaatgagac tgtggtgggg ctgtaccaga agtctgcaat gaagactctg 1860
gctctcctct ttgttggggc aacgggagcg gaagcagagg ctggcggtgg aaagaaaggt 1920
ggtaagaaga agggttcttc tttccagact gtgtcggctc tcttcaggga gaatttgaat 1980

```
aagctgatga ccaacttgag gagcactcac ccccactttg tgcggtgcat catccccaat   2040
gaaactaaaa ctcctggtgc catggagcat gagcttgtcc tgcatcagct gaggtgtaac   2100
ggtgtgctgg aaggcatccg catctgcagg aaaggcttcc caagcagaat cctttatgca   2160
gacttcaaac agagatacaa ggtgttaaat gcaagtgcta tccctgaagg acaattcatc   2220
gatagcaaga aggcttcaga gaagctcctg gggtccattg acattgacca cacccagtat   2280
aaatttggtc acaccaaggt ctttttcaaa gctggtcttc tggggctcct agaggagatg   2340
cgagatgaga agctggccca gctgattacc cgaacccagg ccatgtgcag agggttcttg   2400
gcaagagtgg agtaccagaa aatggtggaa agaagagagt ccatcttctg catccagtac   2460
aatgtccgtg ccttcatgaa tgtcaagcac tggccctgga tgaagctgta tttcaagatc   2520
aaacccctcc tcaaaagtgc agagacagag aaggagatgg ccaacatgaa ggaagaattt   2580
gagaaaacca aagaagagct ggctaagacc gaggcaaaaa ggaaagagct ggaagaaaaa   2640
atggtgactc tgatgcaaga aaaaaatgac ttgcaactcc aggttcaagc tgaagctgac   2700
agcttggctg atgcagagga aaggtgtgac cagctaatca aaaccaaaat ccagctagaa   2760
gccaaaatca aagaggtgac tgagagagct gaggatgagg aagagatcaa tgctgagctg   2820
acagccaaga agaggaaact ggaggatgaa tgttcagaac tcaagaaaga cattgatgac   2880
cttgagctga cactggccaa ggttgagaag gagaaacatg ccacagaaaa caaggtgaaa   2940
aacctcacag aagagatggc gggtctggat gaaaccattg ctaagctgac caaggagaag   3000
aaggctctcc aggaggccca ccagcagacc ctggatgacc tgcaggcaga ggaggacaaa   3060
gtcaacaccc tgaccaaagc taaaatcaaa cttgaacaac aagtggatga tcttgaagga   3120
tctttggaac aagaaaagaa aatccggatg gatctagaaa gagcaaagag aaaactagag   3180
ggagacctaa aattggctca agaatccgca atggatatag aaaatgacaa acaacaactt   3240
gatgaaaagc ttaaaaagaa agagtttgaa atgagcggtc tgcaaagcaa gattgaagat   3300
gaacaagccc ttggtatgca gctgcagaag aaaatcaagg agttacaagc ccgcattgag   3360
gagctggagg aggaaatcga ggcagagcgg gcctcccggg ccaaagcaga gaagcagcgc   3420
tctgatctct cccgggagct ggaggagatc agtgagaggc tggaagaagc cggtggggcc   3480
acctcggccc agattgagat gaacaagaag cgggaagctg agttccagaa aatgcgcagg   3540
gacctggagg aggccaccct acagcatgag gccacggcgg ccaccctgag gaagaagcat   3600
gcagatagtg tggccgagct tggggagcag attgacaacc tgcagcgagt gaagcagaag   3660
ctggagaagg agaagagtga gatgaagatg gagatcgatg accttgctag taacatggag   3720
actgtctcca aagccaaggg aaaccttgaa aagatgtgcc gcgctctaga agatcaactg   3780
agtgaaatta agaccaagga agaggagcag cagcggctga tcaatgacct cacagcacag   3840
agagcgcgcc tgcaaacaga atcaggtgaa tattcacgcc agctagatga aaaggacaca   3900
ctagtttcac agctctcgag gggcaaacaa gcctttactc aacagattga ggaactgaaa   3960
aggcaacttg aagaggagat aaaggccaag agtgccctgg cacatgccct gcagtcctcc   4020
cgccatgact gtgacctgct gcgggaacag tatgaggagg agcaggaagc caaggccgag   4080
ctacagagag caatgtccaa ggccaacagt gaggttgccc agtggaggac caaatatgag   4140
acagatgcca tccagcgcac agaggagctg gaggaggcca agaagaagct ggctcagcgt   4200
ctgcaggatg ctgaggaaca tgtagaagct gtgaatgcca aatgtgcttc ccttgagaag   4260
acgaagcaga ggctccagaa tgaagttgag gacctcatga ttgatgttga gaggacaaat   4320
```

```
gctgcctgtg ccgccctgga caaaaagcaa aggaactttg ataagatcct ggcagaatgg   4380
aaacagaagt gtgaagaaac tcatgctgaa cttgaagctt ctcaaaagga atcccgctca   4440
ctcagcacag aactatttaa gattaagaat gcttatgagg aatctttaga ccaacttgaa   4500
accttgaaac gggaaaataa gaatctgcag caggagattt ctgatctcac tgaacagatt   4560
gcagaaggag gaaagcgcat ccatgaactg gaaaaaataa agaagcaagt tgagcaagaa   4620
aagtctgaac ttcaggctgc cttagaggag gcagaggcat ctcttgaaca tgaagaggga   4680
aagatcctgc gcatccagct tgagttgaac caagtcaagt ctgaggttga taggaaaatt   4740
gctgaaaaag atgaggaaat tgaccagatg aagagaaacc acattagaat cgtggagtcc   4800
atgcagagca cactggatgc tgagatcagg agcaggaatg atgccattag gctcaagaag   4860
aagatggagg gagacctcaa tgaaatggaa atccagctga accatgccaa ccgcatggct   4920
gctgaggccc tgaggaacta taggaacacc caagccatcc tcaaggatac ccagctccac   4980
ctagatgatg ctctccggag ccaagaggac ctgaaggaac agctggctat ggtggagcgc   5040
agagccaacc tgctgcaggc tgagatcgag gaactacgag ccactctgga acagacggag   5100
aggagcagga aaatcgcaga acaggagctc ctggatgcca gtgaacgtgt tcagctcctg   5160
cacacccaga acaccagcct gatcaacacc aagaagaagc tggagacaga catttcccaa   5220
atccagggag agatggaaga catcatccag gaagcccgca atgcagaaga gaaggccaag   5280
aaggccatca ctgatgctgc catgatggct gaggagctga agaaggaaca ggacaccagc   5340
gcccatctgg agcggatgaa gaagaacttg gaacagacgg tgaaggacct gcagcatcgt   5400
ctggatgagg ctgagcagct ggccctgaag ggtgggaaga agcagatcca gaaactggag   5460
gccagggttc gtgaacttga aggtgaagtt gaaagtgaac agaagcgcaa tgttgaagct   5520
gtcaagggtc tacgcaaaca tgagagaaaa gtgaaggaac tcacttacca aactgaggaa   5580
gaccgcaaga atattctcag gctgcaggac ctggtggaca agctgcaagc aaaggtgaaa   5640
tcctacaaga gacaagctga agaagcggag gaacaatcca acgtcaacct ctccaaattc   5700
cggaggatcc agcacgagct ggaggaggcc gaggaaaggg ctgacattgc tgagtcccag   5760
gtcaacaagc tgagggtgaa gagcagggag gttcacacaa aaatcataag tgaagagtaa   5820
tttatctaac tgctgaaagg tgaccaaaga aatgcacaaa atgtgaaaat ctttgtcact   5880
ccatttgta cttatgactt ttggagataa aaaatttatc tgcca                   5925
```

<210> SEQ ID NO 6
<211> LENGTH: 1939
<212> TYPE: PRT
<213> ORGANISM: Homo sapiens

<400> SEQUENCE: 6

```
Met Ser Ser Asp Ser Glu Met Ala Ile Phe Gly Glu Ala Ala Pro Phe
1               5                   10                  15

Leu Arg Lys Ser Glu Arg Glu Arg Ile Glu Ala Gln Asn Lys Pro Phe
            20                  25                  30

Asp Ala Lys Thr Ser Val Phe Val Val Asp Pro Lys Glu Ser Phe Val
        35                  40                  45

Lys Ala Thr Val Gln Ser Arg Glu Gly Gly Lys Val Thr Ala Lys Thr
    50                  55                  60

Glu Ala Gly Ala Thr Val Thr Val Lys Asp Asp Gln Val Phe Pro Met
65                  70                  75                  80

Asn Pro Pro Lys Tyr Asp Lys Ile Glu Asp Met Ala Met Met Thr His
                85                  90                  95
```

```
Leu His Glu Pro Ala Val Leu Tyr Asn Leu Lys Glu Arg Tyr Ala Ala
            100                 105                 110

Trp Met Ile Tyr Thr Tyr Ser Gly Leu Phe Cys Val Thr Val Asn Pro
        115                 120                 125

Tyr Lys Trp Leu Pro Val Tyr Asn Ala Glu Val Val Thr Ala Tyr Arg
    130                 135                 140

Gly Lys Lys Arg Gln Glu Ala Pro Pro His Ile Phe Ser Ile Ser Asp
145                 150                 155                 160

Asn Ala Tyr Gln Phe Met Leu Thr Asp Arg Glu Asn Gln Ser Ile Leu
                165                 170                 175

Ile Thr Gly Glu Ser Gly Ala Gly Lys Thr Val Asn Thr Lys Arg Val
            180                 185                 190

Ile Gln Tyr Phe Ala Thr Ile Ala Val Thr Gly Glu Lys Lys Lys Glu
        195                 200                 205

Glu Val Thr Ser Gly Lys Met Gln Gly Thr Leu Glu Asp Gln Ile Ile
    210                 215                 220

Ser Ala Asn Pro Leu Leu Glu Ala Phe Gly Asn Ala Lys Thr Val Arg
225                 230                 235                 240

Asn Asp Asn Ser Ser Arg Phe Gly Lys Phe Ile Arg Ile His Phe Gly
                245                 250                 255

Thr Thr Gly Lys Leu Ala Ser Ala Asp Ile Glu Thr Tyr Leu Leu Glu
            260                 265                 270

Lys Ser Arg Val Thr Phe Gln Leu Lys Ala Glu Arg Ser Tyr His Ile
        275                 280                 285

Phe Tyr Gln Ile Met Ser Asn Lys Lys Pro Asp Leu Ile Glu Met Leu
    290                 295                 300

Leu Ile Thr Thr Asn Pro Tyr Asp Tyr Ala Phe Val Ser Gln Gly Glu
305                 310                 315                 320

Ile Thr Val Pro Ser Ile Asp Asp Gln Glu Glu Leu Met Ala Thr Asp
                325                 330                 335

Ser Ala Ile Glu Ile Leu Gly Phe Thr Ser Asp Glu Arg Val Ser Ile
            340                 345                 350

Tyr Lys Leu Thr Gly Ala Val Met His Tyr Gly Asn Met Lys Phe Lys
        355                 360                 365

Gln Lys Gln Arg Glu Glu Gln Ala Glu Pro Asp Gly Thr Glu Val Ala
    370                 375                 380

Asp Lys Ala Ala Tyr Leu Gln Asn Leu Asn Ser Ala Asp Leu Leu Lys
385                 390                 395                 400

Ala Leu Cys Tyr Pro Arg Val Lys Val Gly Asn Glu Tyr Val Thr Lys
                405                 410                 415

Gly Gln Thr Val Gln Gln Val Tyr Asn Ala Val Gly Ala Leu Ala Lys
            420                 425                 430

Ala Val Tyr Asp Lys Met Phe Leu Trp Met Val Thr Arg Ile Asn Gln
        435                 440                 445

Gln Leu Asp Thr Lys Gln Pro Arg Gln Tyr Phe Ile Gly Val Leu Asp
    450                 455                 460

Ile Ala Gly Phe Glu Ile Phe Asp Phe Asn Ser Leu Glu Gln Leu Cys
465                 470                 475                 480

Ile Asn Phe Thr Asn Glu Lys Leu Gln Gln Phe Phe Asn His His Met
                485                 490                 495

Phe Val Leu Glu Gln Glu Glu Tyr Lys Lys Glu Gly Ile Glu Trp Thr
            500                 505                 510
```

```
Phe Ile Asp Phe Gly Met Asp Leu Ala Ala Cys Ile Glu Leu Ile Glu
        515                 520                 525

Lys Pro Met Gly Ile Phe Ser Ile Leu Glu Glu Glu Cys Met Phe Pro
    530                 535                 540

Lys Ala Thr Asp Thr Ser Phe Lys Asn Lys Leu Tyr Glu Gln His Leu
545                 550                 555                 560

Gly Lys Ser Asn Asn Phe Gln Lys Pro Lys Pro Ala Lys Gly Lys Pro
                565                 570                 575

Glu Ala His Phe Ser Leu Ile His Tyr Ala Gly Thr Val Asp Tyr Asn
            580                 585                 590

Ile Ala Gly Trp Leu Asp Lys Asn Lys Asp Pro Leu Asn Glu Thr Val
        595                 600                 605

Val Gly Leu Tyr Gln Lys Ser Ala Met Lys Thr Leu Ala Leu Leu Phe
    610                 615                 620

Val Gly Ala Thr Gly Ala Glu Ala Glu Ala Gly Gly Gly Lys Lys Gly
625                 630                 635                 640

Gly Lys Lys Lys Gly Ser Ser Phe Gln Thr Val Ser Ala Leu Phe Arg
                645                 650                 655

Glu Asn Leu Asn Lys Leu Met Thr Asn Leu Arg Ser Thr His Pro His
            660                 665                 670

Phe Val Arg Cys Ile Ile Pro Asn Glu Thr Lys Thr Pro Gly Ala Met
        675                 680                 685

Glu His Glu Leu Val Leu His Gln Leu Arg Cys Asn Gly Val Leu Glu
    690                 695                 700

Gly Ile Arg Ile Cys Arg Lys Gly Phe Pro Ser Arg Ile Leu Tyr Ala
705                 710                 715                 720

Asp Phe Lys Gln Arg Tyr Lys Val Leu Asn Ala Ser Ala Ile Pro Glu
                725                 730                 735

Gly Gln Phe Ile Asp Ser Lys Lys Ala Ser Glu Lys Leu Leu Gly Ser
            740                 745                 750

Ile Asp Ile Asp His Thr Gln Tyr Lys Phe Gly His Thr Lys Val Phe
        755                 760                 765

Phe Lys Ala Gly Leu Leu Gly Leu Leu Glu Glu Met Arg Asp Glu Lys
    770                 775                 780

Leu Ala Gln Leu Ile Thr Arg Thr Gln Ala Met Cys Arg Gly Phe Leu
785                 790                 795                 800

Ala Arg Val Glu Tyr Gln Lys Met Val Glu Arg Arg Glu Ser Ile Phe
                805                 810                 815

Cys Ile Gln Tyr Asn Val Arg Ala Phe Met Asn Val Lys His Trp Pro
            820                 825                 830

Trp Met Lys Leu Tyr Phe Lys Ile Lys Pro Leu Leu Lys Ser Ala Glu
        835                 840                 845

Thr Glu Lys Glu Met Ala Asn Met Lys Glu Glu Phe Glu Lys Thr Lys
    850                 855                 860

Glu Glu Leu Ala Lys Thr Glu Ala Lys Arg Lys Glu Leu Glu Glu Lys
865                 870                 875                 880

Met Val Thr Leu Met Gln Glu Lys Asn Asp Leu Gln Leu Gln Val Gln
                885                 890                 895

Ala Glu Ala Asp Ser Leu Ala Asp Ala Glu Glu Arg Cys Asp Gln Leu
            900                 905                 910

Ile Lys Thr Lys Ile Gln Leu Glu Ala Lys Ile Lys Glu Val Thr Glu
        915                 920                 925

Arg Ala Glu Asp Glu Glu Glu Ile Asn Ala Glu Leu Thr Ala Lys Lys
```

```
    930                 935                 940

Arg Lys Leu Glu Asp Glu Cys Ser Glu Leu Lys Lys Asp Ile Asp Asp
945                 950                 955                 960

Leu Glu Leu Thr Leu Ala Lys Val Glu Lys Glu Lys His Ala Thr Glu
                965                 970                 975

Asn Lys Val Lys Asn Leu Thr Glu Glu Met Ala Gly Leu Asp Glu Thr
            980                 985                 990

Ile Ala Lys Leu Thr Lys Glu Lys  Lys Ala Leu Gln Glu  Ala His Gln
        995                 1000                 1005

Gln Thr  Leu Asp Asp Leu Gln  Ala Glu Glu Asp Lys  Val Asn Thr
    1010                 1015                 1020

Leu Thr  Lys Ala Lys Ile Lys  Leu Glu Gln Gln Val  Asp Asp Leu
    1025                 1030                 1035

Glu Gly  Ser Leu Glu Gln Glu  Lys Lys Ile Arg Met  Asp Leu Glu
    1040                 1045                 1050

Arg Ala  Lys Arg Lys Leu Glu  Gly Asp Leu Lys Leu  Ala Gln Glu
    1055                 1060                 1065

Ser Ala  Met Asp Ile Glu Asn  Asp Lys Gln Gln Leu  Asp Glu Lys
    1070                 1075                 1080

Leu Lys  Lys Lys Glu Phe Glu  Met Ser Gly Leu Gln  Ser Lys Ile
    1085                 1090                 1095

Glu Asp  Glu Gln Ala Leu Gly  Met Gln Leu Gln Lys  Lys Ile Lys
    1100                 1105                 1110

Glu Leu  Gln Ala Arg Ile Glu  Glu Leu Glu Glu Glu  Ile Glu Ala
    1115                 1120                 1125

Glu Arg  Ala Ser Arg Ala Lys  Ala Glu Lys Gln Arg  Ser Asp Leu
    1130                 1135                 1140

Ser Arg  Glu Leu Glu Glu Ile  Ser Glu Arg Leu Glu  Glu Ala Gly
    1145                 1150                 1155

Gly Ala  Thr Ser Ala Gln Ile  Glu Met Asn Lys Lys  Arg Glu Ala
    1160                 1165                 1170

Glu Phe  Gln Lys Met Arg Arg  Asp Leu Glu Glu Ala  Thr Leu Gln
    1175                 1180                 1185

His Glu  Ala Thr Ala Ala Thr  Leu Arg Lys Lys His  Ala Asp Ser
    1190                 1195                 1200

Val Ala  Glu Leu Gly Glu Gln  Ile Asp Asn Leu Gln  Arg Val Lys
    1205                 1210                 1215

Gln Lys  Leu Glu Lys Glu Lys  Ser Glu Met Lys Met  Glu Ile Asp
    1220                 1225                 1230

Asp Leu  Ala Ser Asn Met Glu  Thr Val Ser Lys Ala  Lys Gly Asn
    1235                 1240                 1245

Leu Glu  Lys Met Cys Arg Ala  Leu Glu Asp Gln Leu  Ser Glu Ile
    1250                 1255                 1260

Lys Thr  Lys Glu Glu Glu Gln  Gln Arg Leu Ile Asn  Asp Leu Thr
    1265                 1270                 1275

Ala Gln  Arg Ala Arg Leu Gln  Thr Glu Ser Gly Glu  Tyr Ser Arg
    1280                 1285                 1290

Gln Leu  Asp Glu Lys Asp Thr  Leu Val Ser Gln Leu  Ser Arg Gly
    1295                 1300                 1305

Lys Gln  Ala Phe Thr Gln Gln  Ile Glu Glu Leu Lys  Arg Gln Leu
    1310                 1315                 1320

Glu Glu  Glu Ile Lys Ala Lys  Ser Ala Leu Ala His  Ala Leu Gln
    1325                 1330                 1335
```

```
Ser Ser  Arg His Asp Cys Asp  Leu Leu Arg Glu Gln  Tyr Glu Glu
    1340                 1345                 1350

Glu Gln  Glu Ala Lys Ala Glu  Leu Gln Arg Ala Met  Ser Lys Ala
    1355                 1360                 1365

Asn Ser  Glu Val Ala Gln Trp  Arg Thr Lys Tyr Glu  Thr Asp Ala
    1370                 1375                 1380

Ile Gln  Arg Thr Glu Glu Leu  Glu Glu Ala Lys Lys  Lys Leu Ala
    1385                 1390                 1395

Gln Arg  Leu Gln Asp Ala Glu  Glu His Val Glu Ala  Val Asn Ala
    1400                 1405                 1410

Lys Cys  Ala Ser Leu Glu Lys  Thr Lys Gln Arg Leu  Gln Asn Glu
    1415                 1420                 1425

Val Glu  Asp Leu Met Ile Asp  Val Glu Arg Thr Asn  Ala Ala Cys
    1430                 1435                 1440

Ala Ala  Leu Asp Lys Lys Gln  Arg Asn Phe Asp Lys  Ile Leu Ala
    1445                 1450                 1455

Glu Trp  Lys Gln Lys Cys Glu  Glu Thr His Ala Glu  Leu Glu Ala
    1460                 1465                 1470

Ser Gln  Lys Glu Ser Arg Ser  Leu Ser Thr Glu Leu  Phe Lys Ile
    1475                 1480                 1485

Lys Asn  Ala Tyr Glu Glu Ser  Leu Asp Gln Leu Glu  Thr Leu Lys
    1490                 1495                 1500

Arg Glu  Asn Lys Asn Leu Gln  Gln Glu Ile Ser Asp  Leu Thr Glu
    1505                 1510                 1515

Gln Ile  Ala Glu Gly Gly Lys  Arg Ile His Glu Leu  Glu Lys Ile
    1520                 1525                 1530

Lys Lys  Gln Val Glu Gln Glu  Lys Ser Glu Leu Gln  Ala Ala Leu
    1535                 1540                 1545

Glu Glu  Ala Glu Ala Ser Leu  Glu His Glu Glu Gly  Lys Ile Leu
    1550                 1555                 1560

Arg Ile  Gln Leu Glu Leu Asn  Gln Val Lys Ser Glu  Val Asp Arg
    1565                 1570                 1575

Lys Ile  Ala Glu Lys Asp Glu  Glu Ile Asp Gln Met  Lys Arg Asn
    1580                 1585                 1590

His Ile  Arg Ile Val Glu Ser  Met Gln Ser Thr Leu  Asp Ala Glu
    1595                 1600                 1605

Ile Arg  Ser Arg Asn Asp Ala  Ile Arg Leu Lys Lys  Lys Met Glu
    1610                 1615                 1620

Gly Asp  Leu Asn Glu Met Glu  Ile Gln Leu Asn His  Ala Asn Arg
    1625                 1630                 1635

Met Ala  Ala Glu Ala Leu Arg  Asn Tyr Arg Asn Thr  Gln Ala Ile
    1640                 1645                 1650

Leu Lys  Asp Thr Gln Leu His  Leu Asp Asp Ala Leu  Arg Ser Gln
    1655                 1660                 1665

Glu Asp  Leu Lys Glu Gln Leu  Ala Met Val Glu Arg  Arg Ala Asn
    1670                 1675                 1680

Leu Leu  Gln Ala Glu Ile Glu  Glu Leu Arg Ala Thr  Leu Glu Gln
    1685                 1690                 1695

Thr Glu  Arg Ser Arg Lys Ile  Ala Glu Gln Glu Leu  Leu Asp Ala
    1700                 1705                 1710

Ser Glu  Arg Val Gln Leu Leu  His Thr Gln Asn Thr  Ser Leu Ile
    1715                 1720                 1725
```

```
Asn Thr  Lys Lys Lys Leu Glu  Thr Asp Ile Ser Gln  Ile Gln Gly
    1730                 1735                 1740

Glu Met  Glu Asp Ile Ile Gln  Glu Ala Arg Asn Ala  Glu Glu Lys
    1745                 1750                 1755

Ala Lys  Lys Ala Ile Thr Asp  Ala Ala Met Met Ala  Glu Glu Leu
    1760                 1765                 1770

Lys Lys  Glu Gln Asp Thr Ser  Ala His Leu Glu Arg  Met Lys Lys
    1775                 1780                 1785

Asn Leu  Glu Gln Thr Val Lys  Asp Leu Gln His Arg  Leu Asp Glu
    1790                 1795                 1800

Ala Glu  Gln Leu Ala Leu Lys  Gly Gly Lys Lys Gln  Ile Gln Lys
    1805                 1810                 1815

Leu Glu  Ala Arg Val Arg Glu  Leu Glu Gly Glu Val  Glu Ser Glu
    1820                 1825                 1830

Gln Lys  Arg Asn Val Glu Ala  Val Lys Gly Leu Arg  Lys His Glu
    1835                 1840                 1845

Arg Lys  Val Lys Glu Leu Thr  Tyr Gln Thr Glu Glu  Asp Arg Lys
    1850                 1855                 1860

Asn Ile  Leu Arg Leu Gln Asp  Leu Val Asp Lys Leu  Gln Ala Lys
    1865                 1870                 1875

Val Lys  Ser Tyr Lys Arg Gln  Ala Glu Glu Ala Glu  Glu Gln Ser
    1880                 1885                 1890

Asn Val  Asn Leu Ser Lys Phe  Arg Arg Ile Gln His  Glu Leu Glu
    1895                 1900                 1905

Glu Ala  Glu Glu Arg Ala Asp  Ile Ala Glu Ser Gln  Val Asn Lys
    1910                 1915                 1920

Leu Arg  Val Lys Ser Arg Glu  Val His Thr Lys Ile  Ile Ser Glu
    1925                 1930                 1935

Glu


<210> SEQ ID NO 7
<211> LENGTH: 2633
<212> TYPE: DNA
<213> ORGANISM: Homo sapiens
<220> FEATURE:
<221> NAME/KEY: CDS
<222> LOCATION: (38)..(2584)
<223> OTHER INFORMATION:

<400> SEQUENCE: 7

ccgcggcaag aacatccctc ccagccagca gattaca atg ctg caa act aag gat      55
                                         Met Leu Gln Thr Lys Asp
                                         1               5

ctc atc tgg act ttg ttt ttc ctg gga act gca gtt tct ctg cag gtg      103
Leu Ile Trp Thr Leu Phe Phe Leu Gly Thr Ala Val Ser Leu Gln Val
            10                  15                  20

gat att gtt ccc agc cag ggg gag atc agc gtt gga gag tcc aaa ttc      151
Asp Ile Val Pro Ser Gln Gly Glu Ile Ser Val Gly Glu Ser Lys Phe
        25                  30                  35

ttc tta tgc caa gtg gca gga gat gcc aaa gat aaa gac atc tcc tgg      199
Phe Leu Cys Gln Val Ala Gly Asp Ala Lys Asp Lys Asp Ile Ser Trp
    40                  45                  50

ttc tcc ccc aat gga gaa aag ctc acc cca aac cag cag cgg atc tca      247
Phe Ser Pro Asn Gly Glu Lys Leu Thr Pro Asn Gln Gln Arg Ile Ser
55                  60                  65                  70

gtg gtg tgg aat gat gat tcc tcc tcc acc ctc acc atc tat aac gcc      295
Val Val Trp Asn Asp Asp Ser Ser Ser Thr Leu Thr Ile Tyr Asn Ala
```

```
                75                  80                  85

aac atc gac gac gcc ggc att tac aag tgt gtg gtt aca ggc gag gat      343
Asn Ile Asp Asp Ala Gly Ile Tyr Lys Cys Val Val Thr Gly Glu Asp
            90                  95                  100

ggc agt gag tca gag gcc acc gtc aac gtg aag atc ttt cag aag ctc      391
Gly Ser Glu Ser Glu Ala Thr Val Asn Val Lys Ile Phe Gln Lys Leu
        105                 110                 115

atg ttc aag aat gcg cca acc cca cag gag ttc cgg gag ggg gaa gat      439
Met Phe Lys Asn Ala Pro Thr Pro Gln Glu Phe Arg Glu Gly Glu Asp
    120                 125                 130

gcc gtg att gtg tgt gat gtg gtc agc tcc ctc cca cca acc atc atc      487
Ala Val Ile Val Cys Asp Val Val Ser Ser Leu Pro Pro Thr Ile Ile
135                 140                 145                 150

tgg aaa cac aaa ggc cga gat gtc atc ctg aaa aaa gat gtc cga ttc      535
Trp Lys His Lys Gly Arg Asp Val Ile Leu Lys Lys Asp Val Arg Phe
                155                 160                 165

ata gtc ctg tcc aac aac tac ctg cag atc cgg ggc atc aag aaa aca      583
Ile Val Leu Ser Asn Asn Tyr Leu Gln Ile Arg Gly Ile Lys Lys Thr
            170                 175                 180

gat gag ggc act tat cgc tgt gag ggc aga atc ctg gca cgg ggg gag      631
Asp Glu Gly Thr Tyr Arg Cys Glu Gly Arg Ile Leu Ala Arg Gly Glu
        185                 190                 195

atc aac ttc aag gac att cag gtc att gtg aat gtg cca cct acc atc      679
Ile Asn Phe Lys Asp Ile Gln Val Ile Val Asn Val Pro Pro Thr Ile
    200                 205                 210

cgg gcc agg cag aat att gtg aat gcc acc gcc aac ctc ggc cag tcc      727
Arg Ala Arg Gln Asn Ile Val Asn Ala Thr Ala Asn Leu Gly Gln Ser
215                 220                 225                 230

gtc acc ctg gtg tgc gat gcc gaa cgg ttc cca gag ccc acc atg agc      775
Val Thr Leu Val Cys Asp Ala Glu Arg Phe Pro Glu Pro Thr Met Ser
                235                 240                 245

tgg aca aag gat ggg gaa cag ata gag caa gag gaa gac gat gag aag      823
Trp Thr Lys Asp Gly Glu Gln Ile Glu Gln Glu Glu Asp Asp Glu Lys
            250                 255                 260

tac atc ttc agc gac gat agt tcc cag ctg acc atc aaa aag gtg gat      871
Tyr Ile Phe Ser Asp Asp Ser Ser Gln Leu Thr Ile Lys Lys Val Asp
        265                 270                 275

aag aac gac gag gct gag tac atc tgc att gct gag aac aag gct ggc      919
Lys Asn Asp Glu Ala Glu Tyr Ile Cys Ile Ala Glu Asn Lys Ala Gly
    280                 285                 290

gag cag gat gcg acc atc cac ctc aaa gtc ttt gca aaa ccc aaa atc      967
Glu Gln Asp Ala Thr Ile His Leu Lys Val Phe Ala Lys Pro Lys Ile
295                 300                 305                 310

aca tat gta gag aac cag act gcc atg gaa tta gag gag cag gtc act     1015
Thr Tyr Val Glu Asn Gln Thr Ala Met Glu Leu Glu Glu Gln Val Thr
                315                 320                 325

ctt acc tgt gaa gcc tcc gga gac ccc att ccc tcc atc acc tgg agg     1063
Leu Thr Cys Glu Ala Ser Gly Asp Pro Ile Pro Ser Ile Thr Trp Arg
            330                 335                 340

act tct acc cgg aac atc agc agc gaa gaa aag act ctg gat ggg cac     1111
Thr Ser Thr Arg Asn Ile Ser Ser Glu Glu Lys Thr Leu Asp Gly His
        345                 350                 355

atg gtg gtg cgt agc cat gcc cgt gtg tcg tcg ctg acc ctg aag agc     1159
Met Val Val Arg Ser His Ala Arg Val Ser Ser Leu Thr Leu Lys Ser
    360                 365                 370

atc cag tac act gat gcc gga gag tac atc tgc acc gcc agc aac acc     1207
Ile Gln Tyr Thr Asp Ala Gly Glu Tyr Ile Cys Thr Ala Ser Asn Thr
375                 380                 385                 390

atc ggc cag gac tcc cag tcc atg tac ctt gaa gtg caa tat gcc cca     1255
```

-continued

```
Ile Gly Gln Asp Ser Gln Ser Met Tyr Leu Glu Val Gln Tyr Ala Pro
                395                 400                 405

aag cta cag ggc cct gtg gct gtg tac act tgg gag ggg aac cag gtg      1303
Lys Leu Gln Gly Pro Val Ala Val Tyr Thr Trp Glu Gly Asn Gln Val
            410                 415                 420

aac atc acc tgc gag gta ttt gcc tat ccc agt gcc acg atc tca tgg      1351
Asn Ile Thr Cys Glu Val Phe Ala Tyr Pro Ser Ala Thr Ile Ser Trp
        425                 430                 435

ttt cgg gat ggc cag ctg ctg cca agc tcc aat tac agc aat atc aag      1399
Phe Arg Asp Gly Gln Leu Leu Pro Ser Ser Asn Tyr Ser Asn Ile Lys
    440                 445                 450

atc tac aac acc ccc tct gcc agc tat ctg gag gtg acc cca gac tct      1447
Ile Tyr Asn Thr Pro Ser Ala Ser Tyr Leu Glu Val Thr Pro Asp Ser
455                 460                 465                 470

gag aat gat ttt ggg aac tac aac tgt act gca gtg aac cgc att ggg      1495
Glu Asn Asp Phe Gly Asn Tyr Asn Cys Thr Ala Val Asn Arg Ile Gly
                475                 480                 485

cag gag tcc ttc gaa ttc atc ctt gtt caa gca gac acc ccc tct tca      1543
Gln Glu Ser Phe Glu Phe Ile Leu Val Gln Ala Asp Thr Pro Ser Ser
            490                 495                 500

cca tcc atc gac cag gtg gag cca tac tcc agc aca gcc cag gtg cag      1591
Pro Ser Ile Asp Gln Val Glu Pro Tyr Ser Ser Thr Ala Gln Val Gln
        505                 510                 515

ttt gat gaa cca gag gcc aca ggt ggg gtg ccc atc ctc aaa tac aaa      1639
Phe Asp Glu Pro Glu Ala Thr Gly Gly Val Pro Ile Leu Lys Tyr Lys
    520                 525                 530

gct gag tgg aga gca gtg ggt gaa gaa gta tgg cat tcc aag tgg tat      1687
Ala Glu Trp Arg Ala Val Gly Glu Glu Val Trp His Ser Lys Trp Tyr
535                 540                 545                 550

gat gcc aag gaa gcc agc atg gag ggc atc gtc acc atc gtg ggc ctg      1735
Asp Ala Lys Glu Ala Ser Met Glu Gly Ile Val Thr Ile Val Gly Leu
                555                 560                 565

aag ccc gaa aca acg tac gcc gta agg ctg gcg gcg ctc aat ggc aaa      1783
Lys Pro Glu Thr Thr Tyr Ala Val Arg Leu Ala Ala Leu Asn Gly Lys
            570                 575                 580

ggg ctg ggt gag atc agc gcg gcc tcc gag ttc aag acg cag cca gtc      1831
Gly Leu Gly Glu Ile Ser Ala Ala Ser Glu Phe Lys Thr Gln Pro Val
        585                 590                 595

caa ggg gaa ccc agt gca cct aag ctc gaa ggg cag atg gga gag gat      1879
Gln Gly Glu Pro Ser Ala Pro Lys Leu Glu Gly Gln Met Gly Glu Asp
    600                 605                 610

gga aac tct att aaa gtg aac ctg atc aag cag gat gac ggc ggc tcc      1927
Gly Asn Ser Ile Lys Val Asn Leu Ile Lys Gln Asp Asp Gly Gly Ser
615                 620                 625                 630

ccc atc aga cac tat ctg gtc agg tac cga gcg ctc tcc tcc gag tgg      1975
Pro Ile Arg His Tyr Leu Val Arg Tyr Arg Ala Leu Ser Ser Glu Trp
                635                 640                 645

aaa cca gag atc agg ctc ccg tct ggc agt gac cac gtc atg ctg aag      2023
Lys Pro Glu Ile Arg Leu Pro Ser Gly Ser Asp His Val Met Leu Lys
            650                 655                 660

tcc ctg gac tgg aat gct gag tat gag gtc tac gtg gtg gct gag aac      2071
Ser Leu Asp Trp Asn Ala Glu Tyr Glu Val Tyr Val Val Ala Glu Asn
        665                 670                 675

cag caa gga aaa tcc aag gcg gct cat ttt gtg ttc agg acc tcg gcc      2119
Gln Gln Gly Lys Ser Lys Ala Ala His Phe Val Phe Arg Thr Ser Ala
    680                 685                 690

cag ccc aca gcc atc cca gcc aac ggc agc ccc acc tca ggc ctg agc      2167
Gln Pro Thr Ala Ile Pro Ala Asn Gly Ser Pro Thr Ser Gly Leu Ser
695                 700                 705                 710
```

```
acc ggg gcc atc gtg ggc atc ctc atc gtc atc ttc gtc ctg ctc ctg     2215
Thr Gly Ala Ile Val Gly Ile Leu Ile Val Ile Phe Val Leu Leu Leu
                715                 720                 725

gtg gtt gtg gac atc acc tgc tac ttc ctg aac aag tgt ggc ctg ttc     2263
Val Val Val Asp Ile Thr Cys Tyr Phe Leu Asn Lys Cys Gly Leu Phe
            730                 735                 740

atg tgc att gcg gtc aac ctg tgt gga aaa gcc ggg ccc ggg gcc aag     2311
Met Cys Ile Ala Val Asn Leu Cys Gly Lys Ala Gly Pro Gly Ala Lys
        745                 750                 755

ggc aag gac atg gag gag ggc aag gcc gcc ttc tcg aaa gat gag tcc     2359
Gly Lys Asp Met Glu Glu Gly Lys Ala Ala Phe Ser Lys Asp Glu Ser
    760                 765                 770

aag gag ccc atc gtg gag gtt cga acg gag gag gag agg acc cca aac     2407
Lys Glu Pro Ile Val Glu Val Arg Thr Glu Glu Glu Arg Thr Pro Asn
775                 780                 785                 790

cat gat gga ggg aaa cac aca gag ccc aac gag acc acg cca ctg acg     2455
His Asp Gly Gly Lys His Thr Glu Pro Asn Glu Thr Thr Pro Leu Thr
                795                 800                 805

gag ccc gag aag ggc ccc gta gaa gca aag cca gag tgc cag gag aca     2503
Glu Pro Glu Lys Gly Pro Val Glu Ala Lys Pro Glu Cys Gln Glu Thr
            810                 815                 820

gaa acg aag cca gcg cca gcc gaa gtc aag acg gtc ccc aat gac gcc     2551
Glu Thr Lys Pro Ala Pro Ala Glu Val Lys Thr Val Pro Asn Asp Ala
        825                 830                 835

aca cag aca aag gag aac gag agc aaa gca tga tgggtgaaga gaaccgagca   2604
Thr Gln Thr Lys Glu Asn Glu Ser Lys Ala
    840                 845

aagatcaaaa taaaaagtga cacagcagc                                     2633


<210> SEQ ID NO 8
<211> LENGTH: 848
<212> TYPE: PRT
<213> ORGANISM: Homo sapiens

<400> SEQUENCE: 8

Met Leu Gln Thr Lys Asp Leu Ile Trp Thr Leu Phe Phe Leu Gly Thr
1               5                   10                  15

Ala Val Ser Leu Gln Val Asp Ile Val Pro Ser Gln Gly Glu Ile Ser
            20                  25                  30

Val Gly Glu Ser Lys Phe Phe Leu Cys Gln Val Ala Gly Asp Ala Lys
        35                  40                  45

Asp Lys Asp Ile Ser Trp Phe Ser Pro Asn Gly Glu Lys Leu Thr Pro
    50                  55                  60

Asn Gln Gln Arg Ile Ser Val Val Trp Asn Asp Asp Ser Ser Ser Thr
65                  70                  75                  80

Leu Thr Ile Tyr Asn Ala Asn Ile Asp Asp Ala Gly Ile Tyr Lys Cys
                85                  90                  95

Val Val Thr Gly Glu Asp Gly Ser Glu Ser Glu Ala Thr Val Asn Val
            100                 105                 110

Lys Ile Phe Gln Lys Leu Met Phe Lys Asn Ala Pro Thr Pro Gln Glu
        115                 120                 125

Phe Arg Glu Gly Glu Asp Ala Val Ile Val Cys Asp Val Val Ser Ser
    130                 135                 140

Leu Pro Pro Thr Ile Ile Trp Lys His Lys Gly Arg Asp Val Ile Leu
145                 150                 155                 160

Lys Lys Asp Val Arg Phe Ile Val Leu Ser Asn Asn Tyr Leu Gln Ile
                165                 170                 175
```

```
Arg Gly Ile Lys Lys Thr Asp Glu Gly Thr Tyr Arg Cys Glu Gly Arg
            180                 185                 190

Ile Leu Ala Arg Gly Glu Ile Asn Phe Lys Asp Ile Gln Val Ile Val
        195                 200                 205

Asn Val Pro Pro Thr Ile Arg Ala Arg Gln Asn Ile Val Asn Ala Thr
    210                 215                 220

Ala Asn Leu Gly Gln Ser Val Thr Leu Val Cys Asp Ala Glu Arg Phe
225                 230                 235                 240

Pro Glu Pro Thr Met Ser Trp Thr Lys Asp Gly Glu Gln Ile Glu Gln
                245                 250                 255

Glu Glu Asp Asp Glu Lys Tyr Ile Phe Ser Asp Asp Ser Ser Gln Leu
            260                 265                 270

Thr Ile Lys Lys Val Asp Lys Asn Asp Glu Ala Glu Tyr Ile Cys Ile
        275                 280                 285

Ala Glu Asn Lys Ala Gly Glu Gln Asp Ala Thr Ile His Leu Lys Val
    290                 295                 300

Phe Ala Lys Pro Lys Ile Thr Tyr Val Glu Asn Gln Thr Ala Met Glu
305                 310                 315                 320

Leu Glu Glu Gln Val Thr Leu Thr Cys Glu Ala Ser Gly Asp Pro Ile
                325                 330                 335

Pro Ser Ile Thr Trp Arg Thr Ser Thr Arg Asn Ile Ser Ser Glu Glu
            340                 345                 350

Lys Thr Leu Asp Gly His Met Val Val Arg Ser His Ala Arg Val Ser
        355                 360                 365

Ser Leu Thr Leu Lys Ser Ile Gln Tyr Thr Asp Ala Gly Glu Tyr Ile
    370                 375                 380

Cys Thr Ala Ser Asn Thr Ile Gly Gln Asp Ser Gln Ser Met Tyr Leu
385                 390                 395                 400

Glu Val Gln Tyr Ala Pro Lys Leu Gln Gly Pro Val Ala Val Tyr Thr
                405                 410                 415

Trp Glu Gly Asn Gln Val Asn Ile Thr Cys Glu Val Phe Ala Tyr Pro
            420                 425                 430

Ser Ala Thr Ile Ser Trp Phe Arg Asp Gly Gln Leu Leu Pro Ser Ser
        435                 440                 445

Asn Tyr Ser Asn Ile Lys Ile Tyr Asn Thr Pro Ser Ala Ser Tyr Leu
    450                 455                 460

Glu Val Thr Pro Asp Ser Glu Asn Asp Phe Gly Asn Tyr Asn Cys Thr
465                 470                 475                 480

Ala Val Asn Arg Ile Gly Gln Glu Ser Phe Glu Phe Ile Leu Val Gln
                485                 490                 495

Ala Asp Thr Pro Ser Ser Pro Ser Ile Asp Gln Val Glu Pro Tyr Ser
            500                 505                 510

Ser Thr Ala Gln Val Gln Phe Asp Glu Pro Glu Ala Thr Gly Gly Val
        515                 520                 525

Pro Ile Leu Lys Tyr Lys Ala Glu Trp Arg Ala Val Gly Glu Glu Val
    530                 535                 540

Trp His Ser Lys Trp Tyr Asp Ala Lys Glu Ala Ser Met Glu Gly Ile
545                 550                 555                 560

Val Thr Ile Val Gly Leu Lys Pro Glu Thr Thr Tyr Ala Val Arg Leu
                565                 570                 575

Ala Ala Leu Asn Gly Lys Gly Leu Gly Glu Ile Ser Ala Ala Ser Glu
            580                 585                 590

Phe Lys Thr Gln Pro Val Gln Gly Glu Pro Ser Ala Pro Lys Leu Glu
```

```
        595                 600                 605

Gly Gln Met Gly Glu Asp Gly Asn Ser Ile Lys Val Asn Leu Ile Lys
    610                 615                 620

Gln Asp Asp Gly Gly Ser Pro Ile Arg His Tyr Leu Val Arg Tyr Arg
625                 630                 635                 640

Ala Leu Ser Ser Glu Trp Lys Pro Glu Ile Arg Leu Pro Ser Gly Ser
                645                 650                 655

Asp His Val Met Leu Lys Ser Leu Asp Trp Asn Ala Glu Tyr Glu Val
            660                 665                 670

Tyr Val Val Ala Glu Asn Gln Gln Gly Lys Ser Lys Ala Ala His Phe
        675                 680                 685

Val Phe Arg Thr Ser Ala Gln Pro Thr Ala Ile Pro Ala Asn Gly Ser
    690                 695                 700

Pro Thr Ser Gly Leu Ser Thr Gly Ala Ile Val Gly Ile Leu Ile Val
705                 710                 715                 720

Ile Phe Val Leu Leu Leu Val Val Val Asp Ile Thr Cys Tyr Phe Leu
                725                 730                 735

Asn Lys Cys Gly Leu Phe Met Cys Ile Ala Val Asn Leu Cys Gly Lys
            740                 745                 750

Ala Gly Pro Gly Ala Lys Gly Lys Asp Met Glu Glu Gly Lys Ala Ala
        755                 760                 765

Phe Ser Lys Asp Glu Ser Lys Glu Pro Ile Val Glu Val Arg Thr Glu
    770                 775                 780

Glu Glu Arg Thr Pro Asn His Asp Gly Gly Lys His Thr Glu Pro Asn
785                 790                 795                 800

Glu Thr Thr Pro Leu Thr Glu Pro Glu Lys Gly Pro Val Glu Ala Lys
                805                 810                 815

Pro Glu Cys Gln Glu Thr Glu Thr Lys Pro Ala Pro Ala Glu Val Lys
            820                 825                 830

Thr Val Pro Asn Asp Ala Thr Gln Thr Lys Glu Asn Glu Ser Lys Ala
        835                 840                 845


<210> SEQ ID NO 9
<211> LENGTH: 1692
<212> TYPE: DNA
<213> ORGANISM: Homo sapiens;
<220> FEATURE:
<221> NAME/KEY: CDS
<222> LOCATION: (121)..(1080)
<223> OTHER INFORMATION:
<300> PUBLICATION INFORMATION:
<308> DATABASE ACCESSION NUMBER: X56677
<309> DATABASE ENTRY DATE: 1991-03-19
<313> RELEVANT RESIDUES: (1)..(1692)

<400> SEQUENCE: 9

attcagactg ccagcacttt gctatctaca gccggggctc ccgagcggca gaaagttccg      60

gccactctct gccgcttggg ttgggcgaaa gccaggaccg tgccgcgcca ccgccaggat     120

atg gag cta ctg tcg cca ccg ctc cgc gac gta gac ctg acg gcc ccc      168
Met Glu Leu Leu Ser Pro Pro Leu Arg Asp Val Asp Leu Thr Ala Pro
1               5                   10                  15

gac ggc tct ctc tgc tcc ttt gcc aca acg gac gac ttc tat gac gac      216
Asp Gly Ser Leu Cys Ser Phe Ala Thr Thr Asp Asp Phe Tyr Asp Asp
            20                  25                  30

ccg tgt ttc gac tcc ccg gac ctg cgc ttc ttc gaa gac ctg gac ccg      264
Pro Cys Phe Asp Ser Pro Asp Leu Arg Phe Phe Glu Asp Leu Asp Pro
        35                  40                  45
```

```
cgc ctg atg cac gtg ggc gcg ctc ctg aaa ccc gaa gag cac tcg cac      312
Arg Leu Met His Val Gly Ala Leu Leu Lys Pro Glu Glu His Ser His
    50                  55                  60

ttc ccc gcg gcg gtg cac ccg gcc ccg ggc gca cgt gag gac gag cat      360
Phe Pro Ala Ala Val His Pro Ala Pro Gly Ala Arg Glu Asp Glu His
65                  70                  75                  80

gtg cgc gcg ccc agc ggg cac cac cag gcg ggc cgc tgc cta ctg tgg      408
Val Arg Ala Pro Ser Gly His His Gln Ala Gly Arg Cys Leu Leu Trp
                85                  90                  95

gcc tgc aag gcg tgc aag cgc aag acc acc aac gcc gac cgc cgc aag      456
Ala Cys Lys Ala Cys Lys Arg Lys Thr Thr Asn Ala Asp Arg Arg Lys
            100                 105                 110

gcc gcc acc atg cgc gag cgg cgc cgc ctg agc aaa gta aat gag gcc      504
Ala Ala Thr Met Arg Glu Arg Arg Arg Leu Ser Lys Val Asn Glu Ala
        115                 120                 125

ttt gag aca ctc aag cgc tgc acg tcg agc aat cca aac cag cgg ttg      552
Phe Glu Thr Leu Lys Arg Cys Thr Ser Ser Asn Pro Asn Gln Arg Leu
    130                 135                 140

ccc aag gtg gag atc ctg cgc aac gcc atc cgc tat atc gag ggc ctg      600
Pro Lys Val Glu Ile Leu Arg Asn Ala Ile Arg Tyr Ile Glu Gly Leu
145                 150                 155                 160

cag gct ctg ctg cgc gac cag gac gcc gcg ccc cct ggc gca gcc gcc      648
Gln Ala Leu Leu Arg Asp Gln Asp Ala Ala Pro Pro Gly Ala Ala Ala
                165                 170                 175

ttc tat gcg ccg ggc ccg ctg ccc ccg ggc cgc ggc ggc gag cac tac      696
Phe Tyr Ala Pro Gly Pro Leu Pro Pro Gly Arg Gly Gly Glu His Tyr
            180                 185                 190

agc ggc gac tcc gac gcg tcc agc ccg cgc tcc aac tgc tcc gac ggc      744
Ser Gly Asp Ser Asp Ala Ser Ser Pro Arg Ser Asn Cys Ser Asp Gly
        195                 200                 205

atg atg gac tac agc ggc ccc ccg agc ggc gcc cgg cgg cgg aac tgc      792
Met Met Asp Tyr Ser Gly Pro Pro Ser Gly Ala Arg Arg Arg Asn Cys
    210                 215                 220

tac gaa ggc gcc tac tac aac gag gcg ccc agc gaa ccc agg ccc ggg      840
Tyr Glu Gly Ala Tyr Tyr Asn Glu Ala Pro Ser Glu Pro Arg Pro Gly
225                 230                 235                 240

aag agt gcg gcg gtg tcg agc cta gac tac ctg tcc agc atc gtg gag      888
Lys Ser Ala Ala Val Ser Ser Leu Asp Tyr Leu Ser Ser Ile Val Glu
                245                 250                 255

cgc atc tcc acc gag agc cct gcg gcg ccc gcc ctc ctg ctg gcg gac      936
Arg Ile Ser Thr Glu Ser Pro Ala Ala Pro Ala Leu Leu Leu Ala Asp
            260                 265                 270

gtg cct tct gag tcg cct ccg cgc agg caa gag gct gcc gcc ccc agc      984
Val Pro Ser Glu Ser Pro Pro Arg Arg Gln Glu Ala Ala Ala Pro Ser
        275                 280                 285

gag gga gag agc agc ggc gac ccc acc cag tca ccg gac gcc gcc ccg     1032
Glu Gly Glu Ser Ser Gly Asp Pro Thr Gln Ser Pro Asp Ala Ala Pro
    290                 295                 300

cag tgc cct gcg ggt gcg aac ccc aac ccg ata tac cag gtg ctc tga     1080
Gln Cys Pro Ala Gly Ala Asn Pro Asn Pro Ile Tyr Gln Val Leu
305                 310                 315

gggggatgtg gccgcccaac cccgccaggg atggtgccct agggtccctc gcgcccaaaa   1140

gattgaactt aaatgccccc ctcccaacag cgctttaaaa gcgccatctc ttgaggtagg   1200

agaggcggag aactgaagtt tccgcccccc ccgacagggc aaggacacag cgcggttttt   1260

tccacgcagc acccttctcg gagacccatt gcgatggccg ctccgtgttc ctcggtgggc   1320

cagagctgaa ccttgagggg ctaggttcac gtttctcgcg ccctccatgg tgagaccctc   1380

gcagacctaa ccctgccccg ggatgcaccg gttatttggg ggggcgtgag acagtgcact   1440
```

```
ccggtcccaa atgtagcagg tgtaaccgta acccaccccc aacccgtttc ccggttcagg   1500

accacttttt gtaatacttt ttgtaatcta ttcctgtaaa taagagttcg tttgccagag   1560

aggagcccct ggggctgtat ttatctctga ggcagggtgt gtggtgctac agggaatttg   1620

tacgtttata ccgcaggcgg gcgagccgcg ggcgctcgct caggtgatca aaataaaggc   1680

gctaatttat aa                                                       1692


<210> SEQ ID NO 10
<211> LENGTH: 319
<212> TYPE: PRT
<213> ORGANISM: Homo sapiens;

<400> SEQUENCE: 10

Met Glu Leu Leu Ser Pro Pro Leu Arg Asp Val Asp Leu Thr Ala Pro
1               5                   10                  15

Asp Gly Ser Leu Cys Ser Phe Ala Thr Thr Asp Asp Phe Tyr Asp Asp
            20                  25                  30

Pro Cys Phe Asp Ser Pro Asp Leu Arg Phe Phe Glu Asp Leu Asp Pro
        35                  40                  45

Arg Leu Met His Val Gly Ala Leu Leu Lys Pro Glu Glu His Ser His
    50                  55                  60

Phe Pro Ala Ala Val His Pro Ala Pro Gly Ala Arg Glu Asp Glu His
65                  70                  75                  80

Val Arg Ala Pro Ser Gly His His Gln Ala Gly Arg Cys Leu Leu Trp
                85                  90                  95

Ala Cys Lys Ala Cys Lys Arg Lys Thr Thr Asn Ala Asp Arg Arg Lys
            100                 105                 110

Ala Ala Thr Met Arg Glu Arg Arg Arg Leu Ser Lys Val Asn Glu Ala
        115                 120                 125

Phe Glu Thr Leu Lys Arg Cys Thr Ser Ser Asn Pro Asn Gln Arg Leu
    130                 135                 140

Pro Lys Val Glu Ile Leu Arg Asn Ala Ile Arg Tyr Ile Glu Gly Leu
145                 150                 155                 160

Gln Ala Leu Leu Arg Asp Gln Asp Ala Ala Pro Pro Gly Ala Ala Ala
                165                 170                 175

Phe Tyr Ala Pro Gly Pro Leu Pro Pro Gly Arg Gly Gly Glu His Tyr
            180                 185                 190

Ser Gly Asp Ser Asp Ala Ser Ser Pro Arg Ser Asn Cys Ser Asp Gly
        195                 200                 205

Met Met Asp Tyr Ser Gly Pro Pro Ser Gly Ala Arg Arg Arg Asn Cys
    210                 215                 220

Tyr Glu Gly Ala Tyr Tyr Asn Glu Ala Pro Ser Glu Pro Arg Pro Gly
225                 230                 235                 240

Lys Ser Ala Ala Val Ser Ser Leu Asp Tyr Leu Ser Ser Ile Val Glu
                245                 250                 255

Arg Ile Ser Thr Glu Ser Pro Ala Ala Pro Ala Leu Leu Leu Ala Asp
            260                 265                 270

Val Pro Ser Glu Ser Pro Pro Arg Arg Gln Glu Ala Ala Ala Pro Ser
        275                 280                 285

Glu Gly Glu Ser Ser Gly Asp Pro Thr Gln Ser Pro Asp Ala Ala Pro
    290                 295                 300

Gln Cys Pro Ala Gly Ala Asn Pro Asn Pro Ile Tyr Gln Val Leu
305                 310                 315
```

```
<210> SEQ ID NO 11
<211> LENGTH: 1427
<212> TYPE: DNA
<213> ORGANISM: Homo sapiens;
<220> FEATURE:
<221> NAME/KEY: CDS
<222> LOCATION: (43)..(810)
<223> OTHER INFORMATION:
<300> PUBLICATION INFORMATION:
<308> DATABASE ACCESSION NUMBER: NM_005593
<309> DATABASE ENTRY DATE: 2003-04-07
<313> RELEVANT RESIDUES: (1)..(1427)

<400> SEQUENCE: 11

cctctcgctg ccgtccaggt gcaccgcctg cctctcagca gg atg gac gtg atg        54
                                               Met Asp Val Met
                                               1

gat ggc tgc cag ttc tca cct tct gag tac ttc tac gac ggc tcc tgc      102
Asp Gly Cys Gln Phe Ser Pro Ser Glu Tyr Phe Tyr Asp Gly Ser Cys
5                   10                  15                  20

ata ccg tcc ccc gag ggt gaa ttt ggg gac gag ttt gtg ccg cga gtg      150
Ile Pro Ser Pro Glu Gly Glu Phe Gly Asp Glu Phe Val Pro Arg Val
                25                  30                  35

gct gcc ttc gga gcg cac aaa gca gag ctg cag ggc tca gat gag gac      198
Ala Ala Phe Gly Ala His Lys Ala Glu Leu Gln Gly Ser Asp Glu Asp
            40                  45                  50

gag cac gtg cga gcg cct acc ggc cac cac cag gct ggt cac tgc ctc      246
Glu His Val Arg Ala Pro Thr Gly His His Gln Ala Gly His Cys Leu
        55                  60                  65

atg tgg gcc tgc aaa gcc tgc aag agg aag tcc acc acc atg gat cgg      294
Met Trp Ala Cys Lys Ala Cys Lys Arg Lys Ser Thr Thr Met Asp Arg
    70                  75                  80

cgg aag gca gcc act atg cgc gag cgg agg cgc ctg aag aag gtc aac      342
Arg Lys Ala Ala Thr Met Arg Glu Arg Arg Arg Leu Lys Lys Val Asn
85                  90                  95                  100

cag gct ttc gaa acc ctc aag agg tgt acc acg acc aac ccc aac cag      390
Gln Ala Phe Glu Thr Leu Lys Arg Cys Thr Thr Thr Asn Pro Asn Gln
                105                 110                 115

agg ctg ccc aag gtg gag atc ctc agg aat gcc atc cgc tac atc gag      438
Arg Leu Pro Lys Val Glu Ile Leu Arg Asn Ala Ile Arg Tyr Ile Glu
            120                 125                 130

agc ctg cag gag ttg ctg aga gag cag gtg gag aac tac tat agc ctg      486
Ser Leu Gln Glu Leu Leu Arg Glu Gln Val Glu Asn Tyr Tyr Ser Leu
        135                 140                 145

ccg gga cag agc tgc tcg gag ccc acc agc ccc acc tcc aac tgc tct      534
Pro Gly Gln Ser Cys Ser Glu Pro Thr Ser Pro Thr Ser Asn Cys Ser
    150                 155                 160

gat ggc atg ccc gaa tgt aac agt cct gtc tgg tcc aga aag agc agt      582
Asp Gly Met Pro Glu Cys Asn Ser Pro Val Trp Ser Arg Lys Ser Ser
165                 170                 175                 180

act ttt gac agc atc tac tgt cct gat gta tca aat gta tat gcc aca      630
Thr Phe Asp Ser Ile Tyr Cys Pro Asp Val Ser Asn Val Tyr Ala Thr
                185                 190                 195

gat aaa aac tcc tta tcc agc ttg gat tgc tta tcc aac ata gtg gac      678
Asp Lys Asn Ser Leu Ser Ser Leu Asp Cys Leu Ser Asn Ile Val Asp
            200                 205                 210

cgg atc acc tcc tca gag caa cct ggg ttg cct ctc cag gat ctg gct      726
Arg Ile Thr Ser Ser Glu Gln Pro Gly Leu Pro Leu Gln Asp Leu Ala
        215                 220                 225

tct ctc tct cca gtt gcc agc acc gat tca cag cct cga act cca ggg      774
Ser Leu Ser Pro Val Ala Ser Thr Asp Ser Gln Pro Arg Thr Pro Gly
    230                 235                 240
```

```
gct tct agt tcc agg ctt atc tat cat gtg cta tga actaattttc          820
Ala Ser Ser Ser Arg Leu Ile Tyr His Val Leu
245                 250                 255

tggtctatat gacttcttcc aggagggcct aatacacagg acgaagaagg cttcaaaaag    880

tcccaaacca agacaacatg tacataaaga tttcttttca gttgtaaatt tgtaaagatt    940

accttgccac tttataagaa agtgtattta actaaaaagt catcattgca aataatactt   1000

tcttcttctt tattattctt tgcttagata ttaatacata gttccagtaa tactatttct   1060

gatagggggc cattgattga gggtagcttg ttcgaatgct taacttatat atacatatat   1120

atatattata aatattgctc atcaaaatgt ctctggtgtt tagagcttta ttttttttctt  1180

taaaacatta aaacagctga gaatcagtta aatggaattt taaatatatt taactatttc   1240

ttttctcttt aatcctttag ttatattgta ttaaataaaa atataatact gcctaatgta   1300

tatattttga tcttttcttg taagaaatgt atcttttaaa tgtaagcaca aaatagtact   1360

ttgtggatca tttcaagata taagaaattt tggaaattcc accataaata aaatttttta   1420

ctacaag                                                             1427
```

<210> SEQ ID NO 12
<211> LENGTH: 255
<212> TYPE: PRT
<213> ORGANISM: Homo sapiens;

<400> SEQUENCE: 12

```
Met Asp Val Met Asp Gly Cys Gln Phe Ser Pro Ser Glu Tyr Phe Tyr
1               5                   10                  15

Asp Gly Ser Cys Ile Pro Ser Pro Glu Gly Glu Phe Gly Asp Glu Phe
            20                  25                  30

Val Pro Arg Val Ala Ala Phe Gly Ala His Lys Ala Glu Leu Gln Gly
        35                  40                  45

Ser Asp Glu Asp Glu His Val Arg Ala Pro Thr Gly His His Gln Ala
    50                  55                  60

Gly His Cys Leu Met Trp Ala Cys Lys Ala Cys Lys Arg Lys Ser Thr
65                  70                  75                  80

Thr Met Asp Arg Arg Lys Ala Ala Thr Met Arg Glu Arg Arg Arg Leu
                85                  90                  95

Lys Lys Val Asn Gln Ala Phe Glu Thr Leu Lys Arg Cys Thr Thr Thr
            100                 105                 110

Asn Pro Asn Gln Arg Leu Pro Lys Val Glu Ile Leu Arg Asn Ala Ile
        115                 120                 125

Arg Tyr Ile Glu Ser Leu Gln Glu Leu Leu Arg Glu Gln Val Glu Asn
    130                 135                 140

Tyr Tyr Ser Leu Pro Gly Gln Ser Cys Ser Glu Pro Thr Ser Pro Thr
145                 150                 155                 160

Ser Asn Cys Ser Asp Gly Met Pro Glu Cys Asn Ser Pro Val Trp Ser
                165                 170                 175

Arg Lys Ser Ser Thr Phe Asp Ser Ile Tyr Cys Pro Asp Val Ser Asn
            180                 185                 190

Val Tyr Ala Thr Asp Lys Asn Ser Leu Ser Ser Leu Asp Cys Leu Ser
        195                 200                 205

Asn Ile Val Asp Arg Ile Thr Ser Ser Glu Gln Pro Gly Leu Pro Leu
    210                 215                 220

Gln Asp Leu Ala Ser Leu Ser Pro Val Ala Ser Thr Asp Ser Gln Pro
225                 230                 235                 240
```

```
Arg Thr Pro Gly Ala Ser Ser Ser Arg Leu Ile Tyr His Val Leu
                245                 250                 255
```

<210> SEQ ID NO 13
<211> LENGTH: 675
<212> TYPE: DNA
<213> ORGANISM: Homo sapiens;
<220> FEATURE:
<221> NAME/KEY: CDS
<222> LOCATION: (1)..(675)
<223> OTHER INFORMATION:
<300> PUBLICATION INFORMATION:
<308> DATABASE ACCESSION NUMBER: BT007233
<309> DATABASE ENTRY DATE: 2003-05-13
<313> RELEVANT RESIDUES: (1)..(675)

<400> SEQUENCE: 13

```
atg gag ctg tat gag aca tcc ccc tac ttc tac cag gaa ccc cgc ttc       48
Met Glu Leu Tyr Glu Thr Ser Pro Tyr Phe Tyr Gln Glu Pro Arg Phe
1               5                   10                  15

tat gat ggg gaa aac tac ctg cct gtc cac ctc cag ggc ttc gaa cca       96
Tyr Asp Gly Glu Asn Tyr Leu Pro Val His Leu Gln Gly Phe Glu Pro
            20                  25                  30

cca ggc tac gag cgg acg gag ctc acc ctg agc ccc gag gcc cca ggg      144
Pro Gly Tyr Glu Arg Thr Glu Leu Thr Leu Ser Pro Glu Ala Pro Gly
        35                  40                  45

ccc ctt gag gac aag ggg ctg ggg acc ccc gag cac tgt cca ggc cag      192
Pro Leu Glu Asp Lys Gly Leu Gly Thr Pro Glu His Cys Pro Gly Gln
    50                  55                  60

tgc ctg ccg tgg gcg tgt aag gtg tgt aag agg aag tcg gtg tcc gtg      240
Cys Leu Pro Trp Ala Cys Lys Val Cys Lys Arg Lys Ser Val Ser Val
65                  70                  75                  80

gac cgg cgg cgg gcg gcc aca ctg agg gag aag cgc agg ctc aag aag      288
Asp Arg Arg Arg Ala Ala Thr Leu Arg Glu Lys Arg Arg Leu Lys Lys
                85                  90                  95

gtg aat gag gcc ttc gag gcc ctg aag aga agc acc ctg ctc aac ccc      336
Val Asn Glu Ala Phe Glu Ala Leu Lys Arg Ser Thr Leu Leu Asn Pro
            100                 105                 110

aac cag cgg ctg ccc aag gtg gag atc ctg cgc agt gcc atc cag tac      384
Asn Gln Arg Leu Pro Lys Val Glu Ile Leu Arg Ser Ala Ile Gln Tyr
        115                 120                 125

atc gag cgc ctc cag gcc ctg ctc agc tcc ctc aac cag gag gag cgt      432
Ile Glu Arg Leu Gln Ala Leu Leu Ser Ser Leu Asn Gln Glu Glu Arg
    130                 135                 140

gac ctc cgc tac cgg ggc ggg ggc ggg ccc cag cca ggg gtg ccc agc      480
Asp Leu Arg Tyr Arg Gly Gly Gly Gly Pro Gln Pro Gly Val Pro Ser
145                 150                 155                 160

gaa tgc agc tct cac agc gcc tcc tgc agt cca gag tgg ggc agt gca      528
Glu Cys Ser Ser His Ser Ala Ser Cys Ser Pro Glu Trp Gly Ser Ala
                165                 170                 175

ctg gag ttc agc gcc aac cca ggg gat cat ctg ctc acg gct gac cct      576
Leu Glu Phe Ser Ala Asn Pro Gly Asp His Leu Leu Thr Ala Asp Pro
            180                 185                 190

aca gat gcc cac aac ctg cac tcc ctc acc tcc atc gtg gac agc atc      624
Thr Asp Ala His Asn Leu His Ser Leu Thr Ser Ile Val Asp Ser Ile
        195                 200                 205

aca gtg gaa gat gtg tct gtg gcc ttc cca gat gaa acc atg ccc aac      672
Thr Val Glu Asp Val Ser Val Ala Phe Pro Asp Glu Thr Met Pro Asn
    210                 215                 220

tag                                                                  675
```

<210> SEQ ID NO 14
<211> LENGTH: 224
<212> TYPE: PRT
<213> ORGANISM: Homo sapiens;

<400> SEQUENCE: 14

```
Met Glu Leu Tyr Glu Thr Ser Pro Tyr Phe Tyr Gln Glu Pro Arg Phe
1               5                   10                  15

Tyr Asp Gly Glu Asn Tyr Leu Pro Val His Leu Gln Gly Phe Glu Pro
            20                  25                  30

Pro Gly Tyr Glu Arg Thr Glu Leu Thr Leu Ser Pro Glu Ala Pro Gly
        35                  40                  45

Pro Leu Glu Asp Lys Gly Leu Gly Thr Pro Glu His Cys Pro Gly Gln
    50                  55                  60

Cys Leu Pro Trp Ala Cys Lys Val Cys Lys Arg Lys Ser Val Ser Val
65                  70                  75                  80

Asp Arg Arg Arg Ala Ala Thr Leu Arg Glu Lys Arg Arg Leu Lys Lys
                85                  90                  95

Val Asn Glu Ala Phe Glu Ala Leu Lys Arg Ser Thr Leu Leu Asn Pro
            100                 105                 110

Asn Gln Arg Leu Pro Lys Val Glu Ile Leu Arg Ser Ala Ile Gln Tyr
        115                 120                 125

Ile Glu Arg Leu Gln Ala Leu Leu Ser Ser Leu Asn Gln Glu Glu Arg
    130                 135                 140

Asp Leu Arg Tyr Arg Gly Gly Gly Gly Pro Gln Pro Gly Val Pro Ser
145                 150                 155                 160

Glu Cys Ser Ser His Ser Ala Ser Cys Ser Pro Glu Trp Gly Ser Ala
                165                 170                 175

Leu Glu Phe Ser Ala Asn Pro Gly Asp His Leu Leu Thr Ala Asp Pro
            180                 185                 190

Thr Asp Ala His Asn Leu His Ser Leu Thr Ser Ile Val Asp Ser Ile
        195                 200                 205

Thr Val Glu Asp Val Ser Val Ala Phe Pro Asp Glu Thr Met Pro Asn
    210                 215                 220
```

<210> SEQ ID NO 15
<211> LENGTH: 26
<212> TYPE: DNA
<213> ORGANISM: Artificial Sequence
<220> FEATURE:
<223> OTHER INFORMATION: SRY forward primer

<400> SEQUENCE: 15
gcctcaggac atattaatct ctggag 26

<210> SEQ ID NO 16
<211> LENGTH: 23
<212> TYPE: DNA
<213> ORGANISM: Artificial Sequence
<220> FEATURE:
<223> OTHER INFORMATION: SRY reverse primer

<400> SEQUENCE: 16
gctgatctct gaattctgca tgc 23

<210> SEQ ID NO 17
<211> LENGTH: 26
<212> TYPE: DNA
<213> ORGANISM: Artificial Sequence
<220> FEATURE:

```
<223> OTHER INFORMATION: SRY probe

<400> SEQUENCE: 17

aggcgcaagt tggctcaaca gaatcc                                          26


<210> SEQ ID NO 18
<211> LENGTH: 25
<212> TYPE: DNA
<213> ORGANISM: Artificial Sequence
<220> FEATURE:
<223> OTHER INFORMATION: IL2 forward primer

<400> SEQUENCE: 18

gccttgtgtg ttataagtag gaggc                                           25


<210> SEQ ID NO 19
<211> LENGTH: 21
<212> TYPE: DNA
<213> ORGANISM: Artificial Sequence
<220> FEATURE:
<223> OTHER INFORMATION: IL2 reverse primer

<400> SEQUENCE: 19

agtgccaatt cgatgatgag c                                               21


<210> SEQ ID NO 20
<211> LENGTH: 29
<212> TYPE: DNA
<213> ORGANISM: Artificial Sequence
<220> FEATURE:
<223> OTHER INFORMATION: IL2 probe

<400> SEQUENCE: 20

tctcctcaga aattccacca cagttgctg                                       29
```